United States Patent
Fetalvero et al.

(10) Patent No.: US 11,325,924 B2
(45) Date of Patent: *May 10, 2022

(54) MODULATORS OF SESTRIN-GATOR2 INTERACTION AND USES THEREOF

(71) Applicant: Navitor Pharmaceuticals, Inc., Cambridge, MA (US)

(72) Inventors: Kristina Michelle Fetalvero, Boston, MA (US); Sridhar Narayan, Belmont, MA (US); David John O'Neill, Arlington, MA (US); Eddine Saiah, Brookline, MA (US); Shomit Sengupta, Belmont, MA (US)

(73) Assignee: NAVITOR PHARMACEUTICALS, INC., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/941,821

(22) Filed: Jul. 29, 2020

(65) Prior Publication Data
US 2021/0047347 A1 Feb. 18, 2021

Related U.S. Application Data

(63) Continuation of application No. 16/515,788, filed on Jul. 18, 2019, now Pat. No. 10,752,644, which is a (Continued)

(51) Int. Cl.

| | | |
|---|---|---|
| *C07F 7/08* | (2006.01) |
| *A61K 38/00* | (2006.01) |
| *A61K 31/198* | (2006.01) |
| *A61K 31/223* | (2006.01) |
| *C07C 261/04* | (2006.01) |
| *C07C 311/13* | (2006.01) |
| *C07C 311/19* | (2006.01) |
| *C07C 311/51* | (2006.01) |
| *C07C 229/28* | (2006.01) |
| *C07C 233/40* | (2006.01) |
| *C07C 233/83* | (2006.01) |
| *C07C 237/06* | (2006.01) |
| *C07C 237/12* | (2006.01) |
| *C07C 237/30* | (2006.01) |
| *A61K 31/197* | (2006.01) |
| *A61K 31/221* | (2006.01) |
| *A61K 31/275* | (2006.01) |
| *A61K 31/341* | (2006.01) |
| *A61K 31/41* | (2006.01) |
| *A61K 31/695* | (2006.01) |
| *A61K 45/06* | (2006.01) |
| *C07C 229/12* | (2006.01) |
| *C07C 229/14* | (2006.01) |
| *C07C 229/18* | (2006.01) |
| *C07C 229/20* | (2006.01) |
| *C07C 233/07* | (2006.01) |
| *C07C 233/47* | (2006.01) |
| *C07C 233/49* | (2006.01) |

(Continued)

(52) U.S. Cl.
CPC ............ *C07F 7/081* (2013.01); *A61K 31/197* (2013.01); *A61K 31/198* (2013.01); *A61K 31/221* (2013.01); *A61K 31/223* (2013.01); *A61K 31/275* (2013.01); *A61K 31/341* (2013.01); *A61K 31/41* (2013.01); *A61K 31/695* (2013.01); *A61K 38/00* (2013.01); *A61K 45/06* (2013.01); *C07C 229/12* (2013.01); *C07C 229/14* (2013.01); *C07C 229/18* (2013.01); *C07C 229/20* (2013.01); *C07C 229/28* (2013.01); *C07C 233/07* (2013.01); *C07C 233/40* (2013.01); *C07C 233/47* (2013.01); *C07C 233/49* (2013.01); *C07C 233/51* (2013.01); *C07C 233/63* (2013.01); *C07C 233/83* (2013.01); *C07C 237/06* (2013.01); *C07C 237/12* (2013.01); *C07C 237/30* (2013.01); *C07C 255/61* (2013.01); *C07C 261/04* (2013.01); *C07C 311/06* (2013.01); *C07C 311/10* (2013.01); *C07C 311/13* (2013.01); *C07C 311/14* (2013.01); *C07C 311/19* (2013.01); *C07C 311/51* (2013.01); *C07D 257/04* (2013.01); *C07D 307/33* (2013.01); *C07C 2601/04* (2017.05); *C07C 2601/08* (2017.05); *C07C 2601/14* (2017.05)

(58) Field of Classification Search
None
See application file for complete search history.

(56) References Cited

U.S. PATENT DOCUMENTS

| 4,346,110 A | 8/1982 | Palfreyman et al. |
| 5,639,600 A | 6/1997 | McGrath et al. |

(Continued)

FOREIGN PATENT DOCUMENTS

| EP | 1389617 A1 | 2/2004 |
| WO | WO-1998008853 A1 | 3/1998 |

(Continued)

OTHER PUBLICATIONS

Abe et al., "Mammalian target of Rapamycin (mTOR) Activation Increases Axonal Growth Capacity of Injured Peripheral Nerves," The Journal of Biological Chemistry, vol. 285, No. 36, Sep. 3, 2010 (pp. 28034-28043).
Ali et al., "IL-15-PI3K-AKT-mTOR: A Critical Pathway in the Life Journey of Natural Killer Cells," Frontiers in Immunology, vol. 6, No. 355, Jul. 20, 2015 (9 pages).
Bar-Peled et al., "Regulation of mTORC1 by amino acids", Trends in Cell Biology, Jul. 2014, vol. 24, No. 7, pp. 400-406.

(Continued)

*Primary Examiner* — Po-Chih Chen
(74) *Attorney, Agent, or Firm* — Andrea L. C. Reid; Todd K. Macklin; Dechert LLP

(57) ABSTRACT

The present invention provides compounds, compositions thereof, and methods of using the same.

6 Claims, No Drawings

Related U.S. Application Data continuation of application No. 15/974,734, filed on May 9, 2018, now Pat. No. 10,414,782, which is a continuation of application No. 15/331,362, filed on Oct. 21, 2016, now Pat. No. 10,100,066.

(60) Provisional application No. 62/336,219, filed on May 13, 2016, provisional application No. 62/245,553, filed on Oct. 23, 2015.

(51) Int. Cl.
  C07C 233/51 (2006.01)
  C07C 233/63 (2006.01)
  C07C 255/61 (2006.01)
  C07C 311/06 (2006.01)
  C07C 311/10 (2006.01)
  C07C 311/14 (2006.01)
  C07D 257/04 (2006.01)
  C07D 307/33 (2006.01)

(56) References Cited

U.S. PATENT DOCUMENTS

| | | |
|---|---|---|
| 6,458,781 B1 | 10/2002 | Connor et al. |
| 6,613,934 B1 | 9/2003 | Jegelka et al. |
| 7,087,648 B1 | 8/2006 | McGrath |
| 7,390,799 B2 | 6/2008 | Bruncko et al. |
| 8,138,347 B2 | 3/2012 | Knight et al. |
| 10,100,066 B2 | 10/2018 | Fetalvero et al. |
| 10,414,782 B2 | 9/2019 | Fetalvero et al. |
| 10,752,644 B2 | 8/2020 | Fetalvero et al. |
| 10,912,750 B2 | 2/2021 | Saiah et al. |
| 2003/0203900 A1 | 10/2003 | Quibell |
| 2004/0110982 A1 | 6/2004 | Anderson et al. |
| 2007/0082894 A1 | 4/2007 | Burns et al. |
| 2010/0093706 A1 | 4/2010 | Hauske |
| 2012/0219596 A1 | 8/2012 | Limbach et al. |
| 2012/0225859 A1 | 9/2012 | Burger et al. |
| 2012/0231993 A1 | 9/2012 | Gazic Smilovic et al. |
| 2013/0116430 A1 | 5/2013 | Fujiwara et al. |
| 2013/0296245 A1 | 11/2013 | Li et al. |
| 2014/0186453 A1 | 7/2014 | Zale et al. |
| 2015/0105386 A1 | 4/2015 | Mack et al. |
| 2016/0137606 A1 | 5/2016 | Bissantz et al. |
| 2017/0114080 A1 | 4/2017 | Fetalvero et al. |
| 2017/0369435 A1 | 12/2017 | Pourgholami et al. |
| 2018/0333381 A1 | 11/2018 | Saiah et al. |
| 2019/0240174 A1 | 8/2019 | During |
| 2020/0079800 A1 | 3/2020 | Fetalvero et al. |
| 2020/0131114 A1 | 4/2020 | Lenzini |

FOREIGN PATENT DOCUMENTS

| | | |
|---|---|---|
| WO | 2000026259 A1 | 5/2000 |
| WO | WO-2003063794 A2 | 8/2003 |
| WO | WO-2004019973 A1 | 3/2004 |
| WO | WO-2004089925 A1 | 10/2004 |
| WO | WO-2004106328 A1 | 12/2004 |
| WO | WO-2005007623 A2 | 1/2005 |
| WO | WO-2005113554 A2 | 12/2005 |
| WO | WO-2006078846 A1 | 7/2006 |
| WO | WO-2006117696 A2 | 11/2006 |
| WO | WO-2006122806 A2 | 11/2006 |
| WO | WO-2007016176 A2 | 2/2007 |
| WO | WO-2007044729 A2 | 4/2007 |
| WO | WO-2007053452 A1 | 5/2007 |
| WO | WO-2007070514 A1 | 6/2007 |
| WO | WO-2007084786 A1 | 7/2007 |
| WO | WO-2007129161 A2 | 11/2007 |
| WO | WO-2008039218 A2 | 4/2008 |
| WO | WO-2008109943 A1 | 9/2008 |
| WO | WO-2008118802 A1 | 10/2008 |
| WO | WO-2009114512 A1 | 9/2009 |
| WO | 2011102964 A1 | 8/2011 |
| WO | WO-2013142229 A1 | 9/2013 |
| WO | WO-2014127052 A1 | 8/2014 |
| WO | WO-2014201111 A1 | 12/2014 |
| WO | WO-2017070518 A1 | 4/2017 |
| WO | WO-2017083823 A1 | 5/2017 |
| WO | WO-2018200625 A1 | 11/2018 |
| WO | WO-2020086816 A1 | 4/2020 |

OTHER PUBLICATIONS

Bar-Peled et al., "A Tumor suppressor complex with GAP activity for the RAG GTPases that signal amino acid sufficiency to mTORC1," Science, vol. 340, No. 6136, May 2013 (1100-1106).

Bar-Peled et al., "An expanded Ragulator is a GEF for the Rag GTPases that signal amino acid levels to mTORC1," Cell, vol. 150, No. 6, Sep. 2012 (pp. 1196-1208).

Berge et al., "Pharmaceutical Salts," Journal of Pharmaceutical Sciences, vol. 66, Jan. 1977 (pp. 1-19).

Bowling et al., "Antipsychotics Activate mTORC1-Dependent Translation to Enhance Neuronal Morphological Complexity," Science Signaling vol. 7, No. 308, Jan. 2014 (31 pages).

Brugarolas et al., "Regulation of mTOR function in response to hypoxia by REDD1 and the TSC1/TSC2 tumor suppressor complex," Genes & Development, vol. 18, No. 23, Dec. 2004 (pp. 2893-2904).

Buckbinder et al., "Gene regulation by temperature-sensitive p53 mutants: Identification of p53 response genes," Proceedings of the National Academy of Sciences U.S.A., vol. 91, Oct. 1994 (pp. 10640-10644).

Budanov et al., "The p53 target genes sestrin1 and sestrin2 connect genotoxic stress and mTOR signaling," Cell, vol. 134, No. 3, Aug. 2008 (pp. 451-460).

Buerger et al., "Localization of Rheb to the endomembrane is critical for its signaling function," Biochemical and Biophysical Research Communications, vol. 344, No. 3, Jun. 2006 (pp. 869-880).

Bull et al, "Conjugate additions of organocuprates to a 3-methylene-6-isopropyldiketopiperazine acceptor for the asymmetric synthesis of homochiral a-amino acids", J. Chem. Soc, Perkins Trans. 1, 2001, 3281-3287.

Bures et al, "Chiral imidazole derivatives synthesis from enentiopure N-protected a-amino acids", Asymmetry 16, Jan. 2005, pp. 1347-1354.

Cao et al., "Translational control of entrainment and synchrony of the suprachiasmatic circadian clock by mTOR/4E-BP1 signaling," Neuron, vol. 79, No. 4, Aug. 2013 (pp. 712-724).

CAS STN Abstract, RN 1555441-22-9 (Pub. Feb. 25, 2014).
CAS STN Abstract, RN 1698493-03-6 (Pub. May 5, 2015).
CAS STN Abstract, RN 1779709-85-1 (Pub. Jun. 14, 2015).
CAS STN Abstract, RN 1780718-09-3 (Pub. Jun. 15, 2015).

Chantranupong et al., "The Sestrins interact with GATOR2 to negatively regulate the amino-acid-sensing pathway upstream of mTORC1," Cell Reports, vol. 9, No. 1, Oct. 2014 (pp. 1-8).

Chauhan et al., "Muscle-specific regulation of the mTOR signaling pathway in MuSK antibody seropositive (MuSK+) experimental autoimmune Myasthenia gravis (EAMG)," Neuroscience Research, vol. 77, No. 1-2, Sep.-Oct. 2013 (pp. 102-109).

Chen et al., "Design, Synthesis, Activity, and Structuire of a Novel Class of Matrix Metalloproteinase Inhibitors containing a Heterocyclic P2-P3 Amide Bond Isotere", Bioorganic & Medicinal Chemistry Letters, 1996, vol. 6, No. 13, pp. 1601-1606.

Chi, "Regulation and function of mTOR signaling in T cell fate decisions," National Reviews Immunology, vol. 12, No. 5, Apr. 2012 (pp. 325-338).

Ching et al., "mTOR dysfunction contributes to vacuolar pathology and weakness in valosin-containing protein associated inclusion body myopathy," Human Molecular Genetics, vol. 22, No. 6, Mar. 2013 (pp. 1167-1179).

Cuthbertson et al., "Anabolic signaling deficits underlie amino acid resistance of wasting, aging muscle," FASEB Journal, vol. 19, No. 3, Mar. 2005 (pp. 422-424).

(56) References Cited

OTHER PUBLICATIONS

Deboves et al, "A new route to hydrophobic amino acids using copper-promoted reactions of serine-derived organozinc reagents", J. Chem. Soc., Perkins Tran. 1, 2000, pp. 4284-4292.

Delgoffe et al., "The mTOR kinase differentially regulates effector and regulatory T cell lineage commitment," Immunity, vol. 30, No. 6, Jun. 2009 (pp. 832-844).

Di Polo, "Dendrite pathology and neurodegeneration: focus on mTOR," Neural Regeneration Research, vol. 10, No. 4, Apr. 2015 (pp. 559-561).

Dibble et al., "TBC1D7 is a third subunit of the TSC1-TSC2 complex upstream of mTORC1," Molecular Cell, vol. 47, No. 4, Aug. 2012 (pp. 535-546).

Efeyan et al., "Amino acids and mTORC1: from lysosomes to disease," Trends in Molecular Medicine, vol. 18, No. 9, Sep. 2012 (pp. 524-533).

Garami et al., "Insulin Activation of Rheb, a Mediator of mTOR/S6K/4E-BP Signaling, is Inhibited by TSC1 and 2," Molecular Cell, vol. 11, Jun. 2003 (pp. 1457-1466).

Gordon et al., "Regulation of muscle protein synthesis and the effects of catabolic states," International Journal of Biochemistry and Cell Biology, vol. 45, No. 10, Oct. 2013 (pp. 2147-2157).

Gurpur et al., "Valproic acid activates the PI3K/Akt/mTOR pathway in muscle and ameliorates pathology in a mouse model of Duchenne muscular dystrophy," The American Journal of Pathology, vol. 174, No. 3, Mar. 2009 (pp. 999-1008).

Ham et al., "Leucine as a treatment for muscle wasting: A critical review," Clinical Nutrition, vol. 33, No. 6, Dec. 2014 (pp. 937-945).

Hirose et al., "RagA is a functional homologue of S. cerevisiae Gtr1p involved in the Ran/Gsp1-GTPase pathway," Journal of Cell Science, vol. 111, part 1, Jan. 1998 (pp. 11-21).

Howell et al., "A growing role for mTOR in promoting anabolic metabolism," Biochemical Society Transactions, vol. 41, No. 4, Aug. 2013 (pp. 906-912).

Ignacio et al., "New perspectives on the involvement of mTOR in depression as well as in the action of antidepressant drugs," British Journal of Clinical Pharmacology, vol. 82, No. 5, Nov. 2016 (pp. 1280-1290).

Inoki et al., "Rheb GTPase is a direct target of TSC2 GAP activity and regulates mTOR signaling," Genes & Development, vol. 17, No. 15, Aug. 2003 (pp. 1829-1834).

International Search Report and Written Opinion issued by the United States Patent and Trademark Office as International Searching Authority for International Application No. PCT/US2016/058188 dated Mar. 17, 2017 (11 pages).

Ito et al., "A medium-term rat liver bioassay for rapid in vivo detection of carcinogenic potential of chemicals," Cancer Science, vol. 94, No. 1, Jan. 2003 (pp. 3-8).

Kang et al., "mTORC1 Phosphorylation Sites Encode Their Sensitivity to Starvation and Rapamycin," Science, vol. 341, Jul. 26, 2013 (pp. 364-374).

Katholnig et al., "Immune responses of macrophages and dendritic cells regulated by mTOR signaling," Biochemical Society Transactions, vol. 41, No. 4, Aug. 2013 (pp. 927-933).

Kim et al., "mTOR: a pharmacologic target for autophagy regulation," The Journal of Clinical Investigation, vol. 125, No. 1, Jan. 2015 (pp. 25-32).

Kim et al., "Nutrient Regulation of the mTOR Complex 1 Signaling Pathway," Molecules and Cells, vol. 35, No. 6, Jun. 2013 (pp. 463-473).

Kim et al., "Regulation of TORC1 by Rag GTPases in nutrient response," Nature Cell Biology, vol. 10, No. 8, Aug. 2008 (pp. 935-945).

Kye et al., "SMN regulates axonal local translation via miR-183/mTOR pathway," Human Molecular Genetics, vol. 23, No. 23, Dec. 2014 (pp. 6318-6331).

Laplante et al., "mTOR signaling in growth control and disease," Cell, vol. 149, No. 2, Apr. 2012 (pp. 274-293).

Lee et al., "reinstating aberrant mTORC1 activity in Huntington's disease mice improves disease phenotypes," Neuron, vol. 85, No. 2, Jan. 2015 (pp. 303-315).

Leger et al., "Atrogin-1, MuRF1, and FoXO, as well as phosphorylated GSK-3beta and 4E-BP1 are reduced in skeletal muscle of chronic spinal cord-injured patients," Muscle Nerve, vol. 40, No. 1, Jul. 2009 (pp. 69-78).

Lin et al., "Activation of mTOR Ameliorates Fragile X Premutation rCGG Repeat-Mediated Neurodegeneration," PLOS One, vol. 8, No. 4, e62572, Apr. 2013 (pp. 1-8).

Long et al., "Rheb binds and regulates the mTOR kinase," Current Biology, vol. 15, No. 8, Apr. 2005 (pp. 702-713).

Love, "Demyelinating diseases," The Journal of Clinical Pathology, vol. 59, No. 11, Nov. 2006 (pp. 1151-1159).

Macovei et al., "Polyclonal antibodies: a cheap and efficient tool for screening of enantioselective catalysts", Chem. Dommun, 2012, vol. 48, pp. 4411-4413.

McVey et al., "CHO cells knocked out for TSC2 display an improved productivity of antibodies under fed batch conditions," Biotechnology and Bioengineering, vol. 113, No. 9, Sep. 2016 (pp. 1942-1952).

Nakamura et al., "Role of the mTOR complex 1 pathway in the in vivo maintenance of the intestinal mucosa by oral intake of amino acids," Geriatric & Gerontology International, vol. 12, No. 1, Jan. 2012 (pp. 131-139).

No Author, "substance Record for SID 219681321," PubChem, NIH U.S. National Library of Medicine, National Center for Biotechnology Information, retrieved only at <https://pubchem.ncbi.nlm.nih.gov/substance/219681321#section=Top> accessed Nov. 22, 2016 (6 pages).

No Author, "Substance Record for SID 4757389," PubChem, NIH U.S. National Library of Medicine, National Center for Biotechnology Information, retrieved only at <https://pubchem.ncbi.nlm.nih.gov/substance/4757389#section=Top> accessed Feb. 16, 2017 (5 pages).

No Author, "Substance Record for SID 8685219," PubChem, NIH U.S. National Library of Medicine, National Center for Biotechnology Information, retrieved only at <https://pubchem.ncbi.nlm.nih.gov/substance/8685219/version/1> accessed Nov. 22, 2016, (7 pages).

Nobukuni et al., "Amino acids mediate mTOR/raptor signaling through activation of class 3 phosphatidylinositol 3OH-kinase," Proceedings of the National Academy of Sciences U.S.A., vol. 102, No. 40, Oct. 2005 (pp. 14238-14243).

Norrmen et al., "mTORC1 controls PNS myelination along the mTORC1-RXR-SREBP-lipid biosynthesis axis in Schwann cells," Cell Reports, vol. 9, No. 2, Oct. 2014 (pp. 646-660).

Novarino et al., "Mutation in BCKD-kinase Lead to a Potentially Treatable Form of Autism with Epilepsy," Science, vol. 338, No. 6105, Sep. 2012 (pp. 394-397).

O'Brien et al., "Regulation of T-cell survival and mitochondrial homeostasis by TSC1," European Journal of immunology, vol. 41, No. 11, Nov. 2011 (pp. 3361-3370).

Panchaud et al., "Amino Acid Deprivation Inhibits TORC1 Through a GTPase-Activating Protein Complex for the Rag Family GTPase Gtr1," Science Signaling, vol. 6, No. 277, May 2013.

Park et al., "TSC1 regulates the balance between effector and regulatory T cells," The Journal of Clinical Investigation, vol. 123, No. 12, Dec. 2013 (pp. 5165-5178).

Pasiakos et al., "Leucine-enriched essential amino acid supplementation during moderate steady state exercise enhances postexercise muscle protein synthesis," The American Journal Clinical Nutrition, vol. 94, No. 3, Sep. 2011 (pp. 809-818).

Payne et al., "L-Leucine improves the anemia and developmental defects associates with Diamond-Blackfan anemia and del(5q) MDS by activating the mTOR pathway," Blood, vol. 120, No. 11, Sep. 2012 (pp. 2214-2224).

Pedroso et al., "Reviewing the Effects of L-Leucine Supplementation in the Regulation of Food Intake, energy Balance, and Glucose Homeostasis," Nutrients, vol. 7, No. 5, May 2015 (pp. 3914-3937).

(56) References Cited

OTHER PUBLICATIONS

Peeters et al., "PA26 is a candidate gene for heterotaxia in humans: Identification of a novel PA26-related gene family in human and mouse," Human Genetics, vol. 112, No. 5-6, Jun. 2003 (pp. 573-580).

Peng et al., "Sestrins function as guanine nucleotide dissociation inhibitors for Rag GTPases to control mTORC1 signaling," Cell, vol. 159, No. 1, Sep. 2014 (pp. 122-133).

Pollizzi et al., "mTORC1 and mTORC2 selectively regulate CD8+ T cell differentiation," The Journal of Clinical Investigation, vol. 125, No. 5, May 2015 (pp. 2090-2108).

Punzo et al., "Stimulation of the insulin/,TOR pathway delays cone death in a mouse model of retinitis pigmentosa," Nature Neuroscience, vol. 12, No. 1, Jan. 2009 (pp. 44-52).

Rennie, "Anabolic resistance: the effects of aging, sexual dimorphism, and immobilization on human muscle protein turnover," Applied Physiology, Nutrition, and Metabolism, vol. 34, No. 3, Jun. 2009 (pp. 377-381).

Roccio et al., "Regulation of the small GTPase Rheb by amino acids," Oncogene, vol. 25, Sep. 2006 (pp. 657-664).

Saito et al., "Novel Role of the Small GTPase Rheb: Its Implication in Endocytic Pathway Independent of the Activation of Mammalian Target of Rapamycin," The Journal of Biochemistry, vol. 137, No. 3, Mar. 2005 (pp. 423-430).

Sancak et al., "Ragulator-Rag complex targets mTORC1 to the lysosomal surface and is necessary for its activation by amino acids," Cell, vol. 141, No. 2, Apr. 2010 (pp. 290-303).

Sancak et al., "The Rag GTPases bind raptor and mediate amino acid signaling to mTORC1," Science, vol. 320, No. 5882, Jun. 2008 (pp. 1496-1501).

Saucedo et al., "Rheb promotes cell growth as a component of the insulin/TOR signaling network," Nature Cell Biology, vol. 5, No. 6, Jun. 2003 (pp. 566-571).

Schurmann et al., "Cloning of a Novel Family of Mamalian GTP-binding Proteins (RagA, RagB.sup.S, RagB.sup.1) with Remote Similarity to the Ras-related GTPases," The Journal of Biological Chemistry, vol. 270, No. 48, Dec. 1995 (pp. 28982-28988).

Sekiguchi et al., "Novel G Proteins, Rag C and Rag D, Interact with GTP-binding Proteins, Rag A and Rag B *," The Journal of Biological Chemistry, No. 276, No. 10, Mar. 2001 (pp. 7246-7257).

Smith et al., "The Tuberous Sclerosis Protein TSC2 Is Not Required for the Regulation of the Mammalian Target of Rapamycin by Amino Acids and Certain Cellular Stresses*," The Journal of Biological Chemistry, vol. 280, No. 19, May 2005 (pp. 18717-18727).

Song et al., "A simple method for preparation of N-mono- and N,N-di-alkylated a-amino acids", Tetrahedron Letters, vol. 41, 2000, pp. 8225-8230.

Song et al., "mTOR Attenuates the Inflammatory Response in Cardiomyocytes and Prevents Cardiac Dysfunction in Pathological Hypertrophy," The American Journal of Physiology Cell Physiology, vol. 299, No. 6, Sep. 2010 (pp. C1256-C1266).

Stein et al., "Protein kinetics during and after long-duration spaceflight on MIR," The American Journal of Physiology Endocrinology Metabolism, vol. 276, No. 6 Part 1, Jun. 1999 (pp. E1014-E1021).

Stocker et al., "Rheb Is an Essential Regulator of S6K in Controlling Cell Growth in *Drosophila*," Nature Cell Biology, vol. 5, No. 6, May 2003 (pp. 559-565).

Takikita et al., "Pertubed myelination process of premyelinating oligodendrocyte in Niemann-Pick type C mouse," The Journal Neuropathology and Experimental Neurology, vol. 63, No. 6, Jun. 2004 (pp. 660-673).

Tee et al., "Tuberous Sclerosis Complex-1 and -2 Gene Products Function together to Inhibit Mammalian Target of Rapamycin (mTOR)-mediated Downstream Signaling," Proceedings of the National Academy of Science U.S.A., vol. 99, No. 21, Oct. 15, 2002(pp. 13571-13576).

Tsun et al., "The Folliculin Tumor Suppressor is a GAP for the RagC/D GTPases That Signal Amino Acid Levels to mTORC1," Molecular Cell, vol. 52, No. 4, Nov. 21, 2013 (pp. 495-505).

Tyler et al., "Activation of the mammalian target of rapamycin (mTOR) is essential for oligodendrocyte differentiation," The Journal of Neuroscience, vol. 29, No. 19, May 13, 2009 (pp. 6367-6378).

Wang et al., "The amino acid transporter SLC38A9 is a key component of a lysosomal membrane complex that signals arginine sufficiency to mTORC1," Science, vol. 347, No. 6218, Jan. 2015 (pp. 188-194).

Wang et al., "Tuberous sclerosis 1 (Tsc1)-dependent metabolic checkpoint controls development of dendritic cells," Proceedings of the National Academy of Science U.S.A., vol. 110, No. 50, Dec. 2013 (pp. E4894-E4903).

Wolfson et al., "Sestrin2 is a leucine sensor for the mTORC1 pathway," Science, vol. 351, No. 6268, Jan. 2016 (pp. 43-48).

Xu et al., "Improved transcription and translation with L-leucine stimulation of mTORC1 in Roberts syndrome," BMC Genomics, vol. 17, No. 25, No Month Listed 2016 (18 pages).

Yang et al., "The tumor suppressor Tsc1 enforces quiescence of naive T cells to promote immune homeostasis and function," Nature Immunology, vol. 12, No. 9, Jul. 2011 (pp. 888-897).

Ye et al., "Chemical aminoacylation of tRNAs with fluorinated amino acids for in vitro protein mutagenesis", Bellstein Journal of Organic Chemistry, 2010, vol. 6, No. 40, pp. 1-6.

Zoncu et al., "mTORC1 senses lysosomal amino acids through an inside-out mechanism that requires the vacuolar H(+)-ATPase," Science, vol. 334, No. 6056, Nov. 2011 (pp. 678-683).

PCT International Search Report and Written Opinion from PCT/US2020/058475 dated Feb. 1, 2021.

Andrzejewska et al., "Cystinosin is a Component of the Vacuolar H+-ATPase-Ragulator-Rag Complex Controlling Mammalian Target of Rapamycin Complex 1 Signaling," Journal of the American Society of Nephrology, vol. 27, No. 6, Jun. 2016 (pp. 1678-1688).

Bidinosti et al., "CLK2 inhibition ameliorates autistic features associated with SHANK3 deficiency," Science, vol. 351, No. 6278, Mar. 2016 (pp. 1199-1203).

Cao et al., "Autophagy Is Disrupted in a Knock-in Mouse Model of Juvenile Neuronal Ceroid Lipofuscinosis," Journal of Biological Chemistry, vol. 281, No. 29, Jul. 2006 (pp. 20483-20493).

Child et al., "Cardiac mTORC1 Dysregulation Impacts Stress Adaptation and Survival in Huntington's Disease," Cell Rep. 2018;23(4):1020-1033.

Fossale et al., 2004, "Membrane trafficking and mitochondrial abnormalities precede subunit c deposition in a cerebellar cell model of juvenile neuronal ceroid lipofuscinosis," BMC Neurosci. 5(1):57.

Ivanova et al., "Altered mTOR signalling in nephropathic cystinosis," Journal of Inherited Metabolic Disease, vol. 39, No. 3, May 2016 (pp. 457-464).

Köhler et al., "Inflammation in Depression and the Potential for Anti-Inflammatory Treatment," Current Neuropharmacol. 2016;14(7):732-742.

Lambe et al., "Hypocretin (Orexin) Induces Calcium Transients in Single Spines Postsynaptic to Identified Thalamocortical Boutons in Prefrontal Slice," Neuron, vol. 40, No. 1, Sep. 2003 (pp. 139-150).

Lee et al., "Platelets Support Extracellular Sialylation by Supplying the Sugar Donor Substrate," Journal of Biological Chemistry, vol. 289, No. 13, Mar. 2014 (pp. 8742-8748).

Lee et al., 2014, "Functional effects of a pathogenic mutation in Cereblon (CRBN) on the regulation of protein synthesis via the AMPK-mTOR cascade," J. Biol. Chem. 289(34):23343-23352.

Li et al., "Glutamate N-methyl-D-aspartate receptor antagonists rapidly reverse behavioral and synaptic deficits caused by chronic stress exposure," Biological Psychiatry, vol. 69, No. 8, Apr. 2011 (pp. 754-761).

Li et al., "mTOR-dependent synapse formation underlies the rapid antidepressant effects of NMDA antagonists," Science, vol. 329, No. 5994, Aug. 2010 (pp. 959-964).

Liebau et al., "Dysregulated Autophagy Contributes to Podocyte Damage in Fabry's Disease," PLoS One, vol. 8, No. 5, May 2013 (10 pages).

Liu et al., "GLYX-13 Produces Rapid Antidepressant Responses with Key Synaptic and Behavioral Effects Distinct from Ketamine," Neuropharmacology, vol. 42, No. 6, May 2017 (pp. 1231-1242).

(56) References Cited

OTHER PUBLICATIONS

Liu et al., "Hypocretins (Orexins) Regulate Serotonin Neurons in the Dorsal Raphe Nucleus by Excitatory Direct and Inhibitory Indirect Actions," Journal of Neuroscience, vol. 22, No. 21, Nov. 2002 (pp. 9453-9464).

Malkesman et al., "The female urine sniffing test: a novel approach for assessing reward-seeking behavior in rodents," Biological Psychiatry, vol. 67, No. 9, May 2010 (pp. 864-871).

Manzi and Wasko, "Inflammation-mediated rheumatic diseases and atherosclerosis," Annals of the Rheumatic Diseases, vol. 59, No. 5, May 2000 (pp. 321-325).

Napolitano et al., "Impairment of chaperone-mediated autophagy leads to selective lysosomal degradation defects in the lysosomal storage disease cystinosis," EMBO Molecular Medicine, vol. 7, No. 2, Feb. 2015 (pp. 158-174).

Nelson et al., "Autophagy-lysosome pathway associated neuropathology and axonal degeneration in the brains of alpha-galactosidase A-deficient mice," Acta Neuropathologica Communications, vol. 2, No. 20, Feb. 2014 (pp. 1-15).

PCT International Search Report and Written Opinion from PCT/US2019/057815 dated Jan. 6, 2020.

Pearce et al., "Action of BTN1, the yeast orthologue of the gene mutated in Batten disease," Nature, Genetics, vol. 22, No. 1, May 1999 (pp. 55-58).

Tarlungeanu et al., 2016, "Impaired Amino Acid Transport at the Blood Brain Barrier Is a Cause of Autism Spectrum Disorder," Cell 167(6):1481-1494.

Vergarajauregui et al., "Autophagic dysfunction in mucolipidosis type IV patients," Human Molecular Genetics, vol. 17, No. 17, Sep. 2008 (pp. 2723-2737).

Wang et al., "Lysosomal amino acid transporter SLC38A9 signals arginine sufficiency to mTORC1," Science, vol. 347, No. 6218, Jan. 2015 (pp. 188-194).

Warner-Schmidt and Duman, "VEGF is an essential mediator of the neurogenic and behavioral actions of antidepressants," Proceedings of the National Academy of Sciences of the United States of America, vol. 104, No. 11, Mar. 2007 (pp. 4647-4652).

Wong et al., "*Drosophila* TRPML is Required for TORC1 Activation," Current Biology, vol. 22, No. 17, Sep. 2012 (pp. 1616-1621).

Xu et al., "A Mental Retardation-linked Nonsense Mutation in Cereblon Is Rescued by Proteasome Inhibition," Journal of Biological Chemistry, vol. 288, No. 41, Oct. 2013 (pp. 29573-29585).

Yang et al., "Reduced Excitatory Neurotransmission and Mild Autism-Relevant Phenotypes in Adolescent Shank3 Null Mutant Mice," Journal of Neuroscience, vol. 32, No. 19, May 2012 (pp. 6525-6541).

CAS STN Abstract, RN 1378266-29-5 (Pub. Jun. 14, 2012).

Peláet al., "Racemic synthesis and solid phase peptide synthesis application of the chimeric valine/leucine derivative 2-amino-3,3,4-trimethyl-pentanoic acid," Pharmazie. 2014;69(7):496-9.

MODULATORS OF SESTRIN-GATOR2 INTERACTION AND USES THEREOF

CROSS-REFERENCE TO RELATED APPLICATIONS

This application is a Continuation of U.S. patent application Ser. No. 16/515,788 filed on Jul. 18, 2019, which is a Continuation of U.S. patent application Ser. No. 15/974,734 filed on May 9, 2018, now U.S. Pat. No. 10,414,782, which is a Continuation of U.S. patent application Ser. No. 15/331,362 filed on Oct. 21, 2016, now U.S. Pat. No. 10,100,066, which claims the benefit of U.S. Provisional Application No. 62/336,219 filed on May 13, 2016, and U.S. Provisional Application 62/245,553 filed on Oct. 23, 2015. The content of each of which is hereby incorporated by reference.

TECHNICAL FIELD OF THE INVENTION

The present invention relates to compounds and methods useful for modulating the Sestrin-GATOR2 interaction thereby selectively modulating mTORC1 activity indirectly. The invention also provides pharmaceutically acceptable compositions comprising compounds of the present invention and methods of using said compositions in the treatment of various disorders.

BACKGROUND OF THE INVENTION

The mechanistic target of rapamycin complex 1 (mTORC1) protein kinase is a master growth regulator that senses diverse environmental cues, such as growth factors, cellular stresses, and nutrient and energy levels. When activated, mTORC1 phosphorylates substrates that potentiate anabolic processes, such as mRNA translation and lipid synthesis, and limits catabolic ones, such as autophagy. mTORC1 dysregulation occurs in a broad spectrum of diseases, including diabetes, epilepsy, neurodegeneration, immune response, suppressed skeletal muscle growth, and cancer among others (Howell et al., (2013) Biochemical Society transactions 41, 906-912; Kim et al., (2013) Molecules and cells 35, 463-473; Laplante and Sabatini, (2012) Cell 149, 274-293).

Many upstream inputs, including growth factors and energy levels, signal to mTORC1 through the TSC complex, which regulates Rheb, a small GTPase that is an essential activator of mTORC1 (Brugarolas et al., (2004) Genes & Development 18, 2893-2904; Garami et al., (2003) Molecular Cell 11, 1457-1466; Inoki et al., (2003) Genes & Development 17, 1829-1834; Long et al., (2005) Current Biology 15, 702-713; Sancak et al., (2008) Science (New York, N.Y.) 320, 1496-1501; Saucedo et al., (2003) Nature cell biology 5, 566-571; Stocker et al., (2003) Nature cell biology 5, 559-565; Tee et al., (2002) Proc Natl Acad Sci USA 99, 13571-13576). Amino acids do not appear to signal to mTORC1 through the TSC-Rheb axis and instead act through the heterodimeric Rag GTPases, which consist of RagA or RagB bound to RagC or RagD, respectively (Hirose et al., (1998) Journal of cell science 111 (Pt 1), 11-21; Kim et al., (2008) Nature cell biology 10, 935-945; Nobukuni et al., (2005) Proc Natl Acad Sci USA 102, 14238-14243; Roccio et al., (2005) Oncogene 25, 657-664; Sancak et al., (2008) Science (New York, N.Y.) 320, 1496-1501; Schürmann et al., (1995) The Journal of biological chemistry 270, 28982-28988; Sekiguchi et al., (2001) The Journal of biological chemistry 276, 7246-7257; Smith et al., (2005) The Journal of biological chemistry 280, 18717-18727). The Rag GTPases control the subcellular localization of mTORC1 and amino acids promote its recruitment to the lysosomal surface, where the Rheb GTPase also resides (Buerger et al., (2006) Biochemical and Biophysical Research Communications 344, 869-880; Dibble et al., (2012) Molecular cell 47, 535-546; Saito et al., (2005) Journal of Biochemistry 137, 423-430; Sancak et al., (2008) Science (New York, N.Y.) 320, 1496-1501). Several positive components of the pathway upstream of the Rag GTPases have been identified. The Ragulator complex localizes the Rag GTPases to the lysosomal surface and, along with the vacuolar-ATPase, promotes the exchange of GDP for GTP on RagA/B (Bar-Peled et al., (2012) Cell 150, 1196-1208; Sancak et al., (2010) Cell 141, 290-303; Zoncu et al., (2011) Science Signaling 334, 678-683). The distinct FLCN-FNIP complex acts on RagC/D and stimulates its hydrolysis of GTP into GDP (Tsun et al., 2013). When RagA/B is loaded with GTP and RagC/D with GDP, the heterodimers bind and recruit mTORC1 to the lysosomal surface, where it can come in contact with its activator Rheb GTPase.

Recent work has identified the GATOR1 multi-protein complex as a major negative regulator of the amino acid sensing pathway and its loss causes mTORC1 signaling to be completely insensitive to amino acid starvation (Bar-Peled et al., (2013) Science 340, 1100-1106; Panchaud et al., (2013) Science Signaling 6, ra42). GATOR1 consists of DEPDC5, Nprl2, and Nprl3, and is a GTPase activating protein (GAP) for RagA/B. The GATOR2 multi-protein complex, which has five known subunits (WDR24, WDR59, Mios, Secl3, and Seh1L), is a positive component of the pathway and upstream of or parallel to GATOR1, but its molecular function was, until recently, unknown (Bar-Peled et al., (2013) Science 340, 1100-1106).

Recently, additional information about the mTORC1 pathway has been elucidated by identifying the binding of GATOR2 with one or more of the Sestrins and demonstrating that the resulting Sestrin-GATOR2 complex regulates the subcellular localization and activity of mTORC1. In particular, the presence of Sestrin-GATOR2 complexes inhibits the mTORC1 pathway and decreases mTORC1 activity by preventing translocation of mTORC1 to the lysosomal membrane. Interaction of GATOR2 with the Sestrins, and in particular Sestrin1 and Sestrin2, is antagonized by amino acids, particularly leucine and, to a lesser extent, isoleucine, methionine and valine. In the presence of leucine, GATOR2 does not interact with Sestrin1 or Sestrin2 and mTORC1 is able to migrate to the lysosomal membrane where it is active. Sestrin1 and Sestrin2 directly bind leucine and to a lesser extent, isoleucine and methionine (Chantranupong et al., (2014) Cell Rep.; 9(1):1-8). The binding of leucine by Sestrin1 or -2 is required for disruption of its interaction with GATOR2 and subsequent activation of mTORC1. Sestrin2 mutants incapable of binding leucine cannot signal the presence of leucine to mTORC1, and cells depleted of Sestrin2 and its homologs render mTORC1 insensitive to the absence of leucine (Wolfson et al., (2015) Science pii: ab2674 [Epub ahead of print]).

The Sestrins are three related proteins (Sestrin1, -2 and -3) of poorly characterized molecular functions (Buckbinder et al., (1994) Proc Natl Acad Sci USA 91, 10640-10644; Budanov et al., (2002) Cell 134, 451-460; Peeters et al., (2003) Human genetics 112, 573-580). Sestrin2 inhibits mTORC1 signaling and has been proposed to activate AMPK upstream of TSC as well as interact with TSC (Budanov and Karin, (2008) Cell 134, 451-460), but later studies find inhibition of mTORC1 by Sestrin2 in the absence of AMPK (Peng et al., (2014) Cell 159(1):122-33) further emphasizing the important role the GATOR2 complex plays in modulating mTORC1 in response to Sestrin2.

Modulation of the Sestrin-GATOR2 complex represents a potential therapeutic target for selectively modulating mTORC1 activity indirectly.

SUMMARY OF THE INVENTION

It has now been found that compounds of this invention, and pharmaceutically acceptable compositions thereof, are effective as Sestrin-GATOR2 modulators. Such compounds have the general formula I:

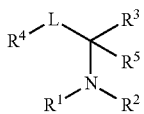

I or a pharmaceutically acceptable salt thereof, wherein each variable is as defined and described herein.

Compounds of the present invention, and pharmaceutically acceptable compositions thereof, are useful for treating a variety of diseases, disorders or conditions, associated with mTORC1. Such diseases, disorders, or conditions include diabetes, epilepsy, neurodegeneration, immune response, suppressed skeletal muscle growth, and cellular proliferative disorders (e.g., cancer) such as those described herein.

DETAILED DESCRIPTION OF CERTAIN EMBODIMENTS

1. General Description of Certain Embodiments of the Invention

Compounds of the present invention, and compositions thereof, are useful as Sestrin-GATOR2 modulators. In certain embodiments, the present invention provides a compound of formula I

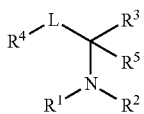

I or a pharmaceutically acceptable salt thereof, wherein:
$R^1$ is H or $C_{1-6}$ alkyl;
$R^2$ is R, —$(CH_2)_n$-phenyl, —C(O)R, —$SO_2$R, or —C(O)N$(R)_2$;
n is 0, 1, or 2;
each R is independently hydrogen, —CN, or an optionally substituted group selected from saturated or unsaturated $C_{1-6}$ aliphatic, phenyl, 4-7 membered saturated or partially unsaturated monocyclic carbocyclic ring, 5-6 membered monocyclic heteroaryl ring having 1-4 heteroatoms, or a 4-8 membered saturated or partially saturated heterocyclic ring with 1-2 heteroatoms independently selected from nitrogen, oxygen, or sulfur;
$R^3$ is Ring A, —C(O)R, —C(O)OR, —C(O)N$(R)_2$, —$SO_3$H, —$SO_2$N$(R)_2$, —S(O)R, —S(O)Ring A, —OR or —B(OR)$_2$ where two OR groups on the same boron are taken together with their intervening atoms to form a 5-8 membered monocyclic saturated or partially unsaturated, ring having 0-3 heteroatoms, in addition to the boron and two oxygens, independently selected from nitrogen, oxygen, or sulfur, or $R^3$ and $R^4$ taken together form an optionally substituted 5-6 membered ring having 0-1 heteroatoms selected from nitrogen, oxygen or sulfur;
L is a covalent bond or a straight or branched $C_{1-6}$ alkylene chain optionally substituted with 1-9 fluoro groups;
Ring A is an optionally substituted ring selected from phenyl or an optionally substituted 5-6 membered heteroaryl ring having 1-4 heteroatoms independently selected from nitrogen, oxygen or sulfur;
$R^4$ is R, —$CF_3$, —OR, —N$(R)_2$, —Si$(R)_3$, or —SR, or $R^3$ and $R^4$ taken together form an optionally substituted 5-6 membered ring having 0-1 heteroatoms selected from nitrogen, oxygen or sulfur; and
$R^5$ is H or $C_{1-4}$ alkyl.

2. Compounds and Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —$(CH_2)_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or $14\pi$ electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}R^\circ$; —$(CH_2)_{0-4}R^\circ$; —$O(CH_2)_{0-4}R^\circ$, —O—$(CH_2)_{0-4}C(O)OR^\circ$; —$(CH_2)_{0-4}CH(OR^\circ)_2$; —$(CH_2)_{0-4}SR^\circ$; —$(CH_2)_{0-4}Ph$, which may be substituted with $R^\circ$; —$(CH_2)_{0-4}O(CH_2)_{0-1}Ph$ which may be substituted with $R^\circ$; —CH=CHPh, which may be substituted with $R^\circ$; —$(CH_2)_{0-4}O(CH_2)_{0-1}$-pyridyl which may be substituted with $R^\circ$; —$NO_2$; —CN; —$N_3$; —$(CH_2)_{0-4}N(R^\circ)_2$; —$(CH_2)_{0-4}N(R^\circ)C(O)R^\circ$; —$N(R^\circ)C(S)R^\circ$; —$(CH_2)_{0-4}N(R^\circ)C(O)NR^\circ_2$; —$N(R^\circ)C(S)NR^\circ_2$; —$(CH_2)_{0-4}N(R^\circ)C(O)OR^\circ$; —$N(R^\circ)N(R^\circ)C(O)R^\circ$; —$N(R^\circ)N(R^\circ)C(O)NR^\circ_2$;

—N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR—, SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; —SiR°$_3$; —(C$_{1-4}$ straight or branched alkylene)O—N(R°)$_2$; or —(C$_{1-4}$ straight or branched alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —SiR$^\bullet$$_3$, —OSiR$^\bullet$$_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger$$_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger$$_2$, —C(S)NR$^\dagger$$_2$, —C(NH)NR$^\dagger$$_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$-Ph, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention.

As used herein, the term "leucine mimetic" is defined as a compound that reduces the amount of Sestrin2 bound to GATOR2 by at least about 40% at 25 µM relative to leucine. In certain embodiments, the "leucine mimetic" reduces the amount of Sestrin2 bound to GATOR2 by at least about 100%, by at least about 150%, or by at least about 200%.

As used herein, the term "leucine antagonist" is defined as a compound that increases the amount of Sestrin2 bound to GATOR2 by at least about 40% at 25 µM relative to leucine (represented as −40% of leucine activity). In certain embodiments, the "leucine antagonist" increases the amount of Sestrin2 bound to GATOR2 by at least about 100%, by at least about 150%, or by at least about 200%.

The terms "measurable affinity" and "measurably inhibit," as used herein, means a measurable change in Sestrin2 binding to GATOR2 between a sample comprising a compound of the present invention, or composition thereof, and Sestrin2, GATOR2 and leucine, and an equivalent sample comprising Sestrin2, GATOR2 and leucine, in the absence of said compound, or composition thereof.

3. Description of Exemplary Embodiments

In certain embodiments, the present invention provides a compound of formula I:

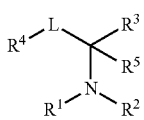

or a pharmaceutically acceptable salt thereof, wherein:
$R^1$ is H or $C_{1-6}$ alkyl;
$R^2$ is R, —(CH$_2$)$_n$-phenyl, —C(O)R, —SO$_2$R, or —C(O)N(R)$_2$;
n is 0, 1, or 2;
each R is independently hydrogen, —CN, or an optionally substituted group selected from saturated or unsaturated $C_{1-6}$ aliphatic, phenyl, 4-7 membered saturated or partially unsaturated monocyclic carbocyclic ring, 5-6 membered monocyclic heteroaryl ring having 1-4 heteroatoms, or a 4-8 membered saturated or partially saturated heterocyclic ring with 1-2 heteroatoms independently selected from nitrogen, oxygen, or sulfur;

$R^3$ is Ring A, —C(O)R, —C(O)OR, —C(O)N(R)$_2$, —SO$_3$H, —SO$_2$N(R)$_2$, —S(O)R, —S(O)Ring A, —OR or —B(OR)$_2$ where two OR groups on the same boron are taken together with their intervening atoms to form a 5-8 membered monocyclic saturated or partially unsaturated, ring having 0-3 heteroatoms, in addition to the boron and two oxygens, independently selected from nitrogen, oxygen, or sulfur, or $R^3$ and $R^4$ taken together form an optionally substituted 5-6 membered ring having 0-1 heteroatoms selected from nitrogen, oxygen or sulfur;

L is a covalent bond or a straight or branched $C_{1-6}$ alkylene chain optionally substituted with 1-9 fluoro groups;

Ring A is an optionally substituted ring selected from phenyl or an optionally substituted 5-6 membered heteroaryl ring having 1-4 heteroatoms independently selected from nitrogen, oxygen or sulfur;

$R^4$ is R, —CF$_3$, —OR, —N(R)$_2$, —Si(R)$_3$, or —SR, or $R^3$ and $R^4$ taken together form an optionally substituted 5-6 membered ring having 0-1 heteroatoms selected from nitrogen, oxygen or sulfur; and $R^5$ is H or $C_{1-4}$ alkyl.

In some embodiments, a provided compound of formula I is other than those compounds depicted in Table 2, below.

As defined generally above, $R^1$ is H or $C_{1-6}$ alkyl. In some embodiments, $R^1$ is H. In other embodiments, $R^1$ is $C_{1-6}$ alkyl. In some embodiments $R^1$ is methyl. In some embodiments $R^1$ is isobutyl. In some embodiments, $R^1$ is selected from those depicted in Table 1, below. In some embodiments, $R^1$ is selected from those depicted in Table 2, below.

As defined generally above, $R^2$ is R, —(CH$_2$)$_n$-phenyl, —C(O)R, —SO$_2$R, or —C(O)N(R)$_2$. In some embodiments, $R^2$ is R. In some embodiments, $R^2$ is —(CH$_2$)$_n$-phenyl. In some embodiments, $R^2$ is —C(O)R. In some embodiments, $R^2$ is —SO$_2$R. In some embodiments, $R^2$ is —C(O)N(R)$_2$. In some embodiments, $R^2$ is methyl. In some embodiments, $R^2$ is —(CH$_2$)-phenyl. In some embodiments, $R^2$ is —C(O)CH$_3$. In some embodiments, $R^2$ is selected from those depicted in Table 1, below. In some embodiments, $R^2$ is selected from those depicted in Table 2, below.

As defined generally above, n is 0, 1, or 2. In some embodiments, n is 0. In some embodiments, n is 1. In some embodiments, n is 2.

As defined generally above, $R^3$ is Ring A, —C(O)R, —C(O)OR, —C(O)N(R)$_2$, —SO$_3$H, —SO$_2$N(R)$_2$, —S(O)R, —S(O)Ring A, —OR or —B(OR)$_2$ where two —OR groups on the same boron are taken together with their intervening atoms to form a 5-8 membered monocyclic saturated or partially unsaturated, ring having 0-3 heteroatoms, in addition to the boron and two oxygens, independently selected from nitrogen, oxygen, or sulfur, or $R^3$ and $R^4$ taken together form an optionally substituted 5-6 membered ring having 0-1 heteroatoms selected from nitrogen, oxygen or sulfur.

In some embodiments, $R^3$ is —C(O)OH. In some embodiments, $R^3$ is —C(O)N(R)$_2$. In some embodiments, $R^3$ is —SO$_3$H. In some embodiments, $R^3$ is —SO$_2$N(R)$_2$. In some embodiments, $R^3$ is —B(OR)$_2$ where two —OR groups on the same boron are taken together with their intervening atoms to form a 5-8 membered monocyclic saturated, partially unsaturated, or heterocyclic ring having 0-3 heteroatoms, in addition to the boron and two oxygens, independently selected from nitrogen, oxygen, or sulfur. In some embodiments, $R^3$ and $R^4$ taken together form an optionally substituted 5-6 membered ring having 0-1 heteroatoms selected from nitrogen, oxygen or sulfur.

In some embodiments, $R^3$ is Ring A. As defined generally above, Ring A is an optionally substituted ring selected from phenyl or an optionally substituted 5-6 membered heteroaryl ring having 1-4 heteroatoms independently selected from nitrogen, oxygen or sulfur. In some embodiments, Ring A is optionally substituted phenyl. In some embodiments, Ring A is an optionally substituted 5-membered heteroaryl ring having 1-4 heteroatoms independently selected from nitrogen, oxygen or sulfur. In some embodiments, Ring A is an optionally substituted 5-membered heteroaryl ring selected from imidazolyl, isoxazolyl, 1H-pyrrolyl (e.g., maleimido), pyrazolyl, oxazolyl, tetrazolyl, thiazolyl and triazolyl. In some embodiments, Ring A is an optionally substituted 6-membered heteroaryl ring having 1-2 nitrogen atoms. In some embodiments, Ring A is an optionally substituted 6-membered ring selected from pyridyl and pyrimidinyl. In some embodiments, Ring A is selected from those depicted in Table 1, below.

In some embodiments, $R^3$ is (pinacolato)boron. In some embodiments, $R^3$ is selected from those depicted in Table 1, below. In some embodiments, $R^3$ is selected from those depicted in Table 2, below.

As defined generally above, L is a covalent bond or a straight or branched $C_{1-6}$ alkylene chain optionally substituted with 1-4 fluoro groups. In some embodiments, L is a covalent bond. In some embodiments, L is a straight or branched $C_{1-6}$ alkylene chain optionally substituted with 1-4 fluoro groups. In some embodiments, L is methylene. In some embodiments, L is n-butylenyl. In some embodiments, L is ethylenyl. In some embodiments, L is n-propylenyl. In some embodiments, L is selected from those depicted in Table 1, below. In some embodiments, L is selected from those depicted in Table 2, below.

In some embodiments, L is a branched $C_{1-6}$ alkylene chain optionally substituted with 1-4 fluoro groups. In certain embodiments, L is —C(CH$_3$)$_2$—. In other embodiments, L is —C(CH$_3$)(CF$_3$)—.

As defined generally above, $R^4$ is R, —CF$_3$, —OR, —N(R)$_2$, —Si(R)$_3$ or —SR, or $R^3$ and $R^4$ taken together form an optionally substituted 5-6 membered ring having 0-1 heteroatoms selected from nitrogen, oxygen or sulfur. In some embodiments, $R^4$ is R. In some embodiments, $R^4$ is —CF$_3$. In some embodiments, $R^4$ is —OR. In some embodiments, $R^4$ is —N(R)$_2$. In some embodiments, $R^4$ is —Si(R)$_3$. In some embodiments, $R^4$ is —SR. In some embodiments, $R^4$ is isopropyl. In some embodiments, $R^4$ is tert-butyl. In some embodiments, $R^4$ is cyclopropyl. In some embodiments, $R^4$ is cyclobutyl. In some embodiments, $R^4$ is sec-butyl. In some embodiments, $R^4$ is methoxyl. In some embodiments, $R^4$ is methylthioyl. In some embodiments, $R^3$ and $R^4$ taken together form an optionally substituted 5-6 membered ring having 0-1 heteroatoms selected from nitrogen, oxygen or sulfur. In some embodiments, $R^4$ is selected from those depicted in Table 1, below. In some embodiments, $R^4$ is selected from those depicted in Table 2, below.

As defined generally above, $R^5$ is H or $C_{1-4}$ alkyl. In some embodiments, $R^5$ is H. In some embodiments, $R^5$ is $C_{1-4}$ alkyl. In some embodiments, $R^5$ is methyl. In some embodiments, $R^5$ is selected from those depicted in Table 1, below. In some embodiments, $R^5$ is selected from those depicted in Table 2, below.

In certain embodiments, the present invention provides for a compound of formula II:

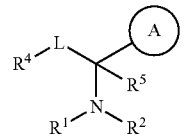

II or a pharmaceutically acceptable salt thereof, wherein each variable is as defined above and as described in embodiments provided herein, both singly and in combination.

In certain embodiments, the present invention provides for a compound of formula

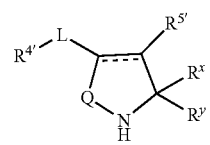

III or a pharmaceutically acceptable salt thereof, wherein:

Q is —C(R')$_2$— or —NH—;

each of $R^x$ and $R^y$ is hydrogen, or $R^x$ and R taken together form =O;

===== is a double bond or a single bond;

each R is independently hydrogen, —CN, or an optionally substituted group selected from $C_{1-6}$ aliphatic, phenyl, 4-7 membered saturated or partially unsaturated monocyclic carbocyclic ring, 5-6 membered monocyclic heteroaryl ring having 1-4 heteroatoms, or a 4-8 membered saturated or partially saturated heterocyclic ring with 1-2 heteroatoms independently selected from nitrogen, oxygen, or sulfur;

each R' is independently hydrogen, halogen, —CN, or an optionally substituted group selected from $C_{1-6}$ aliphatic, phenyl, 4-7 membered saturated or partially unsaturated monocyclic carbocyclic ring, 5-6 membered monocyclic heteroaryl ring having 1-4 heteroatoms, or a 4-8 membered saturated or partially saturated heterocyclic ring with 1-2 heteroatoms independently selected from nitrogen, oxygen, or sulfur;

L is a covalent bond or a straight or branched $C_{1-6}$ alkylene chain optionally substituted with 1-9 fluoro groups;

$R^{4'}$ is R, —CF$_3$, —OR, —N(R)$_2$, —Si(R)$_3$, or —SR; and $R^{5'}$ is H, —OR, or $C_{1-4}$ alkyl.

In some embodiments, Q is —NH—. In some embodiments, Q is —CH$_2$—. In some embodiments, Q is —CHF—.

In some embodiments, L is —CH$_2$—.

In some embodiments, each $R^x$ and R is hydrogen. In some embodiments, $R^x$ and R taken together form =O.

In some embodiments, $R^{5'}$ is H. In some embodiments, $R^{5'}$ is —OH.

In some embodiments, ===== is a single bond. In some embodiments, ===== is a double bond.

In certain embodiments, the present invention provides for a compound of formulae IV-a, IV-b, or IV-c:

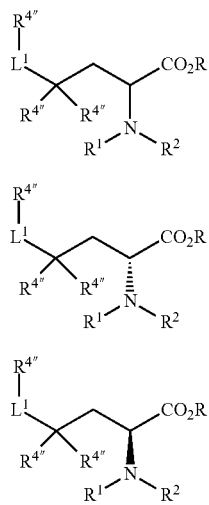

or a pharmaceutically acceptable salt thereof, wherein:

$R^1$ is H or C1-6 alkyl;

$R^2$ is R, —$(CH_2)_n$-phenyl, —C(O)R, —$SO_2$R, or —C(O)N$(R)_2$;

each $R^{4''}$ is independently R, halogen, or —$CF_3$;

each R is independently hydrogen, —CN, or an optionally substituted group selected from saturated or unsaturated $C_{1-6}$ aliphatic, phenyl, 4-7 membered saturated or partially unsaturated monocyclic carbocyclic ring, 5-6 membered monocyclic heteroaryl ring having 1-4 heteroatoms, or a 4-8 membered saturated or partially saturated heterocyclic ring with 1-2 heteroatoms independently selected from nitrogen, oxygen, or sulfur; and $L^1$ is a covalent bond or a straight or branched $C_{1-6}$ alkylene chain optionally substituted with 1-9 fluoro groups.

In some embodiments, $R^1$ is H. In some embodiments, $R^1$ is $C_{1-6}$ alkyl.

In some embodiments, $R^1$ is selected from those depicted in Table 1, below.

In some embodiments, $R^2$ is R. In some embodiments, $R^2$ is —$(CH_2)_n$-phenyl. In some embodiments, $R^2$ is —C(O)R.

In some embodiments, $R^2$ is selected from those depicted in Table 1, below.

In some embodiments, each $R^{4''}$ is independently R, halogen, or —$CF_3$. In some embodiments, $R^{4''}$ is R. In some embodiments, $R^{4''}$ is halogen. In some embodiments, $R^{4''}$ is —$CF_3$. In some embodiments, $R^{4''}$ is selected from those depicted in Table 1, below.

In some embodiments, $L^1$ is a covalent bond or a straight or branched $C_{1-6}$ alkylene chain optionally substituted with 1-9 fluoro groups. In some embodiments, $L^1$ is a covalent bond. In some embodiments, $L^1$ is a straight or branched $C_{1-6}$ alkylene chain optionally substituted with 1-9 fluoro groups. In some embodiments, $L^1$ is selected from those depicted in Table 1, below.

Exemplary compounds of the present invention are set forth in Table 1, below.

TABLE 1

Exemplary Compounds

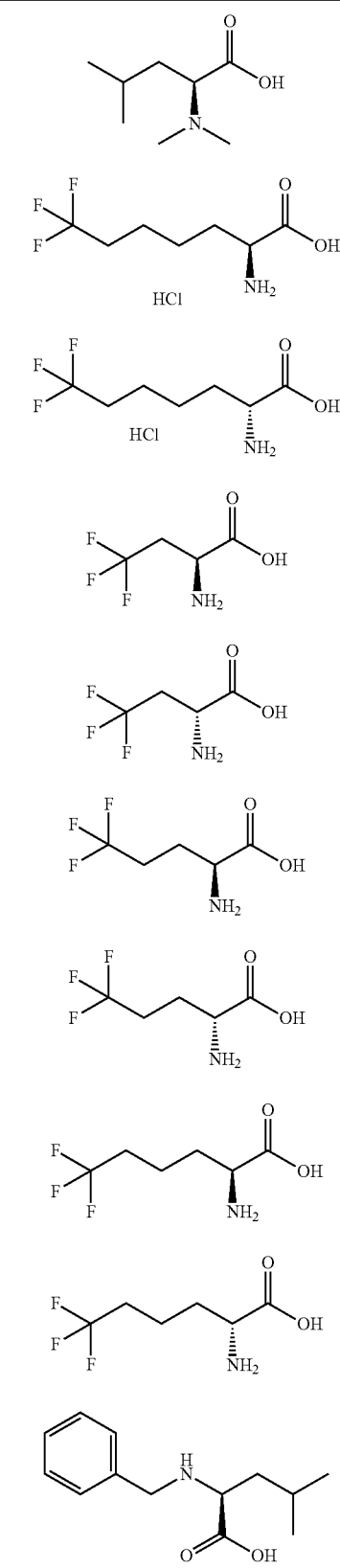

TABLE 1-continued

Exemplary Compounds

| Compound | 
|---|
| I-12 |
| I-13 |
| I-14 |
| I-15 |
| I-16 |
| I-17 |
| I-18 |
| I-19 |
| I-20 |
| I-21 |
| I-22 |
| I-25 |
| I-26 |
| I-36 |
| I-45 |
| I-46 |
| I-47 |
| I-48 |
| I-49 |

TABLE 1-continued

Exemplary Compounds

I-50, I-51, I-52, I-53, I-54, I-55, I-56, I-57, I-58, I-59, I-60, I-61, I-62, I-63, I-64

TABLE 1-continued

Exemplary Compounds

I-65, I-66, I-67, I-68, I-69, I-70, I-71, I-72, I-73, I-74, I-75, I-76, I-77

TABLE 1-continued

Exemplary Compounds

| Compound | ID |
|---|---|
| (structure) | I-78 |
| (structure) | I-79 |
| (structure) | I-80 |
| (structure) | I-81 |
| (structure) | I-82 |
| (structure) | I-83 |
| (structure) | I-84 |
| (structure) | I-85 |
| (structure) | I-86 |
| (structure) | I-87 |
| (structure) | I-88 |
| (structure) | I-89 |
| (structure) | I-90 |
| (structure) | I-91 |
| (structure) | I-92 |

TABLE 1-continued
Exemplary Compounds
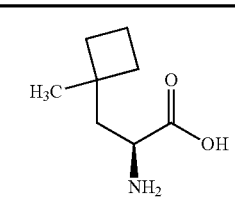 I-93
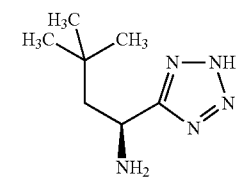 I-94
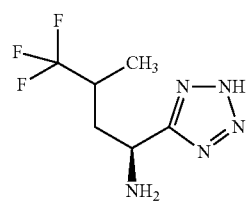 I-95
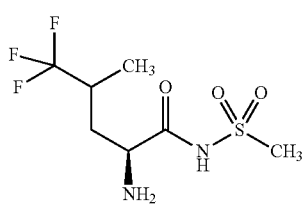 I-96
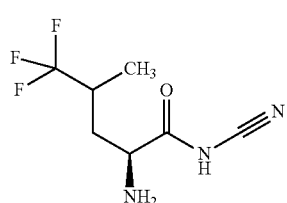 I-97
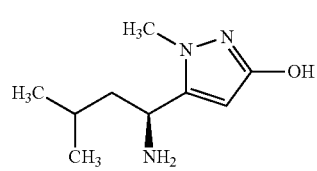 I-98
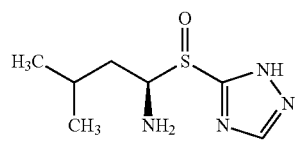 I-99
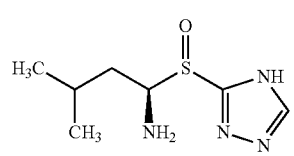 I-100
TABLE 1-continued
Exemplary Compounds
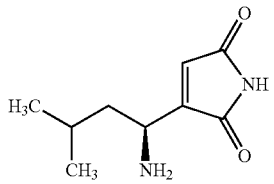 I-101
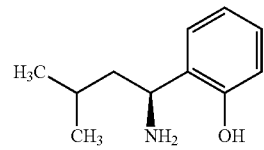 I-102
I-103
I-104
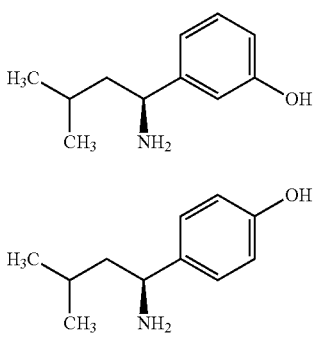 I-105
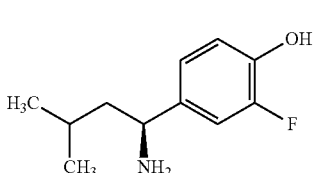 I-106
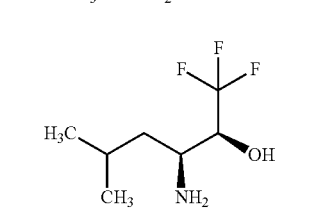 I-107
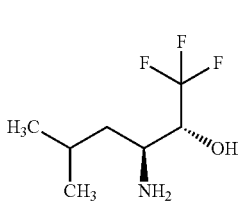 I-108
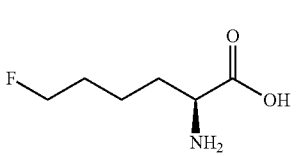 
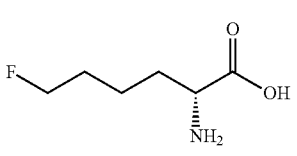 I-109

TABLE 1-continued

Exemplary Compounds

I-110, I-111, I-113, I-114, I-115, I-116, I-117, I-118, I-119, I-120, I-121, I-122, I-123, I-124, I-125, I-126, I-127, I-128, I-129

TABLE 1-continued

Exemplary Compounds

| Structure | ID |
|---|---|
| (3-hydroxy-4-neopentyl-pyrrolidin-2-one) | I-130 |
| (5-neopentyl-1H-pyrazol-3(2H)-one) | I-131 |
| (5-isopentyl-1H-pyrazol-3(2H)-one) | I-132 |
| (5-isobutyl-1H-pyrazol-3(2H)-one) | I-133 |
| (5-fluoro-4-neopentyl-pyrrolidin-2-one) | I-134 |
| (3-hydroxy-5-isobutyl-pyrrolidin-2-one) | I-135 |
| (trifluoromethylthio homoserine) | I-136 |
| (difluoromethylthio homoserine) | I-137 |
| (fluoro methylthio homoserine) | I-138 |
| (difluoro methylthio amino acid) | I-139 |
| (isopropylthio homoserine) | I-140 |
| (tert-butylthio homoserine) | I-141 |
| (cyclopropylthio homoserine) | I-142 |
| (cyclobutylthio homoserine) | I-143 |
| (3,3-difluorocyclobutylthio homoserine) | I-144 |
| (5,5,5-trifluoro-4-methyl-L-norvaline) | I-145 |
| (5,5,5-trifluoro-4-methyl-D-norvaline) | I-146 |
| (L-leucine methanesulfonamide) | I-147 |
| (L-leucine benzenesulfonamide) | I-148 |

TABLE 1-continued
Exemplary Compounds
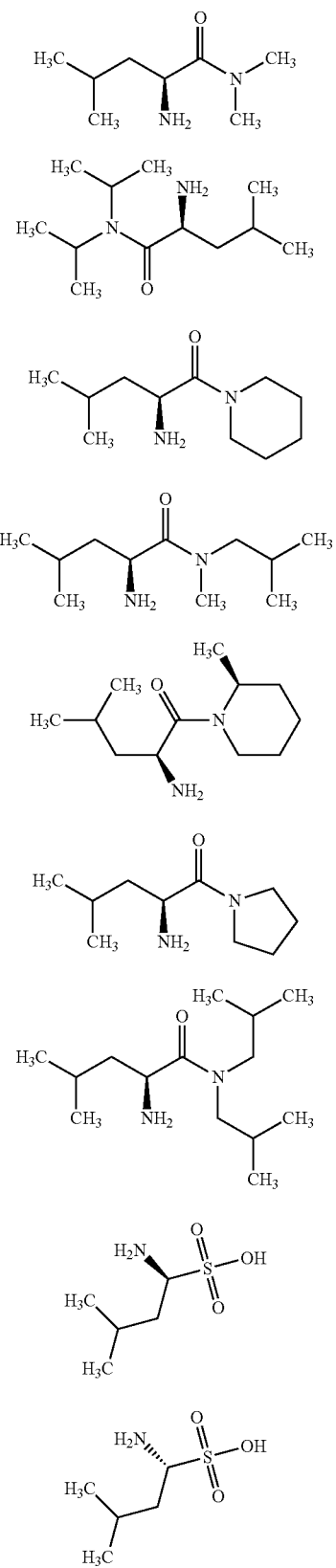
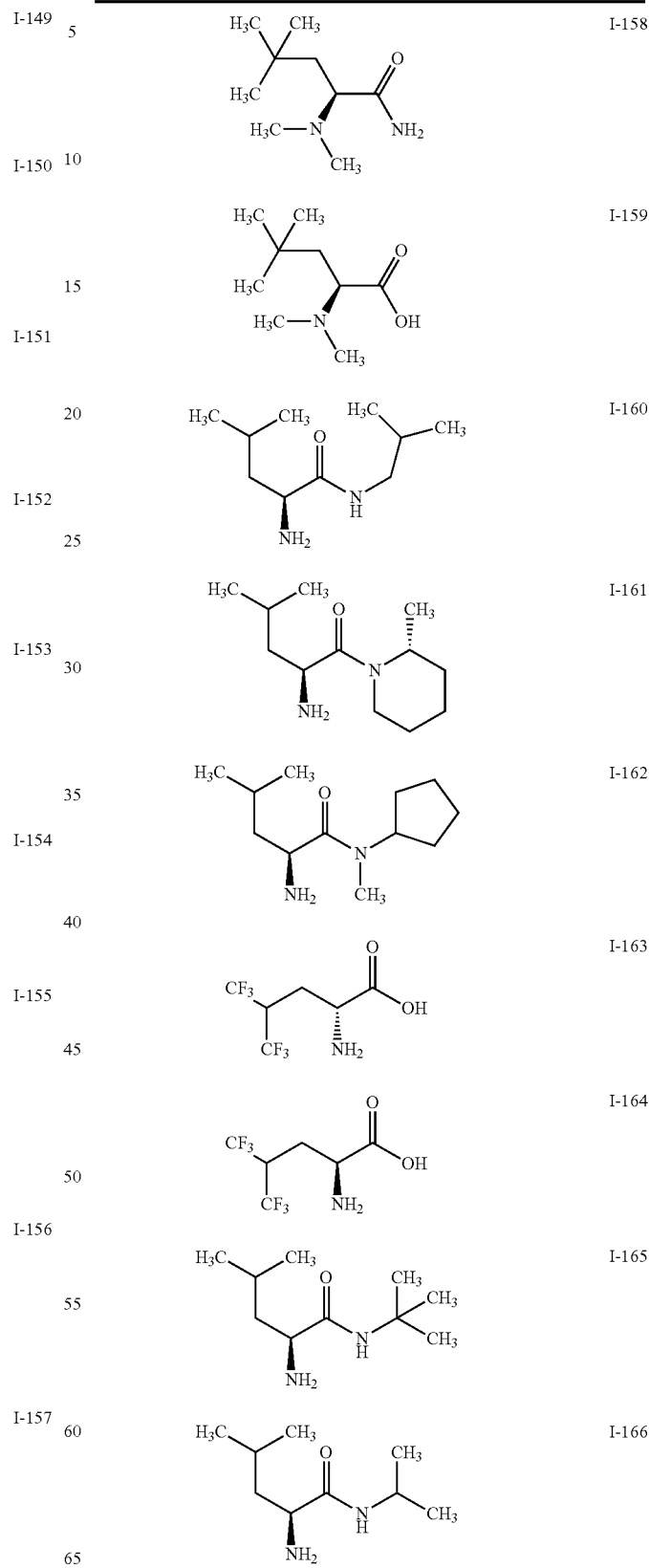

TABLE 1-continued

Exemplary Compounds

| Compound | ID |
|---|---|
| (structure) | I-167 |
| (structure) | I-168 |
| (structure) | I-169 |
| (structure) | I-170 |
| (structure) | I-171 |
| (structure) | I-172 |
| (structure) | I-173 |
| (structure) | I-174 |
| (structure) | I-175 |
| (structure) | I-176 |
| (structure) | I-177 |
| (structure) | I-178 |
| (structure) | I-179 |
| (structure) | I-180 |
| (structure) | I-181 |
| (structure) | I-182 |
| (structure) | I-183 |

TABLE 1-continued
Exemplary Compounds
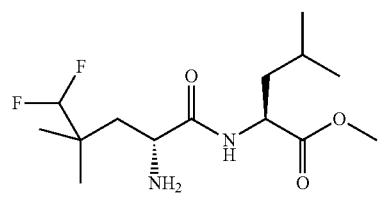 [SMILES: COC(=O)[C@H](CC(C)C)NC(=O)[C@H](N)CC(C)(C)C(F)F] I-184
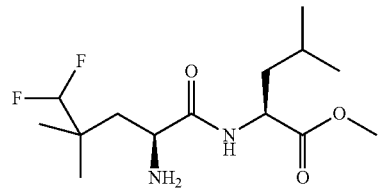 [SMILES: COC(=O)[C@H](CC(C)C)NC(=O)[C@@H](N)CC(C)(C)C(F)F] I-185
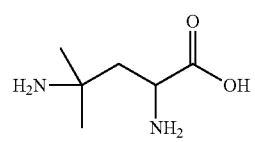 I-186
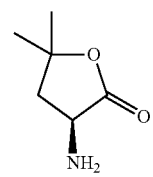 I-187
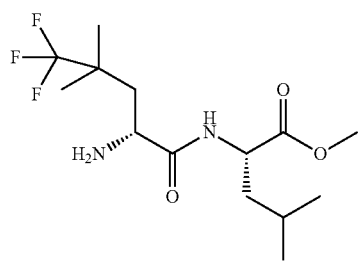 [SMILES: COC(=O)[C@H](CC(C)C)NC(=O)[C@H](N)CC(C)(C)C(F)(F)F] I-188
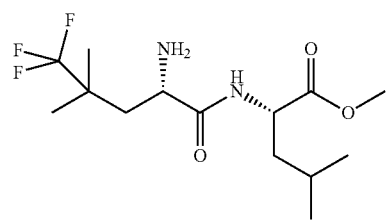 [SMILES: COC(=O)[C@H](CC(C)C)NC(=O)[C@@H](N)CC(C)(C)C(F)(F)F] I-189
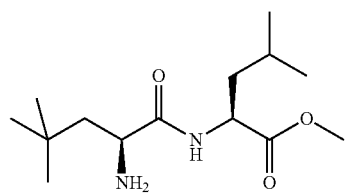 [SMILES: COC(=O)[C@H](CC(C)C)NC(=O)[C@@H](N)CC(C)(C)C] I-190
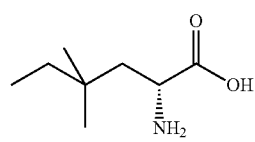 I-191
TABLE 1-continued
Exemplary Compounds
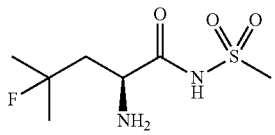 I-192
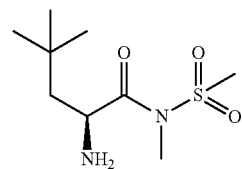 I-193
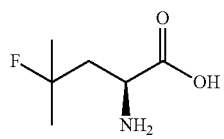 I-194
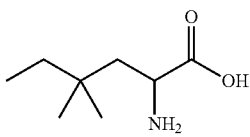 I-195
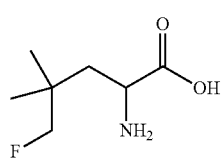 I-196
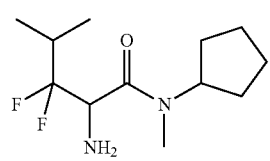 I-197
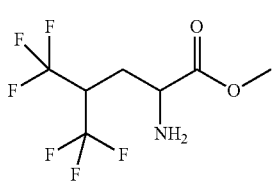 [SMILES: COC(=O)C(N)CC(C(F)(F)F)C(F)(F)F] I-198
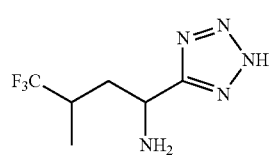 I-199
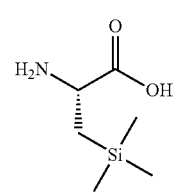 I-200

TABLE 1-continued

Exemplary Compounds

| Compound | ID |
|---|---|
| (structure) | I-201 |
| (structure) | I-202 |
| (structure) | I-203 |
| (structure) | I-204 |
| (structure) | I-205 |
| (structure) | I-206 |
| (structure) | I-207 |
| (structure) | I-208 |
| (structure) | I-209 |
| (structure) | I-210 |
| (structure) | I-211 |
| (structure) | I-212 |
| (structure) | I-213 |
| (structure) | I-214 |
| (structure) | I-215 |
| (structure) | I-216 |
| (structure) | I-217 |
| (structure) | I-218 |
| (structure) | I-219 |

TABLE 1-continued

Exemplary Compounds

| Compound | ID |
|---|---|
| (structure) | I-220 |
| (structure) | I-221 |
| (structure) | I-222 |
| (structure) | I-223 |
| (structure) | I-224 |
| (structure) | I-225 |
| (structure) | I-226 |
| (structure) | I-227 |
| (structure) | I-228 |
| (structure) | I-229 |
| (structure) | I-230 |
| (structure) | I-231 |
| (structure) | I-232 |
| (structure) | I-233 |
| (structure) | I-234 |
| (structure) | I-235 |
| (structure) | I-236 |
| (structure) | I-237 |
| (structure) | I-238 |
| (structure) | I-239 |

TABLE 1-continued
Exemplary Compounds
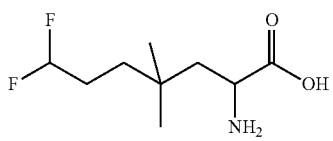 I-240
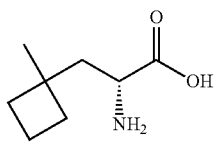 I-241
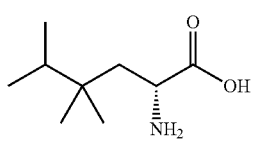 I-242
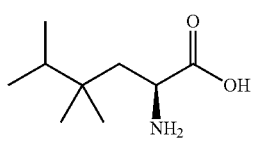 I-243
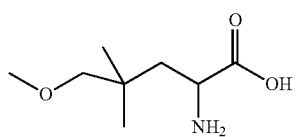 I-244
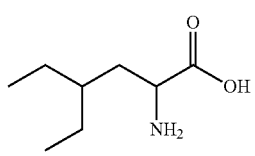 I-245
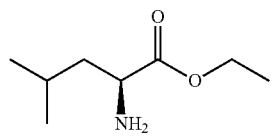 I-246
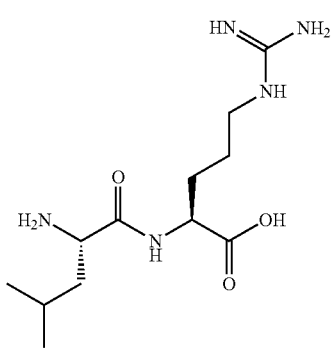 [SMILES: CC(C)C[C@H](N)C(=O)N[C@@H](CCCNC(=N)N)C(=O)O] I-247
TABLE 1-continued
Exemplary Compounds
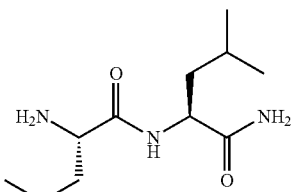 I-248
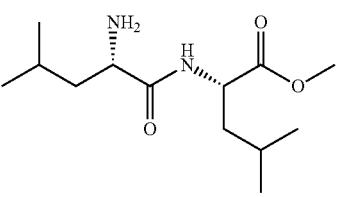 [SMILES: COC(=O)[C@H](CC(C)C)NC(=O)[C@@H](N)CC(C)C] I-249
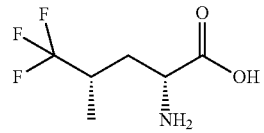 I-250
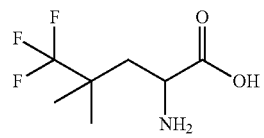 I-251
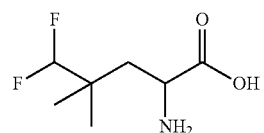 I-252
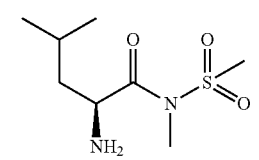 I-253
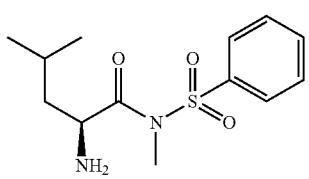 [SMILES: CC(C)C[C@H](N)C(=O)N(C)S(=O)(=O)c1ccccc1] I-254
Exemplary compounds of the invention are set forth in Table 2, below.
TABLE 2
Exemplary Compounds
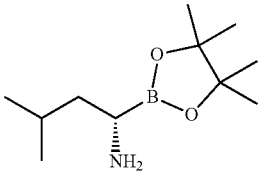 I-10

TABLE 2-continued

Exemplary Compounds

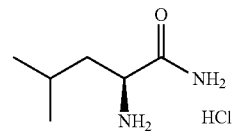 I-23

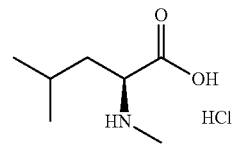 I-24

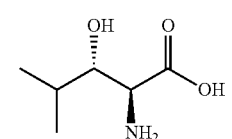 I-27

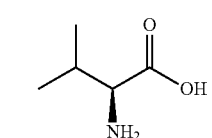 I-28

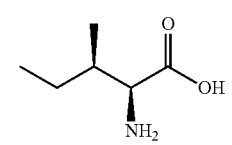 I-29

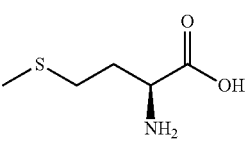 I-30

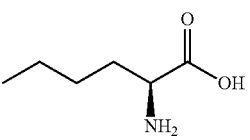 I-31

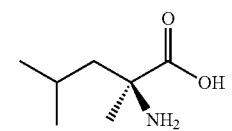 I-32

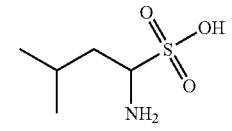 I-33

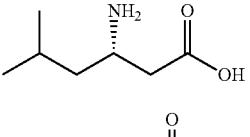 I-34

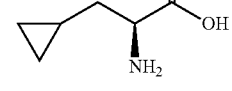 I-35

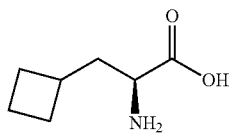 I-37

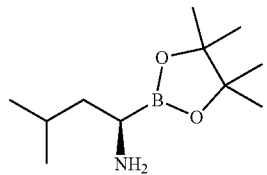 I-38

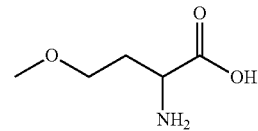 I-39

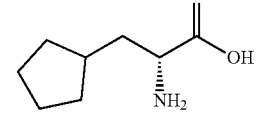 I-40

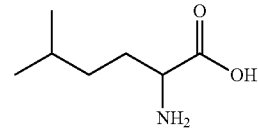 I-41

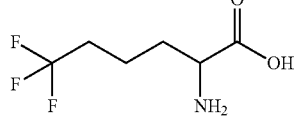 I-42

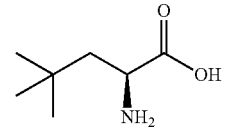 I-43

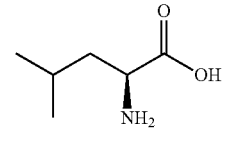 I-44

In some embodiments, the present invention provides a compound set forth in Table 1, above, or a pharmaceutically acceptable salt thereof. In some embodiments, the present invention provides a compound set forth in Table 2, above, or a pharmaceutically acceptable salt thereof.

5. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit or activate the Sestrin-GATOR2 interaction, in a biological sample or in a patient. In certain embodiments, the amount of compound in compositions of this invention is such that is effective to measurably inhibit or activate the Sestrin-GATOR2 interaction, in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a nontoxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a nontoxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Compounds and compositions described herein are generally useful for the inhibition or activation of the Sestrin-GATOR2 interaction. In some embodiments, a provided compound, or composition thereof, is an activator of the Sestrin-GATOR2 interaction.

The activity of a compound utilized in this invention as an inhibitor or activator of the Sestrin-GATOR2 interaction, may be assayed in vitro, in vivo or in a cell line. In vitro assays include assays that determine the inhibition or activation of the Sestrin-GATOR2 interaction. Alternate in vitro assays quantitate the ability of the inhibitor or activator to decrease or increase the binding of Sestrin to GATOR2. Detailed conditions for assaying a compound utilized in this invention as an inhibitor or activator of the Sestrin-GATOR2 interaction, are set forth in the Examples below.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Provided compounds are inhibitors or activators of the Sestrin-GATOR2 interaction and are therefore useful for treating one or more disorders associated with activity of mTORC1. Thus, in certain embodiments, the present invention provides a method for treating an mTORC1-mediated disorder comprising the step of administering to a patient in need thereof a compound of the present invention, or pharmaceutically acceptable composition thereof.

As used herein, the terms "mTORC1-mediated" disorders, diseases, and/or conditions as used herein means any disease or other deleterious condition in which mTORC1, is known to play a role. Accordingly, another embodiment of the present invention relates to treating or lessening the severity of one or more diseases in which mTORC1 is known to play a role.

The methods described herein include methods for the treatment of cancer in a subject. As used in this context, to "treat" means to ameliorate or improve at least one symptom or clinical parameter of the cancer. For example, a treatment can result in a reduction in tumor size or growth rate. A treatment need not cure the cancer or cause remission 100% of the time, in all subjects.

As described herein, the application of agents, e.g., inhibitory nucleic acids or small molecules, that activate the Sestrin-GATOR2 interaction and thereby decrease mTORC1 activity reduces cancer cell proliferation and thus treat cancer in subjects. Thus, in some embodiments, the methods described herein include administering a therapeutically effective dose of one or more agents that activate the Sestrin-GATOR2 interaction and thereby indirectly inhibit the mTORC1 pathway.

As used herein, the term "cancer" refers to cells having the capacity for autonomous growth, i.e., an abnormal state or condition characterized by rapidly proliferating cell growth. The term is meant to include all types of cancerous growths or oncogenic processes, metastatic tissues or malignantly transformed cells, tissues, or organs, irrespective of histopathologic type or stage of invasiveness. The term "tumor" as used herein refers to cancerous cells, e.g., a mass of cancer cells.

Cancers that can be treated or diagnoses using the methods described herein include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

In some embodiments, the methods described herein are used for treating or diagnosing a carcinoma in a subject. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. In some embodiments, the cancer is renal carcinoma or melanoma. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation.

In some embodiments, the cancers that are treated by the methods described herein are cancers that have increased levels of mTORC1 or an increased expression or activity of a mTORC1 relative to normal tissues or to other cancers of the same tissues; methods known in the art and described herein can be used to identify those cancers. In some embodiments, the methods include obtaining a sample comprising cells of the cancer, determining the mTORC1 activity in the sample, and administering a treatment as described herein (e.g., modulator of the Sestrin-GATOR2 interaction). In some embodiments, the cancer is one that is shown herein to have increased levels of mTORC1 activity In some embodiments, the present invention provides a method for treating one or more disorders, diseases, and/or conditions wherein the disorder, disease, or condition includes, but is not limited to, a cellular proliferative disorder.

Cellular Proliferative Disorders

The present invention features methods and compositions for the diagnosis and prognosis of cellular proliferative disorders (e.g., cancer) and the treatment of these disorders by modulating the Sestrin-GATOR2 interaction thereby selectively modulating mTORC1 activity indirectly. Cellular proliferative disorders described herein include, e.g., cancer, obesity, and proliferation-dependent diseases. Such disorders may be diagnosed using methods known in the art.

Cancer

Cancers include, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (e.g., Hodgkin's disease or non-Hodgkin's disease), Waldenstrom's macroglobulinemia, multiple myeloma, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, schwannoma, meningioma, melanoma, neuroblastoma, and retinoblastoma). In some embodiments, the cancer is melanoma or breast cancer.

Other Proliferative Diseases

Other proliferative diseases include, e.g., obesity, benign prostatic hyperplasia, psoriasis, abnormal keratinization, lymphoproliferative disorders (e.g., a disorder in which there is abnormal proliferation of cells of the lymphatic system), chronic rheumatoid arthritis, arteriosclerosis, restenosis, and diabetic retinopathy. Proliferative diseases that are hereby incorporated by reference include those described in U.S. Pat. Nos. 5,639,600 and 7,087,648.

Other Disorders

In some embodiments, the method of activating mTORC1 is used to treat Ribosomopathies (e.g. Diamond-Blackfan anemia, 5q-syndrome, Shwachman-Diamond syndrome, X-linked dyskeratosis, cartilage hair hypoplasia, and Treacher Collins syndrome). (See Payne et al., (2012) Blood. September 13; 120(11):2214-24; Efeyan et al., (2012) Trends Mol Med. September; 18(9): 524-533). Accordingly, in some embodiments, the present invention provides a method of treating a ribosomopathy, in a patient in need thereof, comprising the step of administering to said patient a provided compound or pharmaceutically acceptable composition thereof. In certain embodiments, the present invention provides a method of treating a ribosomopathy selected from Diamond-Blackfan anemia, 5q-syndrome, Shwachman-Diamond syndrome, X-linked dyskeratosis, cartilage hair hypoplasia, or Treacher Collins syndrome, in a patient in need thereof, comprising the step of administering to said patient a provided compound or pharmaceutically acceptable composition thereof.

In some embodiments, the method of activating mTORC1 activity is used to treat Cohesinopathies (e.g. Roberts syndrome and Cornelia de Lange syndrome). (See Xu et al., (2016) BMC Genomics 17:25). Accordingly, in some embodiments, the present invention provides a method of treating a cohesionopathy (e.g. Roberts syndrome and Cornelia de Lange syndrome), in a patient in need thereof, comprising the step of administering to said patient a provided compound or pharmaceutically acceptable composition thereof.

In some embodiments, the method of activating mTORC1 is used to reverse muscle atrophy or to prevent muscle atrophy due to inactivity due to lifestyle, inactivity caused by orthopedic surgery, immobilization, or age of the subject or a disease or condition the subject has or suffers from. (See Cuthbertson et al., (2005) FASEB J. March; 19(3):422-4. Epub 2004 Dec. 13; Rennie, (2009) Appl. Physiol. Nutr. Metab. 34: 377-381; Ham et al., (2014) Clin Nutr. December; 33(6):937-45). Accordingly, in some embodiments, the present invention provides a method of reversing or preventing a muscle atrophy due to inactivity due to lifestyle, inactivity caused by orthopedic surgery, immobilization, or age of the subject or a disease or condition the subject has or suffers from, in a patient in need thereof, comprising the step of administering to said patient a provided compound or pharmaceutically acceptable composition thereof.

In some embodiments, the method of activating mTORC1 is used to reverse muscle atrophy or to prevent muscle atrophy due to a broken bone, a severe burn, a spinal injury, an amputation, a degenerative disease, a condition wherein recovery requires bed rest for the subject, a stay in an intensive care unit, or long-term hospitalization. (See Gordon et al., (2013) Int J Biochem Cell Biol. October; 45(10): 2147-57; Léger et al., (2009) Muscle Nerve. July; 40(1):69-78). Accordingly, in some embodiments, the present invention provides a method of reversing or preventing a muscle atrophy due to a broken bone, a severe burn, a spinal injury, an amputation, a degenerative disease, a condition wherein recovery requires bed rest for the subject, a stay in an intensive care unit, or long-term hospitalization, in a patient in need thereof, comprising the step of administering to said patient a provided compound or pharmaceutically acceptable composition thereof.

In some embodiments, the method of activating mTORC1 is used to treat a disease, condition or disorder resulting in skeletal muscle atrophy, such as sarcopenia, muscle denervation, muscular dystrophy, an inflammatory myopathy, spinal muscular atrophy (SMA), amyotrophic lateral sclerosis (ALS), or myasthenia gravis. (See Kye et al., (2014) Hum Mol Genet. December 1; 23(23): 6318-6331; Gurpur et al., (2009) Am J Pathol. March; 174(3): 999-1008; Chauhan et al., (2013) Neurosci Res. September-October; 77(1-2): 102-9); Ching et al., (2013) Hum Mol Genet. March 15; 22(6):1167-79). Accordingly, in some embodiments, the present invention provides a method of treating a disease, a condition or a disorder resulting in a skeletal muscle atrophy, such as sarcopenia, muscle denervation, muscular dystrophy, an inflammatory myopathy, spinal muscular atrophy (SMA), amyotrophic lateral sclerosis (ALS), or myasthenia gravis, in a patient in need thereof, comprising the step of administering to said patient a provided compound or pharmaceutically acceptable composition thereof.

In some embodiments, the method of activating mTORC1 is used to prevent, sustain or enhance recovery from muscle loss in a subject that is preparing for, participating in or has recently returned from space travel, respectively. (See Stein et al., (1999) Am J Physiol.; 276:E1014-21). Accordingly, in some embodiments, the present invention provides a method of preventing, sustaining or enhancing recovery from a muscle loss in a subject that is preparing for, participating in or has recently returned from space travel, respectively, in a subject in need thereof, comprising the step of administering to said subject a provided compound or pharmaceutically acceptable composition thereof.

In some embodiments, the method of activating mTORC1 is used to sustain or enhance recovery from excessive muscle stress and/or fatigue in a subject that is preparing for, participating in or has recently returned from an armed conflict or military training. (See Pasiakos et al., (2011) Am J Clin Nutr. September; 94(3):809-18). Accordingly, in some embodiments, the present invention provides a method of sustaining or enhancing recovery from an excessive muscle stress and/or fatigue in a subject that is preparing for, participating in or has recently returned from an armed conflict or military training, in a subject in need thereof, comprising the step of administering to said subject a provided compound or pharmaceutically acceptable composition thereof.

In some embodiments, the method of activating mTORC1 is used to prevent autophagy in a patient. In some embodiments, said patient has or suffers from therapy resistant cancer in a manner dependent upon induction of autophagy. (See Kim and Guan, (2015) J Clin Invest. January; 125(1): 25-32). Accordingly, in some embodiments, the present invention provides a method of preventing an autophagy in a patient that has or suffers from therapy resistant cancer in a manner dependent upon induction of autophagy, in a patient in need thereof, comprising the step of administering to said patient a provided compound or pharmaceutically acceptable composition thereof.

In some embodiments, the method of activating mTORC is used to treat or prevent depression. (See Ignácio et al., (2015) Br J Clin Pharmacol. November 27). Accordingly, in some embodiments, the present invention provides a method of treating or preventing depression, in a patient in need thereof, comprising the step of administering to said patient a provided compound or pharmaceutically acceptable composition thereof.

In some embodiments, the method of activating mTORC1 is used to elicit a rapid onset antidepressant activity. Accordingly, in some embodiments, the present invention provides a method of eliciting a rapid onset antidepressant activity, in a patient in need thereof, comprising the step of administering to said patient a provided compound or pharmaceutically acceptable composition thereof.

In some embodiments, the method of activating mTORC1 is used to treat or prevent jet lag through accelerated circadian behavioral re-entrainment in response to a shifted day/light cycle. (See Cao et al., (2013) Neuron. August 21; 79(4):712-24 10.1016). Accordingly, in some embodiments, the present invention provides a method of treating or preventing a jet lag through accelerated circadian behavioral re-entrainment in response to a shifted day/light cycle, in a patient in need thereof, comprising the step of administering to said patient a provided compound or pharmaceutically acceptable composition thereof.

In some embodiments, the method of activating mTORC1 is used to prevent or reverse cardiac muscle atrophy in a subject. In some embodiments, said subject has or has had a disease or condition selected from heart attack, congestive heart failure, heart transplant, heart valve repair, atherosclerosis, other major blood vessel disease, and heart bypass surgery. (See Song et al., (2010) Am J Physiol Cell Physiol. December; 299(6): C1256-C1266). Accordingly, in some embodiments, the present invention provides a method of preventing or reversing a cardiac muscle atrophy in a subject, wherein said subject has or has had a disease or condition selected from heart attack, congestive heart failure, heart transplant, heart valve repair, atherosclerosis, other major blood vessel disease, and heart bypass surgery, in a subject in need thereof, comprising the step of administering to said subject a provided compound or pharmaceutically acceptable composition thereof.

In some embodiments, the method of activating mTORC1 is used to increase strength and/or to increase muscle mass following exercise. In some embodiments, the method is carried out in conjunction with physical therapy, as part of total parenteral nutrition, or to promote functional electrical stimulation. (See Nakamura et al., (2012) Geriatr Gerontol Int. January; 12(1):131-9). Accordingly, in some embodiments, the present invention provides a method of increasing strength and/or increasing muscle mass following exercise. In some embodiments, the method is carried out in conjunction with physical therapy, as part of total parenteral nutrition, or to promote functional electrical stimulation, in a subject in need thereof, comprising the step of administering to said subject a provided compound or pharmaceutically acceptable composition thereof.

In some embodiments, the method of activating mTORC1 is used to decrease food intake. (See Pedroso et al., (2015) Nutrients. May 22; 7(5):3914-37). Accordingly, in some embodiments, the present invention provides a method of decreasing food intake, in a subject in need thereof, comprising the step of administering to said subject a provided compound or pharmaceutically acceptable composition thereof.

In some embodiments, the method of activating mTORC1 is used to treat obesity. Accordingly, in some embodiments, the present invention provides a method of treating obesity, in a subject in need thereof, comprising the step of administering to said subject a provided compound or pharmaceutically acceptable composition thereof.

In some embodiments, the method of activating mTORC1 is used to increase productivity in a manufacturing of therapeutic recombinant proteins from bioreactors. (See McVey et al., (2016) Biotechnol Bioeng. February 16. doi: 10.1002/bit.25951). Accordingly, in some embodiments, the present invention provides a method of increasing productivity in the manufacturing of therapeutic recombinant proteins from bioreactors, comprising the step of adding to said manufacturing a provided compound or pharmaceutically acceptable composition thereof.

In some embodiments, the method of activating mTORC1 in immune cells is used to promote and/or sustain their anti-tumor activity. This includes increasing mTORC1 in immune cells in vitro before adoptive transfer, as well as increasing mTORC1 in immune cells when co-administered with other targeted immunotherapy strategies in vivo. In some embodiments, immune cells include naïve T-cells, CD4+ or CD8+ T-cells, Th1, Th2, $T_{Reg}$ and Th17 cells, dendritic cells, NK-cells and macrophages. (See Yang et al., (2011) Nat Immuno.; 12:888-897; O'Brien et al. (2011) Eur J Immunol.; 41:3361-3370; Delgoffe et al., (2009) Immunity. June 19; 30(6):832-44; Chi, (2012) Nat Rev Immunol. April 20; 12(5): 325-338; Pollizzi et al., (2015) J Clin Invest.; 125(5):2090-2108; Ali et al., (2015) Front Immunol.; 6: 355; Katholnig et al., (2013) Biochem Soc Trans. August; 41(4):927-33; Wang et al., (2013) Proc Natl Acad Sci USA. December 10; 110(50):E4894-903; Yang and Chi, (2013) J Clin Invest. December; 123(12):5165-78). Accordingly, in some embodiments, the present invention provides a method of activating mTORC1 in immune cells to promote and/or sustain their anti-tumor activity. In some embodiments, the present invention provides a method of increasing mTORC1 in immune cells in vitro before adoptive transfer. In some embodiments, the present invention provides a method of increasing mTORC1 in immune cells when co-administered with other targeted immunotherapy strategies in vivo. In certain embodiments, immune cells include naïve T-cells, CD4+ or CD8+ T-cells, Th1, Th2, $T_{Reg}$ and Th17 cells, dendritic cells, NK-cells and macrophages, comprising the step of adding to said immune cells a provided compound or pharmaceutically acceptable composition thereof.

In some embodiments, the method of activating mTORC1 in the retina is used to treat Retinitis pigmentosa and other forms of ocular neurodegeneration. (See Punzo et al., (2009) Nat Neurosci. January; 12(1):44-52). Accordingly, in some embodiments, the present invention provides a method of treating Retinitis pigmentosa and other forms of ocular neurodegeneration, in a subject in need thereof, comprising the step of administering to said subject a provided compound or pharmaceutically acceptable composition thereof.

In some embodiments, the method of activating mTORC1 is used to increase central or peripheral axonal regeneration. (See Namiko et al., (2010) J Biol Chem. 285:28034-28043). Accordingly, in some embodiments, the present invention provides a method of increasing central or peripheral axonal regeneration, in a subject in need thereof, comprising the step of administering to said subject a provided compound or pharmaceutically acceptable composition thereof.

In some embodiments, the method of activating mTORC1 is used to promote re-myelination and neuronal activity after injury or in diseases characterized by de-myelination such as multiple sclerosis and Parkinson's disease. (See Tyler et al., (2009) J Neurosci. May 13; 29(19):6367-78; Norrmén et al., (2014) Cell Rep. October 23; 9(2):646-60; Love (2006). J Clin Pathol. November; 59(11): 1151-1159). Accordingly, in some embodiments, the present invention provides a method of promoting re-myelination and neuronal activity after injury or in diseases characterized by de-myelination, in a subject in need thereof, comprising the step of administering to said subject a provided compound or pharmaceutically acceptable composition thereof. In some embodiments, the present invention provides a method of treating multiple sclerosis in a subject in need thereof, comprising the step of administering to said subject a provided compound or pharmaceutically acceptable composition thereof. In some embodiments, the present invention provides a method of treating Parkinson's disease in a subject in need thereof, comprising the step of administering to said subject a provided compound or pharmaceutically acceptable composition thereof.

In some embodiments, the method of activating mTORC1 is used to treat multiple sclerosis. Accordingly, in some embodiments, the present invention provides a method of treating multiple sclerosis or a variant thereof, in a subject in need thereof, comprising the step of administering to said subject a provided compound or pharmaceutically acceptable composition thereof. In some embodiments, the present invention provides a method of treating Balo's concentric sclerosis, Schilder's disease, acute (Marburg Type) multiple sclerosis, inflammatory demyelinative polyradiculoneuropathy, or tumefactive multiple sclerosis, in a subject in need thereof, comprising the step of administering to said subject a provided compound or pharmaceutically acceptable composition thereof.

In some embodiments, the method of activating mTORC1 is used to treat Devic's disease, acute-disseminated encephalomyelitis, acute haemorrhagic leucoencephalitis, progressive multifocal leucoencephalopathy and Niemann-Pick. (See Takikita et al., (2004) J Neuropathol Exp Neurol. June; 63(6):660-73). Accordingly, in some embodiments, the present invention provides a method of treating Devic's disease, acute-disseminated encephalomyelitis, acute haemorrhagic leucoencephalitis, progressive multifocal leucoencephalopathy and Niemann-Pick, in a subject in need thereof, comprising the step of administering to said subject a provided compound or pharmaceutically acceptable composition thereof.

In some embodiments, the method of activating mTORC1 is used to treat or prevent forms of autism. (See Novarino et al., (2012) Science 19 October, 338:6105, pp. 394-397). Accordingly, in some embodiments, the present invention provides a method of treating or preventing a form of autism, in a subject in need thereof, comprising the step of administering to said subject a provided compound or pharmaceutically acceptable composition thereof.

In some embodiments, the method of activating mTORC1 is used to treat neurodegenerative diseases. Accordingly, in some embodiments, the present invention provides a method of treating a neurodegenerative disease, in a subject in need thereof, comprising the step of administering to said subject a provided compound or pharmaceutically acceptable composition thereof.

In some embodiments, the method of activating mTORC1 is used to treat diseases related to synaptic dysfunction. Accordingly, in some embodiments, the present invention provides a method of treating a disease related to synaptic dysfunction, in a subject in need thereof, comprising the step of administering to said subject a provided compound or pharmaceutically acceptable composition thereof.

In some embodiments, the method of activating mTORC1 in the central nervous system is used to increase dendrite formation and synaptogenesis in neurodegenerative diseases marked by a reduction in dendritic spines and synapse loss such as Alzheimer's disease, amyotrophic lateral sclerosis, stroke and glaucoma. (See Di Polo et al., (2015) Neural Regen Res. April; 10(4): 559-561). Accordingly, in some embodiments, the present invention provides a method of increasing dendrite formation and synaptogenesis in a neurodegenerative disease marked by a reduction in dendritic spines and synapse loss, in a subject in need thereof, comprising the step of administering to said subject a provided compound or pharmaceutically acceptable composition thereof. In some embodiments, the present invention provides a method of treating Alzheimer's disease, amyotrophic lateral sclerosis, stroke or glaucoma in a subject in need thereof, comprising the step of administering to said subject a provided compound or pharmaceutically acceptable composition thereof.

In some embodiments, the method of activating mTORC1 is used to treat diseases such as Alzheimer's disease, amyotrophic lateral sclerosis, schizophrenia, Rett syndrome, Fragile X syndrome, Parkinson's disease, Huntington's disease, stroke and glaucoma. (See Lin et al., PLoS ONE 8(4): e62572, 2013; Lee et al., (2015) Neuron. January 21; 85(2): 303-315; Bowling et al., (2014) Sci Signal. January 14; 7(308): ra4). Accordingly, in some embodiments, the present invention provides a method of treating a disease such as Alzheimer's disease, amyotrophic lateral sclerosis, schizophrenia, Rett syndrome, Fragile X syndrome, Parkinson's disease, Huntington's disease, stroke and glaucoma, in a subject in need thereof, comprising the step of administering to said subject a provided compound or pharmaceutically acceptable composition thereof.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of modulating Sestrin-GATOR2 interaction thereby selectively modulating mTORC1 activity indirectly in a biological sample comprising the step of contacting said biological sample with a compound of this invention, or a composition comprising said compound.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Another embodiment of the present invention relates to a method of modulating Sestrin-GATOR2 interaction thereby selectively modulating mTORC1 activity indirectly in a patient comprising the step of administering to said patient a compound of the present invention, or a composition comprising said compound.

According to another embodiment, the invention relates to a method of modulating Sestrin-GATOR2 interaction thereby selectively modulating mTORC1 activity indirectly in a patient comprising the step of administering to said patient a compound of the present invention, or a composition comprising said compound. In other embodiments, the present invention provides a method for treating a disorder mediated by mTORC1 in a patient in need thereof, comprising the step of administering to said patient a compound according to the present invention or pharmaceutically acceptable composition thereof. Such disorders are described in detail herein.

Depending upon the particular condition, or disease, to be treated, additional therapeutic agents that are normally administered to treat that condition, may also be present in the compositions of this invention. As used herein, additional therapeutic agents that are normally administered to treat a particular disease, or condition, are known as "appropriate for the disease, or condition, being treated."

A compound of the current invention may also be used to advantage in combination with other antiproliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozolomide (Temodal®); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, AZD6244 from AstraZeneca, PD181461 from Pfizer and leucovorin. The term "aromatase inhibitor" as used herein relates to a compound which inhibits estrogen production, for instance, the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane is marketed under the trade name Aromasin™. Formestane is marketed under the trade name Lentaron™. Fadrozole is marketed under the trade name Afema™. Anastrozole is marketed under the trade name Arimidex™. Letrozole is marketed under the trade names Femara™ or Femar™. Aminoglutethimide is marketed under the trade name Orimeten™. A combination of the invention comprising a chemotherapeutic agent which is an aromatase inhibitor is particularly useful for the treatment of hormone receptor positive tumors, such as breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen is marketed under the trade name Nolvadex™. Raloxifene hydrochloride is marketed under the trade name Evista™. Fulvestrant can be administered under the trade name Faslodex™. A combination of the invention comprising a chemotherapeutic agent which is an antiestrogen is particularly useful for the treatment of estrogen receptor positive tumors, such as breast tumors.

The term "anti-androgen" as used herein relates to any substance which is capable of inhibiting the biological effects of androgenic hormones and includes, but is not limited to, bicalutamide (Casodex™). The term "gonadorelin agonist" as used herein includes, but is not limited to abarelix, goserelin and goserelin acetate. Goserelin can be administered under the trade name Zoladex™.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148. Irinotecan can be administered, e.g. in the form as it is marketed, e.g. under the trademark Camptosar™. Topotecan is marketed under the trade name Hycamptin™.

The term "topoisomerase II inhibitor" as used herein includes, but is not limited to the anthracyclines such as doxorubicin (including liposomal formulation, such as Caelyx™) daunorubicin, epirubicin, idarubicin and nemorubicin, the anthraquinones mitoxantrone and losoxantrone, and the podophillotoxines etoposide and teniposide. Etoposide is marketed under the trade name Etopophos™. Teniposide is marketed under the trade name VM 26-Bristol Doxorubicin is marketed under the trade name Acriblastin™ or Adriamycin™. Epirubicin is marketed under the trade name Farmorubicin™. Idarubicin is marketed. under the trade name Zavedos™. Mitoxantrone is marketed under the trade name Novantron.

The term "microtubule active agent" relates to microtubule stabilizing, microtubule destabilizing compounds and microtublin polymerization inhibitors including, but not limited to taxanes, such as paclitaxel and docetaxel; *vinca* alkaloids, such as vinblastine or vinblastine sulfate, vincristine or vincristine sulfate, and vinorelbine; discodermolides; cochicine and epothilones and derivatives thereof. Paclitaxel is marketed under the trade name Taxol™ Docetaxel is marketed under the trade name Taxotere™. Vinblastine sulfate is marketed under the trade name Vinblastin R.P™. Vincristine sulfate is marketed under the trade name Farmistin™.

The term "alkylating agent" as used herein includes, but is not limited to, cyclophosphamide, ifosfamide, melphalan or nitrosourea (BCNU or Gliadel). Cyclophosphamide is marketed under the trade name Cyclostin™. Ifosfamide is marketed under the trade name Holoxan™.

The term "histone deacetylase inhibitors" or "HDAC inhibitors" relates to compounds which inhibit the histone deacetylase and which possess antiproliferative activity. This includes, but is not limited to, suberoylanilide hydroxamic acid (SAHA).

The term "antineoplastic antimetabolite" includes, but is not limited to, 5-fluorouracil or 5-FU, capecitabine, gemcitabine, DNA demethylating compounds, such as 5-azacytidine and decitabine, methotrexate and edatrexate, and folic acid antagonists such as pemetrexed. Capecitabine is marketed under the trade name Xeloda™. Gemcitabine is marketed under the trade name Gemzar™.

The term "platin compound" as used herein includes, but is not limited to, carboplatin, cis-platin, cisplatinum and oxaliplatin. Carboplatin can be administered, e.g., in the form as it is marketed, e.g. under the trademark Carboplat™. Oxaliplatin can be administered, e.g., in the form as it is marketed, e.g. under the trademark Eloxatin™.

The term "compounds targeting/decreasing a protein or lipid kinase activity; or a protein or lipid phosphatase activity; or further anti-angiogenic compounds" as used herein includes, but is not limited to, protein tyrosine kinase and/or serine and/or threonine kinase inhibitors or lipid kinase inhibitors, such as a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, such as an N-phenyl-2-pyrimidine-amine derivative, such as imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-R, especially compounds which inhibit the kinase activity of IGF-I receptor, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the Axl receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, such as imatinib; h) compounds targeting, decreasing or inhibiting the activity of the C-kit receptor tyrosine kinases, which are part of the PDGFR family, such as compounds which target, decrease or inhibit the activity of the c-Kit receptor tyrosine kinase family, especially compounds which inhibit the c-Kit receptor, such as imatinib; i) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, such as an N-phenyl-2-pyrimidine-amine derivative, such as imatinib or nilotinib (AMN107); PD180970; AG957; NSC 680410; PD173955 from ParkeDavis; or dasatinib (BMS-354825); j) compounds targeting, decreasing or inhibiting the activity of members of the protein kinase C (PKC) and Raf family of serine/threonine kinases, members of the MEK, SRC, JAK/pan-JAK, FAK, PDK1, PKB/Akt, Ras/MAPK, PI3K, SYK, TYK2, BTK and TEC family, and/or members of the cyclin-dependent kinase family (CDK) including staurosporine derivatives, such as midostaurin; examples of further compounds include UCN-01, safingol, BAY 43-9006, Bryostatin 1, Perifosine; llmofosine; RO 318220 and RO 320432; GO 6976; lsis 3521; LY333531/LY379196; isochinoline compounds; FTIs; PD184352 or QAN697 (a P13K inhibitor) or AT7519 (CDK inhibitor); k) compounds targeting, decreasing or inhibiting the activity of protein-tyrosine kinase inhibitors, such as compounds which target, decrease or inhibit the activity of protein-tyrosine kinase inhibitors include imatinib mesylate (Gleevec™) or tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); l) compounds targeting, decreasing or inhibiting the activity of the epidermal growth factor family of receptor tyrosine kinases (EGFR$_1$ ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, such as EGF receptor, ErbB2, ErbB3 and ErbB4 or bind to EGF or EGF related ligands, CP 358774, ZD 1839, ZM 105180; trastuzumab (Herceptin™), cetuximab (Erbitux™), Iressa, Tarceva, OSI-774, C1-1033, EKB-569, GW-2016, E1.1, E2.4, E2.5, E6.2, E6.4, E2.11, E6.3 or E7.6.3, and 7H-pyrrolo-[2,3-d]pyrimidine derivatives; m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF, n) compounds targeting, decreasing or inhibiting the kinase activity of one or more JAK family members (JAK1/JAK2/JAK3/TYK2 and/or pan-JAK), including but not limited to PRT-062070, SB-1578, baricitinib, pacritinib, momelotinib, VX-509, AZD-1480, TG-101348, tofacitinib, and ruxolitinib; o) compounds targeting, decreasing or inhibiting the kinase activity of PI3 kinase (PI3K) including but not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib; and; and q) compounds targeting, decreasing or inhibiting the signaling effects of hedgehog protein (Hh) or smoothened receptor (SMO) pathways, including but not limited to cyclopamine, vismodegib, itraconazole, erismodegib, and IPI-926 (saridegib).

The term "PI3K inhibitor" as used herein includes, but is not limited to compounds having inhibitory activity against one or more enzymes in the phosphatidylinositol-3-kinase family, including, but not limited to PI3Kα, PI3Kγ, PI3Kδ, PI3Kβ, PI3K-C2α, PI3K-C2β, PI3K-C2γ, Vps34, p110-α, p110-β, p110-γ, p110-δ, p85-α, p85-β, p55-γ, p150, p101, and p87. Examples of PI3K inhibitors useful in this invention include but are not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib.

The term "Bcl-2 inhibitor" as used herein includes, but is not limited to compounds having inhibitory activity against B-cell lymphoma 2 protein (Bcl-2), including but not limited to ABT-199, ABT-731, ABT-737, apogossypol, Ascenta's pan-Bcl-2 inhibitors, curcumin (and analogs thereof), dual Bcl-2/Bcl-xL inhibitors (Infinity Pharmaceuticals/Novartis Pharmaceuticals), Genasense (G3139), HA14-1 (and analogs thereof; see WO2008118802), navitoclax (and analogs thereof, see U.S. Pat. No. 7,390,799), NH-1 (Shenayng Pharmaceutical University), obatoclax (and analogs thereof, see WO2004106328), S-001 (Gloria Pharmaceuticals), TW series compounds (Univ. of Michigan), and venetoclax. In some embodiments the Bcl-2 inhibitor is a small molecule therapeutic. In some embodiments the Bcl-2 inhibitor is a peptidomimetic.

The term "BTK inhibitor" as used herein includes, but is not limited to compounds having inhibitory activity against Bruton's Tyrosine Kinase (BTK), including, but not limited to AVL-292 and ibrutinib.

The term "SYK inhibitor" as used herein includes, but is not limited to compounds having inhibitory activity against spleen tyrosine kinase (SYK), including but not limited to PRT-062070, R-343, R-333, Excellair, PRT-062607, and fostamatinib Further examples of BTK inhibitory compounds, and conditions treatable by such compounds in combination with compounds of this invention can be found in WO2008039218 and WO2011090760, the entirety of which are incorporated herein by reference.

Further examples of SYK inhibitory compounds, and conditions treatable by such compounds in combination with compounds of this invention can be found in WO2003063794, WO2005007623, and WO2006078846, the entirety of which are incorporated herein by reference.

Further examples of PI3K inhibitory compounds, and conditions treatable by such compounds in combination with compounds of this invention can be found in WO2004019973, WO2004089925, WO2007016176, U.S. Pat. No. 8,138,347, WO2002088112, WO2007084786, WO2007129161, WO2006122806, WO2005113554, and WO2007044729 the entirety of which are incorporated herein by reference.

Further examples of JAK inhibitory compounds, and conditions treatable by such compounds in combination with compounds of this invention can be found in WO2009114512, WO2008109943, WO2007053452, WO2000142246, and WO2007070514, the entirety of which are incorporated herein by reference.

Further anti-angiogenic compounds include compounds having another mechanism for their activity, e.g. unrelated to protein or lipid kinase inhibition e.g. thalidomide (Thalomid™) and TNP-470.

Examples of proteasome inhibitors useful for use in combination with compounds of the invention include, but are not limited to bortezomib, disulfiram, epigallocatechin-3-gallate (EGCG), salinosporamide A, carfilzomib, ONX-0912, CEP-18770, and MLN9708.

Compounds which target, decrease or inhibit the activity of a protein or lipid phosphatase are e.g. inhibitors of phosphatase 1, phosphatase 2A, or CDC125, such as okadaic acid or a derivative thereof.

Compounds which induce cell differentiation processes include, but are not limited to, retinoic acid, α- γ- or δ-tocopherol or α- γ- or δ-tocotrienol.

The term cyclooxygenase inhibitor as used herein includes, but is not limited to, Cox-2 inhibitors, 5-alkyl substituted 2-arylaminophenylacetic acid and derivatives, such as celecoxib (Celebrex™), rofecoxib (Vioxx™), etoricoxib, valdecoxib or a 5-alkyl-2-arylaminophenylacetic acid, such as 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. Etridonic acid is marketed under the trade name Didronel™. Clodronic acid is marketed under the trade name Bonefos™. Tiludronic acid is marketed under the trade name Skelid™ Pamidronic acid is marketed under the trade name Aredia™. Alendronic acid is marketed under the trade name Fosamax™. Ibandronic acid is marketed under the trade name Bondranat™ Risedronic acid is marketed under the trade name Actonel™. Zoledronic acid is marketed under the trade name Zometa™. The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88. The term "biological response modifier" as used herein refers to a lymphokine or interferons.

The term "inhibitor of Ras oncogenic isoforms", such as H-Ras, K-Ras, or N-Ras, as used herein refers to compounds which target, decrease or inhibit the oncogenic activity of Ras; for example, a "farnesyl transferase inhibitor" such as L-744832, DK8G557 or R115777 (Zarnestra™). The term "telomerase inhibitor" as used herein refers to compounds which target, decrease or inhibit the activity of telomerase. Compounds which target, decrease or inhibit the activity of telomerase are especially compounds which inhibit the telomerase receptor, such as telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase include, but are not limited to, bengamide or a derivative thereof.

The term "proteasome inhibitor" as used herein refers to compounds which target, decrease or inhibit the activity of the proteasome. Compounds which target, decrease or inhibit the activity of the proteasome include, but are not limited to, Bortezomib (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c) and bisulfan; and ALK inhibitors, which are compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, such as PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino,17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (Herceptin™), Trastuzumab-DM1, erbitux, bevacizumab (Avastin™), rituximab (Rituxan®), PR064553 (anti-CD40) and 2C4 Antibody. By antibodies is meant intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the current invention can be used in combination with standard leukemia therapies, especially in combination with therapies used for the treatment of AML. In particular, compounds of the current invention can be administered in combination with, for example, farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

Other anti-leukemic compounds include, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065 including, but not limited to, N-hydroxy-3-[4-[[[2-(2-methyl-1H-indol-3-yl)-ethyl]-amino]methyl] phenyl]-2E-2-propenamide, or a pharmaceutically acceptable salt thereof and N-hydroxy-3-[4-[(2-hydroxyethyl){2-(1H-indol-3-yl)ethyl]-amino]methyl]phenyl]-2E-2-propenamide, or a pharmaceutically acceptable salt thereof, especially the lactate salt. Somatostatin receptor antagonists as used herein refer to compounds which target, treat or inhibit the somatostatin receptor such as octreotide, and SOM230. Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in Principles and Practice of Oncology, Devita et al., Eds., 4$^{th}$ Edition, Vol. 1, pp. 248-275 (1993).

Also included are EDG binders and ribonucleotide reductase inhibitors. The term "EDG binders" as used herein refers to a class of immunosuppressants that modulates lymphocyte recirculation, such as FTY720. The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives.

Also included are in particular those compounds, proteins or monoclonal antibodies of VEGF such as 1-(4-chloroanilino)-4-(4-pyridylmethyl)phthalazine or a pharmaceutically acceptable salt thereof, 1-(4-chloroanilino)-4-(4-pyridylmethyl)phthalazine succinate; Angiostatin™; Endostatin™; anthranilic acid amides; ZD4190; ZD6474; SU5416; SU6668; bevacizumab; or anti-VEGF antibodies or anti-VEGF receptor antibodies, such as rhuMAb and RHUFab, VEGF aptamer such as Macugon; FLT-4 inhibitors, FLT-3 inhibitors, VEGFR-2 IgGI antibody, Angiozyme (RPI 4610) and Bevacizumab (Avastin™).

Photodynamic therapy as used herein refers to therapy which uses certain chemicals known as photosensitizing compounds to treat or prevent cancers. Examples of photodynamic therapy include treatment with compounds, such as Visudyne™ and porfimer sodium.

Angiostatic steroids as used herein refers to compounds which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as fluocinolone and dexamethasone.

Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The structure of the active compounds identified by code numbers, generic or trade names may be taken from the actual edition of the standard compendium "The Merck Index" or from databases, e.g. Patents International (e.g. IMS World Publications).

A compound of the current invention may also be used in combination with known therapeutic processes, for example, the administration of hormones or radiation. In certain embodiments, a provided compound is used as a radiosensitizer, especially for the treatment of tumors which exhibit poor sensitivity to radiotherapy.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-1,000 µg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Implantable devices coated with a compound of this invention are another embodiment of the present invention.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

LIST OF ABBREVIATIONS USED IN THE EXPERIMENTAL SECTION

4A MS: 4 Å molecular sieves
AcOH: acetic acid
ACN: acetonitrile
Anhyd: anhydrous
Aq: aqueous
Bn: benzyl
Boc: tert-butoxycarbonyl
CbzCl: benzyl chloroformate
Cbz-OSU: N-(Benzyloxycarbonyloxy)succinimide
$Cu(OAc)_2$: copper(II) acetate
d: days
DAST: diethylaminosulfur trifluoride
DBU: 1,8-diazobicyclo[5.4.0]undec-7-ene
DCE: 1,2-dichloroethane
DCM: dichloromethane
DEA: diethylamine
DIBAL-H: diisobutylaluminium hydride
DIPEA: N,N-diisopropylethylamine
DMA: N,N-dimethylacetamide
DMAP: 4-dimethylaminopyridine
DMF: N,N-dimethylformamide
DMSO-dimethyl sulfoxide
DPPA: diphenylphosphoryl azide
EDC: 1-(3-dimethylaminopropyl)-3-ethylcarbodiimide hydrochloride
ee: enantiomeric excess
ESI: electrospray ionization
$Et_3N$: triethylamine
$Et_2O$: diethyl ether
EtOAc: ethyl acetate
EtOH: ethanol
Fmoc: fluorenylmethyloxycarbonyl
Fmoc-OSu: N-(9-fluorenylmethoxycarbonyloxy)succinimide
h: hours
HATU: 1-[Bis(dimethylamino)methylene]-1H-1,2,3-triazolo[4,5-b]pyridinium 3-oxid hexafluorophosphate
$HCOONH_4$: ammonium formate
HPLC: high performance liquid chromatography
IBX: 2-Iodoxybenzoic acid
IPA: isopropyl alcohol
KOAc: potassium acetate
M: molar
Me: methyl
MeOH: methanol
mins: minutes
mL: milliliters mM: millimolar
mmol: millimoles
MTBE: methyl tert-butyl ether
NaBH$_3$CN: sodium cyanoborohydride
Na$_2$CO$_3$: sodium carbonate
NaHCO$_3$: sodium bicarbonate
NMP: N-methylpyrrolidine
NMR: Nuclear Magnetic Resonance
° C.: degrees Celsius
PBS: phosphate buffered saline
Pd/C: Palladium on carbon
Pd(OH)$_2$/C: Pearlman's catalyst
PE: petroleum ether
PhNH$_2$: aniline
PPh$_3$: triphenylphosphine
Rel: relative
rt: room temperature
sat: saturated
SFC: supercritical fluid chromatography
SOCl$_2$: thionyl chloride
TBAB: Tetra-n-butylammonium bromide
tBuOK: potassium tert-butoxide
TEA: triethylamine
Tf: trifluoromethanesulfonate
TfAA: trifluoromethanesulfonic anhydride
TFA: trifluoroacetic acid
TIPS: triisopropylsilyl
THF: tetrahydrofuran
TMSCN: trimethylsilyl cyanide
pTSA: para-toluenesulfonic acid
TsOH: p-Toluenesulfonic acid Preparation of representative non-limiting examples of provided compounds are described below.

Example 1: (S)-2-(dimethylamino)-4-methylpentanoic acid [I-1]

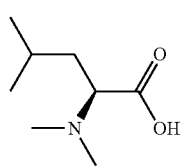

I-1

Synthetic Scheme:

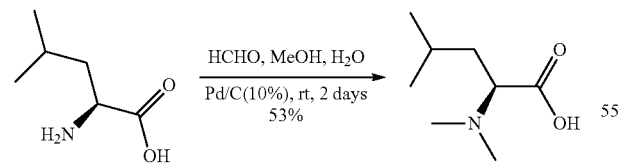

Procedures and Characterization:

Step 1: (S)-2-(dimethylamino)-4-methylpentanoic acid

Formaldehyde (38%, 24.0 g) and Pd/C (10%, 500 mg) were added to a solution of (S)-2-amino-4-methylpentanoic acid (2.0 g, 15.24 mmol) in resulting solution was filtered (60 mL). The mixture was hydrogenated at room temperature for two days and filtered to remove the catalyst. The filtrate was concentrated to dryness and EtOH (30 mL) was added to the residue. The mixture was stirred for 1 h and filtered. The filtrate was concentrated to afford (S)-2-(dimethylamino)-4-methylpentanoic acid (1.3 g, 8.16 mmol, 53%) as a white powder. ESI-MS (EI$^+$, m/z): 160.2 [M+H]$^+$. $^1$H-NMR (400 MHz, MeOD-d$_4$): δ 3.47 (dd, J=4.4 Hz, 10.0 Hz, 1H), 2.85 (S, 6H), 1.89-1.74 (m, 2H), 1.62-1.55 (m, 1H), 1.00 (dd, J=2.8 Hz, 6.8 Hz, 6H).

Examples 2 and 3: (S)-2-amino-7,7,7-trifluoroheptanoic acid hydrochloride [I-2] and (R)-2-amino-7,7,7-trifluoroheptanoic acid hydrochloride [I-3]

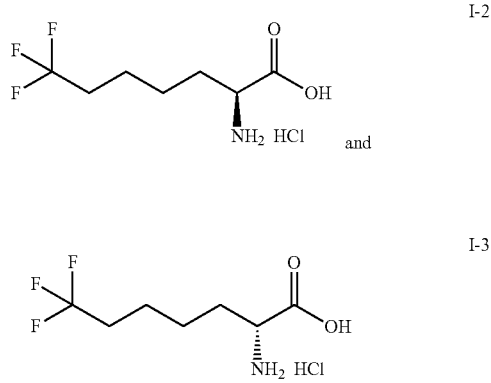

Synthetic Scheme:

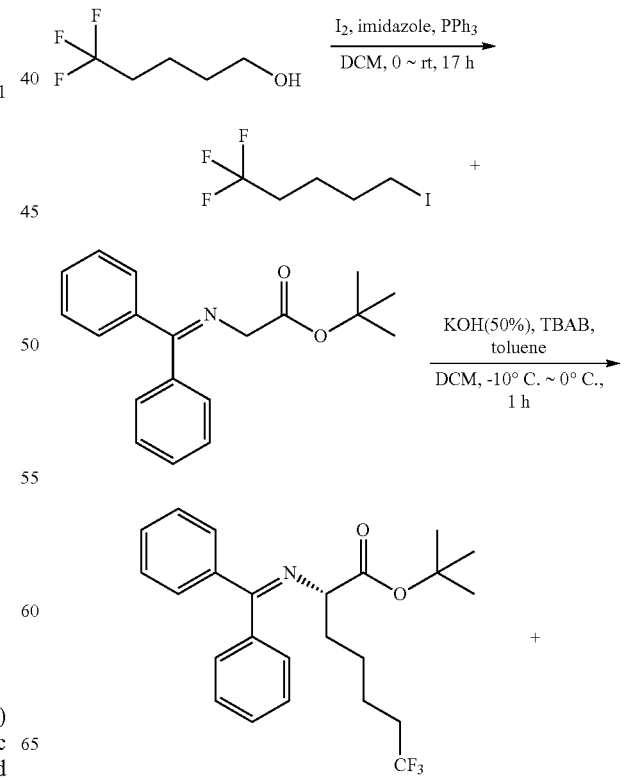

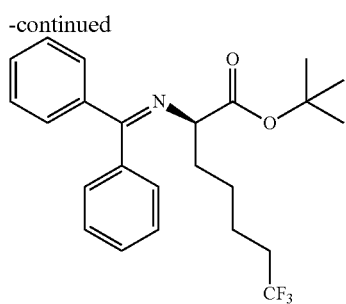

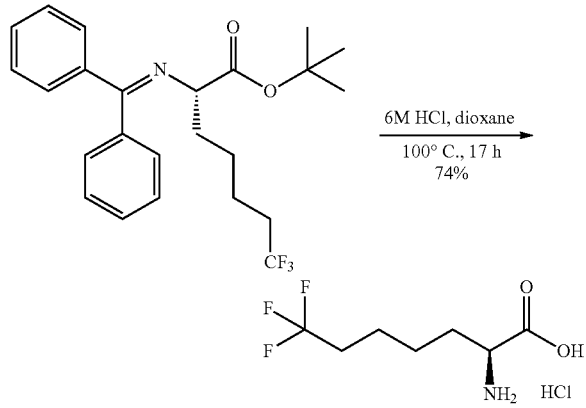

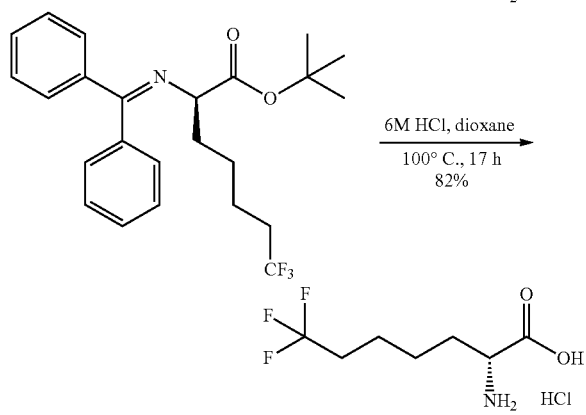

Procedures and Characterization:

Step 1: 1,1,1-Trifluoro-5-iodopentane

To a solution of 5,5,5-trifluoropentan-1-ol (2.0 g, 14.0 mmol), imidazole (1.48 g, 21.7 mmol) and PPh₃ (5.5 g, 21.0 mmol) in DCM (40 mL) was added I2 (4.45 g, 17.5 mmol) with ice-bath. The mixture was warmed to room temperature and stirred overnight. To the mixture of above was added Et₂O (50 mL), and then stirred for 10 mins. The mixture was filtered, and the filtrate was evaporated at 65° C. to remove the solvent under atmospheric pressure, the residue was diluted with Et₂O (30 mL), the mixture was filtered, and the filtrate was used for the next step.

Step 2: (S)-tert-butyl 2-(diphenylmethyleneamino)-7,7,7-trifluoroheptanoate and (R)-tert-butyl 2-(diphenylmethyleneamino)-7,7,7-trifluoroheptanoate To a solution of tert-butyl 2-(diphenylmethyleneamino) acetate (2.0 g, 6.78 mmol) and TBAB (109 mg, 0.339 mmol) in toluene (35 mL) and DCM (15 mL) was added KOH (50%, 20 mL) at −10° C., after 5 mins, the above solution of 1,1,1-trifluoro-5-iodopentane in Et₂O (30 mL) was added dropwise over 5 mins, the result mixture was stirred at −10° C. to 0° C. for 1 h. The solution was diluted with water (200 mL) and extracted with EA (100 mL). The organic phase was washed with water (100 mL×2), and brine (100 mL), dried (Na₂SO₄), filtered and concentrated in vacuum, the crude product was purified by chromatography (silica, ethyl acetate/petroleum ether=1/10) and then chiral-prep-HPLC [column, R, R-whelk-ol 4.6*250 mm 5 um; solvent, MeOH (0.2% Methanol Ammonia)] to afford (S)-tert-butyl 2-(diphenylmethyleneamino)-7,7,7-trifluoroheptanoate (200 mg, 0.48 mmol, 7.1%) and (R)-tert-butyl 2-(diphenylmethyleneamino)-7,7,7-trifluoroheptanoate (200 mg, 0.48 mmol, 7.1%).

(S)-tert-butyl 2-(diphenylmethyleneamino)-7,7,7-trifluoroheptanoate (200 mg, 0.48 mmol, 7.1%). ESI-MS (EI+, m/z): 243.1 [M+H]+. ¹H-NMR (500 MHz, CDCl₃): δ 8.64 (d, J=8.0 Hz, 2H), 7.43-7.46 (m, 3H), 7.38-7.39 (m, 1H), 7.31-7.34 (m, 2H), 7.15-7.17 (m, 2H), 3.91 (dd, J=5.5 Hz, 7.5 Hz, 1H), 2.00-2.05 (m, 2H), 1.88-1.92 (m, 2H), 1.31-1.52 (m, 13H).

(R)-tert-butyl 2-(diphenylmethyleneamino)-7,7,7-trifluoroheptanoate (200 mg, 0.48 mmol, 7.1%). ESI-MS (EI+, m/z): 243.1 [M+H]+. ¹H-NMR (500 MHz, CDCl₃): δ 8.64 (d, J=7.0 Hz, 2H), 7.43-7.46 (m, 3H), 7.38-7.39 (m, 1H), 7.31-7.34 (m, 2H), 7.15-7.17 (m, 2H), 3.92 (dd, J=5.5 Hz, 7.5 Hz, 1H), 2.00-2.05 (m, 2H), 1.88-1.92 (m, 2H), 1.31-1.52 (m, 13H).

Step 3: (S)-2-amino-7,7,7-trifluoroheptanoic acid hydrochloride [I-2]

A solution of (S)-tert-butyl 2-(diphenylmethyleneamino)-7,7,7-trifluoroheptanoate (200 mg, 0.48 mmol) in 6 M HCl (10 mL) and dioxane (5 mL) was heated to 100° C. for 17 hrs. The solution was extracted with Et₂O (10 mL×2), the aqueous phase was concentrated to dryness to afford (S)-2-amino-7,7,7-trifluoroheptanoic acid hydrochloride (I-2) as a white solid (82.7 mg, 0.35 mmol, 74%). ESI-MS (EI+, m/z): 200.1 [M+H]+. 1H NMR (500 MHz, D₂O) δ 3.93 (t, J=6.0 Hz, 1H), 2.10-2.15 (m, 2H), 1.83-1.90 (m, 2H), 1.40-1.56 (m, 4H).

Step 4: (R)-2-amino-7,7,7-trifluoroheptanoic acid hydrochloride [I-3]

A solution of (R)-tert-butyl 2-(diphenylmethyleneamino)-7,7,7-trifluoroheptanoate (200 mg, 0.48 mmol) in 6 M HCl (10 mL) and dioxane (5 mL) was heated to 100° C. for 17 hrs. The solution was extracted with Et₂O (10 mL×2), the aqueous phase was concentrated to dryness to afford (R)-2-amino-7,7,7-trifluoroheptanoic acid hydrochloride (I-3) as a white solid (91.6 mg, 0.39 mmol, 82%). ESI-MS (EI+, m/z): 200.1 [M+H]+. 1H NMR (500 MHz, D₂O) δ 3.92 (t, J=6.0 Hz, 1H), 2.09-2.14 (m, 2H), 1.82-1.89 (m, 2H), 1.39-1.55 (m, 4H).

Examples 4 and 5: (S)-2-amino-4,4,4-trifluorobutanoic acid [I-4] and (R)-2-amino-4,4,4-trifluoro butanoic acid [I-5]

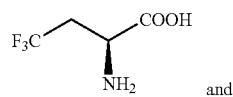

and

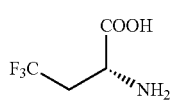

Synthetic Scheme:

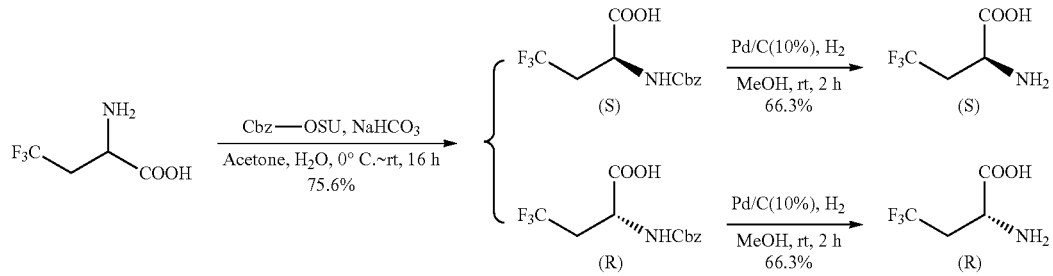

Procedures and Characterization:

Step 1: (S)-2-(benzyloxycarbonylamino)-4,4,4-trifluorobutanoic acid and (R)-2-(benzyloxycarbonylamino)-4,4,4-trifluorobutanoic acid N-(Benzyloxycarbonyloxy)succinimide (1.75 g, 7.01 mmol) was slowly added to a solution of 2-amino-4,4,4-trifluorobutanoic acid (1.0 g, 6.36 mmol) and NaHCO₃ (589 mg, 7.01 mmol) in acetone (60 mL) and resulting solution was filtered (60 mL) at 0° C. The mixture was stirred at rt for 16 hrs. The reaction mixture was extracted with CH₂Cl₂ (2×100 mL) and the aqueous layer was acidified with HCl (3) to about pH 4 and then extracted with EtOAc (3×150 mL). The organic phase was dried over Na₂SO₄ and the solvent was evaporated under vacuum. The resulting crude product was purified by chiral-prep-HPLC (column, AY-H 4.6*250 mm 5 um; solvent, EtOH) to afford (S)-2-(benzyloxycarbonylamino)-4,4,4-trifluoro butanoic acid (700 mg, 2.40 mmol, 37.8%) and (R)-2-(benzyloxy carbonylamino)-4,4,4-trifluorobutanoic acid (700 mg, 2.40 mmol, 37.8%) as white solid. ESI-MS (EI+, m/z): 314.0[M+Na]+.

(S)-2-(benzyloxycarbonylamino)-4,4,4-trifluorobutanoic acid. $^1$H-NMR (500 MHz, DMSO-d₆): δ 13.20 (s, 1H), 7.84 (d, J=9.0 Hz, 1H), 7.40-7.30 (m, 5H), 5.06 (s, 2H), 4.31-4.27 (m, 1H), 2.85-2.58 (m, 2H).

(R)-2-(benzyloxycarbonylamino)-4,4,4-trifluorobutanoic acid. $^1$H-NMR (500 MHz, DMSO-d6): δ 13.21 (s, 1H), 7.85 (d, J=8.5 Hz, 1H), 7.38-7.30 (m, 5H), 5.06 (s, 2H), 4.31-4.27 (m, 1H), 2.83-2.59 (m, 2H).

Step 2: (S)-2-amino-4,4,4-trifluorobutanoic acid [I-4]

A mixture of (S)-2-(benzyloxycarbonylamino)-4,4,4-trifluorobutanoic acid (700 mg, 2.40 mmol) and Pd/C (10%) (200 mg) in MeOH (50 mL) was stirred at rt for 2 h under hydrogen atmosphere. The mixture was filtered, and the filter cake was washed with MeOH (20 mL). The filtrate was concentrated to afford (S)-2-amino-4,4,4-trifluorobutanoic acid (I-4), (250 mg, 1.59 mmol, 66.3%) as a white solid. ESI-MS (EI+, m/z): 158.1 [M+H]+. 1H-NMR (500 MHz, DMSO-d6+1 drop TFA+1 drop D2O): δ 4.32 (t, J=6.0 Hz, 1H), 3.03-2.82 (m, 2H).

Step 3: (R)-2-amino-4,4,4-trifluorobutanoic acid [I-5]

A mixture of (R)-2-(benzyloxycarbonylamino)-4,4,4-trifluorobutanoic acid (700 mg, 2.40 mmol) and Pd/C (10%) (200 mg) in MeOH (50 mL) was stirred at rt for 2 h under hydrogen atmosphere. The mixture was filtered, and the filter cake was washed with MeOH (20 mL). The filtrate was concentrated to afford (R)-2-amino-4,4,4-trifluorobutanoic acid (I-5), (250 mg, 1.59 mmol, 66.3%) as a white solid. ESI-MS (EI⁺, m/z): 158.1 [M+H]⁺. $^1$H-NMR (500 MHz, DMSO-d₆+1 drop TFA+1 drop D₂O): δ 4.31 (t, J=6.0 Hz, 1H), 3.03-2.83 (m, 2H).

Examples 6 and 7: (S)-2-amino-5,5,5-trifluoropentanoic acid [I-6] and (R)-2-amino-5,5,5-trifluoropentanoic acid [I-7]

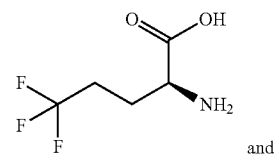

and

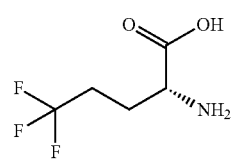

Synthetic Scheme:

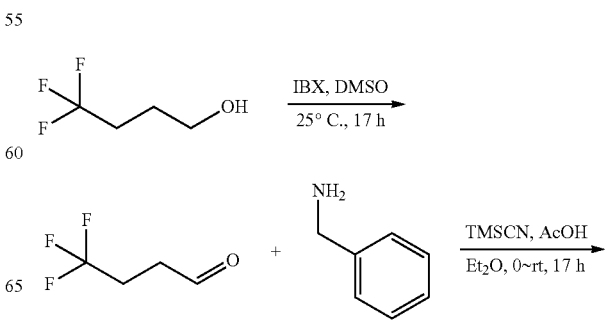

-continued

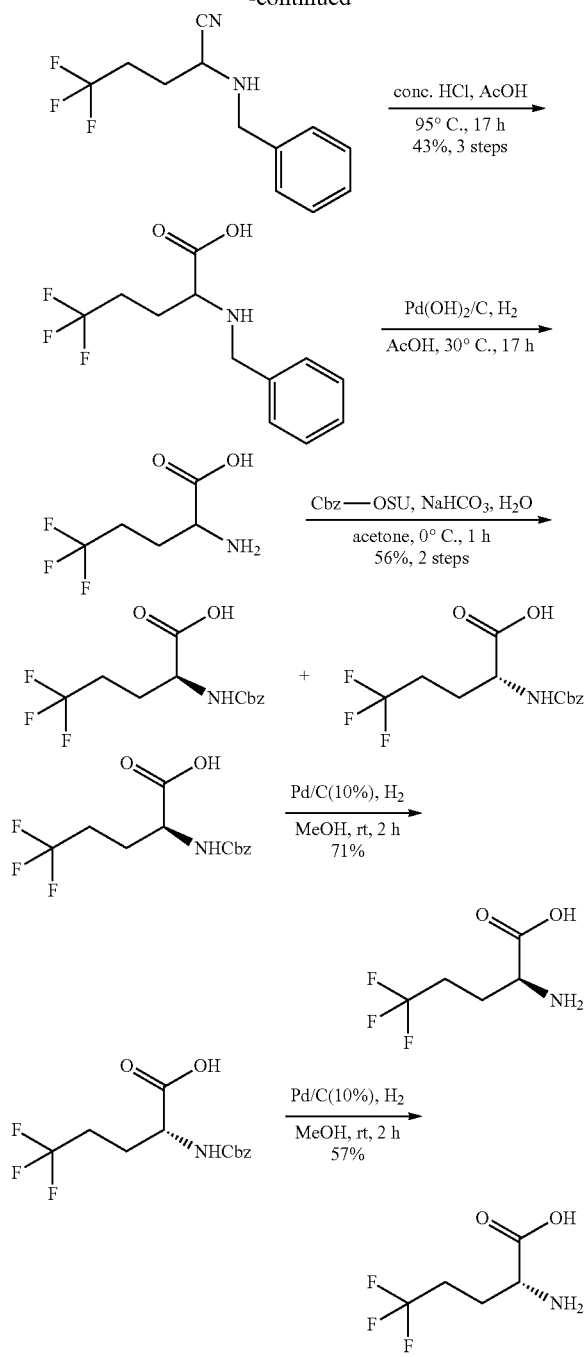

Procedures and Characterization:

Step 1: 4,4,4-Trifluorobutanal

To a solution of 4,4,4-trifluorobutan-1-ol (4.0 g, 31.3 mmol) in DMSO (80 mL) was added IBX (13.0 g, 46.9 mmol) under ice-bath. The mixture was warmed to room temperature and stirred overnight. The reaction mixture was poured into water (200 mL) and extracted with Et2O (100 mL×2), the organic phase was washed with water (100 mL×3), and brine (100 mL), dried (Na2SO4), and the solution was used for the next step.

Step 2: 2-(Benzylamino)-5,5,5-trifluoropentanenitrile

To a solution of above 4,4,4-trifluorobutanal in Et2O (200 mL) was added benzylamine (4 mL), AcOH (3.0 mL) and then TMSCN (3.5 mL) with ice-bath. The mixture was warmed to room temperature and stirred overnight. The solution was diluted with water (200 mL) and extracted with EtOAc (100 mL), the organic phase was washed with water (100 mL×2), and brine (100 mL), dried (Na2SO4), filtered and concentrated in vacuum to afford 2-(benzylamino)-5,5,5-trifluoropentanenitrile (6.7 g, crude) as a brown solid which was used for the next step. ESI-MS (EI+, m/z): 243.1 [M+H]+.

Step 3: 2-(Benzylamino)-5,5,5-trifluoropentanoic acid

A solution of 2-(benzylamino)-5,5,5-trifluoropentanenitrile (6.7 g, crude) in conc. HCl (80 mL) and AcOH (30 mL) was heated to 95° C. for 17 hrs. The solution was concentrated to dryness, diluted with resulting solution was filtered (100 mL) and ACN (50 mL), the pH was adjusted to 3-4 with sat. NaHCO$_3$ solution, the mixture was filtered and dried to afford 2-(benzylamino)-5,5,5-trifluoropentanoic acid (3.5 g, 13.4 mmol, 43% for 3 steps) as a white solid. ESI-MS (EI$^+$, m/z): 262.1 [M+H]$^+$.

Step 4: 2-Amino-5,5,5-trifluoropentanoic acid

A mixture of 2-(benzylamino)-5,5,5-trifluoropentanoic acid (3.3 g, 12.6 mmol) and Pd(OH)2/C (20%, 400 mg) in AcOH (60 mL) was stirred at 30° C. for 17 hrs. The mixture was filtered, and the filtrate was concentrated to dryness to afford 2-amino-5,5,5-trifluoropentanoic acid (3.0 g, crude) as a brown solid. ESI-MS (EI+, m/z): 172.2 [M+H]$^+$.\

Step 5: (S)-2-(Benzyloxycarbonylamino)-5,5,5-trifluoropentanoic acid and (R)-2-(benzyloxycarbonylamino)-5,5,5-trifluoropentanoic acid To a solution of 2-amino-5,5,5-trifluoropentanoic acid (3.0 g, crude) in sat. NaHCO3 solution (100 mL) and acetone (100 mL) was added Cbz-OSu (3.45 g, 13.9 mmol) with ice-bath, after 2 h, The mixture was adjusted to pH 3 with 6 M HCl, extracted with EtOAc (50 mL×2), the organic phase was washed with water (50 mL) and brine (100 mL), dried (Na$_2$SO$_4$), and concentrated in vacuum, The crude product was purified by chromatography (silica, ethyl acetate/petroleum ether=1/2) and then chiral-prep-HPLC [column, AY-H 4.6*250 mm 5 um; solvent, MeOH (0.5% NH$_4$OH)] to afford (S)-2-(benzyloxycarbonylamino)-5,5,5-trifluoropentanoic acid (1.50 g, 4.92 mmol, 28%, 2 steps) and (R)-2-(benzyloxycarbonylamino)-5,5,5-trifluoropentanoic acid (1.50 g, 4.92 mmol, 28%,\ for 2 steps) as white solids.

(S)-2-(benzyloxycarbonylamino)-5,5,5-trifluoropentanoic acid (1.50 g, 4.92 mmol, 28% for 2 steps). ESI-MS (EI+, m/z): 328.0 [M+Na]+. 1H-NMR (500 MHz, DMSO-d6): δ 12.86 (s, 1H), 7.71 (d, J=8.0 Hz, 1H), 7.31-7.39 (m, 5H), 5.05 (s, 2H), 4.05-4.10 (m, 1H), 2.34-2.41 (m, 1H), 2.21-2.29 (m, 1H), 1.84-1.97 (m, 2H).

(R)-2-(benzyloxycarbonylamino)-5,5,5-trifluoropentanoic acid (1.50 g, 4.92 mmol, 28%, 2 steps) ESI-MS (EI+, m/z): 328.0 [M+Na]+. 1H-NMR (500 MHz, DMSO-d6): δ 12.85 (s, 1H), 7.71 (d, J=8.0 Hz, 1H), 7.30-7.39 (m, 5H), 5.05 (s, 2H), 4.05-4.10 (m, 1H), 2.34-2.41 (m, 1H), 2.21-2.29 (m, 1H), 1.84-1.97 (m, 2H).

Step 6: (S)-2-Amino-5,5,5-trifluoropentanoic acid [I-6]

A mixture of (S)-2-(benzyloxycarbonylamino)-5,5,5-trifluoropentanoic acid (500 mg, 1.64 mmol) and Pd/C (10%) (50 mg) in MeOH (20 mL) was stirred at rt for 2 h under hydrogen. The mixture was filtered, and the filter cake was washed with MeOH (20 mL). The filtrate was concentrated to afford (S)-2-amino-5,5,5-trifluoropentanoic acid (I-6), (200 mg, 1.17 mmol, 71%) as a white solid. ESI-MS (EI+, m/z): 172.1 [M+H]+. $^1$H-NMR (400 MHz, DMSO-$d_6$): δ 8.38 (s, 3H), 4.05 (d, J=4.4 Hz, 1H), 2.34-2.55 (m, 2H), 1.95-20.9 (m, 2H).

Step 7: (R)-2-Amino-5,5,5-trifluoropentanoic acid [I-7]

A mixture of (R)-2-(benzyloxycarbonylamino)-5,5,5-trifluoropentanoic acid (500 mg, 1.64 mmol) and Pd/C (10%) (50 mg) in MeOH (20 mL) was stirred at rt for 2 h under hydrogen. The mixture was filtered, and the filter cake was washed with MeOH (20 mL). The filtrate was concentrated to afford (R)-2-amino-5,5,5-trifluoropentanoic acid (I-7), (160 mg, 0.94 mmol, 57%) as a white solid. ESI-MS (EI+, m/z): 172.1 [M+H]+. 1H-NMR (400 MHz, DMSO-d6): δ 8.38 (s, 3H), 4.05 (d, J=4.4 Hz, 1H), 2.34-2.55 (m, 2H), 1.95-20.9 (m, 2H).

Examples 8 and 9: (S)-2-amino-6,6,6-trifluorohexanoic acid [I-8] and (R)-2-amino-6,6,6-trifluorohexanoic acid [I-9]

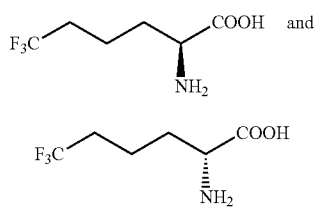

Synthetic Scheme:

Procedure and Characterization:

Step 1: (S)-2-(benzyloxycarbonylamino)-6,6,6-trifluorohexanoic acid and (R)-2-(benzyloxycarbonylamino)-6,6,6-trifluorohexanoic acid Benzyl carbonochloridate (554 mg, 3.25 mmol) was slowly added to a solution of 2-amino-6,6,6-trifluorohexanoic acid (556 mg, 2.5 mmol) and 1 M NaOH (25 mL, 25 mmol) in THF (25 mL) at 0° C., the mixture was stirred at rt for 16 h. The reaction mixture was extracted with DCM (2×100 mL) and the aqueous layer was acidified with HCl (3 M) to about pH 4 and then extracted with EtOAc (3×50 mL). The organic phase was dried over Na2SO4 and the solvent was evaporated under vacuum. The resulting crude product was purified by chiral-prep-HPLC (Column: AY-H (250*4.6 mm 5 um); mobile phase: n-Hexane (0.1% DEA):EtOH (0.1% DEA)=90:10) to afford (S)-2-(benzyloxycarbonylamino)-6,6,6-trifluorohexanoic acid (232 mg, 0.73 mmol, 29%) and (R)-2-(benzyloxycarbonyl amino)-6,6,6-trifluorohexanoic acid (250 mg, 0.78 mmol, 31.3%) as white solids. ESI-MS (EI+, m/z): 342.0 [M+Na]+.

(S)-2-(benzyloxycarbonylamino)-6,6,6-trifluorohexanoic acid, 1H-NMR (500 MHz, DMSO-d6): δ 12.68 (s, 1H), 7.66 (d, J=7.5 Hz, 1H), 7.38-7.32 (m, 5H), 5.04 (s, 2H), 4.00-3.96 (m, 1H), 2.28-2.19 (m, 2H), 1.80-1.51 (m, 4H).

(R)-2-(benzyloxycarbonylamino)-6,6,6-trifluorohexanoic acid, 1H-NMR (500 MHz, DMSO-d6): δ 12.68 (s, 1H), 7.67 (d, J=8.5 Hz, 1H), 7.38-7.30 (m, 5H), 5.04 (s, 2H), 4.00-3.96 (m, 1H), 2.33-2.15 (m, 2H), 1.82-1.51 (m, 4H).

Step 2: (S)-2-amino-6,6,6-trifluorohexanoic acid [I-8]

A mixture of (S)-2-(benzyloxycarbonylamino)-6,6,6-trifluorohexanoic acid (200 mg, 0.63 mmol) and Pd/C (10%) (50 mg) in MeOH (20 mL) was stirred at rt for 2 h under hydrogen atmosphere. The mixture was filtered, and the filter cake was washed with MeOH (20 mL). The filtrate was concentrated to afford (S)-2-amino-6,6,6-trifluorohexanoic acid (I-8), (56.2 mg, 0.30 mmol, 48.2%) as a white solid. ESI-MS (EI+, m/z): 186.1 [M+H]+. $^1$H-NMR (500 MHz, DMSO-$d_6$+1 drop TFA+1 drop $D_2$O): δ 3.99 (t, J=5.5 Hz, 1H), 2.32-2.30 (m, 2H), 1.91-1.83 (m, 2H), 1.70-1.57 (m, 2H).

Step 3: (R)-2-amino-6,6,6-trifluorohexanoic acid [I-9]

A mixture of (R)-2-(benzyloxycarbonylamino)-6,6,6-trifluorohexanoic acid (250 mg, 0.78 mmol) and Pd/C (10%) (50 mg) in MeOH (20 mL) was stirred at rt for 2 h under

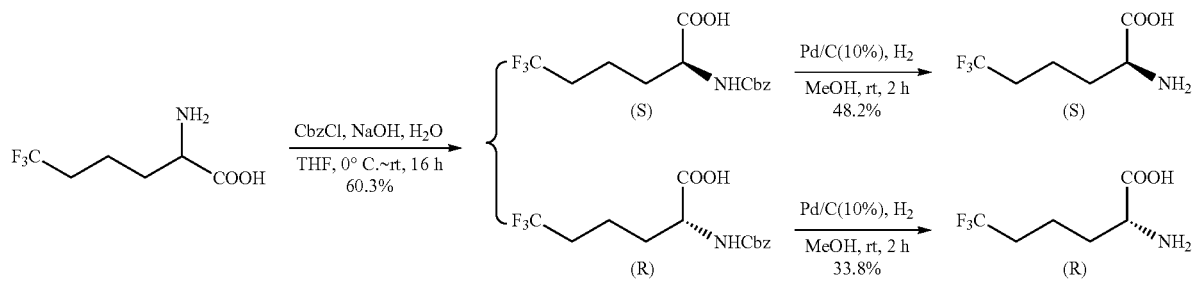

hydrogen atmosphere. The mixture was filtered, and the filter cake was washed with MeOH (20 mL). The filtrate was concentrated to afford (R)-2-amino-6,6,6-trifluorohexanoic acid (I-9), (48.8 mg, 0.26 mmol, 33.8%) as a white solid. ESI-MS (EI+, m/z): 186.1 [M+H]+. ¹H-NMR (500 MHz, DMSO-d6+1 drop TFA+1 drop D2O): δ 3.98 (t, J=6.5 Hz, 1H), 3.33-2.28 (m, 2H), 1.93-1.81 (m, 2H), 1.71-1.54 (m, 2H).

Example 11: (S)-2-(benzylamino)-4-methylpentanoic acid [I-11]

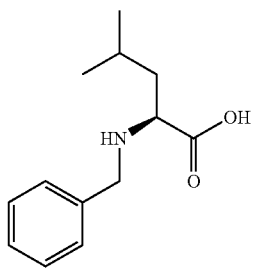 [SMILES: CC(C)C[C@H](NCc1ccccc1)C(=O)O]

Synthetic Scheme:

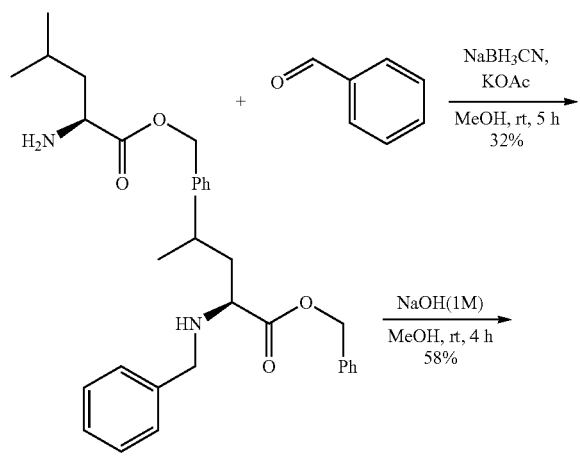

Procedures and Characterization:

Step 1: (S)-Benzyl 2-(benzylamino)-4-methylpentanoate

To a stirred solution of L-leucine benzyl ester p-toluenesulfonate (800 mg, 2.0 mmol) in MeOH (30 mL) was added benzaldehyde (0.26 g, 2.4 mmol) and potassium acetate (0.4 g, 4.1 mmol), and the mixture was stirred for 30 min at rt, then Sodium cyanoborohydride (0.2 g, 3.0 mmol) was added, the mixture was stirred for another 5 h at rt. The mixture was quenched with sat. NaHCO3 solution (50 mL), extracted with EtOAc (50 mL×2), washed with resulting solution was filtered (50 mL) and brine (50 mL). The organic phase was concentrated purified by prep-HPLC (Boston C18 21*250 mm 10 μm, Mobile phase: A: 0.1% trifluoroacetic acid; B: acetonitrile) to afford (S)-benzyl 2-(benzylamino)-4-methylpentanoate (200 mg, 0.64 mmol, 32%) as colorless oil. MS (EI+, m/z): 312.3 [M+H]+. 1H-NMR (500 MHz, MeOD): δ 7.41~7.49 (m, 1OH), 5.34 (dd, J=12.0 Hz, 45.0 Hz, 2H), 4.23 (q, J=12.0 Hz, 2H), 4.07~4.09 (m, 3H), 1.68~1.85 (m, 3H), 0.94 (dd, J=8.5 Hz, 20.5 Hz, 6H).

Step 2: (S)-2-(Benzylamino)-4-methylpentanoic acid [I-11]

To a stirred solution of (S)-benzyl 2-(benzylamino)-4-methylpentanoate (50 mg, 0.16 mmol) in MeOH (5 mL) was added 1 M NaOH (0.5 mL). The reaction was stirred for 4 h at rt. The resulting solution was concentrated and the residue was purified by prep-HPLC (Boston C18 21*250 mm 10 μm, Mobile phase: A: 0.1% trifluoroacetic acid; B: acetonitrile) to afford (S)-2-(benzylamino)-4-methylpentanoic acid (I-11), (21 mg, 0.095 mmol, 58%) as white solid MS (EI+, m/z): 222.2 [M+H]+. 1H-NMR (500 MHz, DMSO-d6): δ 9.32 (s, 1H), 7.43~7.50 (m, 5H), 4.17 (dd, J=13.0 Hz, 44.0 Hz, 2H), 3.82 (t, J=6.5 Hz, 1H), 1.68~1.76 (m, 3H), 0.85~0.90 (m, 6H).

Example 12: (S)-4-methyl-2-(2-phenylacetamido)pentanoic acid [I-12]

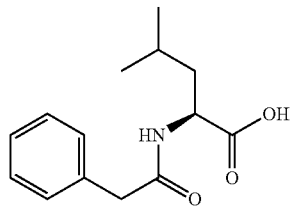 [SMILES: CC(C)C[C@H](NC(=O)Cc1ccccc1)C(=O)O]

Synthetic Scheme:

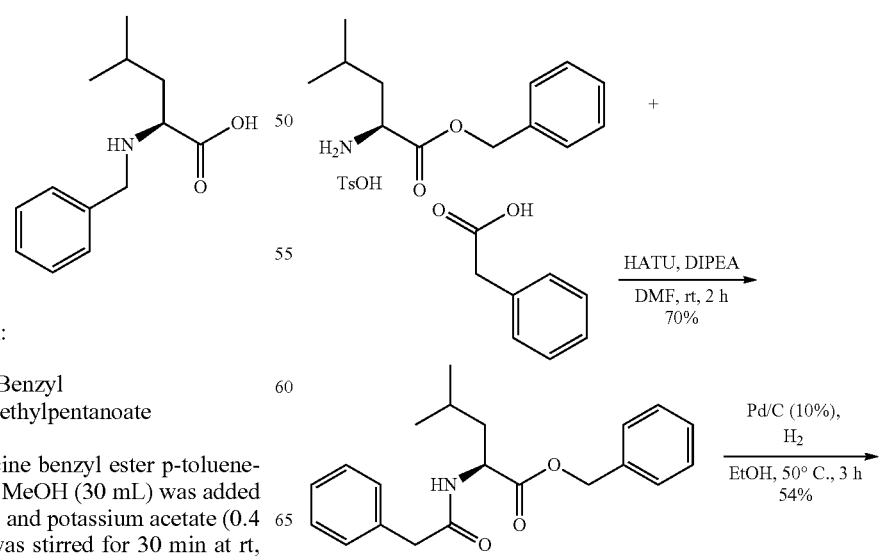

77

-continued

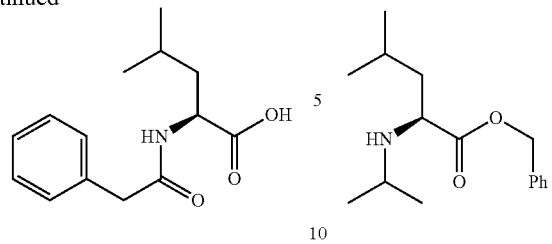

Procedures and Characterization:

Step 1: (S)-Benzyl 4-methyl-2-(2-phenylacetamido)pentanoate

To a solution of L-leucine benzyl ester p-toluenesulfonate (500 mg, 1.27 mmol), 2-phenylacetic acid (260 mg, 1.91 mmol) and HATU (726 mg, 1.91 mmol) in DMF (10 mL) was added DIPEA (410 mg, 3.18 mmol) and the solution was stirred for 2 h at rt. The solution was purified by prep-HPLC (Boston C18 21*250 mm 10 µm, Mobile phase: A: 0.1% trifluoroacetic acid; B: acetonitrile) to afford (S)-benzyl 4-methyl-2-(2-phenylacetamido)pentanoate (300 mg, 0.88 mmol, 70%) as a white solid. MS (EI+, m/z): 340.2 [M+H]+.

Step 2: (S)-4-Methyl-2-(2-phenylacetamido)pentanoic acid [I-12]

To a stirred solution of (S)-benzyl 4-methyl-2-(2-phenylacetamido)pentanoate (250 mg, 0.74 mmol) in EtOH (10 mL) was added a catalytic amount of Pd/C (10%, 20 mg). The reaction was stirred under hydrogen atmosphere for 3 h at 50° C. The resulting solution was filtered and concentrated to afford (S)-4-methyl-2-(2-phenylacetamido)pentanoic acid (I-12), (100 mg, 0.40 mmol, 54%) as a white solid. MS (EI+, m/z): 250.2 [M+H]+. 1H-NMR (500 MHz, MeOD): δ 7.24-7.32 (m, 5H), 4.44 (t, J=7.5 Hz, 1H), 3.58 (s, 2H), 1.64-1.68 (m, 3H), 0.96 (d, J=6.0 Hz, 3H), 0.91 (d, J=6.0 Hz, 3H).

Example 13: (S)-2-(isopropylamino)-4-methylpentanoic acid [I-13]

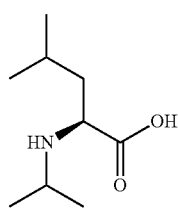

Synthetic Scheme:

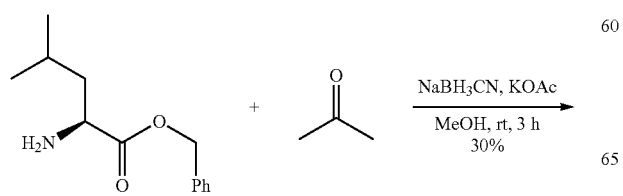

78

-continued

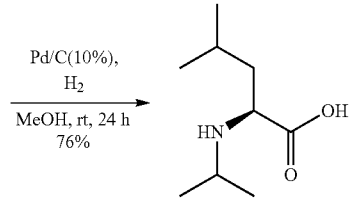

Procedures and Characterization:

Step 1: (S)-Benzyl 2-(isopropylamino)-4-methylpentanoate

To a stirred solution of L-leucine benzyl ester p-toluenesulfonate (1.0 g, 2.53 mmol) in MeOH (30 mL) was added acetone (177 mg, 3.05 mmol) and potassium acetate (0.5 g, 5.08 mmol), and the mixture was stirred for 30 min at rt, then sodium cyanoborohydride (0.24 g, 3.81 mmol) was added, the mixture was stirred for another 3 h at rt. The mixture was quenched with sat. NaHCO3 solution (50 mL), extracted with EtOAc (50 mL×2), washed with resulting solution was filtered (50 mL) and brine (50 mL). The organic phase was concentrated purified by prep-HPLC (Boston C18 21*250 mm 10 µm, Mobile phase: A: 0.1% trifluoroacetic acid; B: acetonitrile) to afford (S)-benzyl 2-(isopropylamino)-4-methylpentanoate (200 mg, 0.76 mmol, 30%) as a colorless oil. MS (EI+, m/z): 264.3 [M+H]+. 1H-NMR (500 MHz, MeOD): δ 7.22~7.29 (m, 5H), 5.07 (dd, J=11.5 Hz, 17.0 Hz, 2H), 3.33 (dd, J=6.5 Hz, 8.5 Hz, 1H), 2.54~2.59 (m, 1H), 1.30~1.48 (m, 3H), 0.72~0.94 (m, 12H).

Step 2: (S)-2-(Isopropylamino)-4-methylpentanoic acid [I-13]

To a stirred solution of (S)-benzyl 2-(isopropylamino)-4-methylpentanoate (200 mg, 0.76 mmol) in MeOH (10 mL), a catalytic amount of Pd/C (10%, 50 mg) were added. The reaction was stirred under hydrogen atmosphere for 24 h at rt. The result solution was filtered and the filtration was concentrated to afford (S)-2-(isopropylamino)-4-methylpentanoic acid (I-13), (100 mg, 0.57 mmol, 76%) as a white solid. MS (EI+, m/z): 174.3 [M+H]+. 1H-NMR (500 MHz, MeOD): δ 3.56 (dd, J=6.0 Hz, 8.5 Hz, 1H), 3.33~3.40 (m, 1H), 1.75~1.86 (m, 2H), 1.53~1.58 (m, 1H), 1.31~1.36 (m, 6H), 0.96~1.02 (m, 6H). 3.85 (dd, J=5.5 Hz, 8.5 Hz, 1H), 2.87 (q, J=6.0 Hz, 1H), 2.68 (dd, J=7.5 Hz, 12.0 Hz, 1H), 1.92~1.99 (m, 1H), 1.65~1.78 (m, 3H), 0.88~0.96 (m, 12H).

Example 14: (S)-2-(isobutylamino)-4-methylpentanoic acid [I-14]

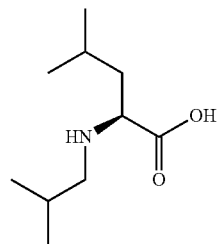

Synthetic Scheme:

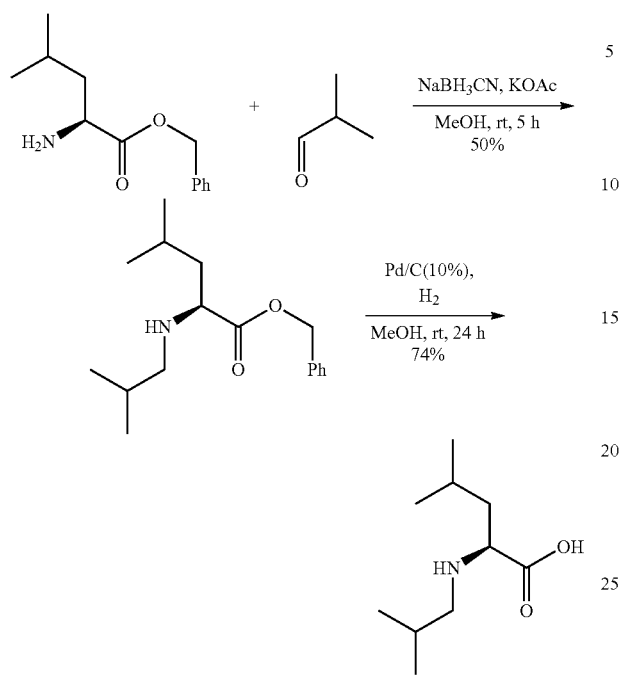

Procedures and Characterization:

Step 1: (S)-Benzyl 2-(isobutylamino)-4-methylpentanoate

To a stirred solution of L-leucine benzyl ester p-toluenesulfonate (1.0 g, 2.53 mmol) in MeOH (30 mL) was added isobutyraldehyde (0.22 g, 3.05 mmol) and potassium acetate (0.5 g, 5.08 mmol), and the mixture was stirred for 30 min at rt, then sodium cyanoborohydride (0.24 g, 3.81 mmol) was added. The mixture was stirred for another 5 h at rt. The mixture was quenched with sat. NaHCO3 solution (50 mL), extracted with EtOAc (50 mL×2), washed with resulting solution was filtered (50 mL) and brine (50 mL). The organic phase was concentrated purified by prep-HPLC (Boston C18 21*250 mm 10 μm, Mobile phase: A: 0.1% trifluoroacetic acid; B: acetonitrile) to afford (S)-benzyl 2-(isobutylamino)-4-methylpentanoate (300 mg, 1.08 mmol, 50%) as a colorless oil. MS (EI+, m/z): 278.2 [M+H]+. 1H-NMR (500 MHz, DMSO-d6): δ 9.16 (s, 1H), 9.14 (d, J=17.5 Hz, 2H), 7.42-7.43 (m, 5H), 5.28 (q, J=12.0 Hz, 2H), 4.08-4.09 (m, 1H), 2.87-2.89 (m, 1H), 2.65-2.66 (m, 1H), 1.91-1.95 (m, 1H), 1.62-1.71 (m, 3H), 0.88~0.94 (m, 12H).

Step 2: (S)-2-(Isobutylamino)-4-methylpentanoic acid [I-14]

To a stirred solution of (S)-benzyl 2-(isobutylamino)-4-methylpentanoate (300 mg, 1.08 mmol) in MeOH (10 mL), a catalytic amount of Pd/C (10%, 50 mg) were added. The reaction was stirred under hydrogen atmosphere for 24 h at rt. The resulting solution was filtered and the filtration was concentrated to afford (S)-2-(isobutylamino)-4-methylpentanoic acid (I-14), (150 mg, 0.8 mmol, 74%) as a white solid. MS (EI+, m/z): 188.3 [M+H]+. 1H-NMR (500 MHz, DMSO-d6): δ 8.82 (s, 2H), 3.85 (dd, J=5.5 Hz, 8.5 Hz, 1H), 2.87 (q, J=6.0 Hz, 1H), 2.68 (dd, J=7.5 Hz, 12.0 Hz, 1H), 1.92~1.99 (m, 1H), 1.65~1.78 (m, 3H), 0.88~0.96 (m, 12H).

Example 15: (S)-2-benzamido-4-methylpentanoic acid [I-15]

Synthetic Scheme:

Procedures and Characterization:

Step 1: (S)-Benzyl 2-benzamido-4-methylpentanoate

To a solution of L-leucine benzyl ester p-toluenesulfonate (500 mg, 1.27 mmol), benzoic acid (223 mg, 1.91 mmol) and HATU (726 mg, 1.91 mmol) in DMF (10 mL) was added DIPEA (410 mg, 3.18 mmol) and the solution was stirred for 2 h at rt. The solution was purified by prep-HPLC (Boston C18 21*250 mm 10 μm, Mobile phase: A: 0.1% trifluoroacetic acid; B: acetonitrile) to afford (S)-benzyl 2-benzamido-4-methylpentanoate (300 mg, 0.92 mmol, 73%) as a white solid. MS (EI+, m/z): 326.2 [M+H]+.

Step 2: (S)-2-Benzamido-4-methylpentanoic acid [I-15]

To a stirred solution of (S)-benzyl 2-benzamido-4-methylpentanoate (100 mg, 0.46 mmol) in EtOH (10 mL) was added a catalytic amount of Pd/C (10%, 20 mg). The reaction was stirred under hydrogen atmosphere for 3 h at 50° C. The resulting solution was filtered and concentrated to afford (S)-2-benzamido-4-methylpentanoic acid (I-15), (100 mg, 0.42 mmol, 65%) as a white solid. MS (EI+, m/z): 236.2 [M+H]+. 1H-NMR (400 MHz, MeOD): δ 7.87 (t, J=6.5 Hz, 2H), 7.47-7.57 (m, 3H), 4.69 (dd, J=4.0 Hz, 11.0 Hz, 1H), 1.75-1.84 (m, 3H), 1.01 (dd, J=6.5 Hz, 10.5 Hz, 6H).

Example 16: (S)-2-isobutyramido-4-methylpentanoic acid [I-16]

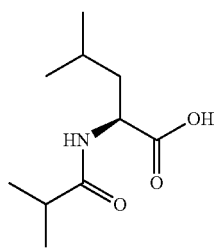

Synthetic Scheme:

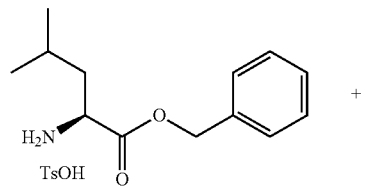

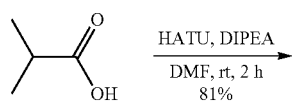

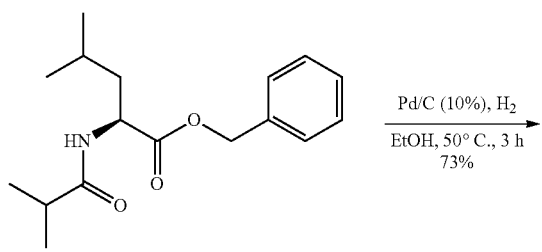

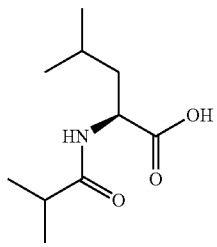

Procedures and Characterization:

Step 1: (S)-Benzyl 2-isobutyramido-4-methylpentanoate

To a solution of L-leucine benzyl ester p-toluenesulfonate (500 mg, 1.27 mmol), isobutyric acid (168 mg, 1.91 mmol) and HATU (726 mg, 1.91 mmol) in DMF (10 mL) was added DIPEA (410 mg, 3.18 mmol) and the solution was stirred for 2 h at rt. The solution was purified by prep-HPLC (Boston C18 21*250 mm 10 μm, Mobile phase: A: 0.1% trifluoroacetic acid; B: acetonitrile) to afford (S)-benzyl 2-isobutyramido-4-methylpentanoate (300 mg, 1.03 mmol, 81%) as a white solid. MS (EI+, m/z): 292.2 [M+H]+.

Step 2: (S)-2-Isobutyramido-4-methylpentanoic acid [I-16]

To a stirred solution of (S)-benzyl 2-(cyclohexanecarboxamido)-4-methylpentanoate (200 mg, 0.69 mmol) in EtOH (10 mL) was added a catalytic amount of Pd/C (10%, 20 mg). The reaction was stirred under hydrogen atmosphere for 3 h at 50° C. The resulting solution was filtered and concentrated to afford (S)-2-isobutyramido-4-methylpentanoic acid (100 mg, 0.50 mmol, 73%) as a white solid. MS (EI+, m/z): 202.2 [M+H]+. 1H-NMR (400 MHz, MeOD): δ 4.43 (t, J=6.4 Hz, 1H), 2.49-2.56 (m, 1H), 1.60-1.74 (m, 3H), 1.12 (dd, J=2.4 Hz, 6.8 Hz, 6H), 0.96 (dd, J=6.4 Hz, 16.0 Hz, 6H).

Example 17: (S)-2-(cyclohexanesulfonamido)-4-methylpentanoic acid [I-17]

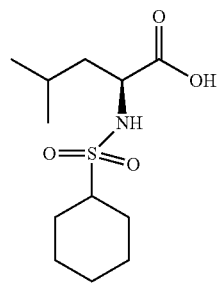 [SMILES: CC(C)C[C@H](NS(=O)(=O)C1CCCCC1)C(=O)O]

Synthetic Scheme:

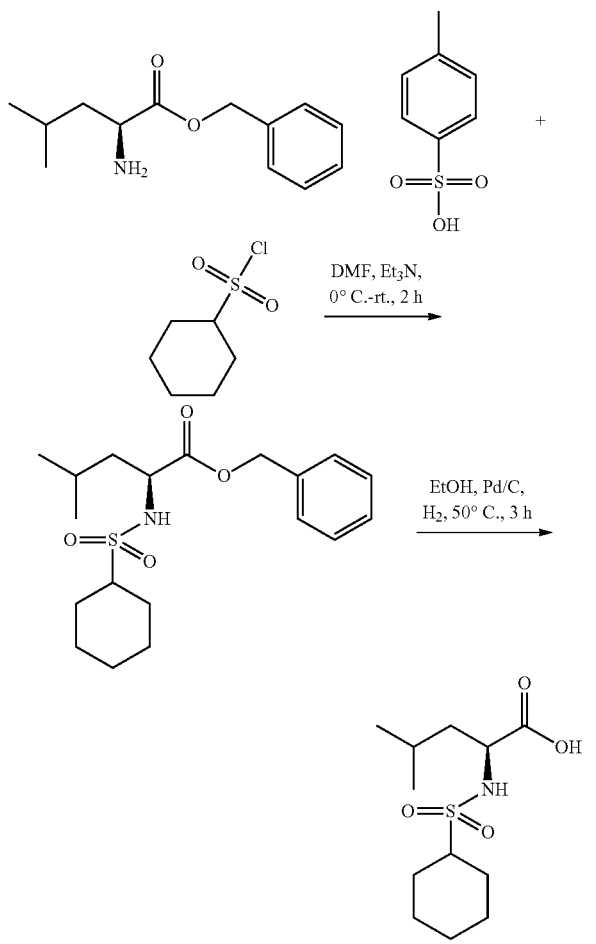

Procedures and Characterization:

Step 1: (S)-Benzyl 2-(cyclohexanesulfonamido)-4-methylpentanoate

To a solution of (S)-benzyl 2-amino-4-methylpentanoate 4-methylbenzenesulfonate (500 mg, 1.27 mmol) and Et3N (642.89 mg, 6.35 mmol) in DMF (3 mL), cooled with an ice-bath, was added cyclohexanesulfonyl chloride (278.53 mg, 1.52 mmol). The mixture was stirred at 25° C. for 2 hrs. The solution was diluted with ethyl acetate (10 mL), washed with resulting solution was filtered (10 mL×3) and brine (10 mL), dried with anhydrous sodium sulfate, filtered and concentrated in vacuo. The crude product was purified by prep-HPLC (Boston C18 21*250 mm 10 μm, Mobile phase: A: 0.1% trifluoroacetic acid; B: acetonitrile) to afford (S)-benzyl 2-(cyclohexanesulfonamido)-4-methylpentanoate (200 mg, 0.544 mmol, 98%) as a white solid. ESI-MS (EI+, m/z): 368.3 [M+H]+. 1H-NMR (500 MHz, DMSO-d6) δ 7.70 (d, J=9.0 Hz, 1H), 7.38 (t, J=6.5 Hz, 4H), 7.37-7.32 (m, 1H), 5.14 (q, J=12.5 Hz, 2H), 3.91 (td, J=5.0 Hz, 9.5 Hz, 1H), 2.69-2.74 (m, 1H), 2.05 (d, J=12.5 Hz, 1H), 1.97 (d, J=12.5 Hz, 1H), 1.74-1.67 (m, 2H), 1.57-1.51 (m, 2H), 1.50-1.44 (m, 1H), 1.36-0.99 (m, 5H), 0.87 (dt, J=10.5 Hz, J=20.5 Hz, 6H).

Step 2: (S)-2-(Cyclohexanesulfonamido)-4-methylpentanoic acid [I-17]

To a solution of (S)-benzyl 2-(cyclohexanesulfonamido)-4-methylpentanoate (192 mg, 0.552 mmol) in EtOH (3 mL), was added Pd/C (20 mg, 10%). The reaction mixture was stirred at 50° C. for 4 h under hydrogen. The mixture was filtered, and the filter cake was washed with MeOH (10 mL). The filtrate was concentrated to afford (S)-2-(cyclohexanesulfonamido)-4-methylpentanoic acid (I-17), (23.3 mg, 0.084 mmol, 100%) as a white solid. ESI-MS (EI+, m/z): 300.2 [M+Na]+. 1H NMR (500 MHz, DMSO-d6) δ 12.75 (s, 1H), 7.47 (d, J=9.0 Hz, 1H), 3.76 (td, J=5.0 Hz, 9.5 Hz, 1H), 2.82-2.69 (m, 1H), 2.18-1.97 (m, 2H), 1.82-1.69 (m, 3H), 1.61 (d, J=12.5 Hz, 1H), 1.54-1.40 (m, 2H), 1.39-1.07 (m, 5H), 0.95-0.80 (m, 6H).

Example 18: (S)-4-methyl-2-(phenylmethylsulfonamido)pentanoic acid [I-18]

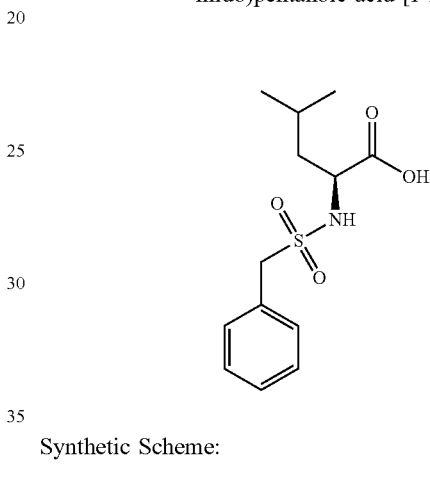

Synthetic Scheme:

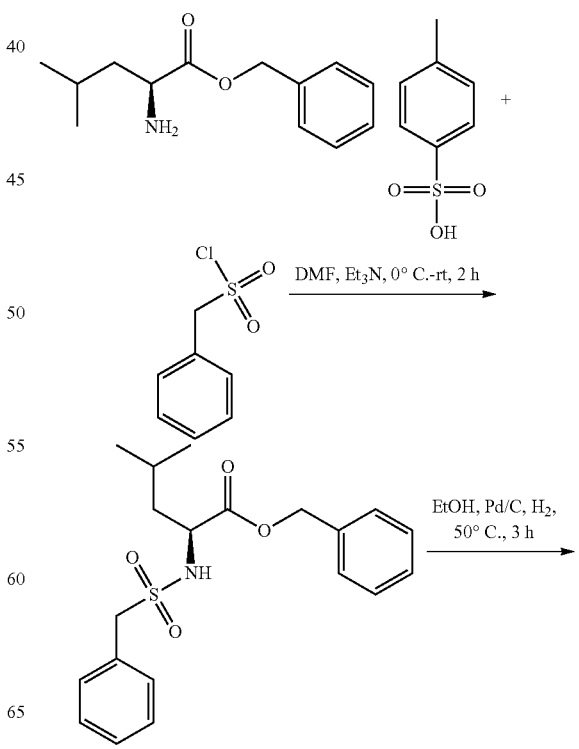

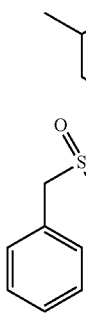

Procedures and Characterization:

Step 1: (S)-Benzyl 4-methyl-2-(phenylmethylsulfonamido)pentanoate

To a solution of (S)-benzyl 2-amino-4-methylpentanoate 4-methylbenzenesulfonate (500 mg, 1.27 mmol) and Et$_3$N (642.89 mg, 6.35 mmol) in DMF (3 mL), cooled with an ice-bath, was added phenylmethanesulfonyl chloride (290.71 mg, 1.52 mmol). The mixture was stirred at 25° C. for 2 hrs. The solution was diluted with ethyl acetate (10 mL), washed with resulting solution was filtered (10 mL×3) and brine (10 mL), dried with anhydrous sodium sulfate, filtered and concentrated in vacuum. The crude product was purified by prep-HPLC (Boston C18 21*250 mm 10 μm, Mobile phase: A: 0.1% trifluoroacetic acid; B: acetonitrile) to afford (S)-benzyl 4-methyl-2-(phenylmethylsulfonamido) pentanoate (149 mg, 0.396 mmol, 90%) as a white solid. ESI-MS (EI+, m/z): 398.0 [M+Na]+. 1H-NMR (500 MHz, DMSO-d6) δ 7.81 (d, J=8.5 Hz, 1H), 7.52-7.18 (m, 9H), 5.15 (s, 2H), 4.28 (dd, J=13.5 Hz, 44.5 Hz, 2H), 3.87 (dd, J=8.0 Hz, 15.0 Hz, 1H), 1.57-1.15 (m, 4H), 0.82 (dd, J=4.5 Hz, 6.0 Hz, 6H).

Step 2: (S)-4-Methyl-2-(phenylmethylsulfonamido) pentanoic acid [I-18]

To a solution of (S)-benzyl 4-methyl-2-(phenylmethyl-sulfonamido)pentanoate (121 mg, 0.322 mmol) in EtOH (3 mL), was added Pd/C (20 mg, 10%). This reaction mixture was stirred at 50° C. for 4 h under hydrogen. The mixture was filtered, and the filter cake was washed with MeOH (10 mL). The filtrate was concentrated to afford (S)-4-methyl-2-(phenylmethylsulfonamido)pentanoic acid (I-18), (41.2 mg, 0.144 mmol, 100%) as a white solid. ESI-MS (EI+, m/z): 308.0 [M+Na]+. 1H NMR (500 MHz, DMSO-d6) δ 12.77 (s, 1H), 7.59 (d, J=8.5 Hz, 1H), 7.47-7.25 (m, 5H), 4.30 (dd, J=13.5 Hz, 37.0 Hz, 2H), 3.75 (dd, J=7.5 Hz, 15.5 Hz, 1H), 1.65 (dt, J=6.5 Hz, 13.5 Hz, 1H), 1.45 (t, J=7.2 Hz, 2H), 0.85 (dd, J=1.5 Hz, 6.5 Hz, 6H).

Example 19: (S)-4-methyl-2-(methylsulfonamido) pentanoic acid [I-19]

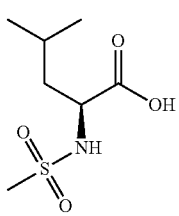

Synthetic Scheme:

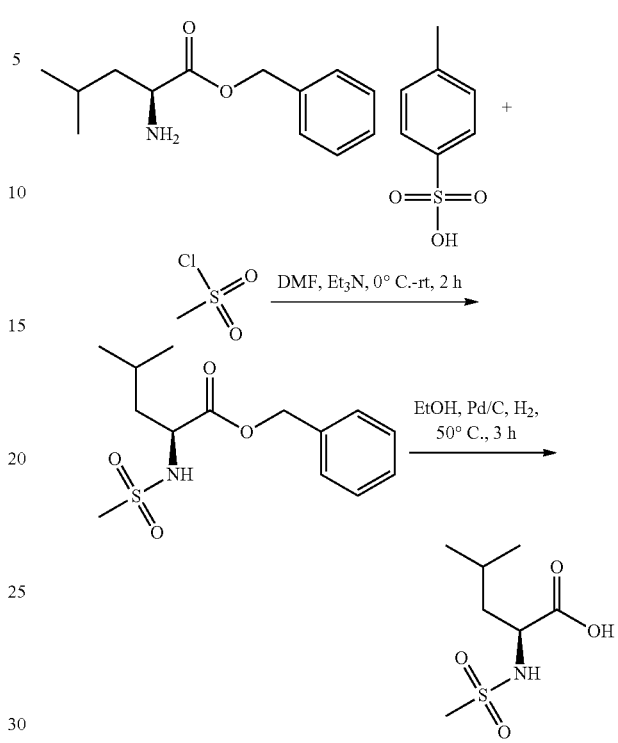

Procedures and Characterization:

Step 1: (S)-Benzyl 4-methyl-2-(methylsulfonamido)pentanoate

To a solution of (S)-benzyl 2-amino-4-methylpentanoate 4-methylbenzenesulfonate (500 mg, 1.27 mmol) and Et$_3$N (642.89 mg, 6.35 mmol) in DMF (3 mL), cooled with an ice-bath, was added methanesulfonyl chloride (290.71 mg, 1.52 mmol), the mixture was stirred at 25° C. for 2 h. The solution was diluted with ethyl acetate (10 mL), washed with resulting solution was filtered (10 mL×3) and brine (10 mL), dried with anhydrous sodium sulfate, filtered and concentrated in vacuo. The crude product was purified by prep-HPLC (Boston C18 21*250 mm 10 μm, Mobile phase: A: 0.1% trifluoroacetic acid; B: acetonitrile) to afford (S)-benzyl 4-methyl-2-(methylsulfonamido)pentanoate (192 mg, 0.641 mmol, 98%) as a white solid. ESI-MS (EI+, m/z): 323.0 [M+Na]+. $^1$H-NMR (500 MHz, DMSO-d$_6$) δ 7.79 (d, J=8.8 Hz, 1H), 7.42-7.36 (m, 4H), 7.37-7.32 (m, 1H), 5.16 (s, 2H), 3.97 (td, J=6.0 Hz, 9.0 Hz, 1H), 2.85 (s, 3H), 1.68 (dq, J=6.5 Hz, 13.0 Hz, 1H), 1.54-1.46 (m, 2H), 0.91-0.82 (m, 6H).

Step 2: (S)-4-Methyl-2-(methylsulfonamido)pentanoic acid [I-19]

To a solution of (S)-benzyl 4-methyl-2-(methylsulfona-mido)pentanoate (149 mg, 0.497 mmol) in EtOH (3 mL) was added Pd/C (20 mg, 10%). This reaction mixture was stirred at 50° C. for 4 h under hydrogen atmosphere. The mixture was filtered, and the filter cake was washed with MeOH (10 mL). The filtrate was concentrated to afford (S)-4-methyl-2-(methylsulfonamido)pentanoic acid (I-19), (31.4 mg, 0.150 mmol, 100%) as a white solid. ESI-MS (EI+, m/z): 232.1 [M+Na]+. 1H NMR (500 MHz, DMSO-d6) δ 12.82 (s, 1H), 7.56 (d, J=9.0 Hz, 1H), 3.82 (dd, J=8.0 Hz, 15.5 Hz, 1H), 2.88 (s, 3H), 1.72 (dt, J=6.5 Hz, 13.0 Hz, 1H), 1.48 (t, J=7.0 Hz, 2H), 0.89 (t, J=7.0 Hz, 6H).

Example 20: (S)-2-amino-4-methyl-N-phenylpentanamide [I-20]

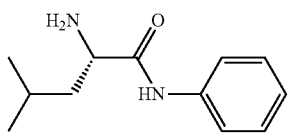

Synthetic Scheme:

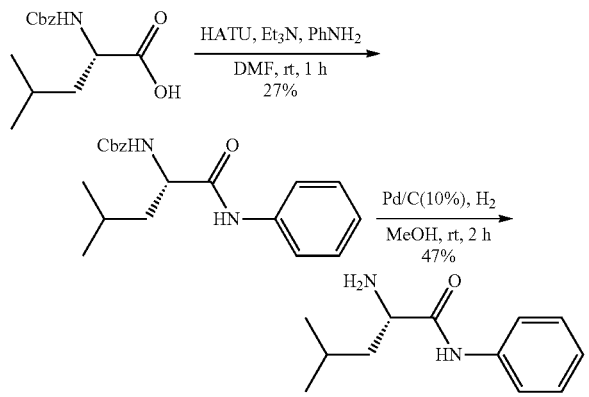

Procedures and Characterization:

Step 1: (S)-benzyl 4-methyl-1-oxo-1-(phenylamino)pentan-2-ylcarbamate

To a solution of (S)-2-(benzyloxycarbonylamino)-4-methylpentanoic acid (1.0 g, 3.77 mmol) in DMF (20 mL) was added aniline (702 mg, 7.55 mmol), HATU (1.72 g, 4.52 mmol) and Et3N (1.14 g, 11.31 mmol) at rt. After 2 hrs, the solution was diluted with EtOAc (80 mL), washed with resulting solution was filtered (80 mL×3) and brine (80 mL), dried (Na2SO4), filtered and concentrated in vacuo. The crude product was purified by chromatography (silica, ethyl acetate/petroleum ether=1/3) to afford (S)-benzyl 4-methyl-1-oxo-1-(phenylamino)pentan-2-ylcarbamate (350 mg, 1.03 mmol, 27%) as a white solid. ESI-MS (EI+, m/z): 341.1 [M+H]+.

Step 2: (S)-2-amino-4-methyl-N-phenylpentanamide [I-20]

A mixture of (S)-benzyl 4-methyl-1-oxo-1-(phenylamino)pentan-2-ylcarbamate (350 mg, 1.03 mmol) and Pd/C (10%, 50 mg) in MeOH (10 mL) was stirred at rt for 2 h under hydrogen. The mixture was filtered, and the filter cake was washed with MeOH (10 mL). The filtrate was concentrated to afford (S)-2-amino-4-methyl-N-phenylpentanamide (I-20), (100 mg, 0.49 mmol, 47%) as a white solid. ESI-MS (EI+, m/z): 207.2 [M+H]+. 1H-NMR (500 MHz, DMSO-d6): δ 9.86 (s, 1H), 7.63 (dd, J=1.0 Hz, 8.5 Hz, 2H), 7.31-7.27 (m, 2H), 7.03 (t, J=7.5 Hz, 1H), 3.31 (dd, J=5.0 Hz, 8.5 Hz, 1H), 1.80-1.71 (m, 1H), 1.50-1.44 (m, 1H), 1.35-1.29 (m, 1H), 0.90 (dd, J=6.5 Hz, 14.0 Hz, 6H).

Example 21: (S)-2-amino-N,4-dimethylpentanamide [I-21]

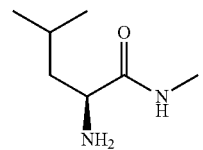

Synthetic Scheme:

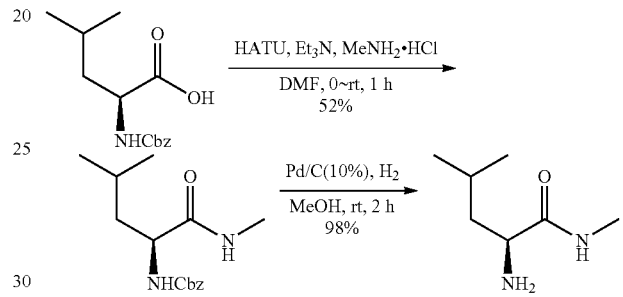

Procedures and Characterization:

Step 1: (S)-Benzyl 4-methyl-1-(methylamino)-1-oxopentan-2-ylcarbamate

To a solution of (S)-2-(benzyloxycarbonylamino)-4-methylpentanoic acid (1.0 g, 3.77 mmol) in DMF (20 mL) was added MeNH2·HCl (509 mg, 7.54 mmol), HATU (1.72 g, 4.52 mmol) and Et3N (1.14 g, 11.31 mmol) at 25° C. After 2 h, the solution was diluted with EtOAc (80 mL), washed with resulting solution was filtered (80 mL×3) and brine (80 mL), dried (Na2SO4), filtered and concentrated in vacuo. The crude product was purified by chromatography (silica, ethyl acetate/petroleum ether=1/3) to afford (S)-benzyl 4-methyl-1-(methylamino)-1-oxopentan-2-ylcarbamate (550 mg, 1.98 mmol, 52%) as a colorless oil. ESI-MS (EI+, m/z): 279.2 [M+H]+.

Step 2: (S)-2-Amino-N,4-dimethylpentanamide [I-21]

A mixture of (S)-benzyl 4-methyl-1-(methylamino)-1-oxopentan-2-ylcarbamate (300 mg, 1.08 mmol) and Pd/C (10%) (50 mg) in MeOH (10 mL) was stirred at rt for 2 h under hydrogen. The mixture was filtered, and the filter cake was washed with MeOH (10 mL). The filtrate was concentrated to afford (S)-2-amino-N,4-dimethylpentanamide (I-21), (152 mg, 1.05 mmol, 98%) as a colorless oil. ESI-MS (EI+, m/z): 145.3 [M+H]+. 1H-NMR (500 MHz, DMSO-d6): δ 7.80 (s, 1H), 3.10 (dd, J=5.0 Hz, 9.0 Hz, 1H), 2.57 (dd, J=3.0 Hz, 5.0 Hz, 3H), 1.81 (s, 2H), 1.66-1.69 (m, 1H), 1.34-1.39 (m, 1H), 1.16-1.22 (m, 1H), 0.81-0.87 (m, 6H).

Example 22: (S)-4-methyl-2-(phenylamino)pentanoic acid [I-22]

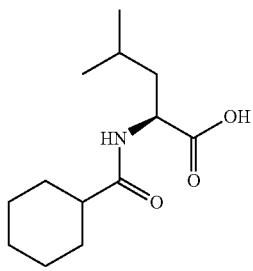 [SMILES: CC(C)C[C@H](NC(=O)C1CCCCC1)C(=O)O]

Synthetic Scheme:

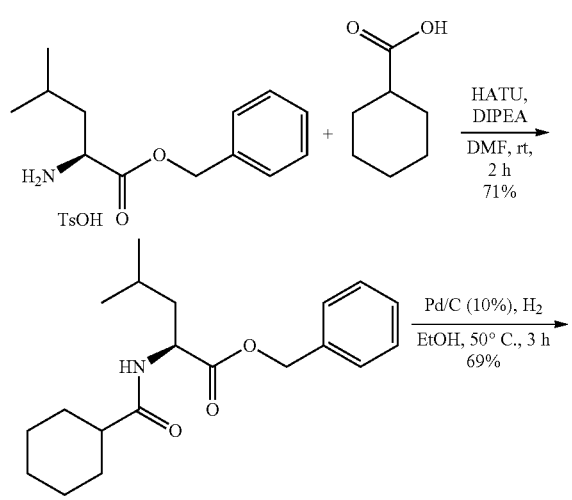

Procedures and Characterization:

Step 1: (S)-Benzyl 2-(cyclohexanecarboxamido)-4-methylpentanoate

To a solution of L-leucine benzyl ester p-toluenesulfonate (500 mg, 1.27 mmol), cyclohexanecarboxylic acid (244 mg, 1.91 mmol) and HATU (726 mg, 1.91 mmol) in DMF (10 mL) was added DIPEA (410 mg, 3.18 mmol) and the solution was stirred for 2 h at rt. The solution was purified by prep-HPLC (Boston C18 21*250 mm 10 μm, Mobile phase: A: 0.1% trifluoroacetic acid; B: acetonitrile) to afford (S)-benzyl 2-(cyclohexanecarboxamido)-4-methylpentanoate (300 mg, 0.91 mmol, 71%) as a white solid. MS (EI+, m/z): 332.3 [M+H]+.

Step 2: (S)-2-(Cyclohexanecarboxamido)-4-methylpentanoic acid [I-22]

To a stirred solution of (S)-benzyl 2-(cyclohexanecarboxamido)-4-methylpentanoate (200 mg, 0.60 mmol) in EtOH (10 mL) was added a catalytic amount of Pd/C (10%, 20 mg). The reaction was stirred under hydrogen atmosphere for 3 h at 50° C. The resulting solution was filtered and concentrated to afford (S)-2-(cyclohexanecarboxamido)-4-methylpentanoic acid (I-22), (100 mg, 0.41 mmol, 69%) as a white solid. MS (EI+, m/z): 242.3 [M+H]+. 1H-NMR (500 MHz, CD$_3$OD): δ 4.43 (t, J=7.5 Hz, 1H), 2.29 (td, J=8.0 Hz, 11.0 Hz, 1H), 1.74-1.85 (m, 4H), 1.63-1.72 (m, 4H), 1.43-1.49 (m, 2H), 1.26-1.36 (m, 3H), 0.96 (dd, J=6.0 Hz, 20.5 Hz, 6H).

Example 25: (S)-4-methyl-2-(phenylsulfonamido)pentanoic acid [I-25]

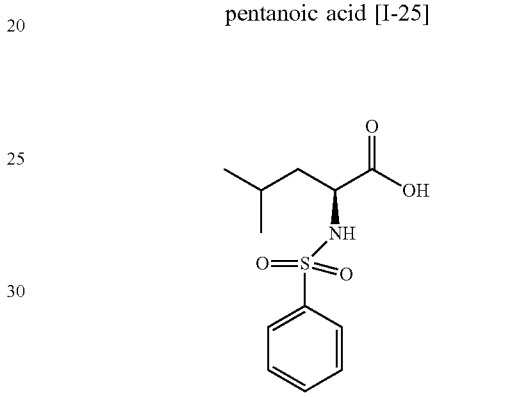

Synthetic Scheme:

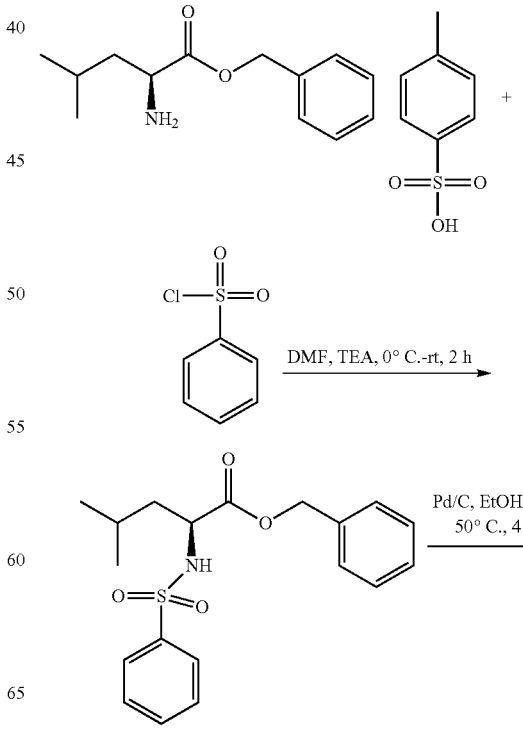

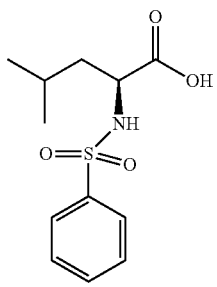 [SMILES: CC(C)C[C@H](NS(=O)(=O)c1ccccc1)C(=O)O]

Procedures and Characterization:

Step 1: (S)-Benzyl 4-methyl-2-(phenylsulfonamido)pentanoate

To a solution of (S)-benzyl 2-amino-4-methylpentanoate 4-methylbenzenesulfonate (300 mg, 0.762 mmol) and Et3N (385.73 mg, 3.81 mmol) in DMF (3 mL), cooled with an ice-bath, was added benzenesulfonyl chloride (148.12 mg, 0.838 mmol). The mixture was stirred at 25° C. for 2 h. The solution was diluted with ethyl acetate (10 mL), washed with resulting solution was filtered (10 mL×3) and brine (10 mL), dried with anhydrous sodium sulfate, filtered and concentrated in vacuo. The crude product (280 mg, purity: 85%, yield: 74%) was used directly in the next step. ESI-MS (EI+, m/z): 384.1 [M+Na]+.

Step 2: (S)-4-Methyl-2-(phenylsulfonamido)pentanoic acid [I-25]

To a solution of (S)-benzyl 4-methyl-2-(phenylsulfonamido)pentanoate (200 mg, 0.553 mmol) in EtOH (3 mL), was added Pd/C (20 mg, 10%). This reaction mixture was stirred at 50° C. for 4 h under hydrogen atmosphere. The mixture was filtered, and the filter cake was washed with MeOH (10 mL). The filtrate was concentrated to afford (S)-4-methyl-2-(phenylsulfonamido)pentanoic acid (I-25), (63.7 mg, 0.234 mmol, 100%) as a white solid. ESI-MS (EI+, m/z): 294.0 [M+Na]+. $^1$H-NMR (500 MHz, DMSO-$d_6$) δ 12.61 (s, 1H), 8.16 (d, J=8.6 Hz, 1H), 7.79-7.73 (m, 2H), 7.62 (t, J=7.3 Hz, 1H), 7.56 (t, J=7.4 Hz, 2H), 3.63 (dd, J=8.5 Hz, 14.5 Hz, 1H), 1.53 (td, J=6.5 Hz, 13.5 Hz, 1H), 1.41-1.31 (m, 2H), 0.79 (d, J=6.6 Hz, 3H), 0.66 (d, J=6.5 Hz, 3H).

Example 26: (S)-4-methyl-2-(phenylamino)pentanoic acid [I-26]

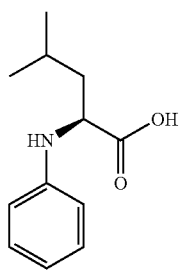

Synthetic Scheme:

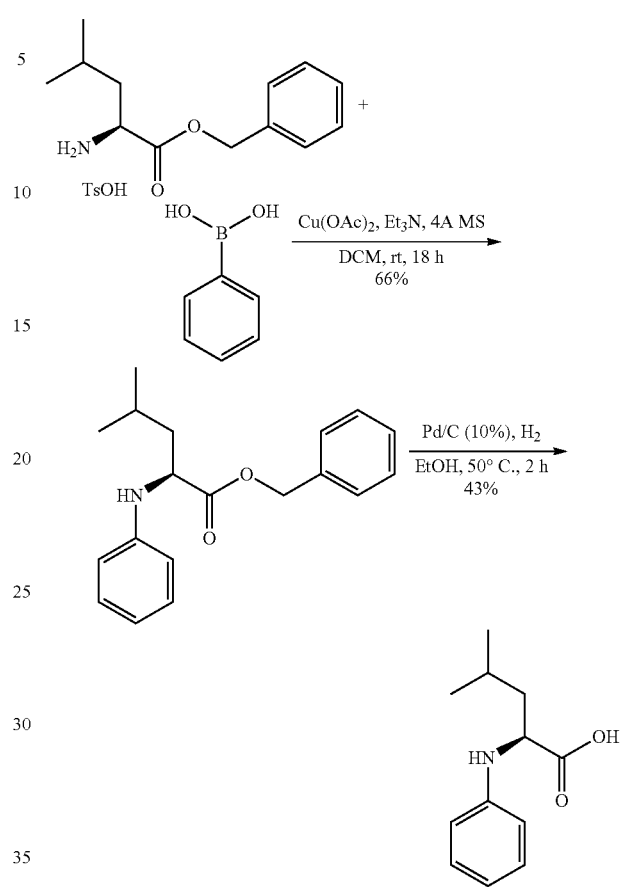

Procedures and Characterization:

Step 1: (S)-Benzyl 4-methyl-2-(phenylamino)pentanoate

To a mixture of L-leucine benzyl ester p-toluenesulfonate (200 mg, 0.51 mmol), phenylboronic acid (186 mg, 1.52 mmol) and Cu(OAc)2 (462 mg, 2.54 mmol) in DCM (10 mL) was added 4A MS (1.0 g) and Et3N (155 mg, 1.52 mmol) and the mixture was stirred for 18 h at rt. The mixture was quenched with resulting solution was filtered (50 mL), extracted with EtOAc (50 mL×2), washed with resulting solution was filtered (50 mL) and brine (50 mL). The organic phase was concentrated purified by chromatography (silica, ethyl acetate/petroleum ether=1/20) to afford (S)-benzyl 4-methyl-2-(phenylamino)pentanoate (100 mg, 0.34 mmol, 66%) as colorless oil. MS (EI+, m/z): 298.2 [M+H]+.

Step 2: (S)-4-methyl-2-(phenylamino)pentanoic acid [I-26]

To a stirred solution of (S)-benzyl 4-methyl-2-(phenylamino)pentanoate (100 mg, 0.34 mmol) in EtOH (10 mL) was added a catalytic amount of Pd/C (10%, 20 mg). The reaction was stirred under hydrogen atmosphere for 2 h at 50° C. The resulting solution was filtered and concentrated to afford (S)-4-methyl-2-(phenylamino)pentanoic acid (I-26), (30 mg, 0.15 mmol, 43%) as a white solid. MS (EI+, m/z): 208.1 [M+H]+. 1H-NMR (400 MHz, CDCl3): δ 7.23

(t, J=8.0 Hz, 2H), 6.83 (t, J=7.6 Hz, 1H), 6.66 (d, J=8.0 Hz, 2H), 3.99 (d, J=8.4 Hz, 1H), 2.87 (q, J=6.0 Hz, 1H), 1.72~1.86 (m, 2H), 1.62~1.68 (m, 1H), 0.85~1.03 (m, 6H).

Example 36: (S)-2-acetamido-4-methylpentanoic acid [I-36]

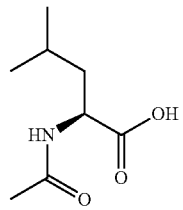

Synthetic Scheme:

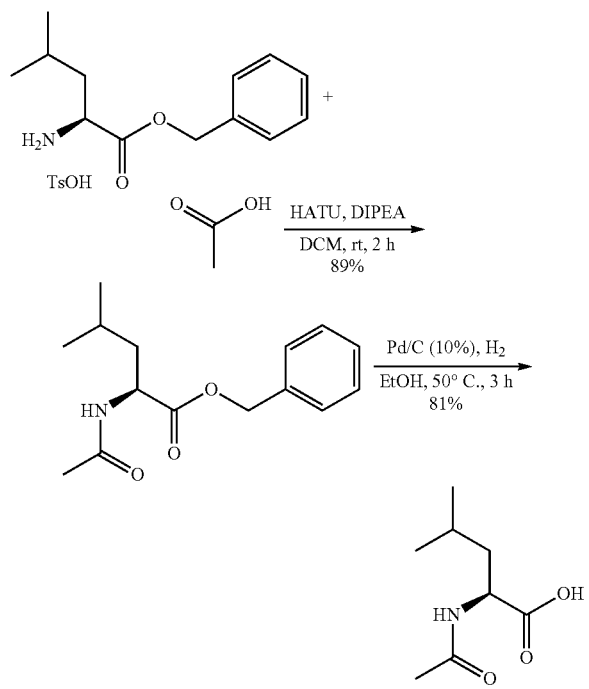

Procedures and Characterization:

Step 1: (S)-Benzyl 2-acetamido-4-methylpentanoate

To a solution of L-leucine benzyl ester p-toluenesulfonate (500 mg, 1.27 mmol), acetic acid (114 mg, 1.91 mmol) and HATU (726 mg, 1.91 mmol) in DMF (10 mL) was added DIPEA (410 mg, 3.18 mmol) and the solution was stirred for 2 h at rt. The solution was purified by prep-HPLC (Boston C18 21*250 mm 10 µm, Mobile phase: A: 0.1% trifluoroacetic acid; B: acetonitrile) to afford (S)-benzyl 2-acetamido-4-methylpentanoate (300 mg, 1.14 mmol, 89%) as a white solid. MS (EI+, m/z): 264.2 [M+H]+.

Step 2: (S)-2-Acetamido-4-methylpentanoic acid [I-36]

To a stirred solution of (S)-benzyl 2-acetamido-4-methylpentanoate (250 mg, 0.74 mmol) in EtOH (10 mL) was added a catalytic amount of Pd/C (10%, 20 mg). The reaction was stirred under hydrogen atmosphere for 3 h at 50° C. The resulting solution was filtered and concentrated to afford (S)-2-acetamido-4-methylpentanoic acid (I-36), (100 mg, 0.57 mmol, 81%) as a white solid. MS (EI+, m/z): 174.2 [M+H]+. $^1$H-NMR (500 MHz, MeOD): δ 4.43 (dd, J=6.0 Hz, 9.5 Hz, 1H), 2.00 (s, 3H), 1.61-1.73 (m, 3H), 0.97 (dd, J=6.0 Hz, 17.5 Hz, 6H).

Example 45: (S,E)-2-(4-methoxy-4-oxobut-2-enamido)-4-methylpentanoic acid

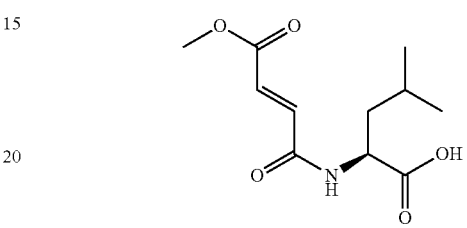

Synthetic Scheme:

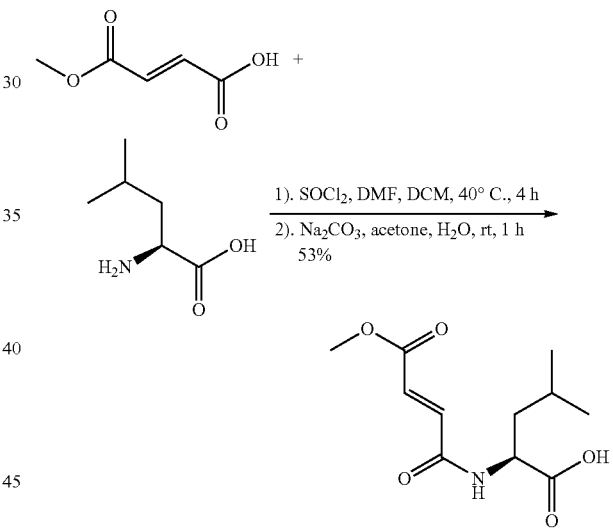

Procedures and Characterization:

Step 1: (S,E)-2-(4-Methoxy-4-oxobut-2-enamido)-4-methylpentanoic acid [I-45]

To a solution of (E)-4-methoxy-4-oxobut-2-enoic acid (1.0 g, 7.69 mmol) in DCM (30 mL) was added SOCl2 (1.83 g, 15.38 mmol), and then DMF (0.1 mL). The solution was heated to 40° C. for 4 h. The solution was concentrated to dryness to afford an oil. The oil was diluted with DCM (10 mL). The solution of (S)-2-amino-4-methylpentanoic acid (1.0 g, 7.62 mmol) in acetone (20 mL) and sat. Na2CO3 (20 mL) solution cooled with an ice-bath was added dropwise. After 1 h, the solution was adjusted pH 2 with 6 MHC solution, extracted with EtOAc (40×2), washed with resulting solution was filtered (80 mL×3) and brine (80 mL), dried (Na2SO4), filtered and concentrated in vacuo. The crude product was purified by chromatography (silica, MeOH/DCM=1/20) to afford (S,E)-2-(4-methoxy-4-oxobut-2-enamido)-4-methylpentanoic acid (I-45), (1.0 g, 4.11 mmol, 53%) as a yellow oil. ESI-MS (EI+, m/z): 244.2 [M+H]+.
$^1$H-NMR (400 MHz, CDCl$_3$): δ 7.32 (d, J=15.2 Hz, 1H), 7.05 (d, J=15.2 Hz, 1H), 6.85-6.89 (m, 2H), 7.30-7.46 (m, 1H), 3.82 (s, 1H), 1.63-1.78 (m, 3H), 0.97 (d, J=4.8 Hz, 6H).

Examples 46 and 47: (R)-2-amino-3,3-difluoro-4-methylpentanoic acid [I-46] and (S)-2-amino-3,3-difluoro-4-methylpentanoic acid [I-47]

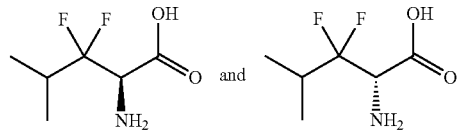

Synthetic Scheme:

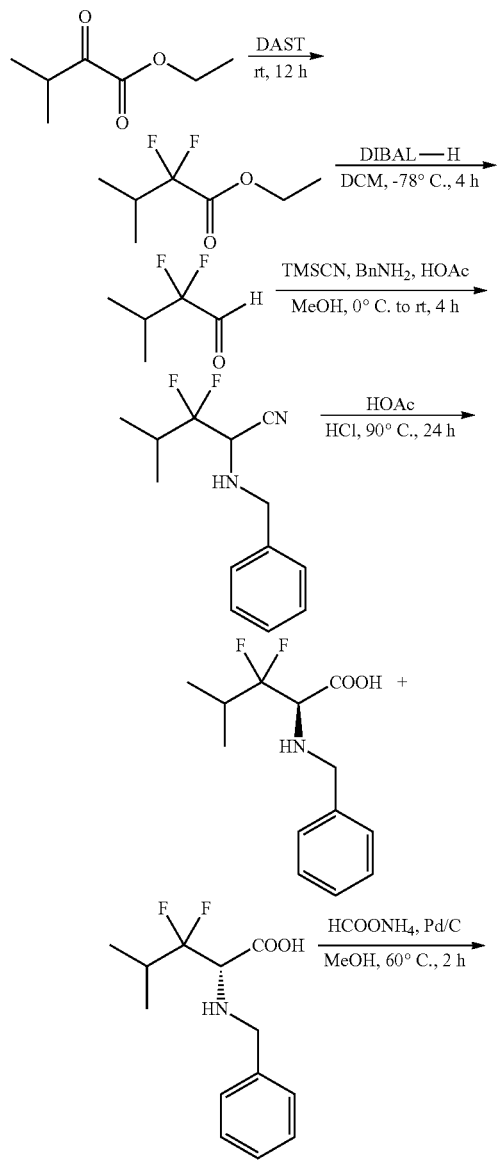

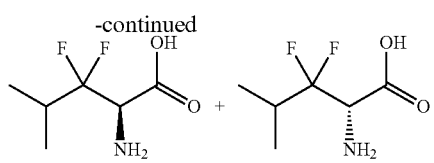

Procedures and Characterization:

Step 1: ethyl 2,2-difluoro-3-methylbutanoate

A mixture of ethyl 3-methyl-2-oxobutanoate (10 g, 0.069 mol) and DAST (16.8 g, 0.10 mol) was stirred at rt for 12 h. After checking by TLC, the reaction mixture was added dropwise slowly to a cold, saturated aqueous sodium bicarbonate solution. The mixture was extracted with Et20 (300 mL×2), and the organic layers were washed with brine, dried and concentrated to give a crude ethyl 2,2-difluoro-3-methylbutanoate (8.3 g) which was used directly in the next step.

Step 2: 2,2-difluoro-3-methylbutanal

To a solution of crude ethyl 2,2-difluoro-3-methylbutanoate (8.3 g) in CH2Cl2 (200 mL) was added dropwise a solution of DIBAL-H in hexanes (1.0 M, 69 mL, 69.0 mmol) at −78° C. under argon, and the mixture was stirred for 30 mins at −78° C. After checking by TLC, the reaction was quenched with saturated citric acid and extracted with Et$_2$O. The extract was washed with saturated citric acid, brine, dried over Na$_2$SO$_4$, and concentrated under reduced pressure to give an oily aldehyde 2,2-difluoro-3-methylbutanal (4.2 g), which was used immediately in the next step without purification.

Step 3: 2-(benzylamino)-3,3-difluoro-4-methylpentanenitrile

A solution of crude 2,2-difluoro-3-methylbutanal (4.2 g) in 50 mL of MeOH was cooled to 0° C. Acetic acid (glacial, 2.1 mL) was added drop-wise, maintaining the temperature around 0° C., followed by trimethylsilyl cyanide (4.2 mL) over a period of 15 minutes. The reaction mixture was warmed to 25° C. and stirred overnight. Cold resulting solution was filtered (200 mL) was charged into the reaction mixture and the reaction mixture was extracted with dichloromethane (2*200 mL). The dichloromethane layer was washed with resulting solution was filtered (2*100 mL), followed by brine (2*50 mL). The dichloromethane layer was dried over anhydrous sodium sulfate and concentrated under reduced pressure to give a crude 2-(benzylamino)-3,3-difluoro-4-methylpentanenitrile (2.8 g) which was used immediately in the next step without purification. ESI-MS (EI+, m/z): 238.2 [M+H]+.

Step 4: 2-(benzylamino)-3,3-difluoro-4-methylpentanoic acid

A solution of crude 2-(benzylamino)-3,3-difluoro-4-methylpentanenitrile (2.8 g) in 50 mL of conc. hydrochloric acid and 10 mL of HOAc was stirred at 90° C. for 24 hrs and concentrated. The residue was purified by prep-HPLC to give 2-(benzylamino)-3,3-difluoro-4-methylpentanoic acid (513 mg) as a white solid. The pure product was purified by chiral-HPLC to give (R)-2-(benzylamino)-3,3-difluoro-4-methylpentanoic acid (80 mg) and (S)-2-(benzylamino)-3, 3-difluoro-4-methylpentanoic acid (63 mg) which both were white solid. ESI-MS (EI+, m/z): 258.2 [M+H]+.

Step 5-A: (R)-2-amino-3,3-difluoro-4-methylpentanoic acid [I-46]

To a solution of (R)-2-(benzylamino)-3,3-difluoro-4-methylpentanoic acid (80 mg, 0.31 mmol) in 20 mL of MeOH was added HCOONH4 (98 mg, 1.56 mmol) and Pd/C (100 mg) at rt. The mixture was stirred at 60° C. for 2 h. The reaction mixture was filtered and concentrated to give a crude product which was purified by reverse-phase silica-gel chromatography to give (R)-2-amino-3,3-difluoro-4-methylpentanoic acid (I-46), (23 mg, 44%) as a white solid; 1H-NMR (500 MHz, D2O): δ 4.27 (dd, J=24.0, 3.5 Hz, 1H), 2.55-2.42 (m, 1H), 1.04 (d, J=7.0 Hz, 3H), 0.993 (d, J=6.5 Hz, 3H).

Step 5-B: (S)-2-amino-3,3-difluoro-4-methylpentanoic acid [I-47]

To a solution of (S)-2-(benzylamino)-3,3-difluoro-4-methylpentanoic acid (63 mg, 0.24 mmol) in 15 mL of MeOH was added HCOONH4 (77 mg, 1.22 mmol) and Pd/C (100 mg) at rt. The mixture was stirred at 60° C. for 2 h. The reaction mixture was filtered and concentrated to give a crude product which was purified by reverse-phase silica-gel chromatography to give (S)-2-amino-3,3-difluoro-4-methylpentanoic acid (I-47), (14 mg, 34%) as a white solid; 1H-NMR (500 MHz, D2O): δ 4.27 (dd, J=24.0, 3.5 Hz, 1H), 2.55-2.42 (m, 1H), 1.04 (d, J=7.0 Hz, 3H), 0.993 (d, J=6.5 Hz, 3H).

Example 147: (S)-2-amino-4-methyl-N-(methylsulfonyl)pentanamide hydrochloride [I-147]

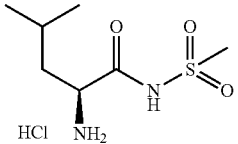

I-147

Synthetic Scheme:

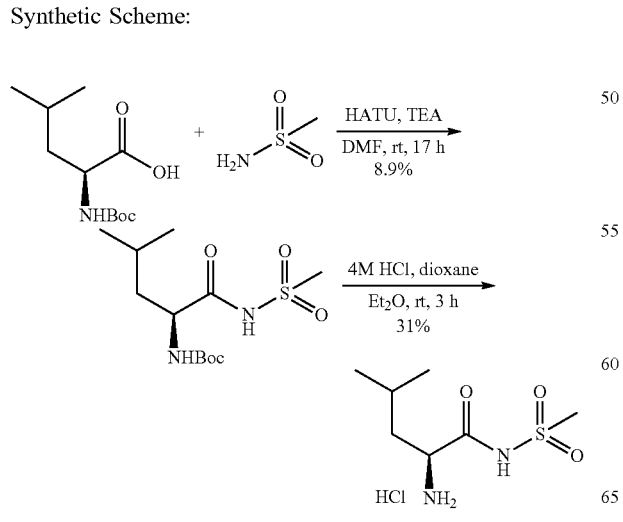

Procedures and Characterization:

Step 1: (S)-tert-butyl 4-methyl-1-(methylsulfonamido)-1-oxopentan-2-ylcarbamate To a solution of (S)-2-(tert-butoxycarbonylamino)-4-methylpentanoic acid (1.0 g, 4.32 mmol), methanesulfonamide (452 mg, 4.75 mmol) and HATU (1.8 g, 4.75 mmol) in DMF (30 mL) was added TEA (1.3 g, 12.9 mmol) and the solution was stirred for 17 h at rt. The solution was purified by prep-HPLC (Boston C18 21*250 mm 10 μm, Mobile phase: A: 0.1% trifluoroacetic acid; B: acetonitrile) to afford (S)-tert-butyl 4-methyl-1-(methylsulfonamido)-1-oxopentan-2-ylcarbamate (130 mg, 0.42 mmol, 8.9%) as a white solid. MS (EI−, m/z): 307.0 [M−H]−.

Step 2: (S)-2-amino-4-methyl-N-(methylsulfonyl)pentanamide hydrochloride[I-147]

A solution of (S)-tert-butyl 4-methyl-1-(methylsulfonamido)-1-oxopentan-2-ylcarbamate (130 mg, 0.42 mmol) in Et2O (15 mL) was added 4 M HCl/dioxane (5 mL) was stirred for 3 h at rt. The solid was filtered to afford (S)-2-amino-4-methyl-N-(methylsulfonyl)pentanamide hydrochloride [I-147] as a white solid (32 mg, 0.13 mmol, 31%). ESI-MS (EI+, m/z): 209.1 [M+H]+. 1H NMR (500 MHz, CD3OD) δ 3.96 (t, J=3.0 Hz, 1H), 3.32 (s, 3H), 1.74-1.79 (m, 3H), 1.02-1.05 (m, 6H).

Example 193: (S)-2-amino-N,4,4-trimethyl-N-(methylsulfonyl)pentanamide hydrochloride[I-193]

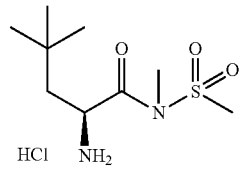

I-193

Synthetic Scheme:

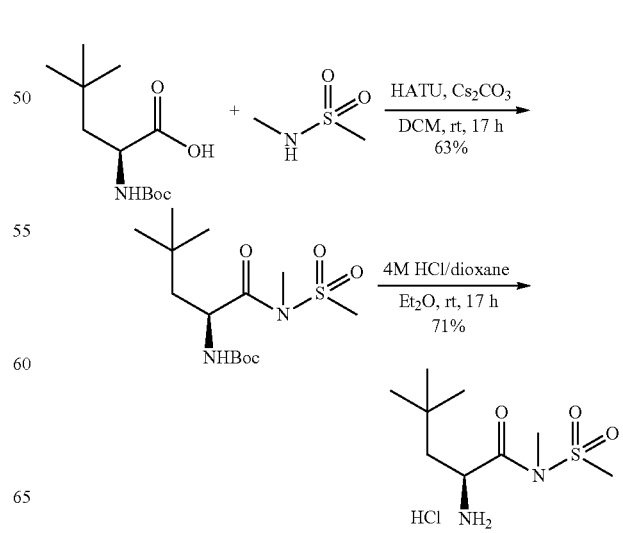

Procedures and Characterization:

Step 1: (S)-tert-butyl 4,4-dimethyl-1-(N-methylmethylsulfonamido)-1-oxopentan-2-ylcarbamate To a solution of (S)-2-(tert-butoxycarbonylamino)-4,4-dimethylpentanoic acid (500 mg, 1.97 mmol) in DCM (60 mL) was added HATU (900 mg, 2.36 mmol) and stirred at rt for 2 h. Then Cs$_2$CO$_3$ (1.92 g, 5.91 mmol), N-methylmethanesulfonamide (322 mg, 2.95 mmol) were added to the mixture and stirred for overnight at rt. The solution was diluted with water (200 mL) and extracted with DCM (100 mL). The organic phase was washed with water (100 mL×2), and brine (100 mL), dried (Na$_2$SO$_4$), filtered and concentrated in vacuum, the crude product was purified by chromatography (silica, ethyl acetate/petroleum ether=1/5) to afford (S)-tert-butyl 4,4-dimethyl-1-(N-methylmethylsulfonamido)-1-oxopentan-2-ylcarbamate (420 mg, 1.25 mmol, 63%) as a yellow oil. ESI-MS (EI+, m/z): 359.1 [M+Na]$^+$.

Step 2: (S)-2-amino-N,4,4-trimethyl-N-(methylsulfonyl)pentanamide hydrochloride[I-193]

A solution of (S)-tert-butyl 4,4-dimethyl-1-(N-methylmethylsulfonamido)-1-oxopentan-2-ylcarbamate (420 mg, 1.25 mmol) in Et$_2$O (20 mL) was added 4 M HCl/dioxane (10 mL) was stirred for 17 h at rt. The solid was filtered to afford (S)-2-amino-N,4,4-trimethyl-N-(methylsulfonyl)pentanamide hydrochloride [I-193] as a white solid (250 mg, 0.13 mmol, 71%). ESI-MS (EI+, m/z): 237.1 [M+H]$^+$. 1H NMR (500 MHz, DMSO) δ 8.55 (s, 3H), 4.59 (s, 1H), 3.50 (s, 3H), 3.26 (s, 3H), 1.81-1.85 (m, 1H), 1.63-1.67 (m, 1H), 0.95 (s, 9H).

Example 192: 2-amino-4-fluoro-4-methyl-N-(methylsulfonyl)pentanamide hydrochloride[I-192]

Procedures and Characterization:

Step 1: tert-butyl 4-fluoro-4-methyl-1-(methylsulfonamido)-1-oxopentan-2-ylcarbamate To a solution of tert-butyl 4-fluoro-4-methyl-1-(methylsulfonamido)-1-oxopentan-2-ylcarbamate (270 mg, 1.08 mmol) in DCM (50 mL) was added HATU (451 mg, 1.19 mmol) and stirred at rt for 2 h. Then Cs$_2$CO$_3$ (1.06 g, 3.24 mmol), methanesulfonamide (206 mg, 2.17 mmol) were added to the mixture and stirred for overnight at rt. The solution was diluted with water (200 mL) and extracted with DCM (100 mL). The organic phase was washed with water (100 mL×2), and brine (100 mL), dried (Na$_2$SO$_4$), filtered and concentrated in vacuum, the crude product was purified by chromatography (silica, ethyl acetate/petroleum ether=1/5) to afford (S)-tert-butyl 4,4-dimethyl-1-(N-methylmethylsulfonamido)-1-oxopentan-2-ylcarbamate (200 mg, 0.6 mmol, 55%) as a yellow oil. ESI-MS (EI+, m/z): 344.1 [M+NH4]$^+$.

Step 2: 2-amino-4-fluoro-4-methyl-N-(methylsulfonyl)pentanamide hydrochloride[I-192]

A solution of (S)-tert-butyl 4,4-dimethyl-1-(N-methylmethylsulfonamido)-1-oxopentan-2-ylcarbamate (200 mg, 0.6 mmol) in Et$_2$O (20 mL) was added 4 M HCl/dioxane (10 mL) was stirred for 17 h at rt. The solid was filtered to afford 2-amino-4-fluoro-4-methyl-N-(methylsulfonyl)pentanamide hydrochloride [I-192] as a white solid (89.8 mg, 0.34 mmol, 57%). ESI-MS (EI+, m/z): 227.1 [M+H]$^+$. 1H NMR (500 MHz, DMSO) δ 8.44 (s, 3H), 4.02 (s, 1H), 3.25 (s, 3H), 2.16-2.25 (m, 1H), 2.03-2.10 (m, 1H), 1.43 (s, 3H), 1.38 (s, 3H).

Example 190: (S)-methyl 2-((S)-2-amino-4,4-dimethylpentanamido)-4-methylpentanoate hydrochloride [I-190]

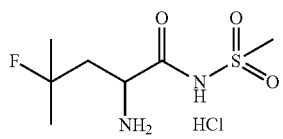

I-192

Synthetic Scheme:

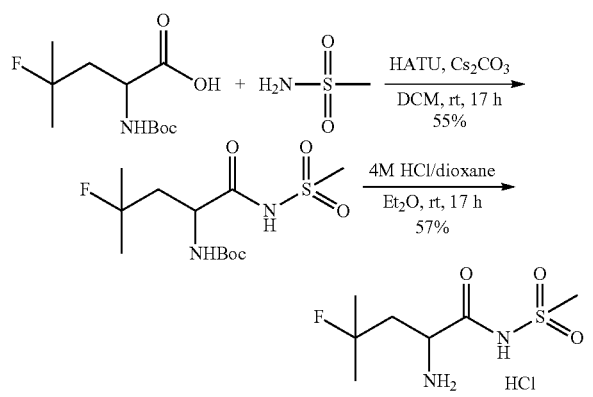

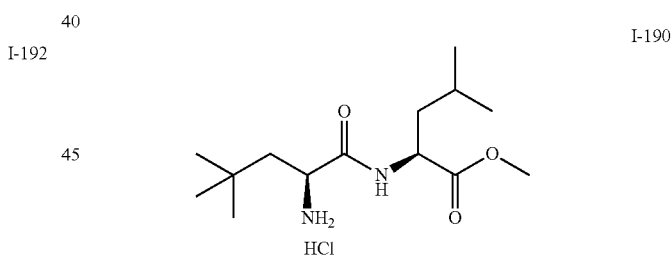

I-190

Synthetic Scheme:

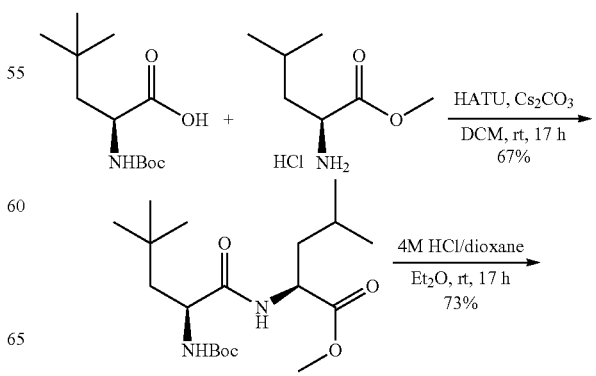

-continued

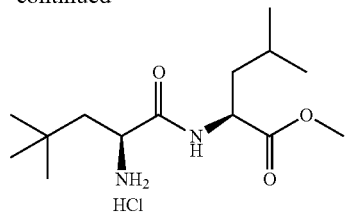

Procedures and Characterization:

Step 1: (S)-methyl 2-((S)-2-(tert-butoxycarbonylamino)-4,4-dimethylpentanamido)-4-methylpentanoate To a solution of (S)-2-(tert-butoxycarbonylamino)-4,4-dimethylpentanoic acid (500 mg, 2.0 mmol) in DCM (80 mL) was added HATU (900 mg, 2.3 mmol) and stirred at rt for 2 h. Then $Cs_2CO_3$ (1.95 g, 6.0 mmol), (S)-methyl 2-amino-4-methylpentanoate hydrochloride (555 mg, 3.0 mmol) were added to the mixture and stirred for overnight at rt. The solution was diluted with water (200 mL) and extracted with DCM (100 mL). The organic phase was washed with water (100 mL×2), and brine (100 mL), dried ($Na_2SO_4$), filtered and concentrated in vacuum, the crude product was purified by chromatography (silica, ethyl acetate/petroleum ether=1/5) to afford (S)-methyl 2-((S)-2-(tert-butoxycarbonylamino)-4,4-dimethylpentanamido)-4-methylpentanoate (500 mg, 1.34 mmol, 67%) as a white solid. ESI-MS (EI+, m/z): 317.2 [M−56]$^+$.

Step 2: (S)-methyl 2-((S)-2-amino-4,4-dimethylpentanamido)-4-methylpentanoate hydrochloride[I-190]

A solution of (S)-methyl 2-((S)-2-(tert-butoxycarbonylamino)-4,4-dimethylpentanamido)-4-methylpentanoate (500 mg, 1.34 mmol) in $Et_2O$ (20 mL) was added 4 M HCl/dioxane (10 mL) was stirred for 17 h at rt. The solid was filtered to afford (S)-methyl 2-(S)-2-amino-4,4-dimethylpentanamido)-4-methylpentanoate hydrochloride [I-190] as a white solid (300 mg, 0.97 mmol, 73%). ESI-MS (EI+, m/z): 273.2 [M+H]$^+$. 1H NMR (500 MHz, DMSO) δ 9.07-9.09 (d, J=7.5 Hz, 1H), 8.42 (s, 3H), 4.29-4.34 (m, 1H), 3.82 (m, 1H), 3.60 (s, 3H), 1.72-1.83 (m, 2H), 1.50-1.62 (m, 3H), 0.86-0.91 (m, 15H).

Example 122: (S)-methyl 2-amino-4,4-dimethylpentanoate hydrochloride[I-122]

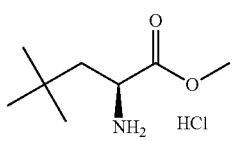

I-122

Synthetic Scheme:

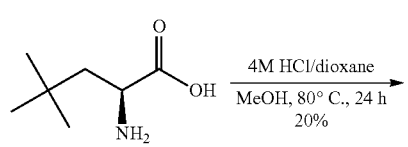

-continued

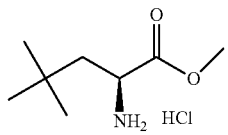

Procedures and Characterization:

Step 1: (S)-methyl 2-amino-4,4-dimethylpentanoate hydrochloride [I-122]

A solution of (S)-2-amino-4,4-dimethylpentanoic acid (100 mg, 0.69 mmol) in MeOH (10 mL) was added 4 M HCl/dioxane (10 mL) stirred at 80° C. for 24 h. The mixture was concentrated and the residue was beating with $Et_2O$ to afford (S)-methyl 2-amino-4,4-dimethylpentanoate hydrochloride [I-122] as a white solid (23.6 mg, 0.12 mmol, 20%). ESI-MS (EI+, m/z): 160.1 [M+H]+. 1H-NMR (500 MHz, CD30D): δ 4.02-4.04 (m, 1H), 3.86 (s, 3H), 1.97-2.02 (m, 1H), 1.64-1.68 (m, 1H), 1.03-1.05 (d, 9H), Example 123: (R)-methyl 2-amino-4,4-dimethylpentanoate hydrochloride [I-123]

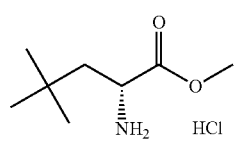

I-123

Synthetic Scheme:

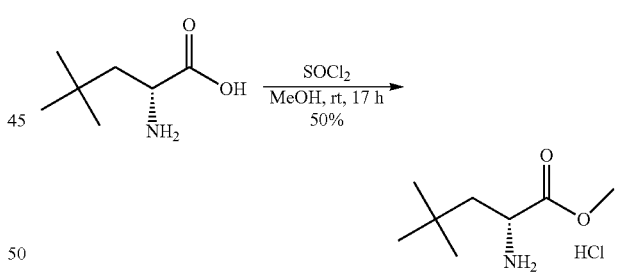

Procedures and Characterization:

Step 1: (R)-methyl 2-amino-4,4-dimethylpentanoate hydrochloride [I-123]

A mixture of (R)-2-amino-4,4-dimethylpentanoic acid (50 mg, 0.34 mmol) in dry MeOH (10 mL) was added $SOCl_2$ (0.5 mL) stirred at rt for 17 h. The mixture was concentrated and the residue was beating with $Et_2O$ to afford (R)-methyl 2-amino-4,4-dimethylpentanoate hydrochloride [I-123] as a white solid (34.2 mg, 0.17 mmol, 50%). ESI-MS (EI+, m/z): 160.1 [M+H]+. 1H-NMR (500 MHz, CD30D): δ 4.02-4.04 (m, 1H), 3.86 (s, 3H), 1.97-2.02 (m, 1H), 1.64-1.68 (m, 1H), 1.03 (s, 9H).

Example 205: 2-amino-N-cyano-5,5,5-trifluoro-4-methylpentanamide hydrochloride [I-205]

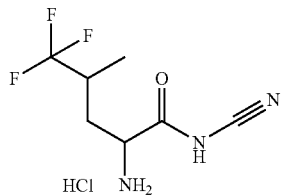

I-205

Synthetic Scheme:

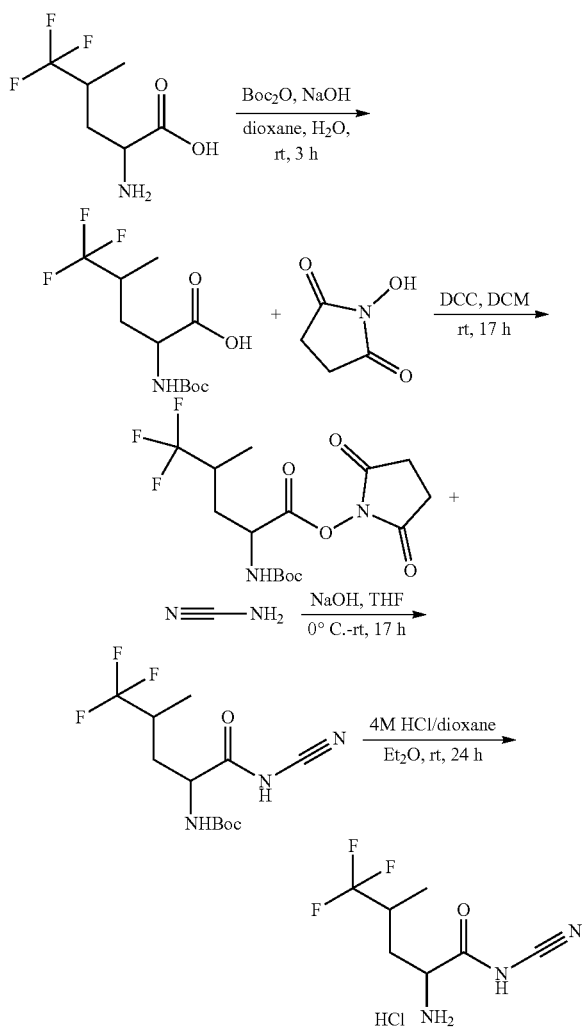

Procedures and Characterization:

Step 1: 2-(tert-butoxycarbonylamino)-5,5,5-trifluoro-4-methylpentanoic acid

A mixture of 2-amino-5,5,5-trifluoro-4-methylpentanoic acid (250 mg, 1.35 mmol), Boc$_2$O (353 mg, 1.62 mmol), NaOH (80 mg, 2.0 mmol) were dissolved in dioxane (10 mL) and H$_2$O (2 mL). The mixture was stirred at rt for 3 h. The solution was diluted with water (200 mL) and extracted with DCM (50 mL). The organic phase was washed with water (20 mL×2), and brine (10 mL), dried (Na$_2$SO$_4$), filtered and concentrated to afford crude 2-(tert-butoxycarbonylamino)-5,5,5-trifluoro-4-methylpentanoic acid (385 mg) as a colorless oil. ESI-MS (EI$^+$, m/z): 307.9 [M+Na]$^+$.

Step 2: 2,5-dioxopyrrolidin-1-yl 2-(tert-butoxycarbonylamino)-5,5,5-trifluoro-4-methylpentanoate A mixture of 2-(tert-butoxycarbonylamino)-5,5,5-trifluoro-4-methylpentanoic acid (385 mg, 1.35 mmol), 1-hydroxypyrrolidine-2,5-dione (197 mg, 1.71 mmol), DCC (353 mg, 1.71 mmol) were dissolved in DCM (15 mL). The mixture was stirred at rt for 17 h. Filtered and the filtrate was washed with brine (20 mL), dried (Na$_2$SO$_4$), filtered and concentrated to afford crude 2,5-dioxopyrrolidin-1-yl 2-(tert-butoxycarbonylamino)-5,5,5-trifluoro-4-methylpentanoate (400 mg) as a white solid. ESI-MS (EI$^+$, m/z): 282.9 [M−100]$^+$.

Step 3: tert-butyl 1-cyanamido-5,5,5-trifluoro-4-methyl-1-oxopentan-2-ylcarbamate A mixture of 2,5-dioxopyrrolidin-1-yl 2-(tert-butoxycarbonylamino)-5,5,5-trifluoro-4-methylpentanoate (300 mg, 0.78 mmol), cyanamide (66 mg, 1.57 mmol), NaOH (156 mg, 3.9 mmol) were dissolved in THF (16 mL). The mixture was stirred at 0° C. for 0.5 h and rt for 17 h. The solution was purified by prep-HPLC (Boston C18 21*250 mm 10 μm, Mobile phase: A: 0.1% trifluoroacetic acid; B: acetonitrile) to afford tert-butyl 1-cyanamido-5,5,5-trifluoro-4-methyl-1-oxopentan-2-ylcarbamate (45 mg, 0.14 mmol) as a white solid. MS (EI+, m/z): 310.3 [M+H]$^+$.

Step 4: 2-amino-N-cyano-5,5,5-trifluoro-4-methylpentanamide hydrochloride [I-205]

A solution of tert-butyl 1-cyanamido-5,5,5-trifluoro-4-methyl-1-oxopentan-2-ylcarbamate (45 mg, 0.14 mmol) in Et$_2$O (20 mL) was added 4 M HCl/dioxane (10 mL) was stirred for 24 h at rt. The solution was purified by prep-HPLC (Boston C18 21*250 mm 10 μm, Mobile phase: A: 0.1% trifluoroacetic acid; B: acetonitrile) to afford 2-amino-N-cyano-5,5,5-trifluoro-4-methylpentanamide hydrochloride [I-205] (12.3 mg, 0.05 mmol, 27%) as a white solid. MS (EI+, m/z): 210.1 [M+H]$^+$. 1H NMR (500 MHz, CD3OD) δ 4.06-4.09 (m, 1H), 2.43-2.65 (m, 1H), 1.67-1.85 (m, 2H), 1.18-1.22 (m, 3H).

Example 206: 2-amino-3-(1-methylcyclobutyl)propanoic acid [I-206]

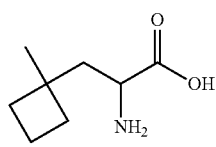

I-206

Synthetic Scheme:

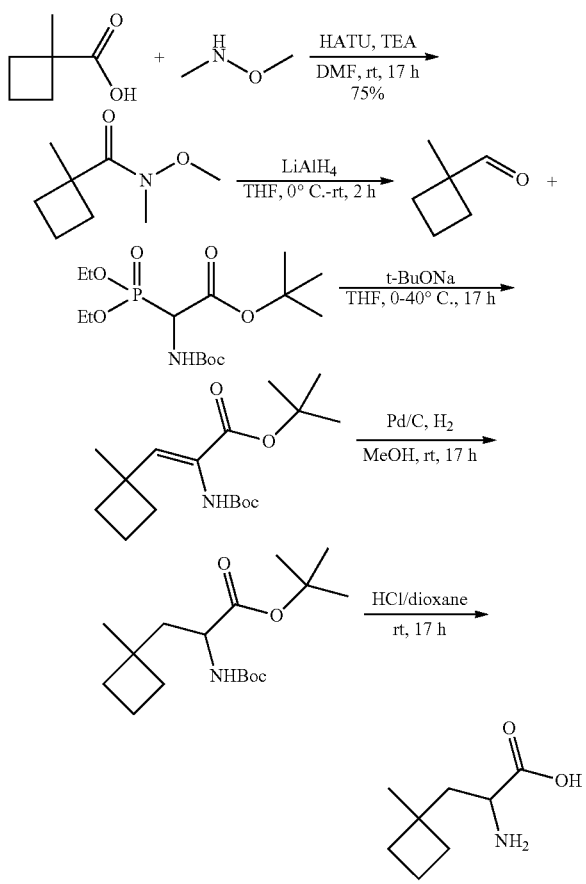

Procedures and Characterization:

Step 1:
N-Methoxy-N,1-dimethylcyclobutanecarboxamide

To a solution of 1-methylcyclobutanecarboxylic acid (11.6 g, 0.1 mol), N,O-dimethylhydroxylamine hydrochloride (19.5 g, 0.2 mol) and HATU (42 g, 0.11 mol) in DMF (300 mL) was added TEA (30.3 g, 0.3 mol) and the solution was stirred for 17 h at rt. The solution was diluted with water (600 mL) and extracted with EtOAc (400 mL×2). The organic phase was washed with 1 N HCl, sat. NaHCO$_3$ and brine (100 mL), dried (Na$_2$SO$_4$), filtered and concentrated in vacuum to afford N-methoxy-N,1-dimethylcyclobutanecarboxamide (12.2 g, 0.07 mol, 75%) as a colorless oil. ESI-MS (EI$^+$, m/z): 158.2 [M+H]$^+$.

Step 2: 1-Methylcyclobutanecarbaldehyde

To a solution of N-methoxy-N,1-dimethylcyclobutanecarboxamide (2.0 g, 12.7 mmol) in dry THF (20 mL) was added 1 M LiAlH$_4$ (19 mL, 19 mmol) dropwise at 0° C. under N$_2$. The mixture was warmed to room temperature and stirred 2 hrs. The solution was quenched with sat. seignette salt slowly and extracted with Et$_2$O (100 mL), the organic phase was washed with water (100 mL×2), and brine (100 mL), dried (Na$_2$SO$_4$), filtered and used for the next step.

Step 3: (Z)-tert-butyl 2-(tert-butoxycarbonylamino)-3-(1-methylcyclobutyl)acrylate To a solution of witting reagent (2.15 g, 5.86 mmol) in dry THF (80 mL) was added t-BuONa (844 mg, 8.79 mmol) at 0° C. and stirred for 1 h. Then the solution of 1-methylcyclobutanecarbaldehyde was added and stirred at rt for 17 hrs. The solution was extracted with EtOAc (100 mL×2). The organic phase was washed with brine (100 mL), dried (Na$_2$SO$_4$), filtered and concentrated in vacuum. The crude product was purified by chromatography (silica, ethyl acetate/petroleum ether=1/30) to afford (Z)-tert-butyl 2-(tert-butoxycarbonylamino)-3-(1-methylcyclobutyl)acrylate (700 mg, 2.2 mmol) as a colorless oil. ESI-MS (EI$^+$, m/z): 200.2 [M−56*2]$^+$.

Step 4: tert-Butyl 2-(tert-butoxycarbonylamino)-3-(1-methylcyclobutyl)propanoate A mixture of (Z)-tert-butyl 2-(tert-butoxycarbonylamino)-3-(1-methylcyclobutyl)acrylate (700 mg, 2.2 mmol) and Pd/C (10%, 100 mg) in MeOH (100 mL) was stirred at 30° C. for 17 hrs. The mixture was filtered, and the filtrate was concentrated to dryness to afford tert-butyl 2-(tert-butoxycarbonylamino)-3-(1-methylcyclobutyl)propanoate (600 mg, crude) as a colorless oil. ESI-MS (EI$^+$, m/z): 158.2 [M−156]$^+$.

Step 5: 2-Amino-3-(1-methylcyclobutyl)propanoic acid [I-206]

A solution of tert-butyl 2-(tert-butoxycarbonylamino)-3-(1-methylcyclobutyl)propanoate (600 mg, crude) in Et$_2$O (20 mL) was added 4 M HCl/dioxane (10 mL) was stirred for 17 h at rt. The solution was concentrated to afford 2-amino-3-(1-methylcyclobutyl)propanoic acid. MS (EI$^+$, m/z): 158.0 [M+H]$^+$.

$^1$H NMR (500 MHz, D$_2$O) δ 3.91 (t, J=7.5 Hz, 1H), 2.06-2.02 (m, 1H), 1.88-1.64 (m, 7H), 1.15 (s, 3H).

Examples 93:
S-2-amino-3-(1-methylcyclobutyl)propanoic acid [I-93]

I-93

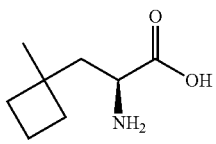

Synthetic Scheme:

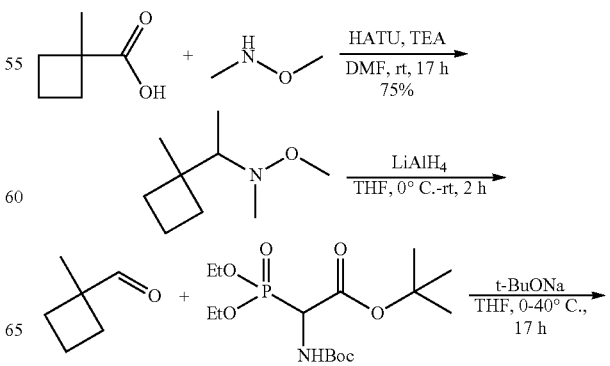

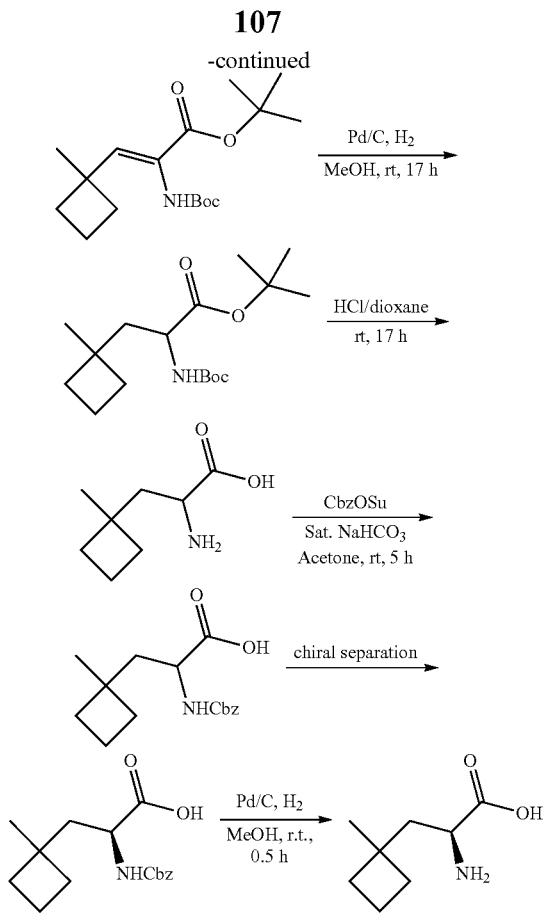

Procedures and Characterization:

The procedure for 2-amino-3-(1-methylcyclobutyl)propanoic acid was same as example 8

Step 6: 2-(benzyloxycarbonylamino)-3-(1-methylcyclobutyl)propanoic acid

A mixture of 2-amino-3-(1-methylcyclobutyl)propanoic acid (300 mg, crude), CbzOSu (714 mg, 2.8 mmol) in Acetone (10 mL) and sat. NaHCO₃ (3 mL) was stirred at rt for 5 h. The solution was purified by prep-HPLC (Boston C18 21*250 mm 10 μm, Mobile phase: A: 0.1% trifluoroacetic acid; B: acetonitrile) to afford 2-(benzyloxycarbonylamino)-3-(1-methylcyclobutyl)propanoic acid (160 mg, 0.54 mmol) as a white solid. MS (EI+, m/z): 292.0[M+H]⁺.

Step 7: (S)-2-(benzyloxycarbonylamino)-3-(1-methylcyclobutyl)propanoic acid 2-(benzyloxycarbonylamino)-3-(1-methylcyclobutyl)propanoic acid (160 mg, 0.54 mmol) was purified by chiral-HPLC to afford (S)-2-(benzyloxycarbonylamino)-3-(1-methylcyclobutyl)propanoic acid (50 mg, 0.17 mmol) as a white solid. MS (EI+, m/z): 292.0[M+H]⁺.

Step 8: (S)-2-amino-3-(1-methylcyclobutyl)propanoic acid [I-93]

A mixture of (S)-2-(benzyloxycarbonylamino)-3-(1-methylcyclobutyl)propanoic acid (50 mg, 0.17 mmol) and Pd/C (10%, 10 mg) in MeOH (10 mL) was stirred at rt for 1 h. The solution was purified by prep-HPLC (Boston C18 21*250 mm 10 μm, Mobile phase: A: 0.1% trifluoroacetic acid; B: acetonitrile) to afford (S)-2-amino-3-(1-methylcyclobutyl)propanoic acid [I-93] (2 mg, 0.01 mmol) as a white solid. MS (EI+, m/z): 292.0[M+H]⁺. 1H NMR (500 MHz, D₂O) δ 3.76-3.79 (t, 1H), 1.96-2.00 (m, 1H), 1.61-1.86 (m, 7H), 1.11 (s, 3H).

Example 204: 2-amino-3-(trimethylsilyl)propanoic acid hydrochloride [I-204]

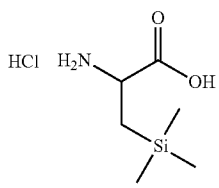

I-204

Synthetic Scheme:

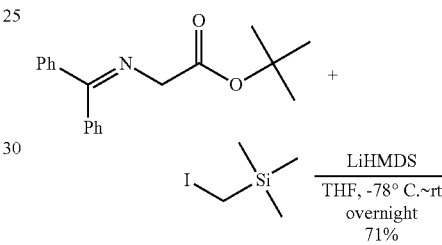

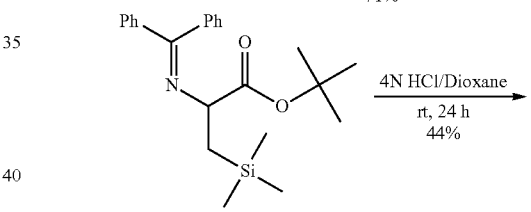

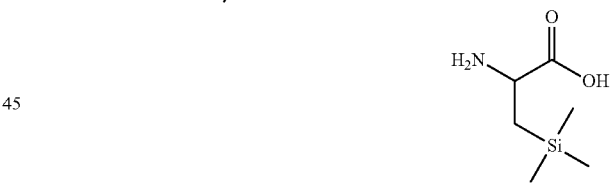

Procedures and Characterization:

Step 1: tert-butyl 2-(diphenylmethyleneamino)-3-(trimethylsilyl)propanoate

A solution of tert-butyl 2-(diphenylmethyleneamino)acetate (2.5 g, 8.47 mmol) in THF (20 mL) was cooled to −78° C., then, LiHMDS (8.47 mL, 8.47 mmol) was added dropwise under N₂. The solution was stirred at −78° C. for 1 h. (iodomethyl)trimethylsilane(1.8 g, 8.47 mmol) was added dropwise. The solution was stirred at −78° C. ~rt overnight. The solution was washed by brine (25 mL*2), dried (Na₂SO₄), concentrated and purified by chromatography (silica, ethyl acetate/petroleum ether=1/30) to afford tert-butyl 2-(diphenylmethyleneamino)-3-(trimethylsilyl)propanoate (2.3 g, 6.04 mmol, 71%) as a yellow solid. ESI-MS (EI+, m/z): 382.3 [M+H]⁺.

Step 2: 2-amino-3-(trimethylsilyl)propanoic acid hydrochloride [I-204]

A solution of tert-butyl 2-(diphenylmethyleneamino)-3-(trimethylsilyl)propanoate (500 mg, 1.31 mmol) in 4 M HCl/dioxane (6 mL) was stirred for 17 h at rt. DCM (80 mL) was added. The solid was filtered to afford 2-amino-3-(trimethylsilyl)propanoic acid hydrochloride [I-204] as a white solid (113 mg, 0.57 mmol, 44%). ESI-MS (EI+, m/z): 162.2 [M+H]$^+$. 1H NMR (500 MHz, CD30D) δ 13.78 (br, 1H), 8.33 (br, 1H), 3.75 (m, 1H), 1.00-1.14 (m, 2H), 0.06 (s, 9H).

Example 201: (S)-2-amino-3-(trimethylsilyl)propanoic acid hydrochloride [I-201]

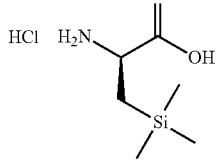

I-201

Synthetic Scheme:

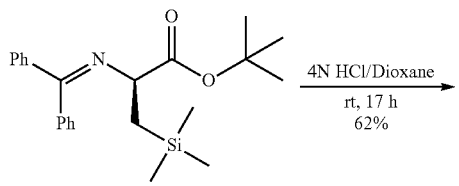

Procedures and Characterization:

Step 1: (S)-2-amino-3-(trimethylsilyl)propanoic acid hydrochloride [I-201]

A solution of (S)-tert-butyl 2-(diphenylmethyleneamino)-3-(trimethylsilyl)propanoate (300 mg, 0.79 mmol) in 4 M HCl/dioxane (3 mL) was stirred for 17 h at rt. DCM (40 mL) was added. The solid was filtered to afford (S)-2-amino-3-(trimethylsilyl)propanoic acid hydrochloride [I-201] as a white solid (92 mg, 0.47 mmol, 62%). ESI-MS (EI$^+$, m/z): 162.2 [M+H]$^+$. 1H NMR (500 MHz, CD30D) δ 13.76 (br, 1H), 8.38 (br, 1H), 3.76 (m, 1H), 1.02-1.16 (m, 2H), 0.06 (s, 9H).

Example 200: (R)-2-amino-3-(trimethylsilyl)propanoic acid hydrochloride [I-200]

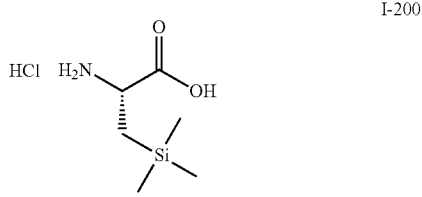

I-200

Synthetic Scheme:

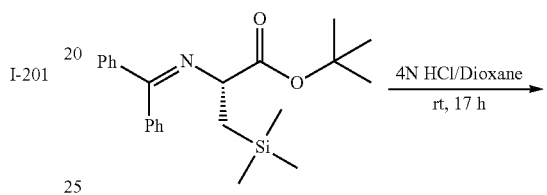

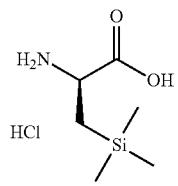

Procedures and Characterization:

Step 1: (R)-2-amino-3-(trimethylsilyl)propanoic acid hydrochloride [I-200]

A solution of (R)-tert-butyl 2-(diphenylmethyleneamino)-3-(trimethylsilyl)propanoate (300 mg, 0.79 mmol) in 4 M HCl/dioxane (3 mL) was stirred for 17 h at rt. DCM (40 mL) was added. The solid was filtered to afford (R)-2-amino-3-(trimethylsilyl)propanoic acid hydrochloride [I-200] as a white solid (80 mg, 0.41 mmol, 52%). ESI-MS (EI+, m/z): 162.2 [M+H]$^+$. 1H NMR (500 MHz, CD30D) δ 13.77 (br, 1H), 8.33 (br, 1H), 3.76 (m, 1H), 1.02-1.14 (m, 2H), 0.06 (s, 9H).

Example 194: (S)-2-amino-4-fluoro-4-methylpentanoic acid [I-194]

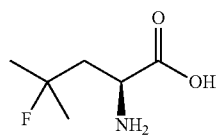

I-194

Synthetic Scheme:

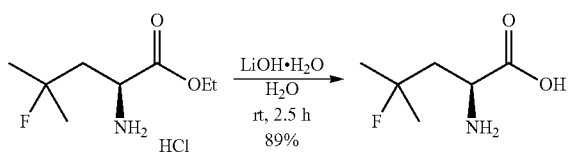

Procedures and Characterization:

Step 1: (S)-2-amino-4-fluoro-4-methylpentanoic acid [I-194]

A mixture of (S)-ethyl 2-amino-4-fluoro-4-methylpentanoate hydrochloride (65 mg, 0.31 mmol), LiOH·H$_2$O (29 mg, 0.69 mmol) in H$_2$O (2 mL) was stirred at rt for 2.5 h. Then, 1N HCl was added to adjust pH=3. The mixture was purified directly by reverse-HPLC (Boston C18 21*250 mm 10 μm, Mobile phase: A: 0.1% trifluoroacetic acid; B: acetonitrile) to afford (S)-2-amino-4-fluoro-4-methylpentanoic acid [I-194] (40 mg, 0.27 mmol, 87%) as a white solid. MS (EI+, m/z): 150.3 [M+H]$^+$. 1H NMR (500 MHz, CD30D) δ 8.10 (br, 2H), 3.79 (m, 1H), 2.19-2.26 (m, 1H), 1.97-2.05 (m, 1H), 1.42 (d, Jz=3.5 Hz, 3H), 1.37 (d, Jz=4.0 Hz, 3H).

Example 94: (S)-3,3-dimethyl-1-(2H-tetrazol-5-yl)butan-1-amine [I-94]

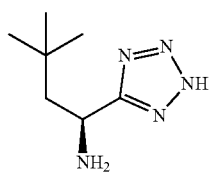

I-94

Synthetic Scheme:

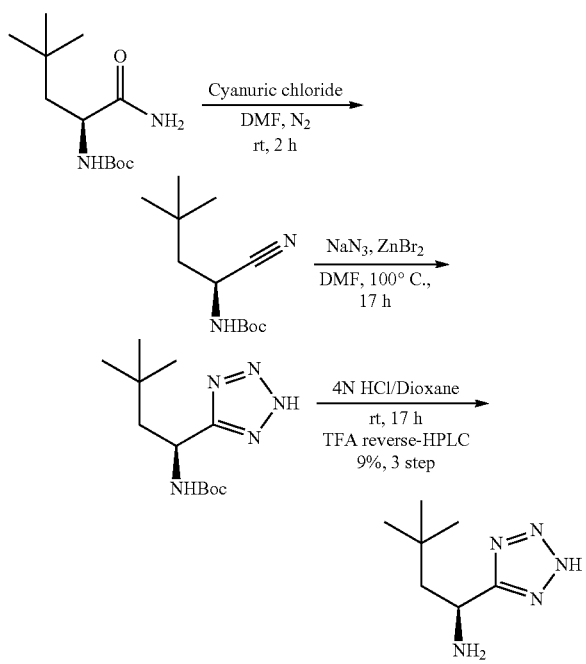

Procedures and Characterization:

Step 1: (S)-tert-butyl 1-cyano-3,3-dimethylbutylcarbamate

To a solution of (S)-tert-butyl 1-amino-4,4-dimethyl-1-oxopentan-2-ylcarbamate (500 mg, 2.1 mmol) in DMF (10 mL) was added Cyanuric chloride (450 mg, 2.5 mmol) and stirred at rt for 2 h. Then, the mixture was diluted by Brine (100 mL), extracted with ethyl acetate (50 mL), dried (Na$_2$SO$_4$) and concentrated to give crude (S)-tert-butyl 1-cyano-3,3-dimethylbutylcarbamate (500 mg) as a yellow dope. ESI-MS (EI+, m/z): 249.2 [M+Na]$^+$.

Step 2: (S)-tert-butyl 3,3-dimethyl-1-(2H-tetrazol-5-yl)butylcarbamate

A mixture of (S)-tert-butyl 1-cyano-3,3-dimethylbutylcarbamate (crude 500 mg), ZnBr$_2$ (900 mg, 4.0 mmol), NaN$_3$ (260 mg, 4.0 mmol) in DMF (20 mL) was stirred for 17 h at 100° C. The mixture was then diluted with Brine (200 mL), extracted with ethyl acetate (60 mL), dried (Na$_2$SO$_4$) and concentrated to give crude (S)-tert-butyl 3,3-dimethyl-1-(2H-tetrazol-5-yl)butylcarbamate (400 mg) as a yellow dope. ESI-MS (EI+, m/z): 214.3 [M+H-56]$^+$.

Step 3: ((S)-3,3-dimethyl-1-(2H-tetrazol-5-yl)butan-1-amine [I-94]

A solution of (S)-tert-butyl 3,3-dimethyl-1-(2H-tetrazol-5-yl)butylcarbamate (crude 300 mg) in 4 M HCl/dioxane (3.5 mL) was stirred for 17 h at rt. Then, the solution was concentrated and purified directly by reverse phase-HPLC (Boston C18 21*250 mm 10 μm, Mobile phase: A: 0.1% trifluoroacetic acid; B: acetonitrile) to afford (S)-3,3-dimethyl-1-(2H-tetrazol-5-yl)butan-1-amine 2,2,2-trifluoroacetic acid salt [I-94] (30 mg, 0.11 mmol, 9% for 3 step) as a white solid. MS (EI+, m/z): 170.2 [M+H]$^+$. 1H NMR (500 MHz, CD30D) δ 8.18 (br, 3H), 4.48 (m, 1H), 2.14 (m, 1H), 1.73 (dd, Jz=3.5, 16.5 Hz 1H), 0.72 (s, 9H).

Example 175: Synthesis of 2-amino-5,5,5-trifluoro-4-methoxypentanoic acid [I-175]

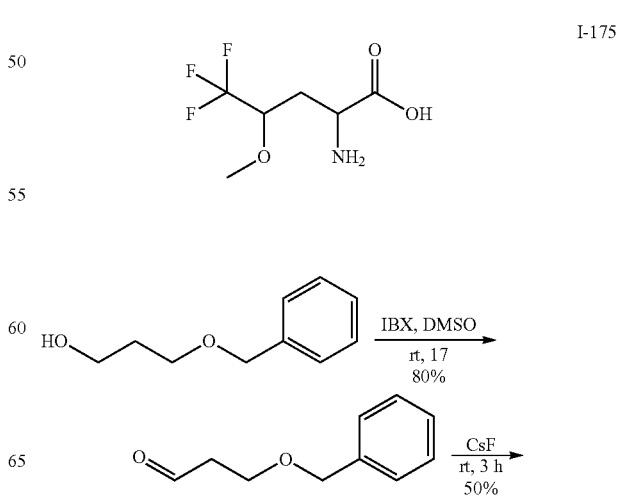

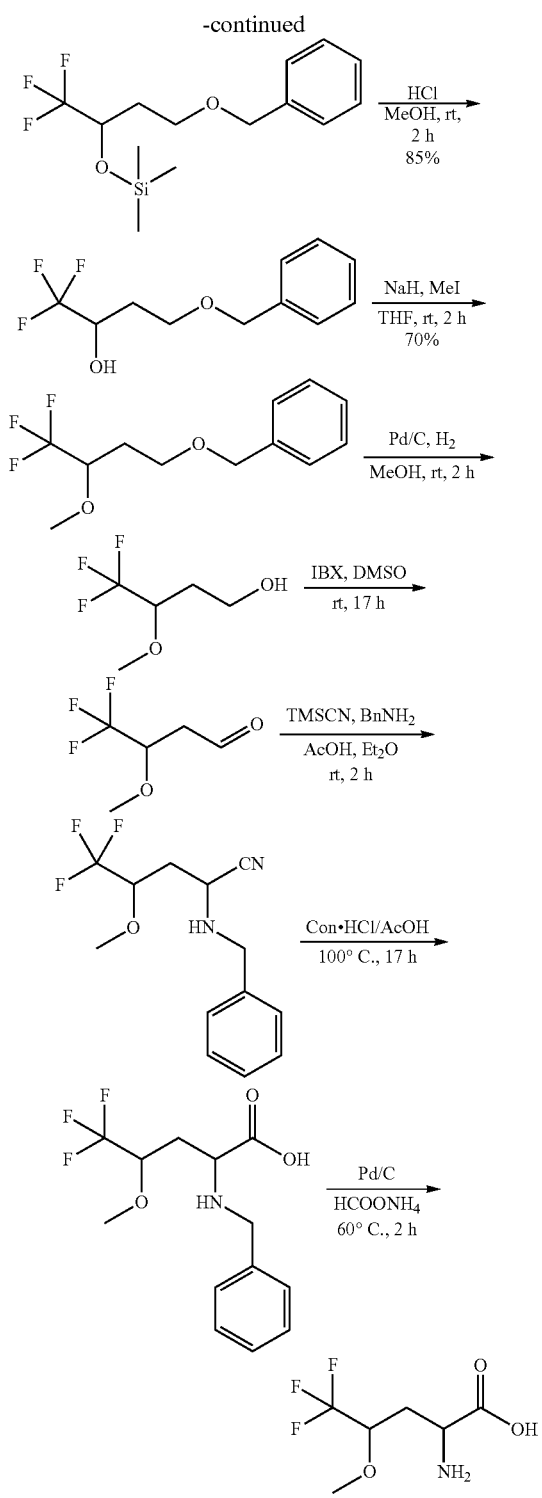

Procedures and Characterization:

Step 1: (S)-Benzyl 4-methyl-2-(phenylmethylsulfonamido)pentanoate

To a solution of 3-(benzyloxy) propan-1-ol (10.0 g, 60.24 mmol) in DMSO (100 mL) was added IBX (20.2 g, 72.29 mmol) under ice-bath. The mixture was warmed to room temperature and stirred at this temperature for 17 hrs. The reaction mixture was poured into water (300 mL) and extracted with EA (200 mL×2), the organic phase was washed with water (200 mL×3), and brine (100 mL), dried (Na$_2$SO$_4$), and the solution was concentrated and the crude was purified by SGC to obtain a light yellow liquid. (8.0 g, 81%). 1H NMR (500 MHz, CDCl3) δ 9.77 (s, 1H), 7.36-7.26 (m, 5H), 4.53 (s, 2H), 3.8-3.83 (m, 2H), 2.71-2.68 (m, 2H).

Step 2: (4-(benzyloxy)-1, 1, 1-trifluorobutan-2-yloxy)trimethylsilane

To a solution of 3-(benzyloxy)propanal (4.0 g, 24.4 mmol) in THF (50 mL) was added trimethyl(trifluoromethyl)silane (10.4 g, 73.2 mmol) at rt, followed by the addition of CsF (0.37 g, 2.44 mmol). The resultant solution was stirred at rt for 2 hrs. Then quenched by water (100 ml) and extracted with EA (100 ml×2), the organic phase was washed with water (100 mL×2), and brine (100 mL), dried (Na$_2$SO$_4$), filtered and concentrated. The crude was purified by ISCO biotage to obtain (4-(benzyloxy)-1, 1, 1-trifluorobutan-2-yloxy)trimethylsilane as a colorless liquid. (4.5 g, 60%)

1H NMR (500 MHz, CDCl$_3$) δ 7.38-7.29 (m, 5H), 4.51 (t, J=12 Hz, 2H), 4.23-4.19 (m, 1H), 3.59-3.57 (m, 2H), 2.04-2.01 (m, 1H), 1.78-1.73 (m, 1H), 0.13 (s, 9H).

Step 3: 4-(benzyloxy)-1, 1, 1-trifluorobutan-2-ol

A solution of 4-(benzyloxy)-1,1,1-trifluorobutan-2-ol (4.5 g, 14.7 mmol) in HCl solution (3 M in MeOH, 50 ml) was stirred at rt for 2 hrs. Then concentrated and purified by ISCO biotage to obtain 4-(benzyloxy)-1, 1, 1-trifluorobutan-2-ol (2.75 g, 80%) as a colorless liquid.

Step 4: ((4, 4, 4-trifluoro-3-methoxybutoxy)methyl)benzene

To a solution of 4-(benzyloxy)-1,1,1-trifluorobutan-2-ol (2.75 g, 11.75 mmol) in THF (100 ml) was added t-BuOK (1.58 g, 14.1 mmol) at 0° C. and stirred at this temperature for 30 min. Then MeI (2.17 g, 15.28 mmol) was added and stirred at rt for another 1 hour. The reaction was quenched by water (100 ml) and extracted with EA (100 ml×2), the organic phase was washed with water (100 mL×2), and brine (100 mL), dried (Na$_2$SO$_4$), filtered and concentrated. The crude was purified by ISCO biotage to obtain ((4, 4, 4-trifluoro-3-methoxybutoxy) methyl) benzene (2.04 g, 70%) as a colorless liquid.

1H NMR (500 MHz, CDCl$_3$) δ 7.38-7.29 (m, 5H), 4.53 (t, J=12 Hz, 2H), 3.78-3.74 (m, 1H), 3.66-3.57 (m, 2H), 3.5 (s, 3H), 2.03-1.96 (m, 1H), 1.78-1.57 (m, 1H).

Step 5: 4, 4, 4-trifluoro-3-methoxybutan-1-ol

The solution of ((4,4,4-trifluoro-3-methoxybutoxy) methyl)benzene (2.04 g, 8.23 mmol) and Pd/C (0.5 g) in MeOH (30 mL) was stirred at rt for 2 hrs, then filtered and concentrated to obtain 4,4,4-trifluoro-3-methoxybutan-1-ol as a colorless liquid. This crude was to next step directly.

Step 6: 4, 4, 4-trifluoro-3-methoxybutanal

To a solution of 4, 4, 4-trifluoro-3-methoxybutan-1-ol (1.3 g crude from last step) in DMSO (20 mL) was added IBX (2.76 g, 9.88 mmol) under ice-bath. The mixture was warmed to room temperature and stirred at this temperature for 17 hrs. The reaction mixture was poured into water (80 mL) and extracted with Et₂O (80 mL×2), the organic phase was washed with water (80 mL×3), and brine (80 mL), and the solution was to next step directly.

Step 7: 2-(benzylamino)-5, 5, 5-trifluoro-4-methoxypentanenitrile

To a solution of above 4, 4, 4-trifluoro-3-methoxybutanal in Et₂O (160 mL) was added benzylamine (2 mL), AcOH (2.0 mL) and then TMSCN (3 mL) with ice-bath. The mixture was warmed to room temperature and stirred at this temperature for 17 hrs. The solution was diluted with water (200 mL) and extracted with EA (100 mL), the organic phase was washed with water (100 mL×2), and brine (100 mL), dried (Na₂SO₄), filtered and concentrated in vacuum to afford 2-(benzylamino)-5,5,5-trifluoro-4-methoxypentanenitrile (2.0 g, crude) as a brown thick oil which was used for the next step. ESI-MS (EI⁺, m/z):

Step 8: 2-(benzylamino)-5, 5, 5-trifluoro-4-methoxypentanoic acid

A solution of 2-(benzylamino)-5, 5, 5-trifluoro-4-methoxypentanenitrile (2.0 g, crude) in conc. HCl (30 mL) and AcOH (10 mL) was heated to 100° C. for 17 hrs. The solution was concentrated to dryness, diluted with H₂O (100 mL) and ACN (50 mL), adjusted pH to 3-4 with sat. NaHCO₃ solution, the mixture was filtered and dried to afford 2-(benzylamino)-5, 5, 5-trifluoro-4-methoxypentanoic acid (0.8 g, 35% for 4 steps) as a brown solid. ESI-MS (EI⁺, m/z): [M+H]⁺.

Step 9: 2-amino-5, 5, 5-trifluoro-4-methoxypentanoic acid [I-175]

A solution of 2-(benzylamino)-5, 5, 5-trifluoro-4-methoxypentanoic acid (300 mg, 1.03 mmol) and HCOONH₄ (650 mg, 10.3 mmol) in MeOH (10 ml) was stirred at 60° C. for 2 hrs, then filtered and concentrated. The crude was purified by reverse-phase biotage to obtain 2-amino-5, 5, 5-trifluoro-4-methoxypentanoic acid [I-175] as a white solid. 1H NMR (500 MHz, methanol-d4) δ 4.23-4.19 (m, 1H), 3.96-3.88 (m, 1H), 3.64-3.6 (m, 3H), 2.29-2.22 (m, 1H), 2.04-1.97 (m, 1H).

Example 176: 2-amino-4,4,5-trimethylhexanoic acid [I-176]

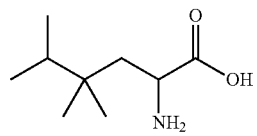
I-176

Synthetic Scheme:

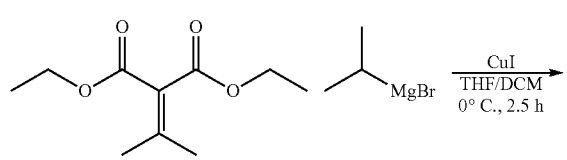

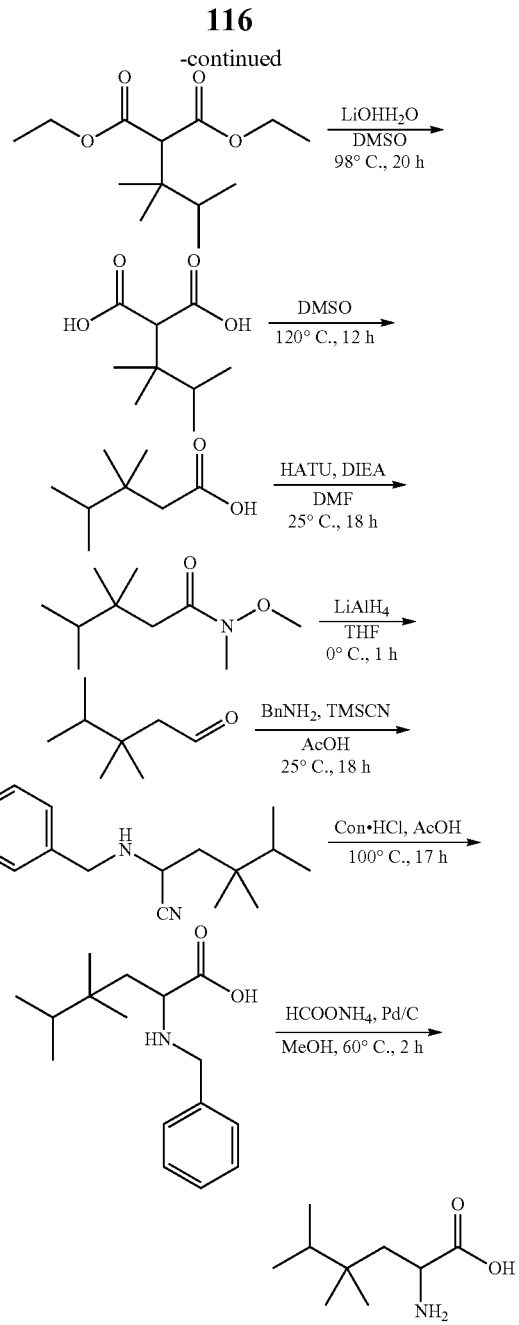

Procedures and Characterization:

Step 1: diethyl 2-(2, 3-dimethylbutan-2-yl)malonate

A solution of diethyl 2-(propan-2-ylidene)malonate (2 g, 10.0 mmol) in THF (60 mL) was cooled to 0° C., followed by copper(I) iodide (2.9 g, 15.0 mmol). The mixture was stirred at 0° C. for 0.5 h. Then isopropylmagnesium bromide (1 mol/L, 30.0 mL, 30.0 mmol) was added dropwise into the above mixture at 0° C. The mixture was stirred at 0° C. for 2 h. The mixture was quenched with HCl (1 mol/L), extracted with EtOAc (60 mL*2). The organic phase was separated, washed with water (100 mL×2), and brine (130 mL), dried (Na₂SO₄), filtered and concentrated in vacuum to afford diethyl 2-(2,3-dimethylbutan-2-yl)malonate (2.4 g, 10.0 mmol, 98%) as a yellow solid. ESI-MS (EI⁺, m/z): 245.3 [M+H]⁺.

Step 2: 2-(2, 3-dimethylbutan-2-yl)malonic acid

A mixture of diethyl 2-(2, 3-dimethylbutan-2-yl)malonate acetamide (2.4 g, 10.0 mmol) and lithium hydroxide hydrate (2.1 g, 50.0 mmol) in DMSO (50 mL) and water (10 mL) was heated to 98° C. and held for 20 h. The mixture was cooled, acidified by HCl (1 mol/L), and partitioned between EtOAc (30 mL) and water (30 mL). The organic phase was separated, washed with water (50 mL×2), and brine (50 mL), dried ($Na_2SO_4$), filtered and concentrated in vacuum to afford 2-(2,3-dimethylbutan-2-yl)malonic acid (1.8 g, 10.0 mmol, 95%) as a yellow oil. ESI-MS (EI$^+$, m/z): 212.2 [M+H]$^+$.

Step 3: 3, 3, 4-trimethylpentanoic acid

A solution of 2-(2, 3-dimethylbutan-2-yl)malonic acid (1.8 g, 10.0 mmol) in DMSO (30 mL) was heated to 120° C. and held for 12 hrs. The mixture was cooled, and partitioned between EtOAc (50 mL) and water (60 mL). The organic phase was separated, washed with water (60 mL×2), and brine (60 mL), dried ($Na_2SO_4$), filtered and concentrated in vacuum to afford 3,3,4-trimethylpentanoic acid (1.4 g, 10.0 mmol, 95%) as a yellow oil. ESI-MS (EI–, m/z): 143.2 [M–H]$^+$.

Step 4: N-methoxy-N,3, 3, 4-tetramethylpentanamide

To a solution 3,3,4-trimethylpentanoic acid (1.4 g, 10.0 mmol) in 30 mL of DMF was added N,O-dimethylhydroxylamine hydrochloride (1.2 g, 12.0 mmol) at 20° C., followed by DIEA (3.8 g, 30.0 mmol). Then HATU (5.8 g, 15.0 mmol) was added. The mixture was heated to 25° C. with stirring and held for 18 h. The reaction mixture was quenched with water, followed by methyl tert-butyl ether (50 mL*2). Phase separation, the organic layer was washed with brine (80 mL*3), dried over $Na_2SO_4$, filtered and concentrated in vacuum to afford N-methoxy-N,3,3,4-tetramethylpentanamide (1.5 g, 90%) as a brown oil. ESI-MS (EI$^+$, m/z): 188.2 [M+H]$^+$.

Step 4: 3, 3, 4-trimethylpentanal

To a solution N-methoxy-N,3, 3, 4-tetramethylpentanamide (1.9 g, 0.01 mol) in 30 mL of THF was added LiAlH4 (1 g, 0.03 mol) at 0° C. The mixture was stirred at 0° C. for 1 h. The reaction mixture was quenched with water, followed by methyl tert-butyl ether (50 mL*2). Phase separation, the organic layer was washed with brine (80 mL*3), dried over $Na_2SO_4$ and filtered. The filtrate was contained 3, 3, 4-trimethylpentanal (1.3 g, 95%) as a colorless solution, which was used into next step directly.

Step 5: 2-(benzylamino)-4, 4, 5-trimethylhexanenitrile

To a solution of above 3, 3, 4-trimethylpentanal in methyl tert-butyl ether (120 mL) was added benzylamine (1.6 mL), AcOH (1.0 mL) and then TMSCN (1.8 mL) with ice-bath. The mixture was warmed 25° C. and stirred overnight. The solution was diluted with water (60 mL) and extracted with EtOAc (30 mL), the organic phase was washed with water (50 mL×2), and brine (50 mL), dried ($Na_2SO_4$), filtered and concentrated in vacuum to afford 2-(benzylamino)-4, 4, 5-trimethylhexanenitrile (2 g, crude) as a brown oil which was used for the next step. ESI-MS (EI+, m/z): 245.4 [M+H]$^+$.

Step 6: 2-(benzylamino)-4, 4, 5-trimethylhexanoic acid

A solution of 2-(benzylamino)-4, 4, 5-trimethylhexanenitrile (2 g, crude) in conc. HCl (60 mL) and AcOH (10 mL) was heated to 95° C. for 18 hrs. The solution was cooled to 15° C., the pH was adjusted to 3-4 with sat. $NaHCO_3$ solution, the mixture was filtered and dried to afford 2-(benzylamino)-4, 4, 5-trimethylhexanoic acid (0.6 g, 2.3 mmol, 30% for 3 steps) as a white solid. ESI-MS (EI$^+$, m/z): 264.4 [M+H]$^+$.

2-amino-4,4,5-trimethylhexanoic acid [I-176]

To a solution of 2-(benzylamino)-4, 4, 5-trimethylhexanoic acid (78 mg, 0.3 mmol) in 8 mL of MeOH was added HCOONH4 (0.13 g, 2.0 mmol) and Pd/C (30 mg) at rt. The mixture was stirred at 60° C. for 2 h. The reaction mixture was filtered and concentrated to give a crude product which was purified by reverse-phase silica-gel chromatography to give 2-amino-6,6,6-trifluoro-4-methylhexanoic acid [I-176] (40 mg, 90%) as a white solid; ESI-MS (EI$^+$, m/z): 174.3 [M+H]$^+$; 1H NMR (500 MHz, MeOD) δ 3.56 (dd, J=7.2, 4.9 Hz, 1H), 2.12 (dd, J=14.7, 4.9 Hz, 1H), 1.66-1.51 (m, 2H), 0.97 (d, J=14.9 Hz, 6H), 0.92 (dd, J=6.8, 3.6 Hz, 6H).

Example 178: 2-amino-4,4-dimethylheptanoic acid [I-178]

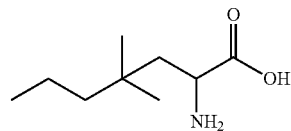

Synthetic Scheme:

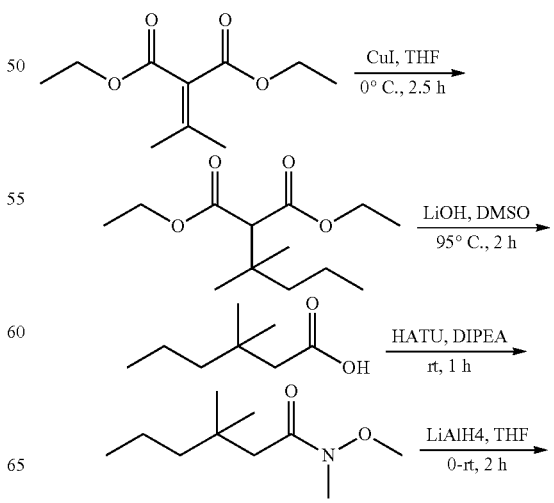

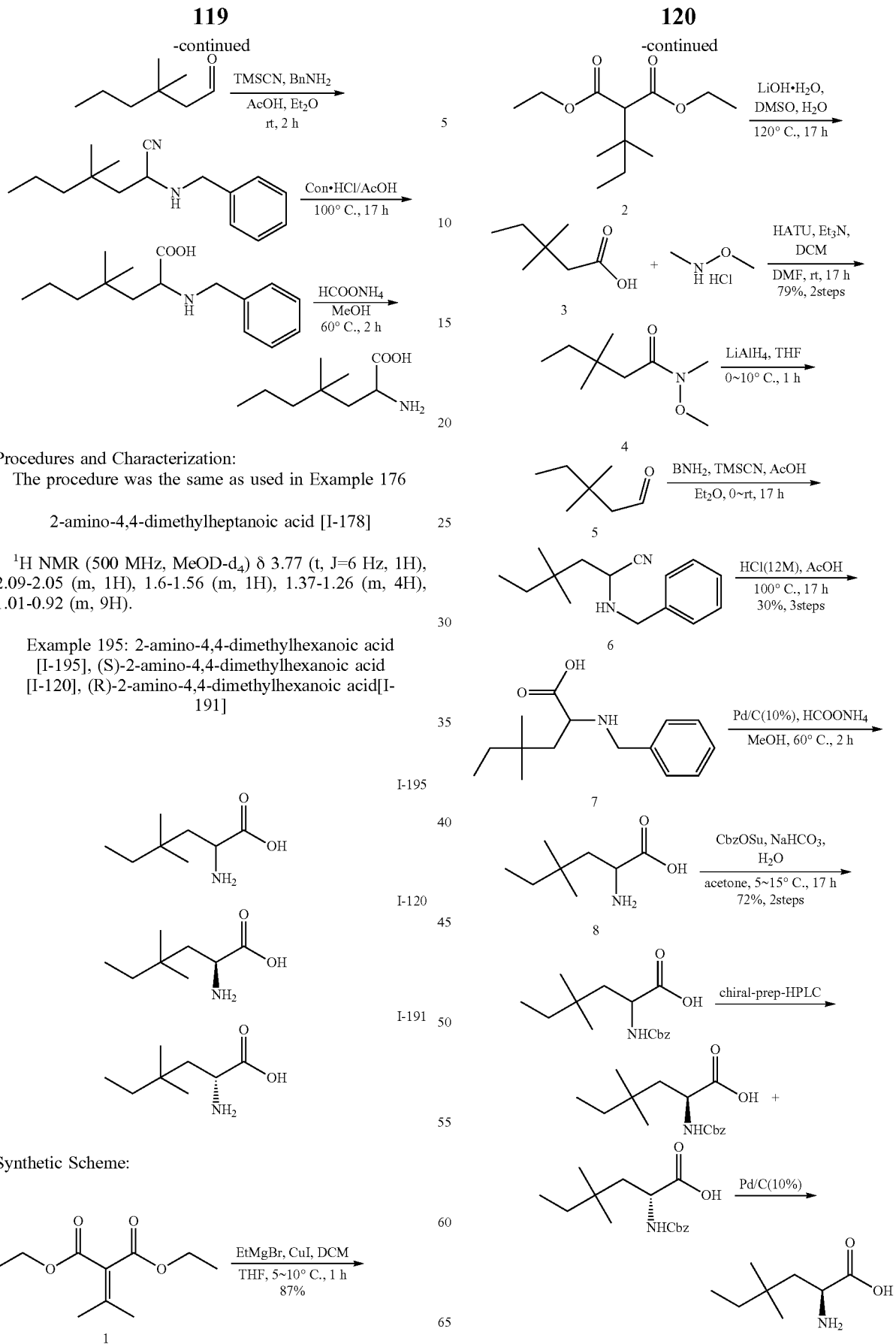
Procedures and Characterization:
The procedure was the same as used in Example 176
2-amino-4,4-dimethylheptanoic acid [I-178]
$^1$H NMR (500 MHz, MeOD-d$_4$) δ 3.77 (t, J=6 Hz, 1H), 2.09-2.05 (m, 1H), 1.6-1.56 (m, 1H), 1.37-1.26 (m, 4H), 1.01-0.92 (m, 9H).
Example 195: 2-amino-4,4-dimethylhexanoic acid [I-195], (S)-2-amino-4,4-dimethylhexanoic acid [I-120], (R)-2-amino-4,4-dimethylhexanoic acid [I-191]
Synthetic Scheme:

Procedures and Characterization:

The procedure was the same as used in Example 176

2-Amino-4,4-dimethylheptanoic acid [I-195]

$^1$H NMR (500 MHz, D$_2$O) δ 3.87 (t, J=6.0 Hz, 1H), 1.93 (dd, J=15.0 Hz, J=5.5 Hz, 1H), 1.57 (dd, J=15.0 Hz, J=6.5 Hz, 1H), 1.22-1.26 (m, 2H), 0.86 (d, (dd, J=2.0 Hz, 6H), 0.76 (t, J=7.5 Hz, 3H).

(S)-2-amino-4,4-dimethylhexanoic acid [I-120]

$^1$H NMR (500 MHz, MeOD-d$_4$) δ 3.43 (dd, J=7.0 Hz, J=5.0 Hz, 1H), 1.95 (dd, J=15.0 Hz, J=5.0 Hz, 1H), 1.42 (dd, J=15.0 Hz, J=7.0 Hz, 1H), 1.23-1.28 (m, 2H), 0.87 (d, (dd, J=4.5 Hz, 6H), 0.80 (t, J=7.5 Hz, 3H).

(R)-2-amino-4,4-dimethylhexanoic acid [I-191]

$^1$H NMR (500 MHz, MeOD-d$_4$) δ 3.43 (dd, J=7.0 Hz, J=5.0 Hz, 1H), 1.95 (dd, J=15.0 Hz, J=5.0 Hz, 1H), 1.42 (dd, J=15.0 Hz, J=7.0 Hz, 1H), 1.23-1.28 (m, 2H), 0.87 (d, (dd, J=4.5 Hz, 6H), 0.80 (t, J=7.5 Hz, 3H).

Example 177:
2-amino-6,6,6-trifluoro-4-methylhexanoic acid
[I-177]

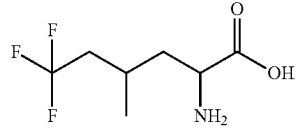

I-177

Synthetic Scheme:

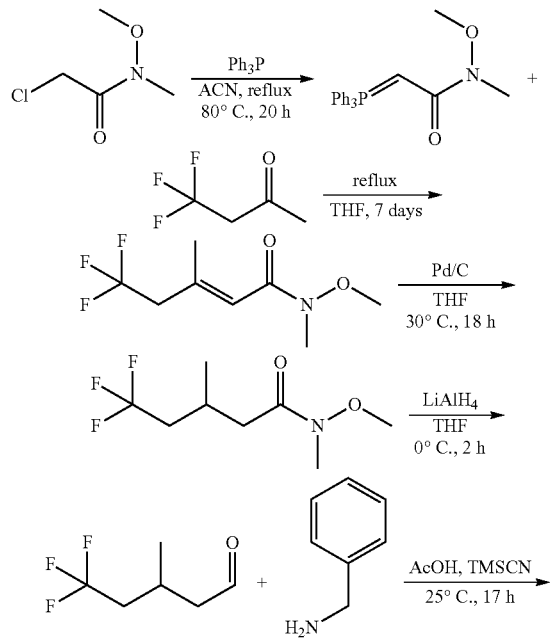

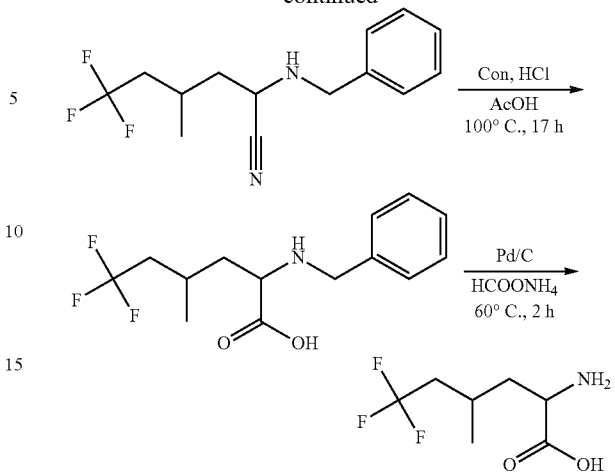

Procedures and Characterization:

Step 1: N-Methoxy-N-methyl-2-(triphenyl-15-phosphanylidene)acetamide

A mixture of (2-chloro-N-methoxy-N-methylacetamide (13.7 g, 0.1 mol) and triphenylphosphane (26.2 g, 0.1 mol) in acetonitrile (200 mL) was heated to 80° C. and held for 20 h. The mixture was cooled and concentrated to remove the solvent below 40° C. The residue was dissolved in dichloromethane (200 mL), followed by 2 N KOH (100 mL). The resulting mixture was stirred at 20° C. for 1 h. Phase separation, the organic layer was washed with brine (200 mL*3), dried over Na$_2$SO$_4$ and filtered. The filtrate was concentrated in vacuum to afford N-methoxy-N-methyl-2-(triphenyl-15-phosphanylidene) acetamide (36 g, 0.1 mol, 98%) as a yellow solid. ESI-MS (EI$^+$, m/z): 364.4 [M+H]$^+$.

Step 2: (E)-5, 5,
5-Trifluoro-N-methoxy-N,3-dimethylpent-2-enamide

A mixture of N-methoxy-N-methyl-2-(triphenyl-15-phosphanylidene) acetamide (36.3 g, 0.1 mol) and 4,4,4-trifluorobutan-2-one (25.2 g, 0.2 mol) in tetrahydrofuran (500 mL) was heated to 70° C. and held for 7 day. The mixture was cooled and concentrated to remove the solvent below 40° C. in vacuum. The residue was purified by silica gel column (200 g, 200~300 mesh, UV 254 nm) eluting with ethyl acetate in petroleum ether from 0 to 35% to afford (E)-5,5,5-trifluoro-N-methoxy-N,3-dimethylpent-2-enamide (6 g, 0.03 mol, 28%) as a yellow oil. ESI-MS (EI$^+$, m/z): 212.2 [M+H]$^+$.

Step 3: 5, 5,
5-Trifluoro-N-methoxy-N,3-dimethylpentanamide

A mixture of (E)-5, 5, 5-trifluoro-N-methoxy-N,3-dimethylpent-2-enamide (6 g, 0.03 mol) and Pd/C (10%, 400 mg) in THE (100 mL) was stirred at 30° C. for 18 hrs. The mixture was filtered, and the filtrate was concentrated in vacuum to dryness to afford 5,5,5-trifluoro-N-methoxy-N,3-dimethylpentanamide (6 g, 0.03 mol, 98%) as a yellow oil. ESI-MS (EI+, m/z): 214.2 [M+H]$^+$.

Step 4: 5, 5, 5-Trifluoro-3-methylpentanal

To a solution 5, 5, 5-trifluoro-N-methoxy-N,3-dimethylpentanamide (6 g, 0.03 mol) in 100 mL of THF was added LiAlH4 (1 g, 0.03 mol) at 0° C. The mixture was stirred at 0° C. for 1 h. The reaction mixture was quenched with water, followed by methyl tert-butyl ether (60 mL*2). Phase separation, the organic layer was washed with brine (80 mL*3), dried over Na₂SO₄ and filtered. The filtrate was contained to afford 5, 5, 5-trifluoro-3-methylpentanal (4.5 g, 95%) as a colorless solution, which was used into next step directly.

Step 5: 2-(Benzylamino)-6, 6, 6-trifluoro-4-methylhexanenitrile

To a solution of above 5, 5, 5-trifluoro-3-methylpentanal in methyl tert-butyl ether (200 mL) was added benzylamine (5 mL), AcOH (4.0 mL) and then TMSCN (5 mL) with ice-bath. The mixture was warmed 20° C. and stirred overnight. The solution was diluted with water (100 mL) and extracted with EtOAc (100 mL), the organic phase was washed with water (100 mL×2), and brine (100 mL), dried (Na₂SO₄), filtered and concentrated in vacuum to afford 2-(benzylamino)-6,6,6-trifluoro-4-methylhexanenitrile (6 g, crude) as a brown oil which was used for the next step. ESI-MS (EI+, m/z): 271.3 [M+H]⁺.

Step 6: 2-(Benzylamino)-6, 6, 6-trifluoro-4-methylhexanoic acid

A solution of 2-(benzylamino)-6, 6, 6-trifluoro-4-methylhexanenitrile (3 g, crude) in conc. HCl (100 mL) and AcOH (20 mL) was heated to 100° C. for 17 hrs. The solution was cooled to 15° C., the pH was adjusted to 3-4 with sat. NaHCO₃ solution, the mixture was filtered and dried to afford 2-(benzylamino)-6, 6, 6-trifluoro-4-methylhexanoic acid (1 g, 13.4 mmol, 33% for 3 steps) as a white solid. ESI-MS (EI⁺, m/z): 290.3 [M+H]⁺.

2-Amino-6, 6, 6-trifluoro-4-methylhexanoic acid [I-177]

To a solution of 2-(benzylamino)-6, 6, 6-trifluoro-4-methylhexanoic acid (88 mg, 0.31 mmol) in 8 mL of MeOH was added HCOONH₄ (0.13 g, 2.0 mmol) and Pd/C (30 mg) at rt. The mixture was stirred at 60° C. for 2 h. The reaction mixture was filtered and concentrated to give a crude product which was purified by reverse-phase silica-gel chromatography to give 2-amino-6,6,6-trifluoro-4-methylhexanoic acid [I-177] (45 mg, 84%) as a white solid; ESI-MS (EI⁺, m/z): 200.2 [M+H]⁺; 1H NMR (500 MHz, DMSO) δ 3.15 (d, J=5.7 Hz, 1H), 2.39-2.24 (m, 1H), 2.19-1.96 (m, 2H), 1.82-1.66 (m, 1H), 1.63-1.35 (m, 1H), 0.98 (dd, J=16.5, 6.2 Hz, 3H).

Example 179: (S)-2-Amino-5-fluoro-4-(fluoromethyl)pentanoic acid [I-179]

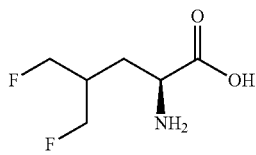

I-179

Synthetic Scheme:

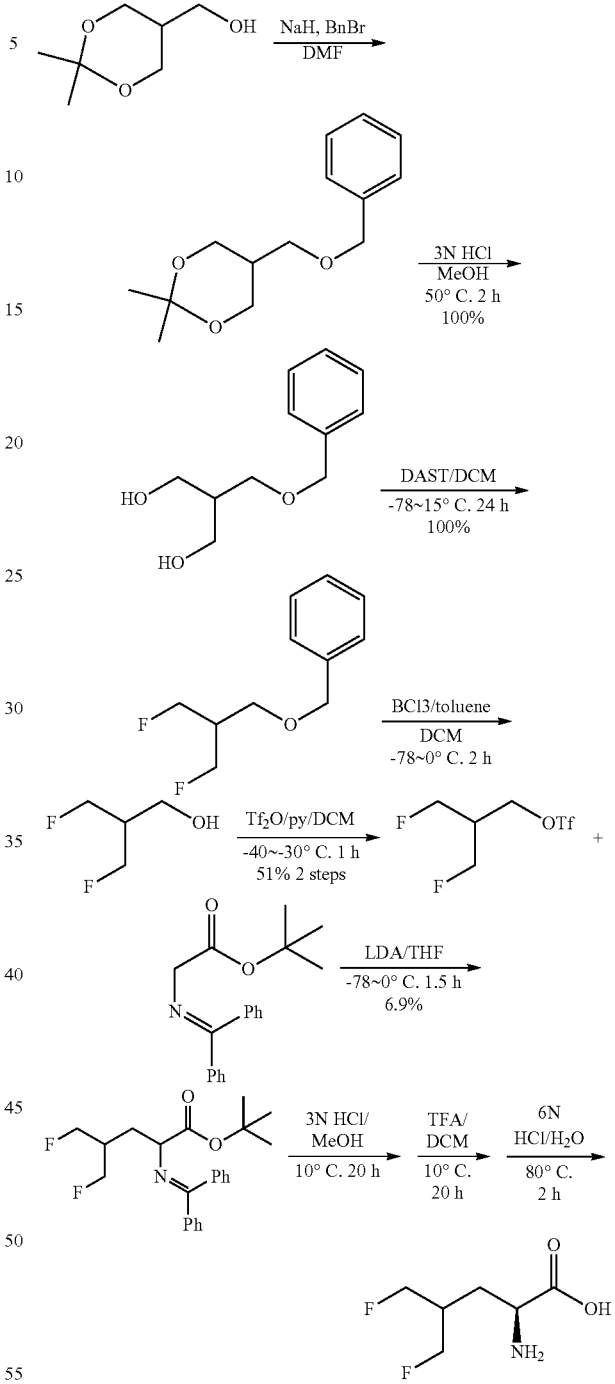

Procedures and Characterization:

Step 1: 5-(Benzyloxymethyl)-2,2-dimethyl-1,3-dioxane

To a solution of (2, 2-dimethyl-1, 3-dioxan-5-yl)methanol (0.29 g, 2.0 mmol) in DMF (10 mL) was added NaH (60% in oil, 0.12 g, 3.0 mmol) at 0° C. The mixture was stirred at 0° C. for 0.2 hours. Then (bromomethyl) benzene (0.45 g, 2.6 mmol) was added. The mixture was warmed to 10° C. for 3 h and held for 18 h. The reaction mixture was quenched with ice-water, followed by EtOAc (60 mL). Phase separation, the organic layer was washed with brine (60 mL*3), dried over Na$_2$SO$_4$ and filtered. The filtrate was concentrated and the residue was purified by silica gel column (20 g, UV 254 nm eluting with EtOAc in PE from 10% to 50%) to afford 5-(benzyloxymethyl)-2,2-dimethyl-1,3-dioxane (1), (0.46 g, 0.2 mol, 95%) as a colorless oil. ESI-MS (EI$^+$, m/z): 237.3 [M+H]$^+$.

Step 2: 2-(Benzyloxymethyl)propane-1,3-diol

To a solution of 5-(benzyloxymethyl)-2,2-dimethyl-1,3-dioxane (930 mg, 3.94 mmol) in MeOH (20 mL) was added 3N aqueous HCl (2 mL). The mixture was stirred at 50° C. for 2 hours. The reaction mixture was concentrated and diluted with DCM (20 mL), washed by brine (15 mL), dried and evaporated to give the crude colorless oil (780 mg, 100%). ESI-MS (EI$^+$, m/z): 197 [M+H]$^+$.

Step 3: ((3-Fluoro-2-(fluoromethyl)propoxy)methyl)benzene

To a pre-cooled solution of 2-(benzyloxymethyl)propane-1,3-diol (780 mg, 3.94 mmol) in DCM (20 mL) was added DAST (1.9 g, 11.8 mmol) drop wise at −78° C. The mixture was stirred at 20° C. for 24 hours. The reaction mixture was quenched by sat. NaHCO$_3$ aqueous (10 mL) at −78° C. DCM phase was separated and washed with brine, dried by MgSO$_4$, filtered through a short silica gel pad and then concentrated to give the crude colorless oil (800 mg, 100%). ESI-MS (EI$^+$, m/z): 223 [M+Na]$^+$. $^1$H NMR (500 MHz, CDCl$_3$) δ 7.37-7.28 (m, 5H), 4.65-4.57 (m, 2H), 4.55-4.48 (m, 4H), 3.57 (d, J=6.2 Hz, 2H), 2.50-2.34 (m, 1H).

Step 4: 3-Fluoro-2-(fluoromethyl)propan-1-ol

To a pre-cooled solution of ((3-fluoro-2-(fluoromethyl)propoxy)methyl)benzene (800 mg, 3.94 mmol) in DCM (20 mL) was added BCl$_3$/toluene (1M, 6 mL, 6.0 mmol) drop wise at −78° C. The mixture was stirred at −78-0° C. for 2 hours. The reaction mixture was quenched by H$_2$O (0.5 mL) at −78° C. DCM phase was dried by MgSO$_4$, filtered and the solution (about 20 mL) was used for next step directly.

Step 5: 3-Fluoro-2-(fluoromethyl)propyl trifluoromethanesulfonate

To a pre-cooled solution of 3-fluoro-2-(fluoromethyl)propan-1-ol (8 mL solution from step 4, 1.6 mmol) was added py (380 mg, 4.8 mmol) then Tf$_2$O (1.36 g, 4.8 mmol) drop wise at −40° C. The mixture was stirred at −30° C. for 1 hour. The reaction mixture was quenched by brine (20 mL) at −40° C. DCM phase was separated and dried by MgSO$_4$, filtered and then concentrated to give the crude tan oil (200 mg, 51%) which was used for next step directly.

Step 6: tert-Butyl 2-(diphenylmethyleneamino)-5-fluoro-4-(fluoromethyl)pentanoate To a pre-cooled solution of tert-butyl 2-(diphenylmethyleneamino)acetate (944 mg, 3.2 mmol) in THF (20 mL) was added LDA (2.5M in THF/toluene/hexane, 1.28 mL, 3.2 mmol) at −78° C. in 25 mins. The mixture was stirred at this temperature for 10 mins. A solution of 3-fluoro-2-(fluoromethyl)propyl trifluoromethanesulfonate (200 mg, 0.82 mmol) in THF (2 mL) was added drop wise at −78° C. The reaction mixture was placed just above the cooling bath and stirred for another 1 h. The reaction mixture was quenched by sat. NH$_4$Cl aqueous (20 mL), extracted with MTBE (30 mL*2), washed with H$_2$O, brine (50 mL each), dried and concentrated to give the crude which was purified by chorography (silica gel, PE to 5% EA/PE) twice to give desired product (22 mg, 6.9%) as white solid. ESI-MS (EI$^+$, m/z): 388 [M+H]$^+$. $^1$H NMR (500 MHz, DMSO) δ 7.56-7.45 (m, 6H), 7.41 (t, J=7.4 Hz, 2H), 7.18 (d, J=6.3 Hz, 2H), 4.50-4.17 (m, 4H), 3.91 (dd, J=7.7, 5.5 Hz, 1H), 2.11-1.97 (m, 1H), 1.87 (dd, J=12.7, 5.5 Hz, 2H), 1.38 (s, 9H).

Step 7: (S)-2-Amino-5-fluoro-4-(fluoromethyl)pentanoic acid hydrochloride

A solution of tert-butyl 2-(diphenylmethyleneamino)-5-fluoro-4-(fluoromethyl)pentanoate (55 mg, 0.14 mmol) in 3N HCl/MeOH (2 mL) was stirred at room temperature for 20 hours. The reaction mixture was concentrated and washed by Et$_2$O to give the crude solid which was dissolved in DCM/TFA (1:1, 2 mL) and stirred at room temperature for 20 hours. The reaction mixture was evaporated and washed by Et$_2$O to give the crude solid which was dissolved in 6NHCl (1 mL) and stirred at 80° C. for 2 h. The reaction mixture was evaporated and lyophilized to give crude product which was purified by RP-biotage using 3 mM HCl/H$_2$O to give desired product (8.3 mg, 29%) as white solid. ESI-MS (EI$^+$, m/z): 168 [M+H]$^+$.

$^1$H NMR (500 MHz, DMSO) δ 7.85 (bs, 3H), 4.48 (dd, J=48.3, 14.2 Hz, 4H), 3.46-3.36 (m, 1H), 2.47-2.26 (m, 1H), 1.78 (dt, J=14.3, 7.3 Hz, 1H), 1.63-1.53 (m, 1H).

Example 187: (S)-3-Amino-5,5-dimethyl-dihydro-furan-2(3H)-one [I-187]

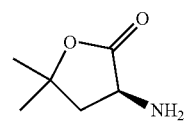

I-187

Synthetic Scheme:

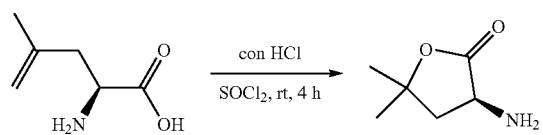

Procedures and Characterization:

Step 1: (S)-3-Amino-5,5-dimethyl-dihydrofuran-2(3H)-one [I-187]

To a round bottom flask containing (S)-2-amino-4-methylpent-4-enoic acid (100 mg) was added Con.HCl (1 mL) and SOCl$_2$ (0.2 mL). The mixture was stirred at room temperature for 4 hours. The reaction mixture was concentrated and washed by Et$_2$O to give the crude solid which was purified by RP-biotage using 0.025% TFA/H$_2$O/MeCN to give desired product (20.2 mg, 11.4%) as white solid. ESI-MS (EI$^+$, m/z): 130.1 [M+H]+. HH NMR (500 MHz, DMSO) δ 8.80 (bs, 3H), 4.58 (dd, J=11.2, 9.3 Hz, 1H), 2.53-2.48 (m, 1H), 2.13 (t, J=11.7 Hz, 1H), 1.45 (s, 3H), 1.40 (s, 3H).
Example 90: Synthesis of (S)-2-amino-5,5-difluoro-4,4-dimethylpentanoic acid [I-90]
Synthetic Scheme:
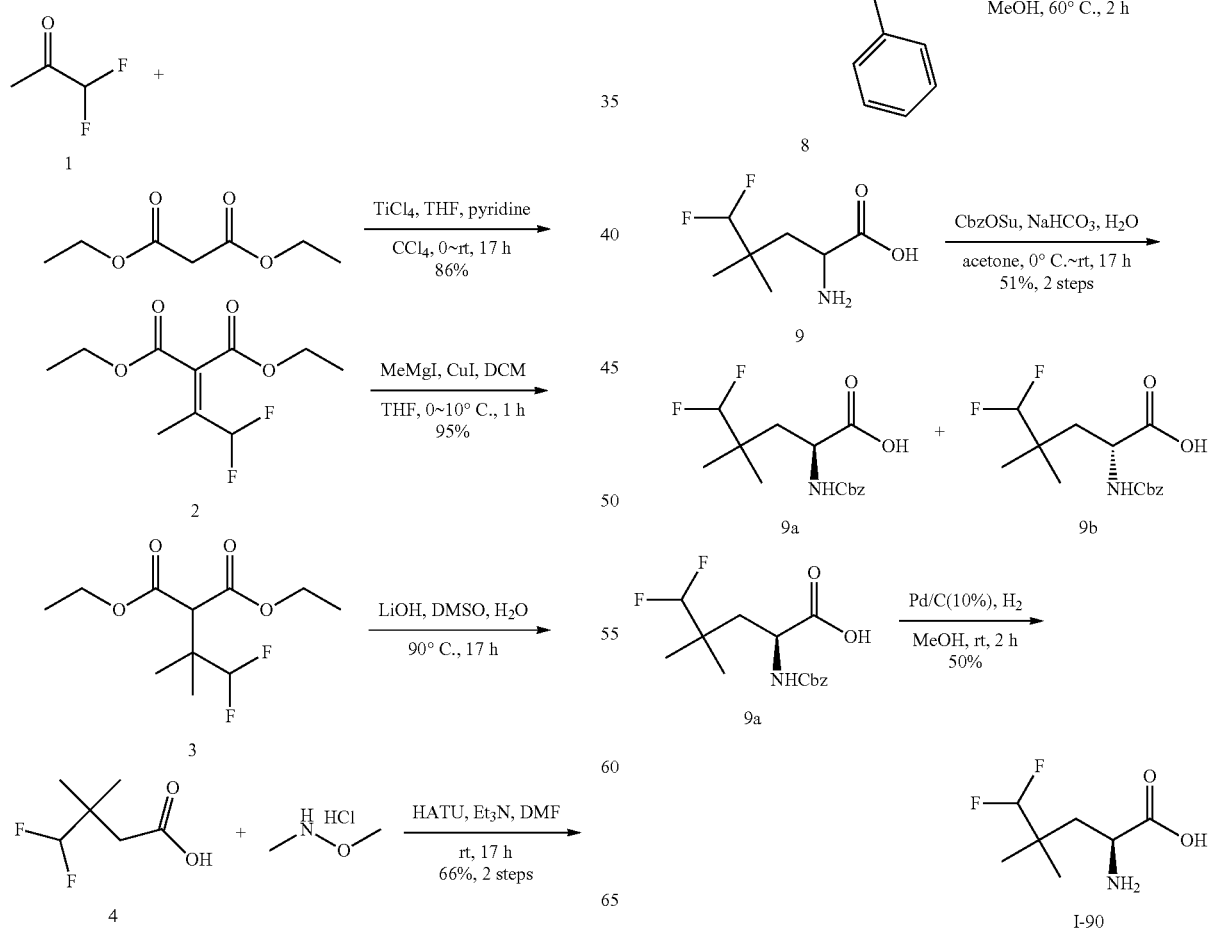

129

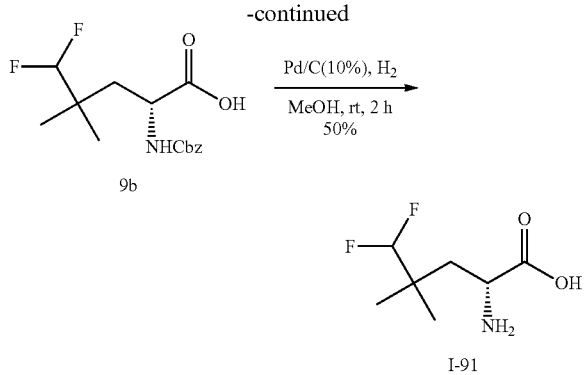

9b

I-91

Procedures and Characterization:

Step 1: Diethyl 2-(1,1,1-trifluoropropan-2-ylidene)malonate

TiCl$_4$ (65.8 mL, 600 mmol) was added dropwise to THF (1 L) with ice-bath over 20 mins, CCl$_4$ (30 mL) was added. To the mixture was added diethyl malonate (48.0 g, 300 mmol) and 1,1-difluoropropan-2-one (56.4 g, 600 mmol). The mixture was warmed to room temperature and stirred overnight. Pyridine (200 mL) was added dropwise over 20 mins with ice-bath, The reaction mixture was poured into water (2 L), filtered, and the filtrate was extracted with EtOAc (500 mL×2), the organic phase was washed with water (600 mL), 1 MHCl (600 mL×2), water (600 mL), sat. NaHCO$_3$ (600 mL) and brine (600 mL), dried (Na$_2$SO$_4$), filtered and concentrated in vacuum and purified by chromatography (silica, ethyl acetate/petroleum ether from 0% to 5%) to afford diethyl 2-(1,1-difluoropropan-2-ylidene) malonate (60.9 g, 258 mmol, 86%) as a colorless liquid. ESI-MS (EI$^+$, m/z): 237.0 [M+H]$^+$. $^1$H-NMR (500 MHz, CDCl$_3$): δ 6.97 (t, J=55.5 Hz, 1H), 4.25-4.33 (m, 4H), 2.03 (s, 3H), 1.29-1.34 (m, 6H).

Step 2: Diethyl 2-(1,1-difluoro-2-methylpropan-2-yl)malonate

To a mixture of diethyl 2-(1,1-difluoropropan-2-ylidene) malonate (10.0 g, 42.3 mmol) and CuI (12.1 g, 63.5 mmol) in DCM (100 mL) and THE (25 mL) was added dropwise MeMgI (42.3 mL, 130.5 mmol) at −20° C. over 1 h, The solution was poured into ice-water (200 mL) and treated with sat. NH$_4$Cl solution (100 mL), the mixture was stirred for 30 mins and filtered, the filtrate was extracted with DCM (100 mL), the organic phase was washed with water (100 mL×2), and brine (100 mL), dried (Na$_2$SO$_4$), filtered and concentrated in vacuum to afford diethyl 2-(1,1-difluoro-2-methylpropan-2-yl)malonate (10.1 g, 40.2 mmol, 95%) as a brown liquid which was used for the next step. ESI-MS (EI$^+$, m/z): 253.1 [M+H]$^+$. $^1$H-NMR (500 MHz, CDCl$_3$): δ 6.05 (t, J=57.5 Hz, 1H), 4.17-4.23 (m, 4H), 3.49 (s, 1H), 1.22-1.28 (m, 6H), 1.20 (s, 6H).

Step 3: 4,4-Difluoro-3,3-dimethylbutanoic acid

A mixture of diethyl 2-(1,1-difluoro-2-methylpropan-2-yl)malonate (6.1 g, 24.2 mmol) and LiOH.H$_2$O (5.1 g, 121 mmol) in DMSO (50 mL) and H$_2$O (0.5 mL) was heated to 90° C. for 7 hrs. The mixture was diluted with water (200 mL), extracted with DCM (100 mL), the aqueous phase was adjusted pH to 3-4 with 6 M HCl solution, extracted with

130

DCM (100 mL×2), dried (Na$_2$SO$_4$), filtered and concentrated in vacuum to afford 4,4-difluoro-3,3-dimethylbutanoic acid (3.6 g, crude) as a brown liquid. ESI-MS (EI$^+$, m/z): 151.1 [M−H]$^-$.

Step 4: 4,4-Difluoro-N-methoxy-N,3,3-trimethylbutanamide

To a solution of 4,4-difluoro-3,3-dimethylbutanoic acid (3.6 g, crude), N,O-dimethylhydroxylamine hydrochloride (4.6 g, 47.4 mmol) and HATU (10.8 g, 28.4 mmol) in DMF (50 mL) was added Et$_3$N (7.18 g, 71.1 mmol), after stirred at rt for 17 hrs. The mixture was filtered, and the filtrate was diluted with water (200 mL), extracted with Et$_2$O (100 mL×2), washed with water (100 mL), 1 M HCl (100 mL), and brine (100 mL), dried (Na$_2$SO$_4$), filtered and concentrated in vacuum to afford 4,4-difluoro-N-methoxy-N,3,3-trimethylbutanamide (3.1 g, 15.9 mmol, 66%, 2 steps) as a brown liquid. ESI-MS (EI$^-$, m/z): 196.0 [M+H]$^+$. $^1$H-NMR (500 MHz, CDCl$_3$): δ 5.95 (t, J=57.5 Hz, 1H), 3.69 (s, 3H), 3.17 (s, 3H), 2.51 (s, 2H), 1.12 (s, 6H).

Step 5: 4,4-Difluoro-3,3-dimethylbutanal

To a solution of 4,4-difluoro-N-methoxy-N,3,3-trimethylbutanamide (3.1 g, 15.9 mmol) in THE (80 mL) was added dropwise LiAlH$_4$ (24 mL, 24 mmol) with ice-bath. After 1 h, the mixture was quenched with citric acid solution (100 mL), the solution was extracted with Et$_2$O (100 mL×2), the organic phase was washed with brine (100 mL), dried (Na$_2$SO$_4$), and the solution was used for the next step.

Step 6: 2-(Benzylamino)-5,5-difluoro-4,4-dimethylpentanenitrile

To the above solution of 4,4-difluoro-3,3-dimethylbutanal in Et$_2$O (200 mL) was added benzylamine (3 mL), AcOH (3 mL) and then TMSCN (3 mL) with ice-bath, the solution was stirred at 0~rt for 17 hrs, and then diluted with EtOAc (100 mL). The solution was washed with H$_2$O (100 mL×2) and then concentrated to afford 2-(benzylamino)-5,5-difluoro-4,4-dimethylpentanenitrile (3.2 g, crude) as a brown liquid. ESI-MS (EI$^+$, m/z): 253.0 [M+H]$^+$.

Step 7: 2-(Benzylamino)-5,5-difluoro-4,4-dimethylpentanoic acid

A solution of 2-(benzylamino)-5,5-difluoro-4,4-dimethylpentanenitrile (1.8 g, crude) in conc. HCl (50 mL) and AcOH (10 mL) was heated to 100° C. for 64 hrs. The mixture was concentrated to remove the solvent, adjusted pH to 12 with 1 M NaOH solution, extracted with PE (100 mL), the aqueous phase was adjusted pH to 5-6 with 6 M HCl. The white solid was formed, filtered, and the filter cake was washed with water (50 mL), dried in vacuum to afford 2-(benzylamino)-5,5-difluoro-4,4-dimethylpentanoic acid (1.3 g, 4.80 mmol, 54%, 3 steps) as a white solid. ESI-MS (EI$^+$, m/z): 272.0

Step 8: 2-Amino-5,5-difluoro-4,4-dimethylpentanoic acid

A mixture of 2-(benzylamino)-5,5-difluoro-4,4-dimethylpentanoic acid (1.3 g, 4.80 mmol), HCOONH$_4$ (1.51 g, 24 mmol) and Pd/C (10%, 200 mg) in MeOH (50 mL) was heated to 60° C. for 1 h. The mixture was filtered, and the filtrate was concentrated to afford 2-amino-5,5-difluoro-4,4-dimethylpentanoic acid (1.0 g, crude) as a white solid. ESI-MS (EI+, m/z): 182.0

Step 9: 2-(Benzyloxycarbonylamino)-5,5-difluoro-4,4-dimethylpentanoic acid

To a solution of 2-amino-5,5-difluoro-4,4-dimethylpentanoic acid (1.0 g, crude) and NaHCO$_3$ (1.27 g, 14.4 mmol) in acetone (30 mL) and H$_2$O (30 mL) was added CbzOSu (2.39 g, 9.6 mmol) with ice-bath. After being stirred for 17 h, the mixture was adjusted pH to 3-4 with 1M HCl solution, and the solution was extracted with EtOAc (50 mL×2), washed with brine (50 mL), dried (Na$_2$SO$_4$), filtered and concentrated in vacuum, the crude product was purified by reverse-phase silica-gel chromatography and then chiral-prep-HPLC [column, CC4 4.6*250 mm 5 um; solvent, MeOH (0.2% Methanol Ammonia)] to afford (S)-2-(benzyloxycarbonylamino)-5,5-difluoro-4,4-dimethylpentanoic acid (400 mg, 1.27 mmol, 26%, 2 steps) and (R)-2-(benzyloxycarbonylamino)-5,5-difluoro-4,4-dimethylpentanoic acid (380 mg, 1.21 mmol, 25%, 2 steps) as two colorless oils. ESI-MS (EI+, m/z): 316.0

Step 10: (S)-2-Amino-5,5-difluoro-4,4-dimethylpentanoic acid

To a solution of (S)-2-(benzyloxycarbonylamino)-5,5-difluoro-4,4-dimethylpentanoic acid (400 mg, 1.27 mmol) and Pd/C (10%, 50 mg) in MeOH (30 mL) was stirred at rt for 2 hrs under hydrogen, the mixture was filtered and concentrated in vacuum and purified by reverse-phase silica-gel chromatography to afford (S)-2-amino-5,5-difluoro-4,4-dimethylpentanoic acid (115.7 mg, 0.64 mmol, 50%). ESI-MS (EI+, m/z): 182.0 $^1$H-NMR (500 MHz, MeOD-d4): δ 5.60 (t, J=56.5 Hz, 1H), 3.97 (t, J=6.0 Hz, 1H), 2.07 (dd, J=15.5 Hz, J=5.5 Hz, 1H), 1.77 (dd, J=15.5 Hz, J=6.5 Hz, 1H), 0.96 (d, J=9.5 Hz, 6H).

Example 88: Synthesis of (S)-2-amino-5,5-difluoro-4,4-dimethylpentanoic acid

I-88

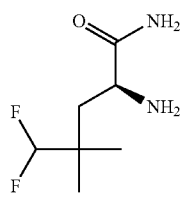

Synthetic Scheme:

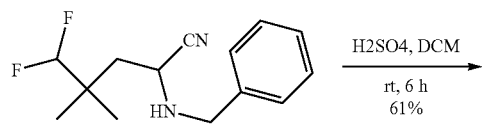

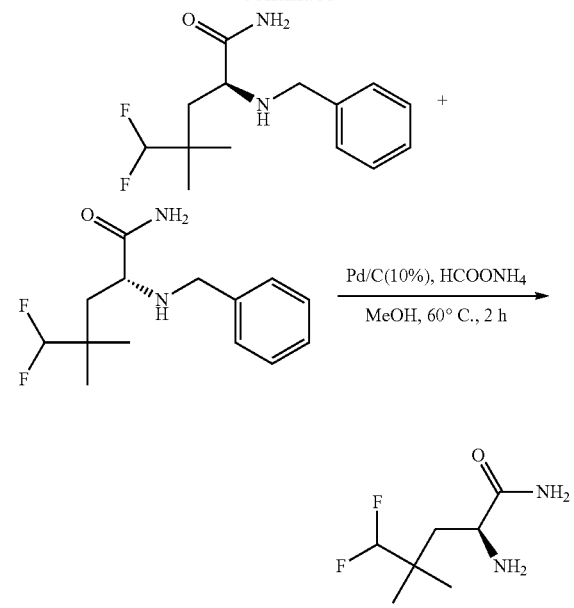

Procedures and Characterization:

Step 1: (S)-2-(Benzylamino)-5,5-difluoro-4,4-dimethylpentanamide

To a solution of 2-(benzylamino)-5,5-difluoro-4,4-dimethylpentanenitrile (1.2 g, 4.76 mmol) in DCM (20 mL) was added dropwise to conc. H$_2$SO$_4$ (10 mL) with ice-bath over 5 mins, the mixture was warmed to room temperature and stirred for 6 hrs. The mixture was poured into ice-water (100 mL), the solution was adjusted PH to 8~9 with 10% NaOH solution, and then extracted with EtOAc (100 mL×2), the organic phase was washed with water (100 mL), and brine (100 mL), dried (Na$_2$SO$_4$), filtered and concentrated in vacuum and purified by chromatography (MeOH/DCM from 0% to 5%) and then chiral-prep-HPLC [column, CC4 4.6*250 mm 5 um; solvent, MeOH (0.2% Methanol Ammonia)] to afford (S)-2-(benzylamino)-5,5-difluoro-4,4-dimethylpentanamide (400 mg, 1.48 mmol, 31%) and (R)-2-(benzylamino)-5,5-difluoro-4,4-dimethylpentanamide (380 mg, 1.41 mmol, 30%) as two colorless liquids. ESI-MS (EI+, m/z): 253.0 [M+H]+.

Step 2: (S)-2-Amino-5,5-difluoro-4,4-dimethylpentanamide

A mixture of (S)-2-(benzylamino)-5,5-difluoro-4,4-dimethylpentanamide (200 mg, 0.74 mmol), HCOONH$_4$ (233 mg, 3.7 mmol) and Pd/C (10%, 40 mg) in MeOH (15 mL) was heated to 60° C. for 1 h. The mixture was filtered, and the filtrate was concentrated and purified by reverse-phase silica-gel chromatography to afford (S)-2-amino-5,5-difluoro-4,4-dimethylpentanamide trifluoroacetic acid (128 mg, 0.44 mmol, 59%) as a white solid. ESI-MS (EI+, m/z): 181.0 [M+H]+. $^1$H-NMR (500 MHz, MeOD-d4): δ 5.66 (t, J=56.5 Hz, 1H), 3.95 (dd, J=8.0 Hz, J=5.0 Hz, 1H), 2.14 (dd, J=10.0 Hz, J=8.0 Hz, 1H), 1.83 (dd, J=14.5 Hz, J=5.5 Hz, 1H), 1.12 (d, J=15.0 Hz, 6H).

Example 185: Synthesis of (S)-methyl 2-((S)-2-amino-5,5-difluoro-4,4-dimethylpentanamido)-4-methylpentanoate[I-185]

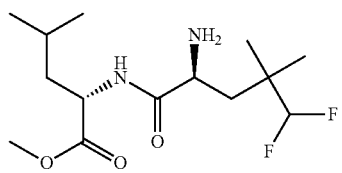

I-185

Synthetic Scheme:

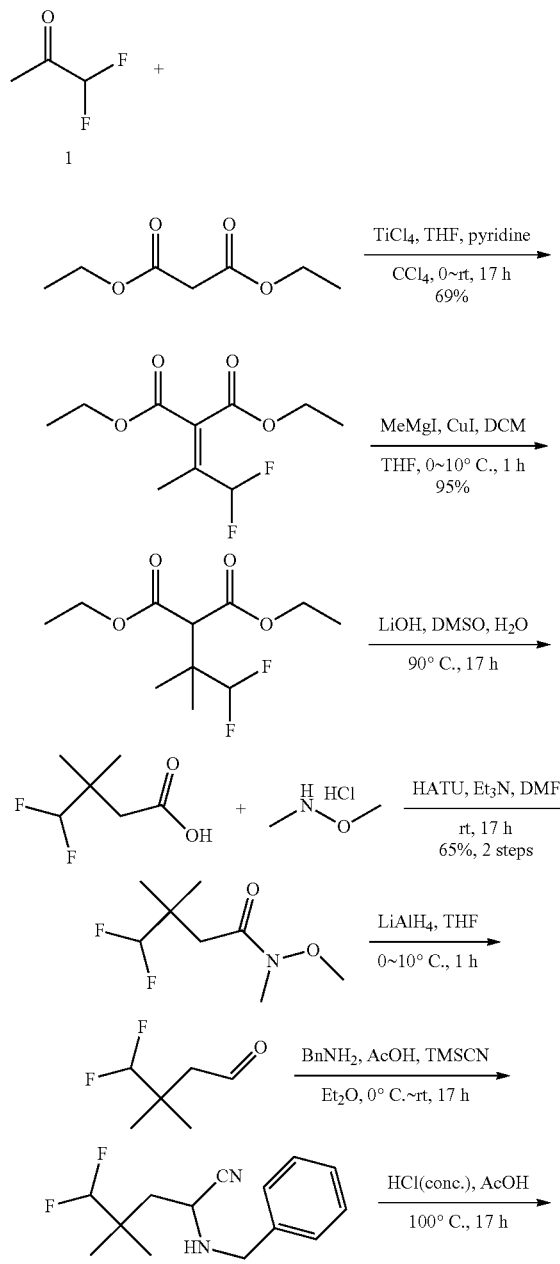

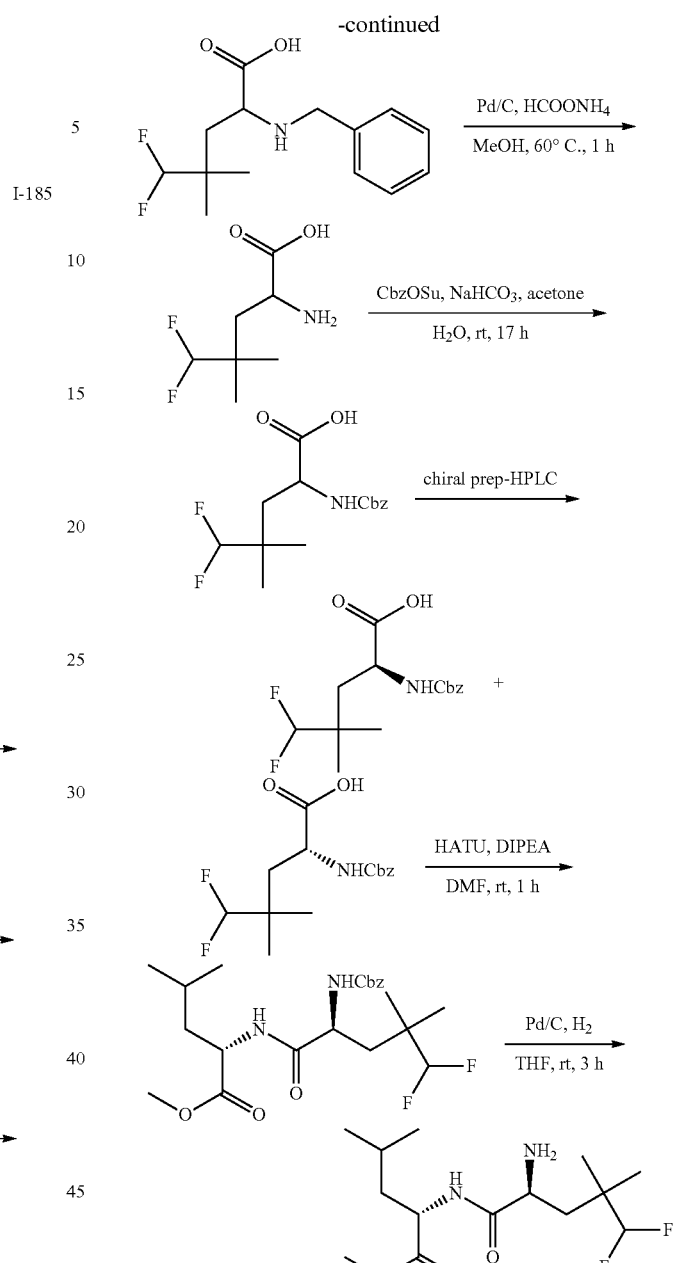

Procedures and Characterization:
The procedure for 2-(benzyloxycarbonylamino)-5,5-difluoro-4,4-dimethylpentanoic acid was same as example 90

Step 1: (S)-methyl 2-((S)-2-(benzyloxycarbonylamino)-5,5-difluoro-4,4-dimethylpentanamido)-4-methylpentanoate The solution of (S)-2-(benzyloxycarbonylamino)-5,5-difluoro-4,4-dimethylpentanoic acid (150 mg, 0.476 mmol), HATU (199 mg, 0.524 mmol), (S)-methyl 2-amino-4-methylpentanoate hydrochloride (104 mg, 0.571 mmol) and DIPEA (123 mg, 0.952 mmol) was stirred at rt for 1 hour, then quenched by ice water (20 ml), extracted with EA (2×30 ml), dried, filtered and concentrated. The crude was purified by reverse-phase silica-gel chromatography biotage to obtain (S)-methyl 2-((S)-2-(benzyloxycarbonylamino)-5,5-difluoro-4,4-dimethylpentanamido)-4-methylpentanoate (95 mg, 45%) as a white solid. ESI-MS (EI+, m/z): 443.0

Step 2: (S)-methyl 2-((S)-2-amino-5,5-difluoro-4,4-dimethylpentanamido)-4-methylpentanoate The solution of (S)-methyl 2-((S)-2-(benzyloxycarbonylamino)-5,5-difluoro-4,4-dimethylpentanamido)-4-methylpentanoate (95 mg, 0.215 mmol) and Pd/C (30 mg) in THF (5 ml) was stirred at rt for 2 hrs, then filtered, concentrated. The crude was purified by reverse-phase silica-gel chromatography biotage to obtain (S)-methyl 2-((S)-2-amino-5,5-difluoro-4,4-dimethylpentanamido)-4-methylpentanoate (45 mg, 69%) as a white solid. ESI-MS (EI+, m/z): 309.0

$^1$H-NMR (500 MHz, DMSO-d6): 9.11 (d, J=7 Hz, 1H), 8.41 (s, 3H), 5.81 (t, J=56.5 Hz, 1H), 4.34-4.31 (m, 1H), 3.89-3.81 (m, 1H), 3.62 (s, 3H), 1.98-1.93 (m, 1H), 1.76-1.73 (m, 1H), 1.65-1.54 (m, 3H), 0.93-0.81 (m, 12H).

Example 184: Synthesis of (S)-methyl 2-((R)-2-amino-5,5-difluoro-4,4-dimethylpentanamido)-4-methylpentanoate [I-184]

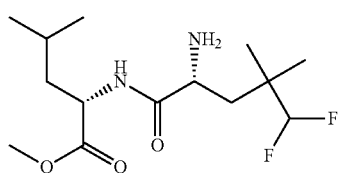

I-184

The procedure was same as Example 90, 185.

(S)-methyl 2-((R)-2-amino-5,5-difluoro-4,4-dimethylpentanamido)-4-methylpentanoate: ESI-MS (EI+, m/z): 309.0

$^1$H-NMR (500 MHz, DMSO-d6): 9.18 (d, J=7 Hz, 1H), 8.38 (s, 3H), 5.79 (t, J=56.5 Hz, 1H), 4.37-4.32 (m, 1H), 3.85-3.78 (m, 1H), 3.58 (s, 3H), 1.97-1.92 (m, 1H), 1.77-1.72 (m, 1H), 1.61-1.51 (m, 3H), 0.94-0.82 (m, 12H).

Example 145: Synthesis of (2S,4R)-2-amino-5,5,5-trifluoro-4-methylpentanoic acid, (2R,4S)-2-amino-5,5,5-trifluoro-4-methylpentanoic acid, (2R,4R)-2-amino-5,5,5-trifluoro-4-methylpentanoic acid and (2S,4S)-2-amino-5,5,5-trifluoro-4-methylpentanoic acid: [3d; I-145]; [3c; I-146]; [3a; I-167]; [3b; I-250]

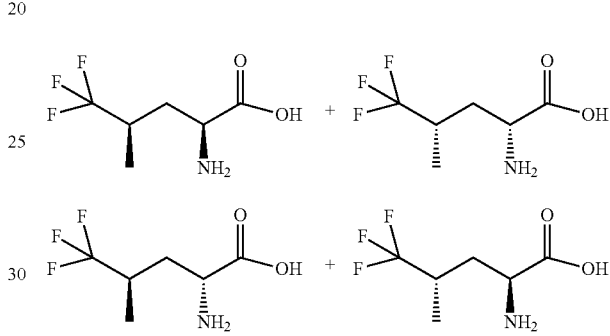

Synthetic Scheme:

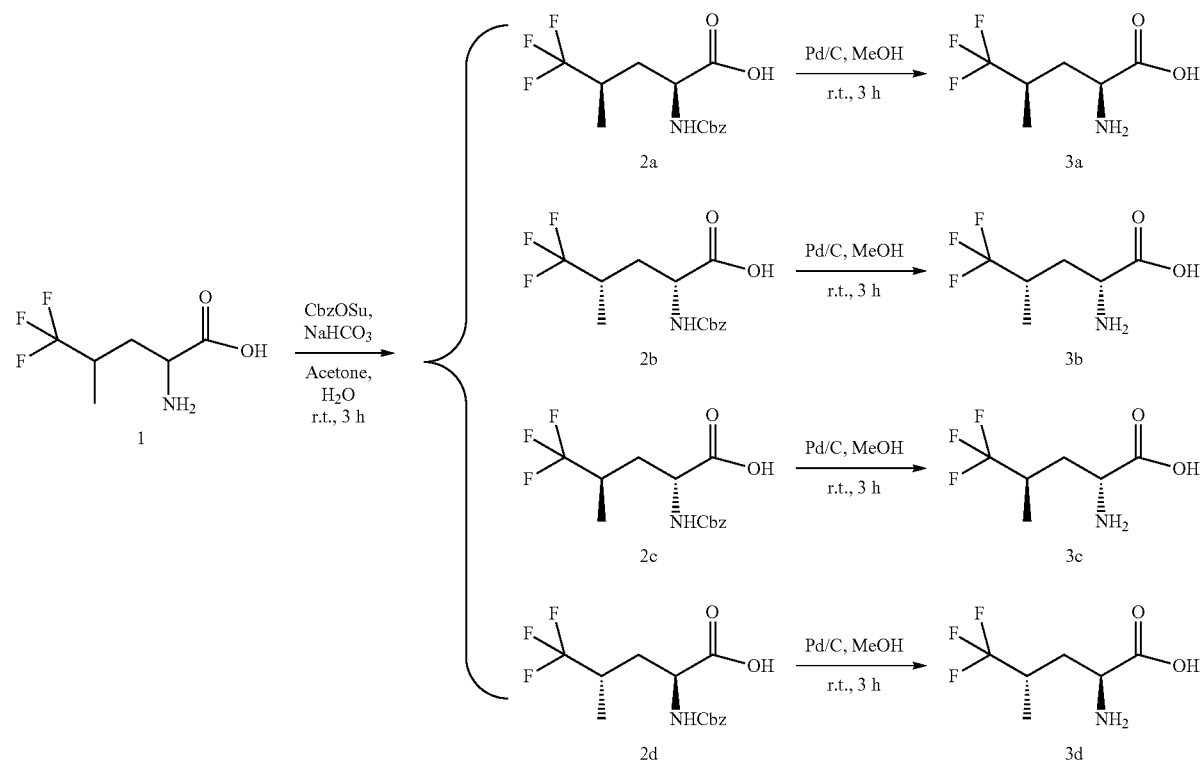

Procedures and Characterization:

Step 1: Synthesis of (2S,4R)-2-(benzyloxycarbonylamino)-5,5,5-trifluoro-4-methylpentanoic acid, (2R,4S)-2-(benzyloxycarbonylamino)-5,5,5-trifluoro-4-methylpentanoic acid, (2R,4R)-2-(benzyloxycarbonylamino)-5,5,5-trifluoro-4-methylpentanoic acid and (2S,4S)-2-(benzyloxycarbonylamino)-5,5,5-trifluoro-4-methylpentanoic acid To a solution of 2-amino-5,5,5-trifluoro-4-methylpentanoic acid (600 mg, 3.2 mmol) in Acetone (10 mL) and NaHCO$_3$ saturated aqueous (10 mL) was added CbzOSu (970 mg, 3.9 mmol). The mixture was stirred at rt for 3 hrs. Then EtOAc (20 mL) and H$_2$O (20 mL) was added, the aqueous was separated and further extracted with EtOAc (2*20 mL), combined the extracts and washed by brine (20 mL), dried by anhydrous Na$_2$SO$_4$, filtered and concentrated, the residue was purified by pre-HPLC to afford 2-(benzyloxycarbonylamino)-5,5,5-trifluoro-4-methylpentanoic acid (750 mg) as a white solid. The pure product was purified by chiral-HPLC to give the four isomers: (2S,4R)-2-(benzyloxycarbonylamino)-5,5,5-trifluoro-4-methylpentanoic acid (150 mg, 15%), (2R,4S)-2-(benzyloxycarbonylamino)-5,5,5-trifluoro-4-methylpentanoic acid (40 mg, 3.9%), (2R,4R)-2-(benzyloxycarbonylamino)-5,5,5-trifluoro-4-methylpentanoic acid (50 mg, 4.9%) and (2S,4S)-2-(benzyloxycarbonylamino)-5,5,5-trifluoro-4-methylpentanoic acid (80 mg, 7.8%) which both were white solid. ESI-MS (EI+, m/z): 342.0 [M+Na]+.

Step 2-A: Synthesis of (2S,4R)-2-amino-5,5,5-trifluoro-4-methylpentanoic acid

A solution of (2S,4R)-2-(benzyloxycarbonylamino)-5,5,5-trifluoro-4-methylpentanoic acid (150 mg, 0.47 mmol) and Pd/C (75 mg) in MeOH (15 mL) was stirred at rt for 3 hrs. The reaction mixture was filtered and concentrated to give (2S,4R)-2-amino-5,5,5-trifluoro-4-methylpentanoic acid (51.7 mg, 59%) as a white solid. ESI-MS (EI$^+$, m/z): 186.2 [M+H]$^+$. $^1$H-NMR (500 MHz, MeOD): δ 3.64-3.60 (m, 1H), 2.77-2.71 (br, 1H), 2.24-2.18 (m, 1H), 1.76-1.69 (m, 1H), 1.25 (d, J=7.0 Hz, 3H).

Step 2-B: Synthesis of (2R,4S)-2-amino-5,5,5-trifluoro-4-methylpentanoic acid

A solution of (2R,4S)-2-(benzyloxycarbonylamino)-5,5,5-trifluoro-4-methylpentanoic acid (40 mg, 0.12 mmol) and Pd/C (20 mg) in MeOH (4 mL) was stirred at rt for 3 hrs. The reaction mixture was filtered and concentrated to give (2R,4S)-2-amino-5,5,5-trifluoro-4-methylpentanoic acid (13.3 mg, 60%) as a white solid. ESI-MS (EI$^+$, m/z): 186.2 [M+H]$^+$. $^1$H-NMR (500 MHz, MeOD): δ 3.51-3.47 (m, 1H), 2.64-2.58 (br, 1H), 2.12-2.06 (m, 1H), 1.63-1.57 (m, 1H), 1.13 (d, J=7.0 Hz, 3H).

Step 2-C: Synthesis of (2R,4R)-2-amino-5,5,5-trifluoro-4-methylpentanoic acid

A solution of (2R,4R)-2-(benzyloxycarbonylamino)-5,5,5-trifluoro-4-methylpentanoic acid (50 mg, 0.16 mmol) and Pd/C (25 mg) in MeOH (5 mL) was stirred at rt for 3 hrs. The reaction mixture was filtered and concentrated to give (2R,4R)-2-amino-5,5,5-trifluoro-4-methylpentanoic acid (18.0 mg, 61%) as a white solid. ESI-MS (EI$^+$, m/z): 186.1 [M+H]$^+$. $^1$H-NMR (500 MHz, MeOD): δ 3.51-3.47 (m, 1H), 2.46-2.44 (br, 1H), 1.95-1.87 (m, 2H), 1.11 (d, J=7.0 Hz, 3H).

Step 2-D: Synthesis of (2S,4S)-2-amino-5,5,5-trifluoro-4-methylpentanoic acid

A solution of (2S,4S)-2-(benzyloxycarbonylamino)-5,5,5-trifluoro-4-methylpentanoic acid (80 mg, 0.25 mmol) and Pd/C (40 mg) in MeOH (8 mL) was stirred at rt for 3 hrs. The reaction mixture was filtered and concentrated to give (2S,4S)-2-amino-5,5,5-trifluoro-4-methylpentanoic acid (38.1 mg, 82%) as a white solid. ESI-MS (EI$^+$, m/z): 186.2 [M+H]$^+$. $^1$H-NMR (500 MHz, MeOD). δ 3.51-3.47 (m, 1H), 2.46-2.44 (br, 1H), 1.95-1.87 (m, 2H), 1.11 (d, J=7.0 Hz, 3H).

Example 128: (S)-2-amino-5,5,5-trifluoro-4,4-dimethylpentanoic acid (I-128)

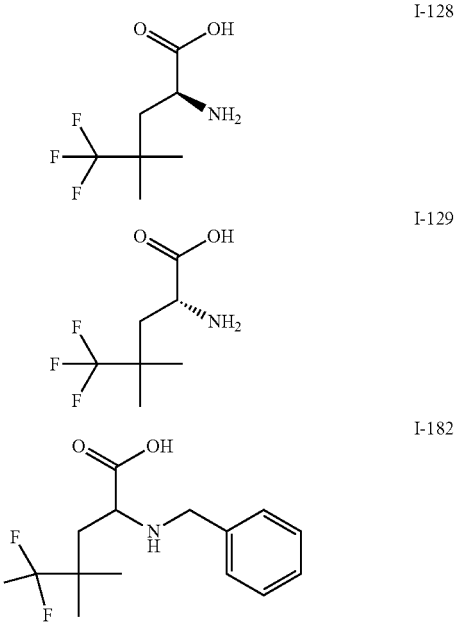

Synthetic Scheme:

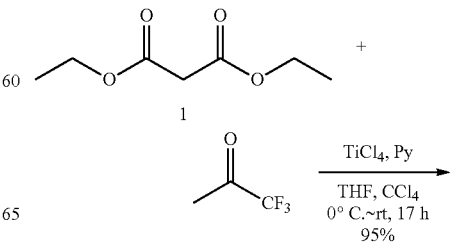

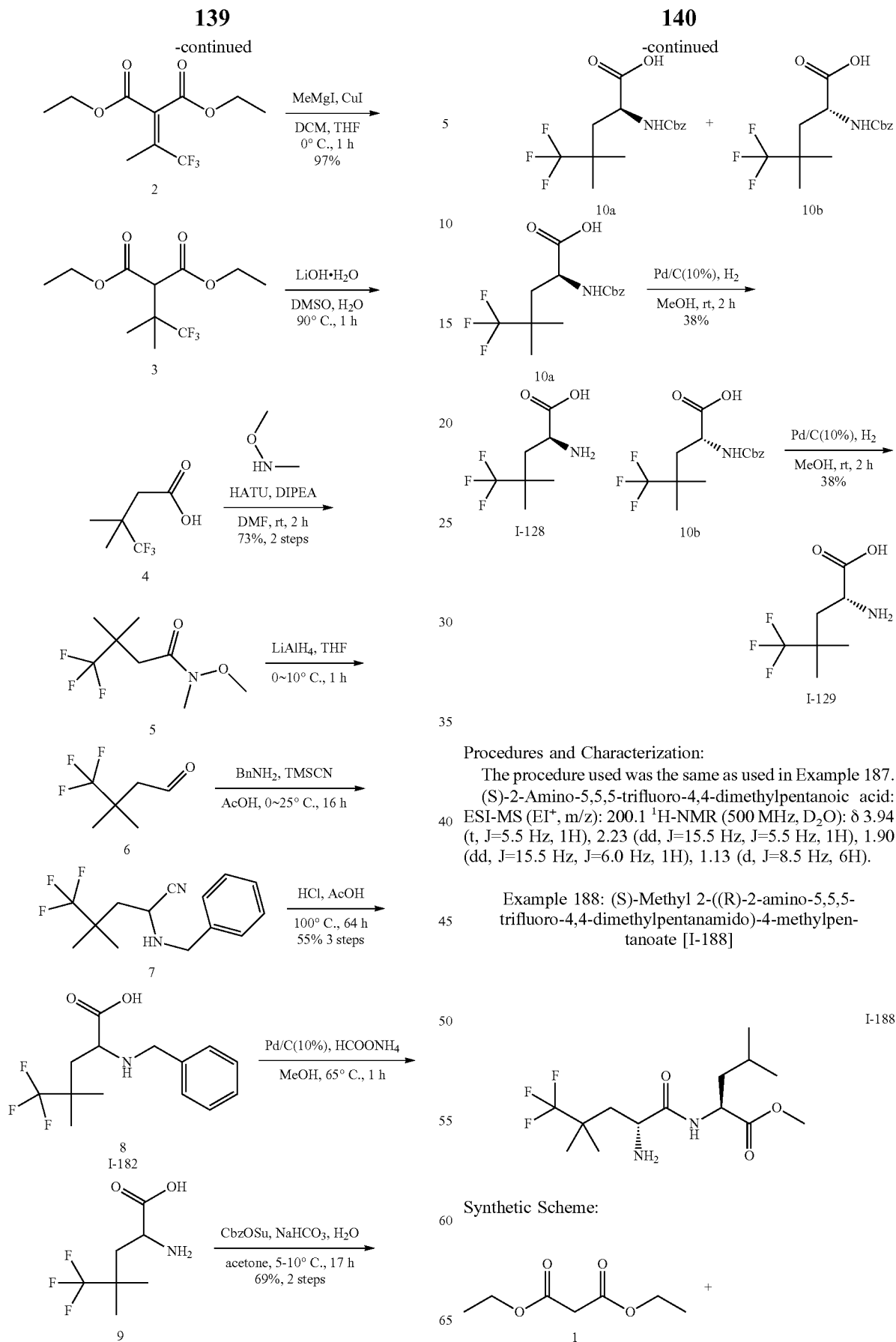
Procedures and Characterization:
The procedure used was the same as used in Example 187.
(S)-2-Amino-5,5,5-trifluoro-4,4-dimethylpentanoic acid: ESI-MS (EI+, m/z): 200.1 $^1$H-NMR (500 MHz, D$_2$O): δ 3.94 (t, J=5.5 Hz, 1H), 2.23 (dd, J=15.5 Hz, J=5.5 Hz, 1H), 1.90 (dd, J=15.5 Hz, J=6.0 Hz, 1H), 1.13 (d, J=8.5 Hz, 6H).
Example 188: (S)-Methyl 2-((R)-2-amino-5,5,5-trifluoro-4,4-dimethylpentanamido)-4-methylpentanoate [I-188]
Synthetic Scheme:

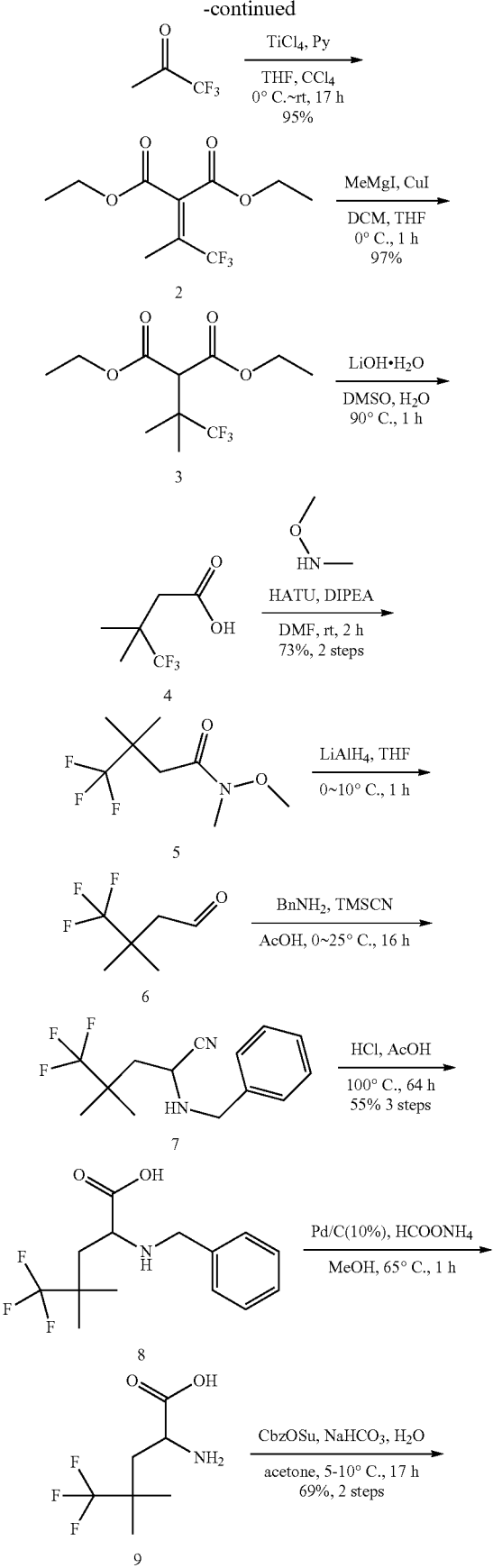

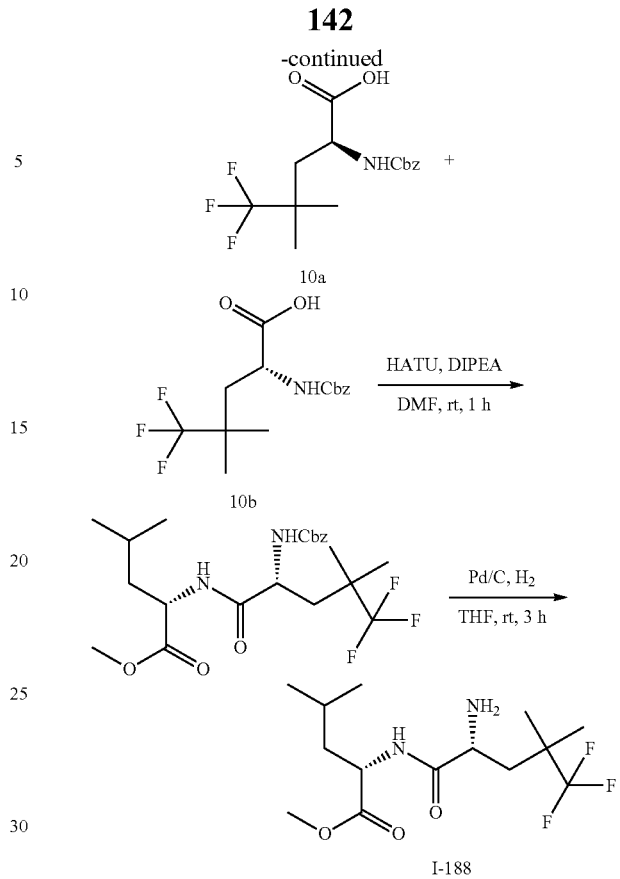

Procedures and Characterization:

The procedure for 2-(benzyloxycarbonylamino)-5,5,5-trifluoro-4,4-dimethylpentanoic acid was same as example 90

Step 1: (S)-methyl 2-((R)-2-(benzyloxycarbonylamino)-5,5,5-trifluoro-4,4-dimethylpentanamido)-4-methylpentanoate The solution of (S)-2-(benzyloxycarbonylamino)-5,5,5-difluoro-4,4-dimethylpentanoic acid (150 mg, 0.45 mmol), HATU (188 mg, 0.495 mmol), (S)-methyl 2-amino-4-methylpentanoate hydrochloride (123 mg, 0.675 mmol) and DIPEA (175 mg, 1.35 mmol) was stirred at rt for 1 hour, then quenched by ice water (20 ml), extracted with EA (2×30 ml), dried, filtered and concentrated. The crude was purified by reverse-phase silica-gel chromatography biotage to obtain (S)-methyl 2-((S)-2-(benzyloxycarbonylamino)-5,5-difluoro-4,4-dimethylpentanamido)-4-methylpentanoate (120 mg, 58%) as a white solid. ESI-MS (EI+, m/z): 461.0

Step 2: (S)-methyl 2-((R)-2-amino-5,5,5-trifluoro-4,4-dimethylpentanamido)-4-methylpentanoate The solution of (S)-methyl 2-((S)-2-(benzyloxycarbonylamino)-5,5,5-difluoro-4,4-dimethylpentanamido)-4-methylpentanoate (120 mg, 0.26 mmol) and Pd/C (30 mg) in THF (10 ml) was stirred at rt for 2 hrs, then filtered, concentrated. The crude was purified by reverse-phase silica-gel chromatography biotage to obtain (S)-methyl 2-((S)-2-amino-5,5,5-trifluoro-4,4-dimethylpentanamido)-4-methylpentanoate (49 mg, 57%) as a white solid. ESI-MS (EI+, m/z): 326.0

¹H-NMR (500 MHz, MeOD-d4): 4.47 (t, J=7.5 Hz, 1H), 3.99-3.97 (m, 1H), 3.77 (s, 3H), 2.33-2.28 (m, 1H), 1.95-1.91 (m, 1H), 1.69-1.68 (m, 3H), 1.24-1.17 (m, 6H), 1.00-0.94 (m, 6H).

Example 189: (S)-methyl 2-((S)-2-amino-5,5,5-trifluoro-4,4-dimethylpentanamido)-4-methylpentanoate [I-189]

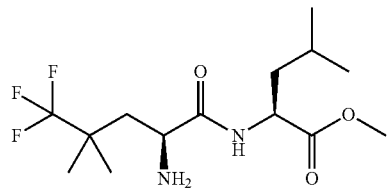

I-189

Synthetic Scheme:
The procedure used was the same as used in Example 188.
Procedures and Characterization:

Example 189: (S)-methyl 2-((S)-2-amino-5,5,5-trifluoro-4,4-dimethylpentanamido)-4-methylpentanoate [I-189]

¹H-NMR (500 MHz, MeOD-d4): 4.52 (t, J=7.5 Hz, 1H), 4.02-3.99 (m, 1H), 3.73 (s, 3H), 2.35-2.30 (m, 1H), 1.95-1.91 (m, 1H), 1.78-1.67 (m, 3H), 1.25 (s, 3H), 1.17 (s, 3H), 1.01-0.97 (m, 6H).

Example 108: (S)-2-amino-6-fluorohexanoic acid [I-108]

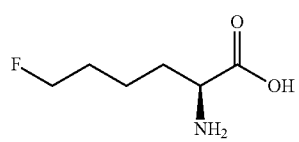

I-108

Example 109: (R)-2-Amino-6-fluorohexanoic acid [I-109]

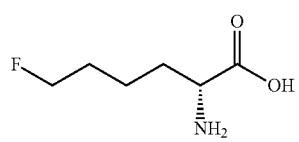

I-109

Synthetic Scheme:

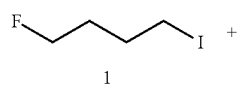

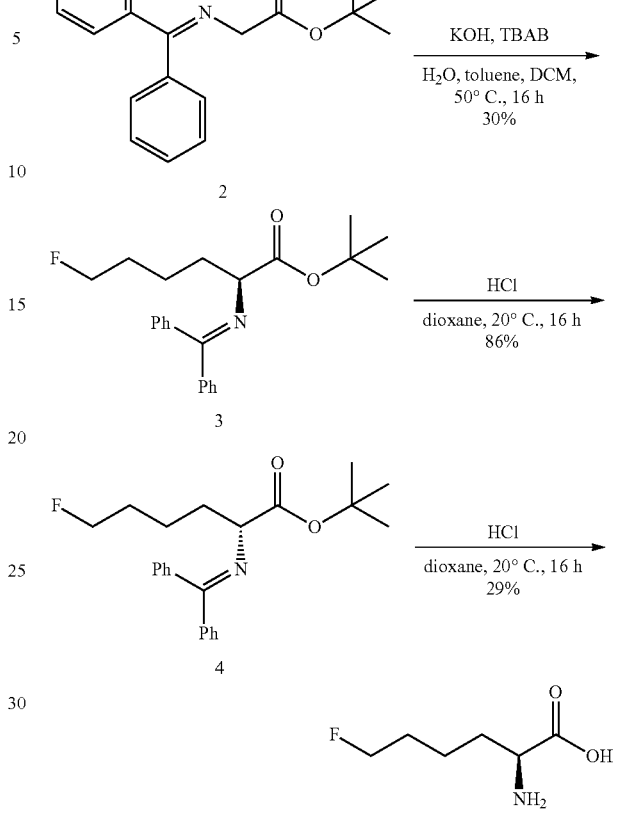

Procedures and Characterization:

Step 1: tert-Butyl 2-(diphenylmethyleneamino)-6-fluorohexanoate

A mixture of 1-fluoro-4-iodobutane (2.0 g, 9.90 mmol), tert-butyl 2-(diphenylmethyleneamino)acetate (2.43 g, 8.25 mmol), TBAB (266 mg, 0.83 mmol) and KOH (aq. 50%) (10 mL) in DCM (10 mL) and toluene (25 mL) was stirred for 16 h at 50° C. The solution was purified by SGC (silica, ethyl acetate/petroleum ether=1/5) to afford (tert-butyl 2-(diphenylmethyleneamino)-6-fluorohexanoate (0.91 g, 2.47 mmol, 30%) as colorless oil. MS (EI+, m/z): 370.2 [M+H]+.

Step 2: (S)-2-Amino-6-fluorohexanoic acid [I-108]

A solution of (S)-tert-butyl 2-(diphenylmethyleneamino)-6-fluorohexanoate (360 mg, 0.97 mmol) in dioxane (10 mL) and HCl (aq. 6M) was stirred for 16 h at rt. The mixture was extracted with ether and water. The water layer was extracted with EA after adjusting pH to 3-4. The org. layer was concentrated to afford (S)-2-amino-6-fluorohexanoic acid [I-108] as white solid (125 mg, 0.84 mmol, 86%). ESI-MS (EI+, m/z): 150.3 [M+H]⁺. 1H NMR (500 MHz, D2O) δ 4.469 (t, J=6.0 Hz, 1H), 4.351 (t, J=6.0 Hz, 1H), 3.950 (t, J=6.0 Hz, 1H), 1.904-1.820 (m, 2H), 1.690-1.588 (m, 2H), 1.456-1.388 (m, 2H).

Step 2: (R)-2-Amino-6-fluorohexanoic acid [I-109]

A solution of (R)-tert-butyl 2-(diphenylmethyleneamino)-6-fluorohexanoate (300 mg, 0.81 mmol) in dioxane (10 mL) and HCl (aq. 6M) was stirred for 16 h at rt. The mixture was extracted with ether and water. The water layer was extracted with EA after adjusting pH to 3-4. The org. layer was purified by HPLC to afford (R)-2-amino-6-fluorohexanoic acid [I-109] as white solid (35 mg, 0.23 mmol, 29%). ESI-MS (EI+, m/z): 150.2 [M+H]⁺. 1H NMR (500 MHz, D2O) δ 4.505 (t, J=6.0 Hz, 1H), 4.410 (t, J=6.0 Hz, 1H), 3.823 (t, J=6.0 Hz, 1H), 1.906-1.827 (m, 2H), 1.722-1.639 (m, 2H), 1.485-1.399 (m, 2H).

Example 198: methyl 2-amino-5,5,5-trifluoro-4-(trifluoromethyl)pentanoate (I-198)

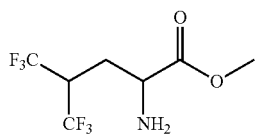

Synthetic Scheme:

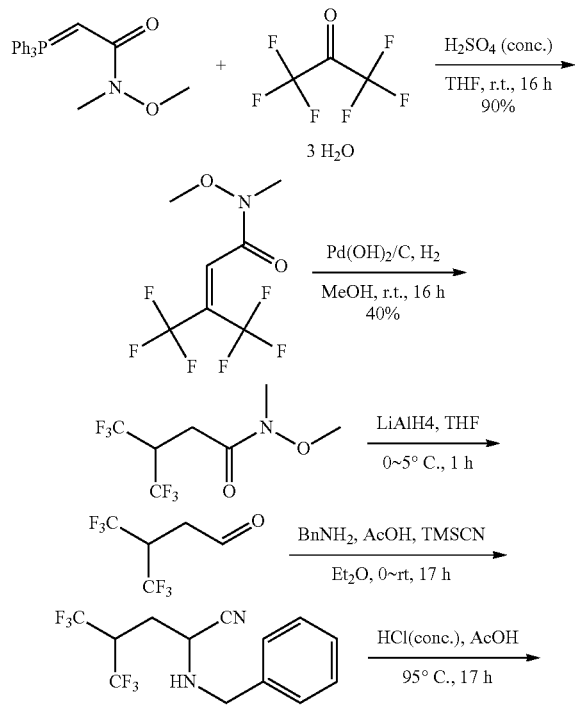

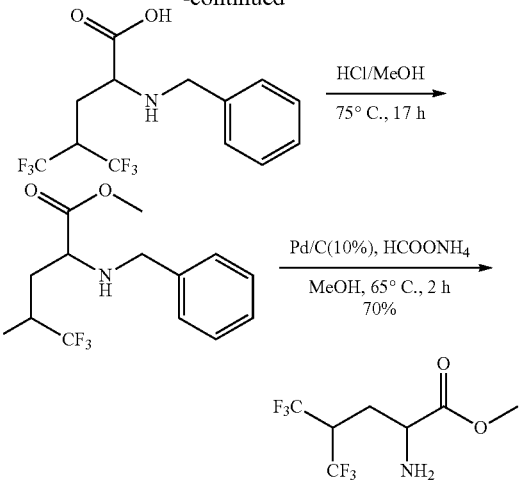

Procedures and Characterization:

Step 1: 4,4,4-Trifluoro-N-methoxy-N-methyl-3-(trifluoromethyl)but-2-enamide

To a stirred solution of Hexafluoroacetone trihydrate (30 g, 136 mmol) was added H₂SO₄ (100 mL, conc.) dropwised slowly over 1 h, and the gaseous Hexafluoroacetone was introduced to the solution of N-methoxy-N-methyl-2-(triphenylphosphoranylidene)-acetamide (10 g, 27.5 mmol) in THF (200 mL). The mixture was stirred at room temperature for 16 hrs. Then Petroleum Ether (200 mL) was added, the white precipitate was filtered off. The filtrate was concentrated, the residue was purified by silica gel chromatography (Petroleum Ether/Ethyl Acetate=5/1~3/1) to afford 4,4,4-trifluoro-N-methoxy-N-methyl-3-(trifluoromethyl)but-2-enamide (6.2 g, 24.7 mmol, 90%) as a slight oil. ESI-MS (EI⁺, m/z): 252.1[M+H]⁺. ¹H-NMR (500 MHz, CDCl₃): δ 7.15 (s, 1H), 3.67 (s, 3H), 3.26 (s, 3H).

Step 2: 4,4,4-Trifluoro-N-methoxy-N-methyl-3-(trifluoromethyl)butanamide

A mixture of 4,4,4-trifluoro-N-methoxy-N-methyl-3-(trifluoromethyl)but-2-enamide (4.5 g, 17.9 mmol), Pd(OH)₂/C (620 mg) in MeOH (100 mL) was stirred at room temperature under hydrogen atmosphere for 16 hrs. Then filtered and concentrated to afford 4,4,4-trifluoro-N-methoxy-N-methyl-3-(trifluoromethyl)butanamide (1.8 g, 7.1 mmol, 40%) as a slight oil. ESI-MS (EI⁺, m/z): 254.1[M+H]⁺.

Step 3: 4,4,4-Trifluoro-3-(trifluoromethyl)butanal

To a solution of 4,4,4-trifluoro-N-methoxy-N-methyl-3-(trifluoromethyl)butanamide (1.8 g, 7.1 mmol) in THF (50 mL) was added dropwise LiAlH₄ (8.5 mL, 8.5 mmol) with ice-bath, after 1 h, the mixture was quenched with citric acid solution (100 mL), the solution was extracted with Et₂O (100 mL×2), the organic phase was washed with brine (100 mL), dried (Na₂SO₄), and the solution was used for the next step.

Step 4: 2-(Benzylamino)-5,5,5-trifluoro-4-(trifluoromethyl)pentanenitrile

To the above solution of 4,4,4-trifluoro-3-(trifluoromethyl)butanal in Et₂O (200 mL) was added benzylamine (2 mL), AcOH (2 mL) and then TMSCN (2 mL) with ice-bath, the solution was stirred at 0~rt for 17 hrs, and then diluted with EtOAc (100 mL). The solution was washed with $H_2O$ (100 mL×2) and then concentrated to afford 2-(benzylamino)-5,5,5-trifluoro-4-(trifluoromethyl)pentanenitrile (2.1 g, crude) as a brown liquid. ESI-MS (EI$^+$, m/z): 311.2 [M+H]$^+$.

Step 5: 2-(Benzylamino)-5,5,5-trifluoro-4-(trifluoromethyl)pentanoic acid

A solution of 2-(benzylamino)-5,5,5-trifluoro-4-(trifluoromethyl)pentanenitrile (2.1 g, crude) in conc. HCl (50 mL) and AcOH (10 mL) was heated to 100° C. for 40 hrs. The mixture was concentrated to remove the solvent, adjusted pH to 12 with 1 M NaOH solution, extracted with PE (100 mL), the aqueous phase was adjusted pH to 5-6 with 6 MHCl, the white solid was formed, filtered, and the filter cake was washed with water (50 mL), dried in vacuum to afford 2-(benzylamino)-5,5,5-trifluoro-4-(trifluoromethyl)pentanoic acid (1.0 g, 3.0 mmol, 42%, 3 steps) as a white solid. ESI-MS (EI$^+$, m/z): 272.0

Step 6: Methyl 2-(benzylamino)-5,5,5-trifluoro-4-(trifluoromethyl)pentanoate

A solution of 2-(benzylamino)-5,5,5-trifluoro-4-(trifluoromethyl)pentanoic acid (800 mg, 2.4 mmol) in HCl/MeOH (50 mL, 2M) was heated to 75° C. for 17 hrs. The solution was concentrated and purified by prep-HPLC (Boston C18 21*250 mm 10 Im Mobile phase: A: 0.1% TFA; B: ACN) to afford methyl 2-(benzylamino)-5,5,5-trifluoro-4-(trifluoromethyl)pentanoate (120 mg, 0.35 mmol, 15%) as a colorless oil. ESI-MS (EI$^+$, m/z): 344.1 [M+H]$^+$.

Step 7: Methyl 2-amino-5,5,5-trifluoro-4-(trifluoromethyl)pentanoate trifluoracetic acid A mixture of methyl 2-(benzylamino)-5,5,5-trifluoro-4-(trifluoromethyl)pentanoate (100 mg, 0.30 mmol), HCOONH$_4$ (92 mg, 1.5 mmol) and Pd/C (10%, 20 mg) in MeOH (10 mL) was heated to 65° C. for 1 h. The mixture was filtered, and the filtrate was concentrated and purified by reverse-phase silica-gel chromatography to afford methyl 2-amino-5,5,5-trifluoro-4-(trifluoromethyl)pentanoate trifluoracetic acid (76 mg, 0.21 mmol, 70%) as a white solid. ESI-MS (EI$^+$, m/z): 254.1 [M+H]$^+$. $^1$H NMR (500 MHz, MeOD-d$_4$) δ 4.26 (dd, J=7.5 Hz, J=6.0 Hz, 1H), 3.91 (m, 4H), 2.49 (dd, J=8.5 Hz, J=5.0 Hz, 1H), 2.33-2.37 (m, 1H).

Example 164: (S)-2-Amino-5,5,5-trifluoro-4-(trifluoromethyl)pentanoic acid (I-164)

I-164

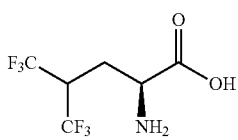

Synthetic Scheme:

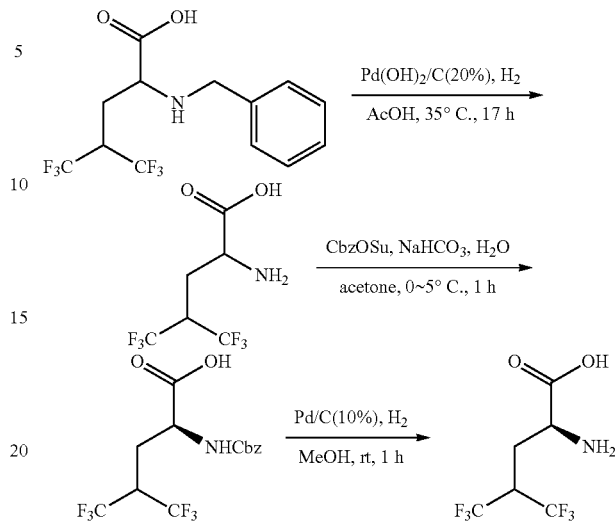

Procedures and Characterization:

Step 1: 2-Amino-5,5,5-trifluoro-4-(trifluoromethyl)pentanoic acid

To a solution of 2-(benzylamino)-5,5,5-trifluoro-4-(trifluoromethyl)pentanoic acid (480 mg, 1.46 mmol) and Pd(OH)$_2$/C (20%, 100 mg) in AcOH (15 mL) was stirred at 35° C. for 17 hrs under hydrogen. The mixture was filtered and the filtrate was concentrated in vacuum to afford 2-amino-5,5,5-trifluoro-4-(trifluoromethyl)pentanoic acid (460 mg, crude) as a white solid. ESI-MS (EI$^+$, m/z): 240.2 [M+H]$^+$.

Step 2: (S)-2-(Benzyloxycarbonylamino)-5,5,5-trifluoro-4-(trifluoromethyl)pentanoic acid To a solution of 2-amino-5,5,5-trifluoro-4-(trifluoromethyl)pentanoic acid (460 mg, crude) and NaHCO$_3$ (368 mg, 4.38 mmol) in acetone (30 mL) and H$_2$O (30 mL) was added CbzOSu (727 mg, 2.92 mmol) with ice-bath. After 17 hrs, the reaction mixture was adjusted pH to 3-4 with 1 MHCl solution, and the solution was extracted with EtOAc (50 mL×2), washed with brine (50 mL), dried (N$_{a2}$SO$_4$), filtered and concentrated in vacuum, the crude product was purified by reverse-phase silica-gel chromatography and then chiral-prep-HPLC [column, CC4 4.6*250 mm 5 um; solvent, MeOH (0.2% Methanol Ammonia)] to afford (S)-2-(benzyloxycarbonylamino)-5,5,5-trifluoro-4-(trifluoromethyl)pentanoic acid (27 mg, 0.072 mmol, 5%, 2 steps) and (R)-2-(benzyloxycarbonylamino)-5,5,5-trifluoro-4-(trifluoromethyl)pentanoic acid (22 mg, 0.059 mmol, 4%, 2 steps) as two colorless oils. ESI-MS (E+, m/z): 396.0 [M+Na]$^+$.

Step 3: (S)-2-Amino-5,5,5-trifluoro-4-(trifluoromethyl)pentanoic acid

A mixture of (S)-2-(benzyloxycarbonylamino)-5,5,5-trifluoro-4-(trifluoromethyl)pentanoic acid (27 mg, 0.072 mmol) and Pd/C (10%, 5 mg) in MeOH (10 mL) was stirred at rt for 1 h. The solution was filtered and purified by reverse-phase silica-gel chromatography to afford (S)-2-amino-5,5,5-trifluoro-4-(trifluoromethyl)pentanoic acid [I-164](8.5 mg, 0.036 mmol, 49%) as a white solid. MS (EI+, m/z): 240.2[M+H]+. 1H NMR (500 MHz, D2O) δ 3.74-3.80 (m, 2H), 2.88-2.31 (m, 1H), 1.91-2.20 (m, 1H).

Example 203: 2-Amino-4-cyclopentylbutanoic acid [I-203]

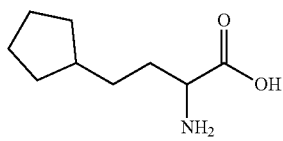

Synthetic Scheme:

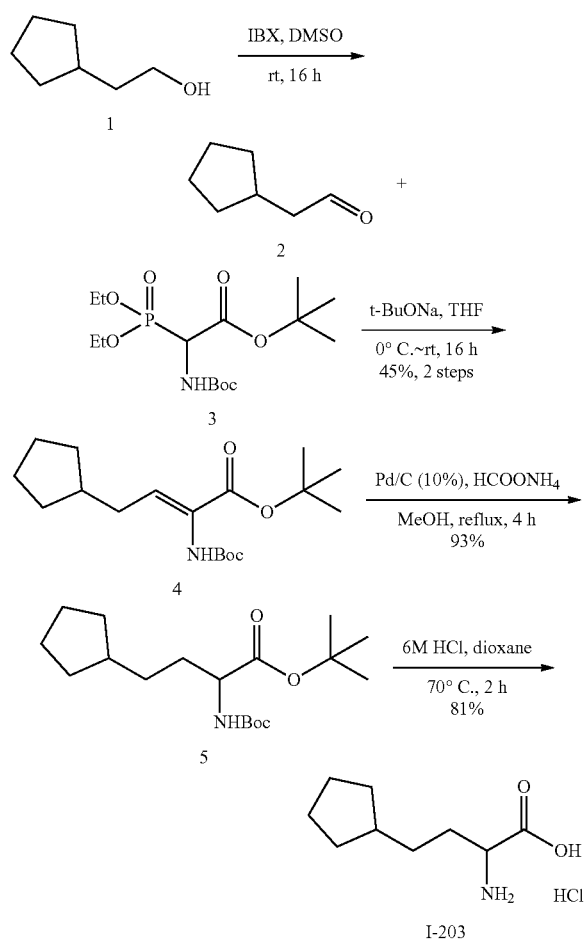

Procedures and Characterization:

Step 1: 2-Cyclopentylacetaldehyde

To a solution of 3-cyclopentylpropan-1-ol (2.0 g, 17.5 mmol) in DMSO (40 mL) was added IBX (7.35 g, 26.3 mmol) under ice-bath. The mixture was warmed to room temperature and stirred overnight. The reaction mixture was poured into water (200 mL) and extracted with Et2O (100 mL×2), the organic phase was washed with water (100 mL×3), and brine (100 mL), dried (Na2SO4), and the solution was used for the next step.

Step 2: (Z)-tert-Butyl 2-(tert-butoxycarbonylamino)-4-cyclopentylbut-2-enoate

To a solution of the witting reagent (2.5 g, 6.8 mmol) in THF (50 mL) was added NaOt-Bu (785 mg, 8.2 mmol) with ice-bath. After 1 h, the above solution of 2-cyclopentylacetaldehyde in Et2O (200 mL) was added. The mixture was warmed to room temperature and stirred overnight. The solution was diluted with water (200 mL) and extracted with EA (100 mL×2), the organic phase was washed with water (100 mL×2), and brine (100 mL), dried (Na2SO4), filtered and concentrated in vacuum and purified by chromatography (silica, ethyl acetate/petroleum ether=1/20) to afford (Z)-tert-butyl 2-(tert-butoxycarbonylamino)-4-cyclopentylbut-2-enoate (1.0 g, 3.1 mmol, 45%, 2 steps) as a colorless liquid. ESI-MS (EI+, m/z): 326.2 [M+H]+.

Step 3: tert-Butyl 2-(tert-butoxycarbonylamino)-4-cyclopentylbutanoate

A mixture of (Z)-tert-butyl 2-(tert-butoxycarbonylamino)-4-cyclopentylbut-2-enoate (240 mg, 0.74 mmol) HCOONH4 (233 mg, 3.7 mmol) and Pd/C (10%, 30 mg) in MeOH (15 mL) was heated to reflux for 4 hrs. The mixture was filtered and concentrated, diluted with Et2O (50 mL), washed with water (50 mL) and brine (50 mL), dried (Na2SO4), filtered and concentrated in vacuum to afford tert-butyl 2-(tert-butoxycarbonylamino)-4-cyclopentylbutanoate (224 mg, 0.69 mmol, 93%) as a colorless liquid. ESI-MS (EI+, m/z): 328.2 [M+H]+.

Step 4: 2-Amino-4-cyclopentylbutanoic acid

A solution of tert-butyl 2-(tert-butoxycarbonylamino)-4-cyclopentylbutanoate (224 mg, 0.69 mmol) in 6 M HCl (20 mL) and dioxane (10 mL) was heated to 70° C. for 2 hrs. The mixture was concentrated in vacuum, diluted with water (30 mL), extracted with Et2O (20 mL×2), and the filtrate was concentrated to dryness to afford 2-amino-4-cyclopentylbutanoic acid (114.9 mg, 0.52 mmol, 81%) as a white solid. ESI-MS (EI+, m/z): 172.3 [M+H]+. 1H-NMR (500 MHz, D2O): δ 3.91 (t, J=6.0 Hz, 1H), 1.82-1.89 (m, 2H), 1.66-1.72 (m, 3H), 1.28-1.52 (m, 6H), 1.00-1.01 (m, 2H).

Example 202: 2-Amino-5-cyclopentylpentanoic acid [I-202]

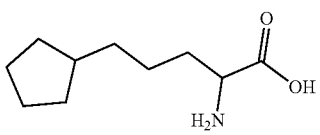

Synthetic Scheme:

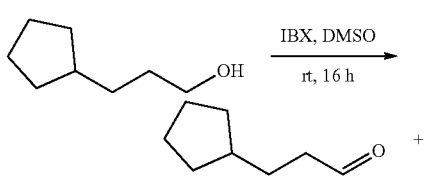

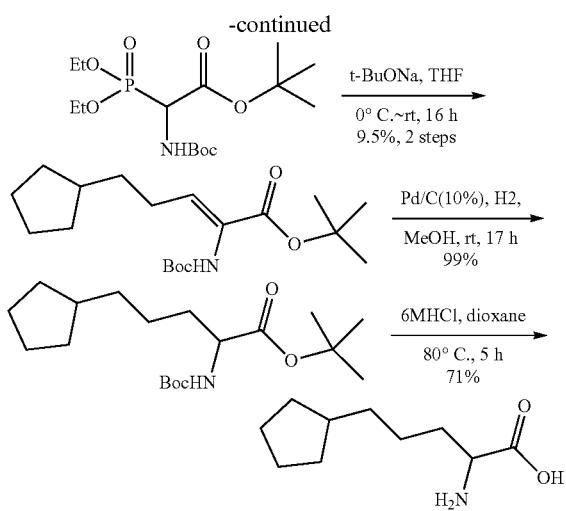

Procedures and Characterization:

Step 1: 3-Cyclopentylpropanal

To a solution of 3-cyclopentylpropan-1-ol (1.0 g, 7.8 mmol) in DMSO (20 mL) was added IBX (3.28 g, 11.7 mmol) under ice-bath. The mixture was warmed to room temperature and stirred overnight. The reaction mixture was poured into water (100 mL) and extracted with $Et_2O$ (60 mL×2), the organic phase was washed with water (100 mL×3), and brine (100 mL), dried ($Na_2SO_4$), and the solution was used for the next step.

Step 2: (E)-tert-Butyl 2-(tert-butoxycarbonylamino)-5-cyclopentylpent-2-enoate To a solution of the witting reagent (500 mg, 1.36 mmol) in THF (15 mL) was added NaOt-Bu (157 mg, 1.63 mmol) with ice-bath. After 1 h, the above solution of 3-cyclopentylpropanal in $Et_2O$ (100 mL) was added. The mixture was warmed to room temperature and stirred overnight. The solution was diluted with water (200 mL) and extracted with EtOAc (100 mL), the organic phase was washed with water (100 mL×2), and brine (100 mL), dried ($Na_2SO_4$), filtered and concentrated in vacuum and purified by chromatography (silica, ethyl acetate/petroleum ether=1/20) to afford (E)-tert-butyl 2-(tert-butoxycarbonylamino)-5-cyclopentylpent-2-enoate (250 mg, 0.74 mmol, 9.5%, 2 steps) as a colorless liquid. ESI-MS (EI$^+$, m/z): 340.2 [M+H]$^+$.

Step 3: tert-Butyl 2-(tert-butoxycarbonylamino)-5-cyclopentylpentanoate

A mixture of 2-(tert-butoxycarbonylamino)-5-cyclopentylpent-2-enoate (250 mg, 0.74 mmol) and Pd/C (10%, 30 mg) in MeOH (15 mL) was stirred at rt for 17 hrs under hydrogen. The mixture was filtered and concentrated to afford tert-butyl 2-(tert-butoxycarbonylamino)-5-cyclopentylpentanoate (250 mg, 0.73 mmol, 99%) as a colorless liquid. ESI-MS (EI$^+$, m/z): 342.2 [M+H]$^+$.

Step 4: 2-Amino-5-cyclopentylpentanoic acid

A solution of 2-(tert-butoxycarbonylamino)-5-cyclopentylpentanoate (250 mg, 0.73 mmol) in 6 MHCl (20 mL) and dioxane (10 mL) was heated to 80° C. for 5 hrs. The mixture was concentrated in vacuum, diluted with water (30 mL), extracted with $Et_2O$ (20 mL×2), and the filtrate was concentrated to dryness to afford 2-amino-5-cyclopentylpentanoic acid (115 mg, 0.52 mmol, 71%) as a white solid. ESI-MS (EI$^+$, m/z): 186.2 [M+H]$^+$. $^1$H-NMR (400 MHz, $D_2O$): δ 3.84 (t, J=6.0 Hz, 1H), 1.79-1.84 (m, 2H), 1.61-1.67 (m, 3H), 1.25-1.49 (m, 8H), 0.95-0.99 (m, 2H).

Example 197: Synthesis of 2-Amino-N-cyclopentyl-3,3-difluoro-N,4-dimethylpentanamide[I-197]

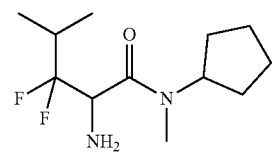

Synthetic Scheme:

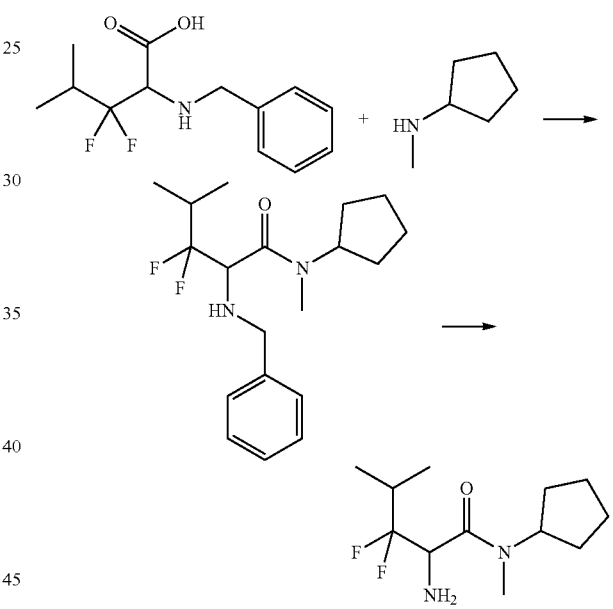

Procedures and Characterization:

Step 1: 2-(Benzylamino)-N-cyclopentyl-3,3-difluoro-N,4-dimethylpentanamide

A mixture of 2-(benzylamino)-3,3-difluoro-4-methylpentanoic acid (80 mg, 0.31 mmol), N-methylcyclopentanamine (62 mg, 0.62 mmol), HATU (141 mg, 0.37 mmol) and $Et_3N$ (94 mg, 0.93) in DMF (2 mL) was stirred at rt for 3 hrs. The mixture was purified by prep-HPLC (Boston C18 21*250 mm 10 Im Mobile phase: A: 0.1% TFA; B: ACN) to afford 2-(benzylamino)-N-cyclopentyl-3,3-difluoro-N,4-dimethylpentanamide (45 mg, 0.13 mmol, 43%) as a white solid. ESI-MS (EI$^+$, m/z): 339.0

Step 2: 2-Amino-N-cyclopentyl-3,3-difluoro-N,4-dimethylpentanamide

A mixture of 2-(benzylamino)-N-cyclopentyl-3,3-difluoro-N,4-dimethylpentanamide (45 mg, 0.13 mmol), HCOONH₄ (41 mg, 0.65 mmol) and Pd/C (10%, 10 mg) in MeOH (5 mL) was heated to 60° C. for 1 h. The mixture was filtered, and the filtrate was concentrated and purified by reverse-phase silica-gel chromatography to afford 2-amino-N-cyclopentyl-3,3-difluoro-N,4-dimethylpentanamide (16.3 mg, 0.066 mmol, 49%) as a white solid. ESI-MS (EI⁺, m/z): 249.2 1H NMR (500 MHz, MeOD-d₄) δ 5.26 (dd, J=15.5 Hz, J=6.0 Hz, 0.5H), 5.08 (dd, J=16.5 Hz, J=5.0 Hz, 1H), 4.28-4.31 (m, 0.5H), 2.97 (d, J=48.5 Hz, 3H), 2.38 (m, 1H), 1.65-1.99 (m, 8H), 11.16 (dt, J=6.5 Hz, J=3.0 Hz, 6H).

Example 196:
2-Amino-5-fluoro-4,4-dimethylpentanoic acid
[I-196]

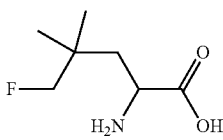

I-196

Synthetic Scheme:

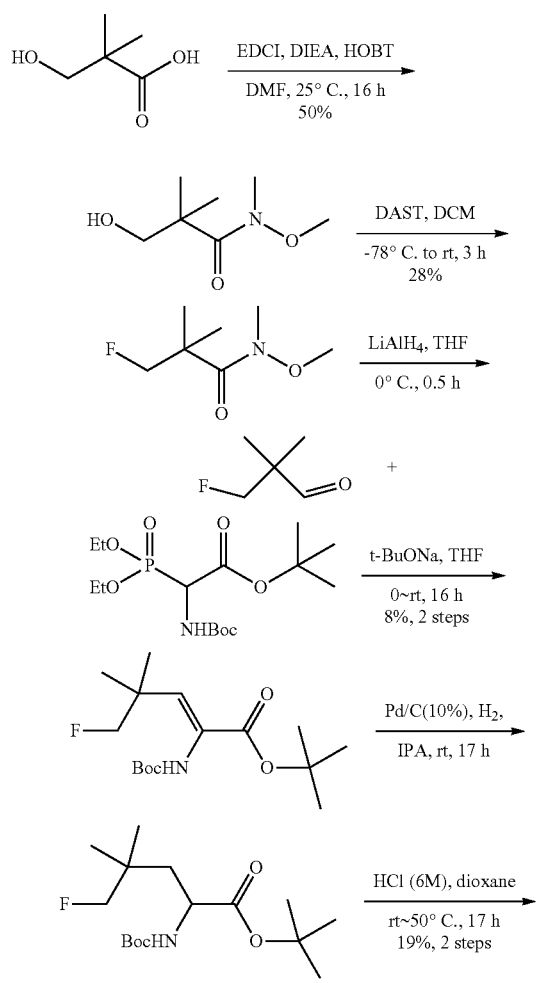

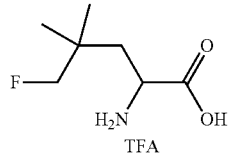

Procedures and Characterization:

Step 1:
3-Hydroxy-N-methoxy-N,2,2-trimethylpropanamide

The mixture of 3-hydroxy-2,2-dimethylpropanoic acid (10 g, 84.7 mmol), N,O-dimethylhydroxylamine hydrochloride (16.4 g, 101.7 mmol), EDCI (24.4 g, 127.1 mmol), HOBT (17.2 g, 127.1 mmol) and DIPEA (28 mL, 169.5 mmol) in DMF (200 mL) was stirred at rt for 16 hrs. The reaction mixture was extracted with EtOAc (200 mL×3) and water (100 mL), combined the organic layers which washed with 1 N HCl (30 mL*2), 1 N NaHCO₃ (30 mL×2) and brine (50 mL), dried, concentrated to afford a residue which purified by chromatography (silica, ethyl acetate/petroleum ether=1/2) to afford 3-hydroxy-N-methoxy-N,2,2-trimethylpropanamide (6.9 g, 50%) as a colorless oil. ESI-MS (EI⁺, m/z): 162.2 [M+H]⁺.

Step 2:
3-Fluoro-N-methoxy-N,2,2-trimethylpropanamide

To a mixture of 3-hydroxy-N-methoxy-N,2,2-trimethylpropanamide (4.5 g, 27.9 mmol) in DCM (40 mL), cooled to −78° C. was added DAST (7.4 mL, 55.9 mmol) dropwise. Then stirred at rt for 1-2 h, cooled to −78° C. again, DAST (4 mL, 27.9 mmol) was added dropwise. The reaction mixture was stirred at rt for further 1 h. The reaction mixture was being cooled to −78° C., sat.NH₄Cl (15 mL) was added slowly, DCM (50 mL) was added, separated the organic layer, washed with sat.NH₄Cl (30 mL), brine (30 mL×2), dried, concentrated to give a residue which purified by chromatography (silica, ethyl acetate/petroleum ether=1/4) to afford 3-fluoro-N-methoxy-N,2,2-trimethylpropanamide (1.9 g, 28%) as a colorless oil. ESI-MS (EI⁺, m/z): 164.2 [M+H]⁺.

Step 3: 3-Fluoro-2,2-dimethylpropanal

To a mixture of 3-fluoro-N-methoxy-N,2,2-trimethylpropanamide (1.0 g, 61.3 mmol) in THF (10 mL), cooled to 0° C. was added LiAlH₄ (6.1 mL, 61.3 mmol, 1 M in THF) dropwise. Then stirred at this temperature for 0.5-1 h. Sat. NH₄Cl (10 mL) was added slowly, extracted with Et₂O (20 mL×3), washed with water (15 mL×2) and brine (15 mL), dried, used for the next step directly. ESI-MS (EI⁺, m/z): no MS.

Step 4: (Z)-tert-Butyl 2-(tert-butoxycarbonylamino)-5-fluoro-4,4-dimethylpent-2-enoate The mixture of 3-fluoro-2,2-dimethylpropanal (about 630 mg, 6.1 mmol, Et₂O solution from above step), tert-butyl 2-(tert-butoxycarbonylamino)-2-diethoxyphosphoryl-acetate (2.25 g, 6.1 mmol) and t-BuONa (1.2 g, 12.3 mmol) in THF (15 mL) was stirred at rt for 16 hrs. Sat.NH₄Cl (15 mL) was added, extracted with EA (30 mL×3), combined with organic layers, washed with water (15 mL) and brine (15 mL), dried, concentrated to give a residue which purified by chromatography (silica, petroleum ether to DCM) to afford (Z)-tert-butyl 2-(tert-butoxycarbonylamino)-5-fluoro-4,4-dimethylpent-2-enoate (190 mg, 0.60 mmol, 8%) as a white solid. ESI-MS (EI+, m/z): 206 [M−111]⁺.

Step 5: tert-Butyl 2-(tert-butoxycarbonylamino)-5-fluoro-4,4-dimethylpentanoate

A mixture of (Z)-tert-butyl 2-(tert-butoxycarbonylamino)-5-fluoro-4,4-dimethylpent-2-enoate (190 mg, 0.60 mmol) and Pd/C (10%, 30 mg) in IPA (15 mL) was stirred at rt for 17 hrs under hydrogen. The mixture was filtered and concentrated to afford tert-butyl 2-(tert-butoxycarbonylamino)-5-fluoro-4,4-dimethylpentanoate (200 mg, crude) as a colorless liquid. ESI-MS (EI⁺, m/z): 342.2 [M+Na]⁺.

Step 6: 2-Amino-5-fluoro-4,4-dimethylpentanoic acid trifluoroacetic acid

A solution of tert-butyl 2-(tert-butoxycarbonylamino)-5-fluoro-4,4-dimethylpentanoate (200 mg, crude) in 6MHCl (20 mL) and dioxane (10 mL) was heated to 50° C. for 17 hrs. The mixture was concentrated in vacuum, diluted with water (30 mL), extracted with Et₂O (20 mL×2), and the filtrate was concentrated in vacuum and purified by reverse-phase silica-gel chromatography to afford 2-amino-5-cyclopentylpentanoic acid trifluoroacetic acid (31.7 mg, 0.11 mmol, 19%) as a white solid. ESI-MS (EI⁺, m/z): 164.2 [M+H]+. ¹H-NMR (500 MHz, D₂O): δ 4.16 (d, J=47.5 Hz, 1H), 3.97 (t, J=5.5 Hz, 1H), 2.03 (dd, J=15.5 Hz, J=5.5 Hz, 1H), 1.71 (dd, J=15.5 Hz, J=6.0 Hz, 1H), 0.91 (dd, J=15.0 Hz, J=2.0 Hz, 6H).

Example 186: Synthesis of 2,4-Diamino-4-methylpentanoic acid [I-186]

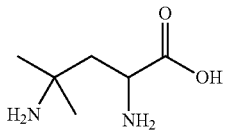

I-186

Synthetic Scheme:

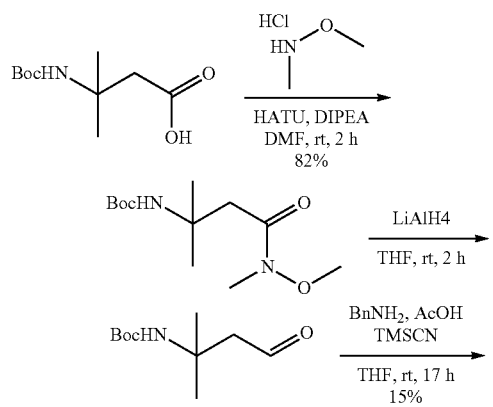

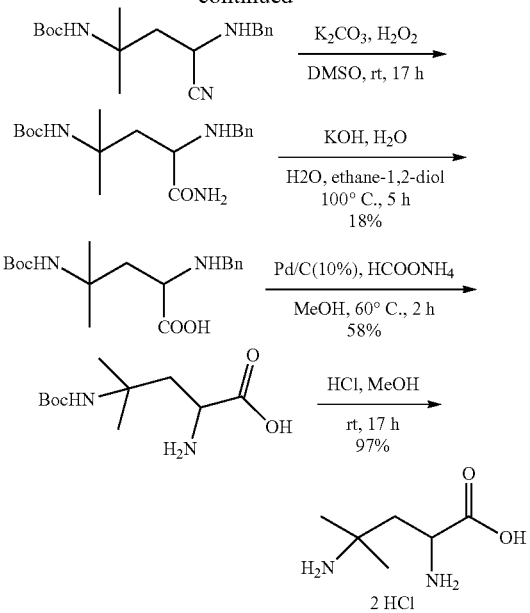

Procedures and Characterization:

Step 1: tert-Butyl 4-(methoxy(methyl)amino)-2-methyl-4-oxobutan-2-ylcarbamate

A solution of 3-(tert-butoxycarbonylamino)-3-methylbutanoic acid (1 g, 4.61 mmol), N,O-dimethylhydroxylamine hydrochloride (536 mg, 5.53 mmol), HATU (2.26 g, 5.99 mmol), in DMF (15 mL) was added DIPEA (1.49 g, 11.53 mmol). The solution was stirred at rt for 2 hrs, Then, the mixture was diluted by brine (100 mL), extracted by EtOAc (50 mL×2). The combined the organic layers, concentrated and purified by chromatography (silica, ethyl acetate/petroleum ether=1/3) to afford tert-butyl 4-(methoxy(methyl)amino)-2-methyl-4-oxobutan-2-ylcarbamate (1.0 g, 3.8 mmol, 82%) as a colourless oil. ESI-MS (EI⁺, m/z): 261.2 [M+H]⁺.

Step 2: tert-Butyl 2-methyl-4-oxobutan-2-ylcarbamate

A solution of tert-butyl 4-(methoxy(methyl)amino)-2-methyl-4-oxobutan-2-ylcarbamate (3.8 g, 14.6 mmol) in THF (50 mL) was added LiAlH₄ (16 mL, 1 M in THF) at r.t. The solution was stirred at rt for 2 hrs, quenched by Na₂SO₄.10H₂O, filtered and washed by THF to afford tert-butyl 2-methyl-4-oxobutan-2-ylcarbamate as a yellow solution (about 14 mmol in 110 mL THF). MS (EI⁺, m/z): 146.3 [M+H-56]⁺.

Step 3: tert-Butyl 4-(benzylamino)-4-cyano-2-methylbutan-2-ylcarbamate

A solution of tert-butyl 2-methyl-4-oxobutan-2-ylcarbamate (crude about 14 mmol in 110 mL of THF) was added BnNH₂ (2.2 mL) and AcOH (2.2 mL). The solution was stirred at rt for 10 mins. TMSCN (2.2 mL) was added. The mixture was stirred at rt for 17 hrs. Then, the reaction mixture was concentrated and by chromatography (silica, ethyl acetate/petroleum ether=1/4) to afford tert-butyl 4-(benzylamino)-4-cyano-2-methylbutan-2-ylcarbamate (670 mg, 2.11 mmol, 15%) as a yellow dope. MS (EI+, m/z): 318.3 [M+H]+.

Step 4: tert-Butyl 5-amino-4-(benzylamino)-2-methyl-5-oxopentan-2-ylcarbamate A mixture of tert-butyl 4-(benzylamino)-4-cyano-2-methylbutan-2-ylcarbamate (640 mg, 2.00 mmol), $K_2CO_3$ (550 mg, 3.98 mmol) in DMSO (16 mL) was added 30% $H_2O_2$ (0.64 mL, 5.67 mmol) and stirred for 17 hrs at r.t. Then, the reaction mixture was diluted by $H_2O$ (200 mL), extracted by EtOAc (100 mL×2). The combined the organic layers were concentrated to afford 2-(benzylamino)-4-(tert-butoxycarbonylamino)-4-methylpentanoic acid (crude 890 mg) as a yellow dope. MS (EI+, m/z): 336.0 [M+H]+.

Step 5: 2-(Benzylamino)-4-(tert-butoxycarbonylamino)-4-methylpentanoic acid

A mixture of tert-butyl 5-amino-4-(benzylamino)-2-methyl-5-oxopentan-2-ylcarbamate (crude 890 mg, about 2.0 mmol), KOH (406 mg, 7.25 mmol) in ethane-1,2-diol (9 mL) and $H_2O$ (9 mL) was stirred for 5 hrs at 100° C. Then, the reaction mixture was diluted by brine (200 mL), extracted by THF/EA=2:1 (90 mL×5), combined the organic layers, concentrated and purified by reverse-HPLC (Boston C18 21*250 mm 10 μm, Mobile phase: A: 0.1% trifluoroacetic acid; B: acetonitrile) to afford 2-(benzylamino)-4-(tert-butoxycarbonylamino)-4-methylpentanoic acid (120 mg, 0.36 mmol, 18%) as a white solid. MS (EI+, m/z): 337.3 [M+H]+.

Step 6: 2-Amino-4-(tert-butoxycarbonylamino)-4-methylpentanoic acid

A mixture of 2-(benzylamino)-4-(tert-butoxycarbonylamino)-4-methylpentanoic acid (140 mg, 0.42 mmol), $HCOONH_4$ (132 mg, 2.1 mmol) and Pd/C (10%, 20 mg) in MeOH (15 mL) was heated to 60° C. for 1 h. The mixture was filtered, and the filtrate was concentrated and purified by reverse-phase silica-gel chromatography to afford 2-amino-4-(tert-butoxycarbonylamino)-4-methylpentanoic acid (60 mg, 0.24 mmol, 58%) as a white solid. ESI-MS (EI+, m/z): 247.2

Step 7: 2,4-Diamino-4-methylpentanoic acid

A solution of 2-amino-4-(tert-butoxycarbonylamino)-4-methylpentanoic acid (60 mg, 0.24 mmol) in 6 M HCl (10 mL) and dioxane (0 mL) was stirred at rt for 17 hrs. The solution was concentrated in vacuum to afford 2,4-diamino-4-methylpentanoic acid (51.8 mg, 0.236 mmol, 97%) as a white solid. ESI-MS (EI+, m/z): 147.1 1H NMR (500 MHz, $D_2O$) δ 4.04 (dd, J=9.5 Hz, J=3.5 Hz, 1H), 2.32 (dd, J=15.0 Hz, J=9.5 Hz, 1H), 1.94 (dd, J=15.0 Hz, J=3.0 Hz, 1H), 1.38 (dd, J=9.5 Hz, J=5.0 Hz, 6H).

Example 199: Synthesis of 4,4,4-Trifluoro-3-methyl-1-(2H-tetrazol-5-yl)butan-1-amine [I-199]

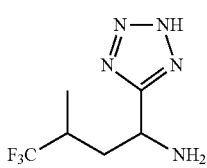

I-199

Synthetic Scheme:

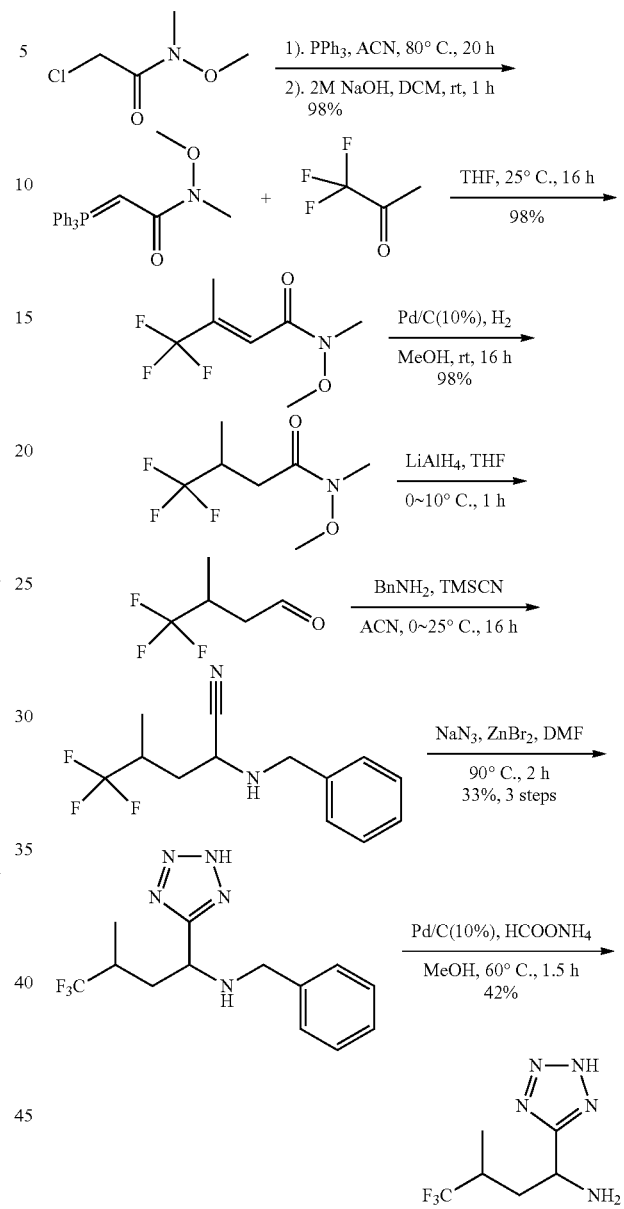

Procedures and Characterization:

Step 1: N-Methoxy-N-methyl-2-(triphenyl-15-phosphanylidene)acetamide

A mixture of 2-chloro-N-methoxy-N-methylacetamide (13.7 g, 0.1 mol) and triphenylphosphane (26.2 g, 0.1 mol) in acetonitrile (200 mL) was heated to 80° C. and held for 20 hrs. The mixture was cooled and concentrated to remove the solvent below 40° C. The residue was dissolved in dichloromethane (200 mL), followed by 2 N KOH (100 mL). The resulting mixture was stirred at 20° C. for 1 h. The organic layer was washed with brine (200 mL×3), dried over $Na_2SO_4$ and filtered. The filtrate was concentrated in vacuum to afford N-methoxy-N-methyl-2-(triphenyl-15-phosphanylidene) acetamide (36 g, 0.1 mol, 98%) as a yellow solid. ESI-MS (EI+, m/z): 364.4 [M+H]+.

Step 2: (E)-4,4,4-Trifluoro-N-methoxy-N,3-dimethylbut-2-enamide

A mixture of N-methoxy-N-methyl-2-(triphenyl-15-phosphanylidene) acetamide (36.3 g, 0.1 mol) and 1, 1, 1-trifluoropropan-2-one (22.4 g, 0.2 mol) in tetrahydrofuran (500 mL) was heated to 20° C. and held for 20 hrs. The mixture was cooled and concentrated to remove the solvent below 40° C. in vacuum. The residue was purified by silica gel column (200 g, 200~300 mesh, UV 254 nm) eluting with ethyl acetate in petroleum ether from 0 to 25% to afford (E)-4,4,4-trifluoro-N-methoxy-N,3-dimethylbut-2-enamide (19.5 g, 0.1 mol, 98%) as a yellow oil. ESI-MS (EI$^+$, m/z): 198.2 [M+H]$^+$.

Step 3: 4,4,4-Trifluoro-N-methoxy-N,3-dimethylbutanamide

A mixture of (E)-4, 4, 4-trifluoro-N-methoxy-N,3-dimethylbut-2-enamide (2 g, 0.01 mol) and Pd/C (10%, 200 mg) in THF (50 mL) was stirred at 26° C. for 18 hrs. The mixture was filtered, and the filtrate was concentrated in vacuum to dryness to afford 4,4,4-trifluoro-N-methoxy-N,3-dimethylbutanamide (2 g, 0.01 mol, 98%) as a yellow oil. ESI-MS (EI$^+$, m/z): 200.2 [M+H]$^+$.

Step 4: 4,4,4-trifluoro-3-methylbutanal

To a solution 4,4,4-trifluoro-N-methoxy-N,3-dimethylbutanamide (2 g, 0.01 mol) in 40 mL of THF was added LiAlH$_4$ (0.4 g, 0.01 mol) at 0° C. The mixture was stirred at 0° C. for 1 h. The reaction mixture was quenched with water, followed by methyl tert-butyl ether (30 mL×2). The organic layer was washed with brine (50 mL×3), dried over Na$_2$SO$_4$ and filtered. The filtrate was contained to afford 4,4,4-trifluoro-3-methylbutanal (1.4 g, crude) as a colorless solution, which was used into next step directly.

Step 5: 2-(Benzylamino)-5, 5, 5-trifluoro-4-methylpentanenitrile

To a solution of above 4,4,4-trifluoro-3-methylbutanal in methyl tert-butyl ether (100 mL) was added benzylamine (1.5 mL), AcOH (1.0 mL) and then TMSCN (1.5 mL) with ice-bath. The mixture was warmed 20° C. and stirred overnight. The solution was diluted with water (30 mL) and extracted with EtOAc (30 mL). The organic phase was washed with water (30 mL×2), and brine (50 mL), dried (Na$_2$SO$_4$), filtered and concentrated in vacuum to afford 2-(benzylamino)-5, 5, 5-trifluoro-4-methyl pentanenitrile (2.6 g, crude) as a brown oil which was used for the next step. ESI-MS (EI$^+$, m/z): 257.3 [M+H]$^+$.

Step 6: N-Benzyl-4,4,4-trifluoro-3-methyl-1-(2H-tetrazol-5-yl)butan-1-amine

To a solution of 2-(benzylamino)-5,5,5-trifluoro-4-methylpentanenitrile (0.3 g, crude) in DMF (10 mL) was added NH$_4$Cl (0.15 g, 0.003 mol) and NaN$_3$ (0.21 g, 0.003 mol) was heated to 95° C. for 18 hrs. The solution was cooled to 15° C. and extracted with EtOAc (20 mL), the organic phase was washed with water (20 mL×2), and brine (20 mL), dried (Na$_2$SO$_4$), filtered and concentrated in vacuum to afford N-benzyl-4,4,4-trifluoro-3-methyl-1-(2H-tetrazol-5-yl)butan-1-amine (0.1 g, 0.5 mmol, 33% for 3 steps) as a white solid. ESI-MS (EI$^+$, m/z): 300.3 [M+H]$^+$.

4,4,4-Trifluoro-3-methyl-1-(2H-tetrazol-5-yl)butan-1-amine trifluoracetic acid To a solution of N-benzyl-4,4,4-trifluoro-3-methyl-1-(2H-tetrazol-5-yl)butan-1-amine (160 mg, 0.54 mmol) in MeOH (15 mL) was added HCOONH$_4$ (0.17 g, 2.7 mmol) and Pd/C (30 mg) at rt. The mixture was stirred at 60° C. for 2 hrs. The reaction mixture was filtered and concentrated to give a crude product which was purified by reverse-phase silica-gel chromatography to give 4,4,4-trifluoro-3-methyl-1-(2H-tetrazol-5-yl)butan-1-amine trifluoracetic acid (72.8 mg, 0.23 mmol, 42%) as a white solid; ESI-MS (EI$^+$, m/z): 210.2 [M+H]$^+$; 1H NMR (500 MHz, DMSO-d$_6$) δ 4.67-4.93 (m, 1H), 2.31-2.41 (m, 1H), 2.00-2.12 (m, 2H), 0.99 (dd, J=16.8, J=6.4 Hz, 6H).

Example 210 Western Blot Assay

This screening assay measured test compound activity in vitro on GATOR2/Sestrin2 complexes purified via immunoprecipitation of stably expressed FLAG-WDR24 from HEK293T cells. HEK293T cells (293 Ts) were engineered to stably express N-terminally tagged FLAG-WDR24 via transduction by lentivirus. Lentiviruses were produced by co-transfection of the lentiviral transfer vector pLJM60 with the AVPR envelope and CMV VSV-G packaging plasmids into HEK-293T cells using the XTremeGene 9 transfection reagent (Roche Diagnostics). The media was changed 24 hours post-transfection to Dulbecco's Modified Eagle's media (DMEM) supplemented with 30% Inactivated Fetal Serum. The virus-containing supernatants were collected 48 and 72 hours after transfection and passed through a 0.45 m filter to eliminate cells. Target cells in 6-well tissue culture plates were infected in media containing 8 g/mL polybrene and spin infections were performed by centrifugation at 2,200 rpm for 1 hour. Twenty-four hours after infection, the virus was removed and the cells selected with the appropriate antibiotic. Cells were then grown in DMEM supplemented with 10% fetal bovine serum and antibiotics.

To screen for leucine mimetic compounds, 2,000,000 FLAG-WDR24 expressing 293T cells were plated in a 10 cm tissue culture plate. Seventy-two hours later, cells were placed in standard RPMI media formulated with no amino acids and supplemented with 5 mM Glucose (-AA RPMI, US Biological Life Sciences) for 1 hour then subsequently lysed in lysis buffer (40 mM HEPES, 1% Triton, 10 mM sodium β-glycerophosphate, 10 mM sodium pyrophosphate, 2.5 mM MgCl2 and protease inhibitors). To isolate the FLAG-WDR24/endogenous-Sestrin2 complex, crude lysate (equivalent to 2-4 mg of total protein) in a volume of 1 ml was subjected to immunoprecipitation with 30 μl of anti-flag resin (SIGMA) for 2 hours at 4° C., washed twice in cold lysis buffer plus 0.5M NaCl and resuspended in 1 ml of cold cytosolic buffer (40 mM HEPES pH 7.4, 140 mM KCl, 10 mM NaCl, 2.5 mM MgCl2, 0.1% TritonX-100). Test compounds or controls (resulting solution was filtered or leucine) were then added to each immunoprecipitation sample at various concentrations and incubated with rotation at 4° C. for 60 minutes. After the incubation period, samples were centrifuged to pellet the FLAG-WDR24/endogenous-Sestrin2 complex bound to the anti-flag resin, the supernatant was completely removed and resin was resuspended in SDS-PAGE sample buffer and boiled for 5 minutes. Samples were then processed by SDS-PAGE and western blots were performed with anti-FLAG (SIGMA) and anti-Sestrin2 (Cell Signaling Technology) antibodies as described in L. Chantranupong, et al., Cell Reports 9:1-8 (2014).

The resulting western blots were scanned and band intensities corresponding to Sestrin2 and FLAG-WDR24 were quantified using the LI-COR® imaging platform. To determine the amount of Sestrin2 bound to GATOR2 for each condition, the band intensity for Sestrin2 was normalized to the band intensity of FLAG-WDR24. For every batch of compounds tested, a negative control (resulting solution was filtered) and a positive control (leucine, 25 µM, SIGMA) were also performed. The depletion of bound endogenous Sestrin2 to FLAG-WDR24 by leucine was normalized to represent 100% activity. Compounds were assayed in duplicate and activity of each compound was quantified as percent of leucine activity and averaged. Repeated attempts of the assay resulted in a standard deviation of 20% in the average activity of leucine compared to water; therefore, test compounds that reduce the amount of Sestrin2 bound to GATOR2 by at least 40% at 25 µM in duplicate were considered statistically significant and were characterized as leucine mimetics. Some compounds increased the amount of Sestrin2 bound to FLAG-WDR24. Compounds that increased the amount of Sestrin2 bound to GATOR2 by more than 40% (represented as less than −40% of leucine activity) were characterized as leucine antagonists.

Example 211. Method of Identifying Compounds that Mimic or Antagonize the Activity of Leucine Upon Sestrin2 and the Sestrin2/GATOR2 Interaction Introduction Sestrin1 and Sestrin2 interact with GATOR2 via the GATOR2 components WDR24 and Seh1L under insufficient leucine levels. Under leucine sufficient conditions, leucine directly binds Sestrin2 inducing the disassociation of Sestrin2 from GATOR2. The goal of the following methods is to identify compounds that mimic the effect of leucine in binding to Sestrin2 and disrupting the Sestrin2/GATOR2. In addition, the methods identify compounds that antagonize leucine binding to Sestrin2 and prevent the disassociation of Sestrin2 from GATOR2 in response to leucine.

Method 1 (In Vitro PPI Assay)

This screening assay measured compound activity in vitro on GATOR2/Sestrin2 complexes purified via immunoprecipitation of stably expressed Flag-WDR24 from HEK293T cells. HEK293T cells (293 Ts) were engineered to stably express N-terminally tagged Flag-WDR24 via transduction by lentivirus. Lentiviruses were produced by co-transfection of the lentiviral transfer vector pLJM60 with the AVPR envelope and CMV VSV-G packaging plasmids into HEK-293T cells using the XTremeGene 9 transfection reagent. The media was changed 24 hours post-transfection to Dulbecco's Modified Eagle's media (DMEM) supplemented with 30% Inactivated Fetal Serum The virus-containing supernatants were collected 48 and 72 hours after transfection and passed through a 0.45 m filter to eliminate cells. Target cells in 6-well tissue culture plates were infected in media containing 8 g/mL polybrene and spin infections were performed by centrifugation at 2,200 rpm for 1 hour. 24 hours after infection, the virus was removed and the cells selected with the appropriate antibiotic. Cells are then grown in DMEM supplemented with 10% fetal bovine serum and antibiotics.

To screen for leucine mimetic compounds, 2,000,000 Flag-WDR24 expressing 293 Ts are plated in a 10 cm tissue culture plate. 72 hours later, cells were placed in standard RPMI media formulated with no amino acids and supplemented with 5 mM Glucose (-AA RPMI, USBiological Life Sciences) for 1 hour then subsequently lysed in lysis buffer (40 mM HEPES, 1% Triton, 10 mM Sodium Beta-Glycerophosphate, 10 mM Sodium Pyrophosphate, 2.5 mM MgCl2 and protease inhibitors). The Flag-WDR24/endogenous-Sestrin2 complex was isolated as follows: crude lysate (equivalent to 2-4 mg of total protein) in a volume of 1 ml was subjected to immunoprecipitation (IP) with 30 µl of anti-flag resin (SIGMA) for 2 hours at 4° C., washed twice in cold lysis buffer plus 0.5M NaCl and resuspended in 1 ml of cold cytosolic buffer (40 mM HEPES pH 7.4, 140 mM KCl, 10 mM NaCl, 2.5 mM $MgCl_2$, 0.1% TritonX-100). Compounds were then added to each sample at a given concentration of 25 µM and incubated with rotation at 4° C. for 30 minutes. After the incubation period, samples were centrifuged to pellet the Flag-WDR24/endogenous-Sestrin2 complex bound to the anti-flag resin, the supernatant was completely removed and resin was resuspended in sodium dodecyl sulfate-polyacrylamide gel electrophoresis (SDS-PAGE) sample buffer and boiled for 5 minutes. Samples were then processed by SDS-PAGE and western blots are performed with anti-Flag (SIGMA) and anti-Sestrin2 (Cell Signaling Technology) antibodies as described in L. Chantranupong, et al., Cell Reports 9:1-8 (2014).

The resulting western blots were scanned and band intensities corresponding to Sestrin2 and Flag-WDR24 were quantified using the LI-COR® imaging platform. To determine amount of Sestrin2 bound to GATOR2 for each condition, the band intensity for Sestrin2 was normalized to the band intensity of Flag-WDR24. For every batch of compounds tested, a negative control (water) and a positive control (leucine, 25 µM, SIGMA)) were also performed. The depletion of bound endogenous Sestrin2 to Flag-WDR24 by leucine is normalized to represent 100% activity. Compounds are assayed in duplicate and activity of each compound is quantified as percent of leucine activity and averaged. A table listing quantified data from compounds tested is presented in Table 3. Repeated attempts of the assay resulted in a standard deviation of 20% in the average activity of leucine compared to water; therefore, compounds where both duplicates reduce the amount of Sestrin2 bound to GATOR2 by at least 40% at 25 µM were considered statistically significant and were referred to as leucine mimetics. Some compounds increased the amount of Sestrin2 bound to Flag-WDR24 (shown as negative percent activity of leucine in Table 3). Compounds that showed less than −40% of leucine activity were also considered hits and were referred to as leucine antagonists.

Method 2 (Cell-Based mTORC1 Activation)

To demonstrate efficacy of compounds identified as leucine mimetics in intact cells, mTORC1 signaling in response to compound treatment post leucine starvation was measured via western blotting. Upon leucine starvation, addition of exogenous leucine activates mTORC1 when signaling is measured 10 to 90 minutes after addition of leucine, as described in Wang, S., Tsun, Z., et al. Science 347(6218): 188-194 (2015). Therefore, a similar assay was designed to test whether compounds identified as leucine mimetics activate mTORC1 in a similar manner. Briefly, 800,000 HEK293T cells were plated in each well of a 6-well plate in DMEM supplemented with 10% fetal bovine serum and antibiotics. The next day, cells were placed in modified DMEM without leucine (Thermo Scientific) or serum for 1 hour followed by addition of leucine mimetic (n=3) at a given concentration for some period of time greater than 10 minutes. Cells were then lysed, processed for SDS-PAGE and western blotting was performed with antibodies directed against the mTORC1 substrates phosphorylated S6 Kinase (Thr389) and phosphorylated 4EBP1 (Thr37/46) (Cell Signaling Technology) and loading controls (beta-actin, Santa Cruz Biotechnology) as described in Kang, S. A., et al. Science 341(6144): 364-374 (2013). The intensity of the bands corresponding to the phosphorylated substrates were then normalized to the actin band using the LI-COR® imaging platform. Compounds that significantly increased mTORC1 signaling relative to leucine-starved cells treated with no compound (student t-test, $p<0.05$) were considered active in cells. As a positive control, leucine was added at 100 μM to leucine-starved cells for 60 minutes.

Method 3 (Cell-Based mTORC1 Activation)

To demonstrate efficacy of compounds identified as leucine antagonists or to determine whether weak leucine mimetics enhance the activity of leucine in intact cells, the same paradigm as above was repeated but with the following changes: cells were placed in leucine minus DMEM media (as described in Method 3) for 60 minutes followed by compound (n=3) for some period of time greater than or equal to 60 minutes. After compound treatment, the cells were stimulated with 30 and 100 μM of leucine for 60 minutes. mTORC1 signaling was measured via western blotting as described in Method 2. Compounds that reduced levels of actin-normalized phosphorylated substrates of mTORC1 in response to leucine at either 30 μM or 100 μM in a statistically significant manner (student t-test, $p<0.05$) were considered active in cells. Compounds that increased levels of actin-normalized phosphorylated substrates of mTORC1 in response to leucine at either 30 μM or 100 μM in a statistically significant manner (student t-test, $p<0.05$) were considered leucine enhancers in cells. As a control, leucine-starved cells were pre-treated with water prior to addition of leucine. Alternatively, potential leucine antagonists were assayed in HEK293T cells in the same manner described above but without leucine starvation and stimulation. Western blots were performed to determine whether baseline mTORC1 signaling was attenuated upon compound treatment under replete culturing conditions.

Method 4

The ability of compounds to modulate the interaction between Sestrin2 and GATOR2 in cells were measured by repeating the assay described in Methods 2 and 3 but in HEK293T cells engineered to stably express Flag-WDR24 plated in 10 cm tissue culture dishes. The interaction between endogenous Sestrin 2 and Flag-WDR24 was measured from lysate obtained from cells after compound treatment (n=3) as described in Method 1. Briefly, to measure the amount of endogenous Sestrin2 bound to Flag-WDR24 after cell treatment, an immunoprecipitation was performed with the anti-flag resin and the resulting samples were processed for SDS-PAGE and western blotting to measure amounts of endogenous Sestrin 2 bound to Flag-WDR24. Compounds that modulated the amount of Sestrin2 bound to GATOR2 in a statistically significant manner (student t-test, $p<0.05$) were considered hits.

Method 5 (ALPHALisa Cell-Based Assay)

To demonstrate efficacy of compounds identified as leucine mimetics in intact cells in a plate-based format, mTORC1 signaling in response to compound treatment post leucine starvation was measured via AlphaLISA. Briefly, 1,000,000 HEK293T cells were plated in T-75 cell culture flasks in DMEM supplemented with 10% fetal bovine serum. After cells reached confluency, they were placed in modified DMEM without leucine (Thermo Scientific) with 10% dialyzed fetal bovine serum for 1 hour. Cells were then trypsinized, and replated in 96-well black clear bottom plates at 50,000 cells/well in DMEM without leucine with 10% dialyzed fetal bovine serum. Cells were allowed to adhere to the plate for 2 hours, followed by addition of compounds (n=4) at a given concentration for some period of time greater than 1 hour. After time point is reached, cells were lysed and assayed by p-p70 S6K (Thr389) SureFire Ultra AlphaLISA kit according to manufacturer's instructions (http.//www.perkinelmer.com/CMSResources/Images/44-176283MAN_SureFire_TGR70S_p70_pT389.pdf).

Compounds that significantly increased mTORC1 signaling relative to leucine-starved cells treated with no compound (student t-test, $p<0.05$) were considered mTORC1 activators. Compounds that significantly decreased mTORC1 signaling relative to leucine-starved cells treated with no compound (student t-test, $p<0.05$) were considered inhibitors in cells. As a positive control, leucine was added at 100 uM to leucine-starved cells for the period of time equal to compound treatment.

Method 6, Thermalshift Protocol (Tm Shift):

Full-length, codon-optimized human Sestrin2 was N-terminally fused with His-MBP tag and cloned into the pMAL6H-C5XT bacterial expression vector. This vector was transformed into *Escherichia coli* LOBSTR (DE3) cells (Kerafast). Cells were grown at 37° C. to 0.6 OD, then protein production was induced with 0.2 mM IPTG at 18° C. for 12-14 h. Cells were collected by centrifugation at 6,000 g, resuspended in lysis buffer (50 mM potassiumphosphate, pH 8.0, 500 mM NaCl, 30 mM imidazole, 1 mM DTT, 10 μg/ml Benzonase and 1 mM PMSF) and lysed by sonication. The lysate was cleared by centrifugation at 10,000 g for 20 min. Sestrin2 protein was isolated from the soluble fraction to near 100% purity through affinity capture of the His tag followed by ion exchange and size exclusion chromatography. For the thermal shift assay, Sestrin2 protein was diluted to 2 mg/ml in dilution buffer (10 mM Tris HCl pH 7.4, 150 mM NaCl, 1 mM DTT, 0.1 mM EDTA). Prior to performing the thermal shift assay, 2 μl of Sestrin2 protein was combined with 8 μl ROX dye (Thermo Fisher), 1 μL vehicle or compound, and 14 μL dilution buffer per well of a 96-well-plate, and incubated on ice for 1 hour to allow for compound binding. The thermal shift assay was then run on an Agilent MX3005p and each compound was assayed in triplicate at 10 μM, 100 μM and 1000 μM. Incubation with leucine shifted the melting temperature of Sestrin2 by 2.16 to 11.61 degrees Celsius in a dose dependent manner. A positive shift of 2 degrees or more is considered statistically significant based on the CV % variability of repeated thermal shift measurements of Sestrin2 incubated with vehicle.

Method 7, Indirect Ligand Binding Assay (ILBA)

The binding of Sestrin2 to leucine or other ligand was detected either in intact cells, in vitro or with purified protein through immune-detection with the rabbit monoclonal anti-Sestrin2 antibody from Cell Signaling Technology (CST, Cat #8487). Binding of the CST antibody to native (non-denatured) Sestrin2 was modulated by the binding of leucine in such a way that the affinity of the antibody decreases upon leucine binding. Similarly, the affinity of the CST antibody for native Sestrin2 decreased upon compounds binding to native in a manner similar as leucine. Conversely, compounds that destabilized Sestrin2 as measured by thermal shift assay increased the affinity of the CST antibody for non-denatured Sestrin2. As a result, multiple formats of this indirect ligand-binding assay (ILBA) were developed that measure the affinity of the CST anti-Sestrin2 antibody after binding of leucine or compound. In one version, the assay was performed with crude lysate generated from a human cell line after a 1-hour period of amino acid starvation (cells are lysed in 1% Triton, 10 mM beta-glycerol phosphate, 10 mM sodium pyrophosphate, 40 mM HEPES [pH 7.4], 150 mM NaCl and 2.5 mM MgCl$_2$). Lysate was then incubated with leucine or other compound for 1 hour on ice or at room temperature. After compound incubation, samples were subjected to immunoprecipitation with the CST anti-Sestrin2 antibody for 1.5 hours followed by a 30-minute incubation with protein-A sepharose as described in L. Chantranupong, et al., Cell Reports 9:1-8 (2014). The sepharose conjugated antibody-protein complex was precipitated via centrifugation and the flow-through was subjected to a second round of immunoprecipitation with a rabbit polyclonal anti-Sestrin2 antibody (Protein Tech, #10795-1-AP) to determine that total Sestrin2 protein levels between samples were equal. SDS-PAGE was performed with the immunoprecipitation samples followed by western-blot with the mouse monoclonal anti-Sestrin2 antibody from SIGMA (cat #WH0083667M3). Leucine binding induced a significant decrease in the intensity of the band corresponding to Sestrin2 by 50% or more on the immunoblot with samples immunoprecipitated with the anti-Sestrin2 antibody from CST but led to no change in the Sestrin2 band on the immunoblot with samples immunoprecipitated with the Protein Tech antibody. This version of the assay also measured increased instability of Sestrin2 induced by incubation with compounds. The assay was performed in the same manner, but compounds that destabilized Sestrin2 (as measured by thermal shift assay) resulted in an increase in immunoblot band intensity corresponding to Sestrin2 immunoprecipitated using the CST antibody.

This assay was also performed in cultured human cells over-expressing Sestrin2 N-terminally fused to a Flag tag. In this version of the assay, the procedure remained the same, but immunoblotting was performed with a mouse anti-Flag antibody (#F3165, SIGMA). The decrease in affinity of the CST antibody upon leucine or γ-methylleucine binding was not observed when an LBA was performed with a point mutant form of Sestrin2 unable to bind leucine.

In another version of the assay, cultured human cells were subjected to some combination of amino acid starvation for 1-hour followed by stimulation with leucine or compounds. One hour after stimulation, cells were lysed and processed as described above with the exception of the 1-hour ligand-binding step.

The indirect ligand-binding assay was also performed in a multi-well format using ALPHAlisa technology (Perkin Elmer). This version of the assay required biotinylated anti-Sestrin2 antibody, Streptavidin donor beads (Perkin Elmer) coupled with either anti-Flag acceptor beads (Perkin Elmer) for detection of overexpressed Flag-Sestrin2, or coupled with mouse anti-Sestrin2 antibody (SIGMA) and anti-mouse acceptor beads (Perkin Elmer) for detection of endogenous Sestrin2.

The assay was performed as described above, but with the following modifications: for the leucine or compound binding portion of the assay, crude lysate generated from cells transiently or stably overexpressing human Flag-Sestrin2 after 1 hour of amino acid starvation was diluted to 0.8 mg/ml of total protein in lysis buffer and arrayed in a multi-well plate such as a 96-well plate. For detection of endogenous Sestrin2, crude lysate was diluted to 4 mg/ml of total protein in lysis buffer. Leucine or compound was added to each well and the plate was incubated on ice or at room temperature for 1 hour with gentle agitation. During the ligand-binding step, biotinylated anti-Sestrin2 antibody (CST) was diluted to 5 nM in ALPHAlisa immunoassay buffer (Perkin Elmer), and 5 nM of mouse anti-Sestrin2 antibody (SIGMA was combined with a 4× stock of the anti-mouse acceptor bead (40 µg/ml) for assays detecting endogenous Sestrin2. For detection of Flag-Sestrin2, a 4× stock of anti-Flag acceptor beads (40 µg/ml) in immunoassay buffer was prepared. After the ligand-binding step, 5 µL of lysate was combined with 10 µL of the biotinylated anti-Sestrin2 antibody, 12.5 µL of the mouse Sestrin2 antibody/anti-mouse acceptor bead mix or anti-Flag acceptor beads, and 10 µL of ALPHAlisa immunoassay buffer and was incubated at room temperature for 1 hour. Finally, 12.5 µL of streptavidin donor beads (160 µg/ml in immunoassay buffer) were added for an additional hour in the dark prior to reading the plate on an Envision plate reader.

The ALPHAlisa assay was also performed as described but with purified Sestrin2 protein at a final reaction concentration of 3 ng/ml diluted in immunoassay buffer.

Finally, the ALPHAlisa was performed with lysate from cells treated with leucine or compound under amino acid starved conditions prior to lysing. Cell-based treatment was performed in a multi-well plate, and 15 µL of lysate (1 mg/ml total protein) was used per ALPHAlisa reaction in combination with 10 µL of biotinylated antibody, 12.5 µL of the antibody/acceptor bead mix and 12.5 µL of the streptavidin donor bead mix.

The indirect ligand-binding assay was also performed with a capture-based method such as a sandwich ELISA as performed in the art. In one version of the assay, the ILBA was performed using the MULTI-ARRAY® technology developed by Meso-Scale Discovery (MSD). The MSD system was based on electrochemiluminescence detection of antibody binding to analyte. The ILBA was performed with crude lysate expressing endogenous Sestrin2 or overexpressed Flag-Sestrin2 and leucine treatment was performed either in vitro or in cells prior to lysis. For the in vitro ILBA with endogenous Sestrin2, crude lysate (0.8 mg/ml total protein) was prepared and leucine binding was performed in the same manner described for the ALPHAlisa ILBA. After ligand binding was complete, biotinylated anti-Sestrin2 antibody from CST was added to each well to a final concentration of 0.25 µg/ml and was incubated with gentle agitation for 1 hour at 4° C. Capture of each sample into a well of a 96-well plate was accomplished in one of the following ways: streptavidin-coated MSD plates or bare MSD plates coated with mouse anti-Sestrin2 antibody from SIGMA. Capture required 25 µL of sample per well followed by 1-hour incubation with shaking at 350 rpm. After sample capture, wells were washed three times with Tris buffered saline with 0.1% Tween (TBS-T). If the samples were captured onto the streptavidin-coated plate, mouse monoclonal anti-Sestrin2 antibody (SIGMA) was then added to a final concentration of 1 µg/ml for 1 hour with shaking at 350 rpm. Wells were washed again in TBS-T, and anti-mouse secondary SULFO-TAG antibody at a final concentration of 1 µg/ml (MSD) was added for an hour with shaking at 350 rpm. Finally, wells were washed three times with TBS-T and 2× Read Buffer (MSD) was added and the plate was read immediately on a MSD instrument. If samples were captured with bare plates coated with the mouse anti-Sestrin2 antibody, after washing, a streptavidin secondary SULFO-TAG antibody (MSD) was added at a final concentration of 1 µg/ml for 1 hour with shaking followed by washes and incubation with Read Buffer prior to analysis.

In another version of this assay, crude lysate overexpressing Flag-Sestrin2 was analyzed and captured or detected with the mouse monoclonal anti-Flag antibody (SIGMA) using the same MSD-based protocol as described above.

For all assays, compounds that decreased the signal corresponding to immunoreactivity of Sestrin2 in a significant manner were considered leucine mimetics while compounds that increased the signal in a significant manner were considered potential leucine antagonists Table 3 shows the activity of selected compounds of this invention. The compound numbers correspond to the compound numbers in Tables 1 and 2. Compounds having an activity designated as "A" provided a % activity relative to leucine of ≥40%, compounds having an activity designated as "B" provided a % activity relative to leucine of ≤−40%; compounds having an activity designated as "C" provided a % activity relative to leucine of between −40 and 40%. Compounds having an activity designated as "D" provided a shift relative to DMSO control of 0.5 to 2 fold, compounds having an activity designated as "E" provided a shift relative to DMSO of 2.1-5 fold, compounds having an activity designated as "F" provided a shift relative to DMSO of 5.1-10 fold and compounds having an activity designated as "G" provided a shift relative to DMSO of 10.1 to 14 fold, at the designated concentrations.

Activity for the % activity relative to leucine assay was determined using assay Method 1. Activity for the cell-based mTORC1 activation assay was determined using assay Method 2.

TABLE 3

Assay Data for Exemplary Compounds

| Compound Number | Activity of Leucine: % Activity | Cell-Based mTORC1 Activation | Cell-Based mTORC1 Activation Concentration (μM) |
|---|---|---|---|
| I-1 | B | | |
| I-2 | B | | |
| I-3 | B | | |
| I-4 | C | | |
| I-5 | B | | |
| I-6 | C | | |
| I-7 | B | | |
| I-8 | B | | |
| I-9 | C | E | 100 |
| I-10 | C | D | 30 and 100 |
| I-11 | C | | |
| I-12 | C | | |
| I-13 | C | | |
| I-14 | B | | |
| I-15 | C | | |
| I-16 | C | | |
| I-17 | C | | |
| I-18 | C | | |
| I-19 | C | | |
| I-20 | C | | |
| I-21 | C | | |
| I-22 | C | | |
| I-23 | C | D to F | 100 |
| I-24 | A | | |
| I-25 | C | | |
| I-26 | C | | |
| I-27 | A | | |
| I-28 | C | | |
| I-29 | A | | |
| I-30 | A | | |
| I-31 | A | | |
| I-32 | A | | |
| I-33 | C | | |
| I-34 | C | | |
| I-35 | A | | |
| I-36 | B | | |
| I-37 | A | E to F | 100 |
| I-38 | C | | |
| I-39 | C | | |
| I-40 | A | | |
| I-41 | A | | |
| I-42 | A | D to F | 100 |
| I-43 | A | D to E | 100 |
| I-44 | A | D | 100 |

TABLE 3-continued

Assay Data for Exemplary Compounds

| Compound Number | Activity of Leucine: % Activity | Cell-Based mTORC1 Activation | Cell-Based mTORC1 Activation Concentration (μM) |
|---|---|---|---|
| I-45 | B | | |
| I-46 | C | D | 100 |
| I-47 | C | D | 100 |
| I-48 | C | | |
| I-49 | C | | |
| I-50 | C | | |
| I-145 | A | | |
| I-146 | A | | |
| I-147 | A | | |
| I-148 | A | | |
| I-149 | C | | |
| I-150 | C | | |
| I-151 | C | | |
| I-152 | C | | |
| I-153 | C | | |
| I-154 | C | | |
| I-155 | C | | |
| I-156 | C | | |
| I-157 | B to C | | |
| I-158 | C | | |
| I-159 | A | | |
| I-160 | C | | |
| I-161 | C | | |
| I-162 | C | | |
| I-163 | A | | |
| I-164 | A | | |
| I-165 | A to C | | |
| I-166 | C | | |
| I-167 | A | D to F | 100 |
| I-168 | | D to E | 100 |

Table 4 shows selected compounds of this invention active in the ALPHALisa cell-based assay (Method 5). The compound numbers correspond to the compound numbers in Tables 1 and 2. Compounds listed in Table 4 are mTORC1 activators and have an activity of >2-fold versus the positive leucine control.

TABLE 4

Exemplary Compounds Active in the ALPHALisa Cell-based Assay Compound Number

I-44
I-43
I-42
I-167
I-253
I-145
I-252
I-251
I-250
I-88
I-56
I-96
I-206
I-122
I-90
I-128
I-195
I-194
I-193
I-93
I-249
I-120
I-190
I-189
I-248
I-247
I-246
I-185

TABLE 4-continued

Exemplary Compounds Active in the ALPHALisa Cell-based Assay
Compound Number

I-183
I-179
I-178
I-177
I-176
I-175
I-207
I-245
I-210
I-244
I-243
I-241
I-240
I-239
I-238
I-237
I-236
I-235
I-234
I-233
I-232
I-231
I-230
I-229
I-228

Table 5 shows selected compounds of this invention active in the Thermalshift assay (Method 6). The compound numbers correspond to the compound numbers in Tables 1 and 2. Compounds listed in Table 5 exhibited a positive shift of 2 degrees or more.

TABLE 5

Exemplary Compounds Active in the Thermalshift Assay
Compound Number

I-44
I-43
I-42
I-31
I-27
I-4
I-47
I-167
I-164
I-163
I-254
I-253
I-145
I-252
I-251
I-250
I-206
I-122
I-203
I-90
I-201
I-129
I-128
I-196
I-195
I-194
I-93
I-120
I-191
I-179
I-178
I-177
I-176
I-175
I-209
I-208
I-207

TABLE 5-continued

Exemplary Compounds Active in the Thermalshift Assay
Compound Number

I-245
I-210
I-244
I-237
I-235
I-233
I-232
I-231
I-229

We claim:

1. A method of treating Huntington's disease in a patient in need thereof, comprising the step of administering a compound of formula I:

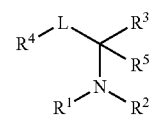

or a pharmaceutically acceptable salt thereof, wherein:
$R^1$ is hydrogen;
$R^2$ is hydrogen;
$R^3$ is —C(O)OH;
L is

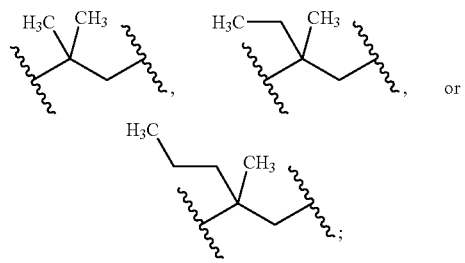

$R^4$ is —CF$_3$, —CH$_2$F, —CHF$_2$, —CH$_2$CHF$_2$, —CH$_2$CF$_3$, or —CH$_2$CH$_2$CHF$_2$; and
$R^5$ is hydrogen.

2. The method of claim 1, wherein said compound is selected from any one of:

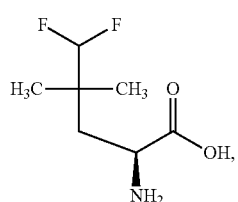

I-90

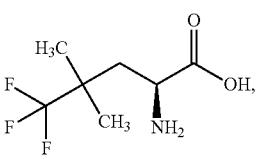

I-128

-continued

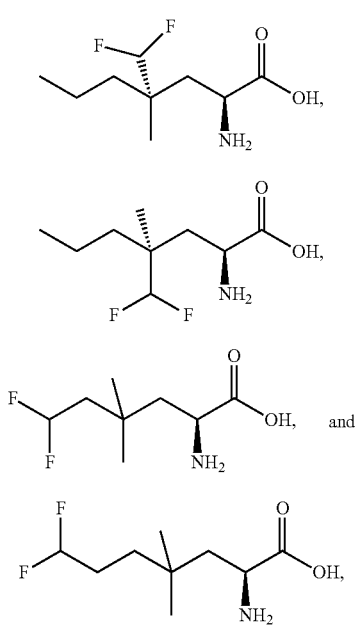

I-229

I-232

I-234 and

I-238 or a pharmaceutically acceptable salt thereof.

3. The method of claim 1, wherein said compound is selected from:

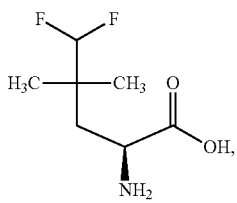

I-90 or a pharmaceutically acceptable salt thereof.

4. The method of claim 1, wherein said compound or pharmaceutically acceptable salt thereof is administered as a pharmaceutically acceptable composition comprising a pharmaceutically acceptable carrier, adjuvant, or vehicle.

5. A method of treating Huntington's disease in a patient in need thereof, comprising the step of administering a compound selected from:

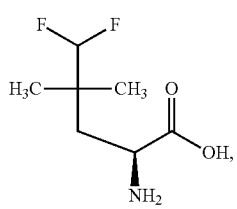

I-90

-continued

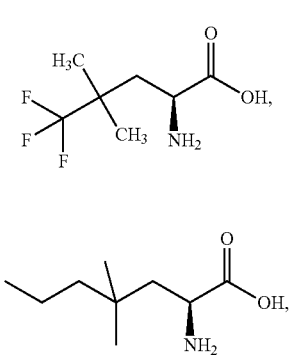

I-128

I-210

I-229

I-230

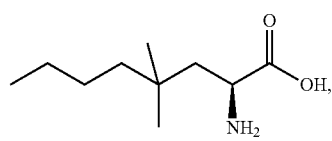

I-232

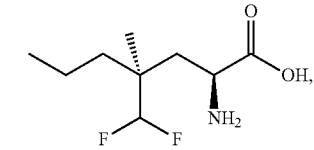

I-234 and

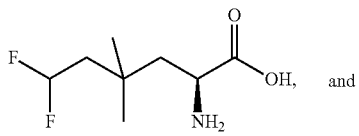

I-238

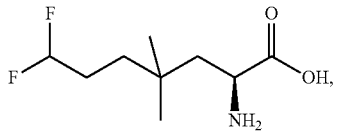

or a pharmaceutically acceptable salt thereof.

6. The method of claim 1, wherein said compound or pharmaceutically acceptable salt thereof is administered as a pharmaceutically acceptable composition comprising a pharmaceutically acceptable carrier, adjuvant, or vehicle.

* * * * *